(12) United States Patent
Jo et al.

(10) Patent No.: US 8,445,443 B2
(45) Date of Patent: May 21, 2013

(54) CELL PERMEABLE P18 RECOMBINANT PROTEINS, POLYNUCLEOTIDES ENCODING THE SAME, AND ANTICANCER COMPOSITION COMPRISING THE SAME

(75) Inventors: Daewoong Jo, Seoul (KR); Seolhwa Kim, Gwangju (KR); Jung-Hee Lim, Seoul (KR); Kisuk Park, Seoul (KR); Se-Eun Kang, Busan (KR)

(73) Assignee: Procell Therapeutics Inc., Seoul (KR)

(*) Notice: Subject to any disclaimer, the term of this patent is extended or adjusted under 35 U.S.C. 154(b) by 533 days.

(21) Appl. No.: 12/676,491

(22) PCT Filed: Sep. 4, 2008

(86) PCT No.: PCT/KR2008/005222
§ 371 (c)(1),
(2), (4) Date: Mar. 4, 2010

(87) PCT Pub. No.: WO2009/031836
PCT Pub. Date: Mar. 12, 2009

(65) Prior Publication Data
US 2010/0305041 A1    Dec. 2, 2010

Related U.S. Application Data

(60) Provisional application No. 60/969,762, filed on Sep. 4, 2007.

(30) Foreign Application Priority Data

Jun. 25, 2008    (KR) .................. 10-2008-0059938

(51) Int. Cl.
*C12N 15/62* (2006.01)

(52) U.S. Cl.
USPC .......... 514/19.3; 514/19.8; 514/1.2; 514/21.5; 514/21.6

(58) Field of Classification Search
None
See application file for complete search history.

(56) References Cited

U.S. PATENT DOCUMENTS

2004/0172684 A1* 9/2004 Kovalic et al. ............... 800/284

FOREIGN PATENT DOCUMENTS

WO    WO 95/34295 A1    12/1995

OTHER PUBLICATIONS

UniProtKB/TrEMBL Accession No. C2HMP7, accessed at http://www.uniprot.org/uniprot/C2HMP7, Feb. 8, 2013.*
Extended European Search Report issued Jan. 17, 2012, in Patent Application No. 08828990.5.
Marie A. Bogoyevitch, et al., "Taking the Cell by Stealth or Storm? Protein Transduction Domains (PTDs) as Versatile Vectors for Delivery", DNA and Cell Biology, vol. 21, No. 12, XP 1145670, 2002, pp. 879-894.
Bryan R. Meade, et al., "Exogenous siRNA delivery using peptide transduction domains/cell penetrating peptides", Advanced Drug Delivery Reviews, vol. 59, 2007, pp. 134-140.
Martha Schreiber, et al., "Comparison of the effectiveness of adenovirus vectors expressing cyclin kinase inhibitors $p16^{INK4A}$, $p18^{INK4C}$, $p19^{INK4D}$, $p21^{WAF1/CIP1}$, and $p27^{KIP1}$ in inducing cell cycle arrest, apoptosis and inhibition of tumorigenicity", Oncogene, vol. 18(9), Mar. 4, 1999, pp. 1663-1676.
Hiroshi Harada, et al., "Antitumor Protein Therapy; Application of the Protein Transduction Domain to the Development of a Protein Drug for Cancer Treatment", Breast Cancer, vol. 13, No. 1, Jan. 2006, pp. 16-26.
Mike S. S. Chang, et al., "Dissecting Intracellular Signaling Pathways with Membrane-Permeable Peptides", Science's STKE, vol. 2000 (47), pl. 1, Aug. 29, 2000, pp. 1-10 and cover page.
Anne Scheller, et al., "Evidence for an amphipathicity independent cellular uptake of amphipathic cell-penetrating peptides", European Journal Biochemistry, vol. 267, 2000, pp. 6043-6049.
Jacek Hawiger, "Noninvasive intracellular delivery of functional peptides and proteins", Current Opinion in Chemical Biology, vol. 3(1), Feb. 1999, pp. 89-94.
D. G. De Rooji, et al. "Regulation of Spermatogonial Proliferation", Annals New York Academy of Sciences 564, The Seminiferous Tubule, Part V, 1989, pp. 140-153.
Jayne M. Stommel, et al., "A New Twist in the Feedback Loop; Stress-Activated MDM2 Destabilization is Required for p53 Activation", Cell Cycle, vol. 4, Issue 3, Mar. 2005, pp. 411-417.
Yunyuan V. Wang, et al., "Quantitative analyses reveal the importance of regulated Hdmx degradation for p53 activation", PNAS, vol. 104, No. 30, Jul. 24, 2007, pp. 12365-12370.
Xiantao Wang, et al., "$p27^{Kip1}$ overexpression causes apoptotic death of mammalian cells", Oncogene (1997) 15, pages 2991-2997.
Feng Bai, et al., "Haploinsufficiency of $p18^{INK4C}$ Sensitizes Mice to Carcinogen-Induced Tumorigenesis", Molecular and Cellular Biology, vol. 23, No. 4, Feb. 2003, pp. 1269-1277.

(Continued)

*Primary Examiner* — Christina Bradley
*Assistant Examiner* — Kristina M Hellman
(74) *Attorney, Agent, or Firm* — Oblon, Spivak, McClelland, Maier & Neustadt, L.L.P.

(57) ABSTRACT

The present invention discloses cell permeable p18 recombinant proteins where a macromolecule transduction domain (MTD) is fused to a tumor suppressor p18. Also disclosed are polynucleotides encoding the cell permeable p18 recombinant proteins, an expression vector containing the cell permeable p18 recombinant protein, and a pharmaceutical composition for treating p18 deficiency or failure which contains the cell permeable p18 recombinant protein as an effective ingredient. The cell permeable p18 recombinant proteins of the present invention are capable of efficiently introducing a haploinsufficient tumor suppressor p18 into a cell, and thus, can activate cell signaling mechanisms involved in the activation of ATM and p53 that induce cell cycle arrest and apoptosis in response to DNA damage or oncogenic signals. Therefore, the cell permeable p18 recombinant proteins of the present invention can be effectively used as an anticancer agent.

24 Claims, 41 Drawing Sheets

OTHER PUBLICATIONS

David A. Alcorta, et al., "Involvement of the cyclin-dependent kinase inhibitor p16 (INK4a) in replicative senescence of normal human fibroblasts", Proc. Natl. Acad. Sci. Biochemistry, vol. 93, Nov. 1996, pp. 13742-13747.

Thenaa K. Said, et al., "Interaction of Retinoblastoma Protein and D Cyclins During Cell-Growth Inhibition by Hexamethylenebisacetamide in TM2H Mouse Epithelial Cells", Molecular Carcinogenesis, 22, 1998, pp. 128-143.

Junan Li, et al., "Tumor Suppressor INK4: Determination of the Solution Structure of p18$^{INK4C}$ and Demonstration of the Functional Significance of Loops in p18$^{INK4C}$ and p16$^{INK4A}$", Biochemistry, 38, 1999, pp. 2930-2940.

Michael B. Kastan, "Checkin two steps", Nature, vol. 410, Apr. 12, 2001, pp. 766-767.

Daewoong Jo, et al., "Epigenetic regulation of gene structure and function with a cell-permeable Cre recombinase", Research Article, Nature Biotechnology, vol. 19, Oct. 2001, pp. 929-933.

Dimitrios Balomenos, et al., "Cell-cycle regulation in immunity, tolerance and autoimmunity", Viewpoint, Immunology Today, vol. 21, No. 11, Nov. 2000, pp. 551-555.

Shu Lu, et al., "Atm-haploinsufficiency enhances susceptibility to carcinogen-induced mammary tumors", Carcinogenesis, vol. 27, No. 4, 2006, pp. 848-855.

Robert T. Abraham, "Part-time cop nabs deviant DNA", Nature Medicine, News and Views, vol. 11, No. 3, Mar. 2005, pp. 257-258.

Bum-Joon Park, et al., "The haploinsufficient Tumor Suppressor p18 Upregulates p53 via Interactions with ATM/ATR", Cell, vol. 120, Jan. 28, 2005, pp. 209-221.

John E. French, et al., "Loss of heterozygosity frequency at the *Trp53* locus in *p53*-deficient (+/−) mouse tumors is carcinogen- and tissue-dependent", Carcinogenesis, vol. 21, No. 1, 2001, pp. 99-106.

Fumio Ide, et al., "*p53* Haploinsufficiency Profoundly Accelerates the Onset of Tongue Tumors in Mice Lacking the Xeroderma Pigmentosum Group A Gene", American Journal of Pathology, Short Communication, vol. 163, No. 5, Nov. 2003, pp. 1729-1733.

Anne K. Baumgärtner, et al., "High Frequency of Genetic Aberrations in Enteropathy-Type T-Cell Lymphoma", Laboratory Investigation, vol. 83, No. 10, Oct. 2003, pp. 1509-1516.

Kinneret Savitsky, et al., "The complete sequence of the coding region of the ATM gene reveals similarity to cell cycle regulators in different species", Human Molecular Genetics, vol. 4, No. 11, 1995, pp. 2025-2032.

James Turkson, et al., "Novel peptidomimetic inhibitors of Signal transducer and activator of transcription 3 dimerization and biological activity", Molecular Cancer Therapeutics, No. 3, Mar. 16, 2004, pp. 261-269.

Rolfs A, et al., "cyclin-dependent kinase inhibitor 2C (p18, inhibits CDK4) [synthetic construct]", Synthetic Construct, GenBank Accession No. ABM85633, Mar. 10, 2008, 3 pages.

* cited by examiner

M1: 1 kb marker
M2: 100 bp marker
1: Hp18 −517 bp
2: HM$_1$p18 −612 bp
3: Hp18M$_1$ −612 bp
4: HM$_1$p18M$_1$ −648 bp
5: Hp18NM$_1$ −288 bp
6: Hp18SM$_1$ −289 bp
7: Hp18CM$_1$ −255 bp
8: Hp18NSM$_1$ −486 bp
9: Hp18SCM$_1$ −435 bp M: 1 kb marker
1: HM$_2$p18 −603 bp
2: Hp18M$_2$ −603 bp
3: HM$_2$p18M$_2$ −630 bp
4: HM$_3$p18 −603 bp
5: Hp18M$_3$ −603 bp
6: HM$_3$p18M$_3$ −630 bp M: 100 bp
1: Hp18       -517 bp
2: HM$_1$p18   -612 bp
3: Hp18M$_1$   -612 bp
4: HM$_1$p18M$_1$ -648 bp
5: Hp18NM$_1$  -288 bp
6: Hp18SM$_1$  -289 bp
7: Hp18CM$_1$  -255 bp
8: Hp18NSM$_1$ -486 bp
9: Hp18SCM$_1$ -435 bp M: 1 kb marker
1: HM$_2$p18     -603 bp
2: Hp18M$_2$     -603 bp
3: HM$_2$p18M$_2$ -630 bp
4: HM$_3$p18     -603 bp
5: Hp18M$_3$     -603 bp
6: HM$_3$p18M$_3$ -630 bp M: 100 bp
1: Hp18        -517 bp
2: HM$_1$p18   -612 bp
3: Hp18M$_1$   -612 bp
4: HM$_1$p18M$_1$ -648 bp
5: Hp18NM$_1$  -288 bp
6: Hp18SM$_1$  -289 bp
7: Hp18CM$_1$  -255 bp
8: Hp18NSM$_1$ -486 bp
9: Hp18SCM$_1$ -435 bp M: 1 kb marker
1: HM$_2$p18      -603 bp
2: Hp18M$_2$      -603 bp
3: HM$_2$p18M$_2$ -630 bp
4: HM$_3$p18      -603 bp
5: Hp18M$_3$      -603 bp
6: HM$_3$p18M$_3$ -630 bp

SEQUENCE LISTING

```
<160> NUMBER OF SEQ ID NOS: 244

<210> SEQ ID NO 1
<211> LENGTH: 507
<212> TYPE: DNA
<213> ORGANISM: Homo sapiens
<220> FEATURE:
<223> OTHER INFORMATION: Human p18
<220> FEATURE:
<221> NAME/KEY: CDS
<222> LOCATION: (1)..(504)

<400> SEQUENCE: 1 atg gcc gag cct tgg ggg aac gag ttg gcg tcc gca gct gcc agg ggg       48
Met Ala Glu Pro Trp Gly Asn Glu Leu Ala Ser Ala Ala Ala Arg Gly
1               5                   10                  15 gac cta gag caa ctt act agt ttg ttg caa aat aat gta aac gtc aat       96
Asp Leu Glu Gln Leu Thr Ser Leu Leu Gln Asn Asn Val Asn Val Asn
            20                  25                  30 gca caa aat gga ttt gga agg act gcg ctg cag gtt atg aaa ctt gga      144
Ala Gln Asn Gly Phe Gly Arg Thr Ala Leu Gln Val Met Lys Leu Gly
        35                  40                  45 aat ccc gag att gcc agg aga ctg cta ctt aga ggt gct aat ccc gat      192
Asn Pro Glu Ile Ala Arg Arg Leu Leu Leu Arg Gly Ala Asn Pro Asp
    50                  55                  60 ttg aaa gac cga act ggt ttc gct gtc att cat gat gcg gcc aga gca      240
Leu Lys Asp Arg Thr Gly Phe Ala Val Ile His Asp Ala Ala Arg Ala
65                  70                  75                  80 ggt ttc ctg gac act tta cag act ttg ctg gag ttt caa gct gat gtt      288
Gly Phe Leu Asp Thr Leu Gln Thr Leu Leu Glu Phe Gln Ala Asp Val
                85                  90                  95 aac atc gag gat aat gaa ggg aac ctg ccc ttg cac ttg gct gcc aaa      336
Asn Ile Glu Asp Asn Glu Gly Asn Leu Pro Leu His Leu Ala Ala Lys
            100                 105                 110 gaa ggc cac ctc cgg gtg gtg gag ttc ctg gtg aag cac acg gcc agc      384
Glu Gly His Leu Arg Val Val Glu Phe Leu Val Lys His Thr Ala Ser
        115                 120                 125 aat gtg ggg cat cgg aac cat aag ggg gac acc gcc tgt gat ttg gcc      432
Asn Val Gly His Arg Asn His Lys Gly Asp Thr Ala Cys Asp Leu Ala
    130                 135                 140 agg ctc tat ggg agg aat gag gtt gtt agc ctg atg cag gca aac ggg      480
Arg Leu Tyr Gly Arg Asn Glu Val Val Ser Leu Met Gln Ala Asn Gly
145                 150                 155                 160 gct ggg gga gcc aca aat ctt caa taa                                  507
Ala Gly Gly Ala Thr Asn Leu Gln
                165

<210> SEQ ID NO 2
<211> LENGTH: 168
<212> TYPE: PRT
<213> ORGANISM: Homo sapiens
<220> FEATURE:
<223> OTHER INFORMATION: Human p18

<400> SEQUENCE: 2

Met Ala Glu Pro Trp Gly Asn Glu Leu Ala Ser Ala Ala Ala Arg Gly
1               5                   10                  15
```

-continued

```
Asp Leu Glu Gln Leu Thr Ser Leu Leu Gln Asn Asn Val Asn Val Asn
            20                  25                  30

Ala Gln Asn Gly Phe Gly Arg Thr Ala Leu Gln Val Met Lys Leu Gly
        35                  40                  45

Asn Pro Glu Ile Ala Arg Arg Leu Leu Arg Gly Ala Asn Pro Asp
 50                  55                  60

Leu Lys Asp Arg Thr Gly Phe Ala Val Ile His Asp Ala Ala Arg Ala
 65                  70                  75                  80

Gly Phe Leu Asp Thr Leu Gln Thr Leu Leu Glu Phe Gln Ala Asp Val
                85                  90                  95

Asn Ile Glu Asp Asn Gly Asn Leu Pro Leu His Leu Ala Ala Lys
            100                 105                 110

Glu Gly His Leu Arg Val Val Glu Phe Leu Val Lys His Thr Ala Ser
        115                 120                 125

Asn Val Gly His Arg Asn His Lys Gly Asp Thr Ala Cys Asp Leu Ala
130                 135                 140

Arg Leu Tyr Gly Arg Asn Glu Val Val Ser Leu Met Gln Ala Asn Gly
145                 150                 155                 160

Ala Gly Gly Ala Thr Asn Leu Gln
                165

<210> SEQ ID NO 3
<211> LENGTH: 36
<212> TYPE: DNA
<213> ORGANISM: Artificial Sequence
<220> FEATURE:
<223> OTHER INFORMATION: kFGF-4 derived MTD
<220> FEATURE:
<223> OTHER INFORMATION: Description of Artificial Sequence: Synthetic
      oligonucleotide

<400> SEQUENCE: 3
gcagccgttc ttctccctgt tcttcttgcc gcaccc                             36

<210> SEQ ID NO 4
<211> LENGTH: 12
<212> TYPE: PRT
<213> ORGANISM: Unknown
<220> FEATURE:
<223> OTHER INFORMATION: kFGF-4 derived MTD
<220> FEATURE:
<223> OTHER INFORMATION: Description of Unknown: Kaposi fibroblast
      growth factor 4 peptide

<400> SEQUENCE: 4

Ala Ala Val Leu Leu Pro Val Leu Leu Ala Ala Pro
1               5                   10

<210> SEQ ID NO 5
<211> LENGTH: 27
<212> TYPE: DNA
<213> ORGANISM: Artificial Sequence
<220> FEATURE:
<223> OTHER INFORMATION: JO-101 MTD
<220> FEATURE:
<223> OTHER INFORMATION: Description of Artificial Sequence: Synthetic
      oligonucleotide

<400> SEQUENCE: 5
ctgattctgc tgctgctgcc gattatt                                       27

<210> SEQ ID NO 6
<211> LENGTH: 9
<212> TYPE: PRT
```

```
<213> ORGANISM: Theileria annulata
<220> FEATURE:
<223> OTHER INFORMATION: JO-101 MTD

<400> SEQUENCE: 6

Leu Ile Leu Leu Leu Leu Pro Ile Ile
1               5

<210> SEQ ID NO 7
<211> LENGTH: 27
<212> TYPE: DNA
<213> ORGANISM: Artificial Sequence
<220> FEATURE:
<223> OTHER INFORMATION: JO-103 MTD
<220> FEATURE:
<223> OTHER INFORMATION: Description of Artificial Sequence: Synthetic
      oligonucleotide

<400> SEQUENCE: 7
ctggcgctgc cggtgctgct gctggcg                                         27

<210> SEQ ID NO 8
<211> LENGTH: 9
<212> TYPE: PRT
<213> ORGANISM: Homo sapiens
<220> FEATURE:
<223> OTHER INFORMATION: JO-103 MTD

<400> SEQUENCE: 8

Leu Ala Leu Pro Val Leu Leu Leu Ala
1               5

<210> SEQ ID NO 9
<211> LENGTH: 15
<212> TYPE: DNA
<213> ORGANISM: Artificial Sequence
<220> FEATURE:
<223> OTHER INFORMATION: SV40 large T antigen-derived NLS
<220> FEATURE:
<223> OTHER INFORMATION: Description of Artificial Sequence: Synthetic
      oligonucleotide

<400> SEQUENCE: 9
aagaagaaga ggaag                                                      15

<210> SEQ ID NO 10
<211> LENGTH: 5
<212> TYPE: PRT
<213> ORGANISM: Artificial Sequence
<220> FEATURE:
<223> OTHER INFORMATION: SV40 large T antigen-derived NLS
<220> FEATURE:
<223> OTHER INFORMATION: Description of Artificial Sequence: Synthetic
      peptide

<400> SEQUENCE: 10

Lys Lys Lys Arg Lys
1               5

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      Hp18-5' primer

<400> SEQUENCE: 11
ccgcatatga agaagaagag gaaggccgag ccttggggga acgag                     45
```

```
<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      Hp18-3' primer

<400> SEQUENCE: 12
ccgcatatgt cattgaagat ttgtggctcc                                          30

<210> SEQ ID NO 13
<211> LENGTH: 84
<212> TYPE: DNA
<213> ORGANISM: Artificial Sequence
<220> FEATURE:
<223> OTHER INFORMATION: Description of Artificial Sequence: Synthetic
      HM1p18-5' primer

<400> SEQUENCE: 13
ccgcatatga agaagaagag gaaggcagcc gttcttctcc ctgttcttct tgccgcaccc         60
gccgagcctt gggggaacga gttg                                               84

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      Hp18M1-3' primer

<400> SEQUENCE: 14
ccgcatatgt cagggtgcgg caagaagaac agggagaaga acggctgctt gaagatttgt         60
ggctccccca gc                                                            72

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic
      Hp18NM1-3' primer

<400> SEQUENCE: 15
ccgcatatgt caaataatcg gcagcagcag cagaatcagt tgaagatttg tggctccccc         60
agc                                                                      63

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      Hp18S-5' primer

<400> SEQUENCE: 16
ccgcatatga agaagaagag gaaggctaat cccgatttga aagac                         45

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      Hp18SM1-3' primer
```

<400> SEQUENCE: 17
ccgcatatgt cagggtgcgg caagaagaac agggagaaga acggvtgcct ccaccacccg    60
gaggtggcct tc    72

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      Hp18C-5' primer

<400> SEQUENCE: 18
ccgcatatga agaagaagag gaagttcctg gtgaagcaca cggcc    45

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: Synthetic
      HM2p18-5' primer

<400> SEQUENCE: 19
ccgcatatga agaagaagag gaagctgatt ctgctgctgc tgccgattat tgccgagcct    60
tgggggaacg agttg    75

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
      Hp18M2-3' primer

<400> SEQUENCE: 20
ccgcatatgt caaataatcg gcagcagcag cagaatcagt tgaagatttg tggctccccc    60
agc    63

<210> SEQ ID NO 21
<211> LENGTH: 75
<212> TYPE: DNA
<213> ORGANISM: Artificial Sequence
<220> FEATURE:
<223> OTHER INFORMATION: Description of Artificial Sequence: Synthetic
      HM3p18-5' primer

<400> SEQUENCE: 21
ccgcatatga agaagaagag gaagctggcg ctgccggtgc tgctgctggc ggccgagcct    60
tgggggaacg agttg    75

<210> SEQ ID NO 22
<211> LENGTH: 63
<212> TYPE: DNA
<213> ORGANISM: Artificial Sequence
<220> FEATURE:
<223> OTHER INFORMATION: Description of Artificial Sequence: Synthetic
      Hp18M3-3' primer

<400> SEQUENCE: 22
ccgcatatgt cacgccagca gcagcaccgg cagcgccagt tgaagatttg tggctccccc    60
agc    63

<210> SEQ ID NO 23
<211> LENGTH: 582
<212> TYPE: DNA
<213> ORGANISM: Artificial Sequence
<220> FEATURE:
<223> OTHER INFORMATION: His-p18 recombinant protein
<220> FEATURE:
<223> OTHER INFORMATION: Description of Artificial Sequence: Synthetic polynucleotide
<220> FEATURE:
<221> NAME/KEY: CDS
<222> LOCATION: (1)..(579)

<400> SEQUENCE: 23

```
atg ggc agc agc cat cat cat cat cat cac agc agc ggc ctg gtg ccg        48
Met Gly Ser Ser His His His His His His Ser Ser Gly Leu Val Pro
1               5                   10                  15 cgc ggc agc cat atg aag aag aag agg aag gcc gag cct tgg ggg aac        96
Arg Gly Ser His Met Lys Lys Lys Arg Lys Ala Glu Pro Trp Gly Asn
            20                  25                  30 gag ttg gcg tcc gca gct gcc agg ggg gac cta gag caa ctt act agt      144
Glu Leu Ala Ser Ala Ala Ala Arg Gly Asp Leu Glu Gln Leu Thr Ser
        35                  40                  45 ttg ttg caa aat aat gta aac gtc aat gca caa aat gga ttt gga agg      192
Leu Leu Gln Asn Asn Val Asn Val Asn Ala Gln Asn Gly Phe Gly Arg
    50                  55                  60 act gcg ctg cag gtt atg aaa ctt gga aat ccc gag att gcc agg aga      240
Thr Ala Leu Gln Val Met Lys Leu Gly Asn Pro Glu Ile Ala Arg Arg
65                  70                  75                  80 ctg cta ctt aga ggt gct aat ccc gat ttg aaa gac cga act ggt ttc      288
Leu Leu Leu Arg Gly Ala Asn Pro Asp Leu Lys Asp Arg Thr Gly Phe
                85                  90                  95 gct gtc att cat gat gcg gcc aga gca ggt ttc ctg gac act tta cag      336
Ala Val Ile His Asp Ala Ala Arg Ala Gly Phe Leu Asp Thr Leu Gln
            100                 105                 110 act ttg ctg gag ttt caa gct gat gtt aac atc gag gat aat gaa ggg      384
Thr Leu Leu Glu Phe Gln Ala Asp Val Asn Ile Glu Asp Asn Glu Gly
        115                 120                 125 aac ctg ccc ttg cac ttg gct gcc aaa gaa ggc cac ctc cgg gtg gtg      432
Asn Leu Pro Leu His Leu Ala Ala Lys Glu Gly His Leu Arg Val Val
    130                 135                 140 gag ttc ctg gtg aag cac acg gcc agc aat gtg ggg cat cgg aac cat      480
Glu Phe Leu Val Lys His Thr Ala Ser Asn Val Gly His Arg Asn His
145                 150                 155                 160 aag ggg gac acc gcc tgt gat ttg gcc agg ctc tat ggg agg aat gag      528
Lys Gly Asp Thr Ala Cys Asp Leu Ala Arg Leu Tyr Gly Arg Asn Glu
                165                 170                 175 gtt gtt agc ctg atg cag gca aac ggg gct ggg gga gcc aca aat ctt      576
Val Val Ser Leu Met Gln Ala Asn Gly Ala Gly Gly Ala Thr Asn Leu
            180                 185                 190 caa taa                                                              582
Gln
```

<210> SEQ ID NO 24
<211> LENGTH: 193
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Gly Ser Ser His His His His His His Ser Ser Gly Leu Val Pro
1               5                   10                  15
```

```
Arg Gly Ser His Met Lys Lys Lys Arg Lys Ala Glu Pro Trp Gly Asn
             20                  25                  30
Glu Leu Ala Ser Ala Ala Ala Arg Gly Asp Leu Glu Gln Leu Thr Ser
         35                  40                  45
Leu Leu Gln Asn Asn Val Asn Val Asn Ala Gln Asn Gly Phe Gly Arg
     50                  55                  60
Thr Ala Leu Gln Val Met Lys Leu Gly Asn Pro Glu Ile Ala Arg Arg
65                  70                  75                  80
Leu Leu Leu Arg Gly Ala Asn Pro Asp Leu Lys Asp Arg Thr Gly Phe
                 85                  90                  95
Ala Val Ile His Asp Ala Ala Arg Ala Gly Phe Leu Asp Thr Leu Gln
            100                 105                 110
Thr Leu Leu Glu Phe Gln Ala Asp Val Asn Ile Glu Asp Asn Glu Gly
        115                 120                 125
Asn Leu Pro Leu His Leu Ala Ala Lys Glu Gly His Leu Arg Val Val
    130                 135                 140
Glu Phe Leu Val Lys His Thr Ala Ser Asn Val Gly His Arg Asn His
145                 150                 155                 160
Lys Gly Asp Thr Ala Cys Asp Leu Ala Arg Leu Tyr Gly Arg Asn Glu
                165                 170                 175
Val Val Ser Leu Met Gln Ala Asn Gly Ala Gly Gly Ala Thr Asn Leu
            180                 185                 190
Gln

<210> SEQ ID NO 25
<211> LENGTH: 618
<212> TYPE: DNA
<213> ORGANISM: Artificial Sequence
<220> FEATURE:
<223> OTHER INFORMATION: His-MTD1-p18 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(615)

<400> SEQUENCE: 25 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag gca gcc gtt ctt ctc cct      96
Arg Gly Ser His Met Lys Lys Lys Arg Lys Ala Ala Val Leu Leu Pro
            20                  25                  30 gtt ctt ctt gcc gca ccc gcc gag cct tgg ggg aac gag ttg gcg tcc     144
Val Leu Leu Ala Ala Pro Ala Glu Pro Trp Gly Asn Glu Leu Ala Ser
        35                  40                  45 gca gct gcc agg ggg gac cta gag caa ctt act agt ttg ttg caa aat     192
Ala Ala Ala Arg Gly Asp Leu Glu Gln Leu Thr Ser Leu Leu Gln Asn
    50                  55                  60 aat gta aac gtc aat gca caa aat gga ttt gga agg act gcg ctg cag     240
Asn Val Asn Val Asn Ala Gln Asn Gly Phe Gly Arg Thr Ala Leu Gln
65                  70                  75                  80 gtt atg aaa ctt gga aat ccc gag att gcc agg aga ctg cta ctt aga     288
Val Met Lys Leu Gly Asn Pro Glu Ile Ala Arg Arg Leu Leu Leu Arg
                85                  90                  95 ggt gct aat ccc gat ttg aaa gac cga act ggt ttc gct gtc att cat     336
Gly Ala Asn Pro Asp Leu Lys Asp Arg Thr Gly Phe Ala Val Ile His
            100                 105                 110
```

```
gat gcg gcc aga gca ggt ttc ctg gac act tta cag act ttg ctg gag    384
Asp Ala Ala Arg Ala Gly Phe Leu Asp Thr Leu Gln Thr Leu Leu Glu
        115                 120                 125 ttt caa gct gat gtt aac atc gag gat aat gaa ggg aac ctg ccc ttg    432
Phe Gln Ala Asp Val Asn Ile Glu Asp Asn Glu Gly Asn Leu Pro Leu
    130                 135                 140 cac ttg gct gcc aaa gaa ggc cac ctc cgg gtg gtg gag ttc ctg gtg    480
His Leu Ala Ala Lys Glu Gly His Leu Arg Val Val Glu Phe Leu Val
145                 150                 155                 160 aag cac acg gcc agc aat gtg ggg cat cgg aac cat aag ggg gac acc    528
Lys His Thr Ala Ser Asn Val Gly His Arg Asn His Lys Gly Asp Thr
                165                 170                 175 gcc tgt gat ttg gcc agg ctc tat ggg agg aat gag gtt gtt agc ctg    576
Ala Cys Asp Leu Ala Arg Leu Tyr Gly Arg Asn Glu Val Val Ser Leu
            180                 185                 190 atg cag gca aac ggg gct ggg gga gcc aca aat ctt caa taa            618
Met Gln Ala Asn Gly Ala Gly Gly Ala Thr Asn Leu Gln
        195                 200                 205
```

<210> SEQ ID NO 26
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Met Gly Ser Ser His His His His His His Ser Ser Gly Leu Val Pro
1               5                   10                  15

Arg Gly Ser His Met Lys Lys Arg Lys Ala Ala Val Leu Leu Pro
            20                  25                  30

Val Leu Leu Ala Ala Pro Ala Glu Pro Trp Gly Asn Glu Leu Ala Ser
        35                  40                  45

Ala Ala Ala Arg Gly Asp Leu Glu Gln Leu Thr Ser Leu Leu Gln Asn
    50                  55                  60

Asn Val Asn Val Asn Ala Gln Asn Gly Phe Gly Arg Thr Ala Leu Gln
65                  70                  75                  80

Val Met Lys Leu Gly Asn Pro Glu Ile Ala Arg Arg Leu Leu Leu Arg
                85                  90                  95

Gly Ala Asn Pro Asp Leu Lys Asp Arg Thr Gly Phe Ala Val Ile His
            100                 105                 110

Asp Ala Ala Arg Ala Gly Phe Leu Asp Thr Leu Gln Thr Leu Leu Glu
        115                 120                 125

Phe Gln Ala Asp Val Asn Ile Glu Asp Asn Glu Gly Asn Leu Pro Leu
    130                 135                 140

His Leu Ala Ala Lys Glu Gly His Leu Arg Val Val Glu Phe Leu Val
145                 150                 155                 160

Lys His Thr Ala Ser Asn Val Gly His Arg Asn His Lys Gly Asp Thr
                165                 170                 175

Ala Cys Asp Leu Ala Arg Leu Tyr Gly Arg Asn Glu Val Val Ser Leu
            180                 185                 190

Met Gln Ala Asn Gly Ala Gly Gly Ala Thr Asn Leu Gln
        195                 200                 205
```

<210> SEQ ID NO 27
<211> LENGTH: 618
<212> TYPE: DNA
<213> ORGANISM: Artificial Sequence
<220> FEATURE:

<223> OTHER INFORMATION: His-p18-MTD1 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(615)

<400> SEQUENCE: 27

```
atg ggc agc agc cat cat cat cat cat cac agc agc ggc ctg gtg ccg     48
Met Gly Ser Ser His His His His His His Ser Ser Gly Leu Val Pro
1               5                   10                  15 cgc ggc agc cat atg aag aag aag agg aag gcc gag cct tgg ggg aac     96
Arg Gly Ser His Met Lys Lys Lys Arg Lys Ala Glu Pro Trp Gly Asn
            20                  25                  30 gag ttg gcg tcc gca gct gcc agg ggg gac cta gag caa ctt act agt    144
Glu Leu Ala Ser Ala Ala Ala Arg Gly Asp Leu Glu Gln Leu Thr Ser
        35                  40                  45 ttg ttg caa aat aat gta aac gtc aat gca caa aat gga ttt gga agg    192
Leu Leu Gln Asn Asn Val Asn Val Asn Ala Gln Asn Gly Phe Gly Arg
    50                  55                  60 act gcg ctg cag gtt atg aaa ctt gga aat ccc gag att gcc agg aga    240
Thr Ala Leu Gln Val Met Lys Leu Gly Asn Pro Glu Ile Ala Arg Arg
65                  70                  75                  80 ctg cta ctt aga ggt gct aat ccc gat ttg aaa gac cga act ggt ttc    288
Leu Leu Leu Arg Gly Ala Asn Pro Asp Leu Lys Asp Arg Thr Gly Phe
                85                  90                  95 gct gtc att cat gat gcg gcc aga gca ggt ttc ctg gac act tta cag    336
Ala Val Ile His Asp Ala Ala Arg Ala Gly Phe Leu Asp Thr Leu Gln
            100                 105                 110 act ttg ctg gag ttt caa gct gat gtt aac atc gag gat aat gaa ggg    384
Thr Leu Leu Glu Phe Gln Ala Asp Val Asn Ile Glu Asp Asn Glu Gly
        115                 120                 125 aac ctg ccc ttg cac ttg gct gcc aaa gaa ggc cac ctc cgg gtg gtg    432
Asn Leu Pro Leu His Leu Ala Ala Lys Glu Gly His Leu Arg Val Val
    130                 135                 140 gag ttc ctg gtg aag cac acg gcc agc aat gtg ggg cat cgg aac cat    480
Glu Phe Leu Val Lys His Thr Ala Ser Asn Val Gly His Arg Asn His
145                 150                 155                 160 aag ggg gac acc gcc tgt gat ttg gcc agg ctc tat ggg agg aat gag    528
Lys Gly Asp Thr Ala Cys Asp Leu Ala Arg Leu Tyr Gly Arg Asn Glu
                165                 170                 175 gtt gtt agc ctg atg cag gca aac ggg gct ggg gga gcc aca aat ctt    576
Val Val Ser Leu Met Gln Ala Asn Gly Ala Gly Gly Ala Thr Asn Leu
            180                 185                 190 caa gca gcc gtt ctt ctc cct gtt ctt ctt gcc gca ccc tga            618
Gln Ala Ala Val Leu Leu Pro Val Leu Leu Ala Ala Pro
        195                 200                 205
```

<210> SEQ ID NO 28
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Met Gly Ser Ser His His His His His His Ser Ser Gly Leu Val Pro
1               5                   10                  15

Arg Gly Ser His Met Lys Lys Lys Arg Lys Ala Glu Pro Trp Gly Asn
            20                  25                  30

Glu Leu Ala Ser Ala Ala Ala Arg Gly Asp Leu Glu Gln Leu Thr Ser
```

```
                        35                  40                  45
Leu Leu Gln Asn Asn Val Asn Val Asn Ala Gln Asn Gly Phe Gly Arg
 50                  55                  60

Thr Ala Leu Gln Val Met Lys Leu Gly Asn Pro Glu Ile Ala Arg Arg
 65                  70                  75                  80

Leu Leu Leu Arg Gly Ala Asn Pro Asp Leu Lys Asp Arg Thr Gly Phe
                 85                  90                  95

Ala Val Ile His Asp Ala Ala Arg Ala Gly Phe Leu Asp Thr Leu Gln
                100                 105                 110

Thr Leu Leu Glu Phe Gln Ala Asp Val Asn Ile Glu Asp Asn Glu Gly
            115                 120                 125

Asn Leu Pro Leu His Leu Ala Ala Lys Glu Gly His Leu Arg Val Val
        130                 135                 140

Glu Phe Leu Val Lys His Thr Ala Ser Asn Val Gly His Arg Asn His
145                 150                 155                 160

Lys Gly Asp Thr Ala Cys Asp Leu Ala Arg Leu Tyr Gly Arg Asn Glu
                165                 170                 175

Val Val Ser Leu Met Gln Ala Asn Gly Ala Gly Gly Ala Thr Asn Leu
            180                 185                 190

Gln Ala Ala Val Leu Leu Pro Val Leu Leu Ala Ala Pro
        195                 200                 205

<210> SEQ ID NO 29
<211> LENGTH: 654
<212> TYPE: DNA
<213> ORGANISM: Artificial Sequence
<220> FEATURE:
<223> OTHER INFORMATION: His-MTD1-p18-MTD1 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(651)

<400> SEQUENCE: 29 atg ggc agc agc cat cat cat cat cat cac agc agc ggc ctg gtg ccg      48
Met Gly Ser Ser His His His His His His Ser Ser Gly Leu Val Pro
 1               5                  10                  15 cgc ggc agc cat atg aag aag aag agg aag gca gcc gtt ctt ctc cct      96
Arg Gly Ser His Met Lys Lys Lys Arg Lys Ala Ala Val Leu Leu Pro
                20                  25                  30 gtt ctt ctt gcc gca ccc gcc gag cct tgg ggg aac gag ttg gcg tcc     144
Val Leu Leu Ala Ala Pro Ala Glu Pro Trp Gly Asn Glu Leu Ala Ser
            35                  40                  45 gca gct gcc agg ggg gac cta gag caa ctt act agt ttg ttg caa aat     192
Ala Ala Ala Arg Gly Asp Leu Glu Gln Leu Thr Ser Leu Leu Gln Asn
 50                  55                  60 aat gta aac gtc aat gca caa aat gga ttt gga agg act gcg ctg cag     240
Asn Val Asn Val Asn Ala Gln Asn Gly Phe Gly Arg Thr Ala Leu Gln
 65                  70                  75                  80 gtt atg aaa ctt gga aat ccc gag att gcc agg aga ctg cta ctt aga     288
Val Met Lys Leu Gly Asn Pro Glu Ile Ala Arg Arg Leu Leu Leu Arg
                 85                  90                  95 ggt gct aat ccc gat ttg aaa gac cga act ggt ttc gct gtc att cat     336
Gly Ala Asn Pro Asp Leu Lys Asp Arg Thr Gly Phe Ala Val Ile His
                100                 105                 110 gat gcg gcc aga gca ggt ttc ctg gac act tta cag act ttg ctg gag     384
Asp Ala Ala Arg Ala Gly Phe Leu Asp Thr Leu Gln Thr Leu Leu Glu
            115                 120                 125
```

```
ttt caa gct gat gtt aac atc gag gat aat gaa ggg aac ctg ccc ttg      432
Phe Gln Ala Asp Val Asn Ile Glu Asp Asn Glu Gly Asn Leu Pro Leu
    130                 135                 140 cac ttg gct gcc aaa gaa ggc cac ctc cgg gtg gtg gag ttc ctg gtg      480
His Leu Ala Ala Lys Glu Gly His Leu Arg Val Val Glu Phe Leu Val
145                 150                 155                 160 aag cac acg gcc agc aat gtg ggg cat cgg aac cat aag ggg gac acc      528
Lys His Thr Ala Ser Asn Val Gly His Arg Asn His Lys Gly Asp Thr
                165                 170                 175 gcc tgt gat ttg gcc agg ctc tat ggg agg aat gag gtt gtt agc ctg      576
Ala Cys Asp Leu Ala Arg Leu Tyr Gly Arg Asn Glu Val Val Ser Leu
            180                 185                 190 atg cag gca aac ggg gct ggg gga gcc aca aat ctt caa gca gcc gtt      624
Met Gln Ala Asn Gly Ala Gly Gly Ala Thr Asn Leu Gln Ala Ala Val
        195                 200                 205 ctt ctc cct gtt ctt ctt gcc gca ccc tga                              654
Leu Leu Pro Val Leu Leu Ala Ala Pro
    210                 215

<210> SEQ ID NO 30
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Gly Ser Ser His His His His His His Ser Ser Gly Leu Val Pro
1               5                   10                  15

Arg Gly Ser His Met Lys Lys Arg Lys Ala Ala Val Leu Leu Pro
            20                  25                  30

Val Leu Leu Ala Ala Pro Ala Glu Pro Trp Gly Asn Glu Leu Ala Ser
        35                  40                  45

Ala Ala Ala Arg Gly Asp Leu Glu Gln Leu Thr Ser Leu Leu Gln Asn
    50                  55                  60

Asn Val Asn Val Asn Ala Gln Asn Gly Phe Gly Arg Thr Ala Leu Gln
65                  70                  75                  80

Val Met Lys Leu Gly Asn Pro Glu Ile Ala Arg Arg Leu Leu Arg
                85                  90                  95

Gly Ala Asn Pro Asp Leu Lys Asp Arg Thr Gly Phe Ala Val Ile His
            100                 105                 110

Asp Ala Ala Arg Ala Gly Phe Leu Asp Thr Leu Gln Thr Leu Leu Glu
        115                 120                 125

Phe Gln Ala Asp Val Asn Ile Glu Asp Asn Glu Gly Asn Leu Pro Leu
    130                 135                 140

His Leu Ala Ala Lys Glu Gly His Leu Arg Val Val Glu Phe Leu Val
145                 150                 155                 160

Lys His Thr Ala Ser Asn Val Gly His Arg Asn His Lys Gly Asp Thr
                165                 170                 175

Ala Cys Asp Leu Ala Arg Leu Tyr Gly Arg Asn Glu Val Val Ser Leu
            180                 185                 190

Met Gln Ala Asn Gly Ala Gly Gly Ala Thr Asn Leu Gln Ala Ala Val
        195                 200                 205

Leu Leu Pro Val Leu Leu Ala Ala Pro
    210                 215

<210> SEQ ID NO 31
<211> LENGTH: 294
```

```
<212> TYPE: DNA
<213> ORGANISM: Artificial Sequence
<220> FEATURE:
<223> OTHER INFORMATION: His-p18N-MTD1 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(291)

<400> SEQUENCE: 31 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag gcc gag cct tgg ggg aac      96
Arg Gly Ser His Met Lys Lys Lys Arg Lys Ala Glu Pro Trp Gly Asn
            20                  25                  30 gag ttg gcg tcc gca gct gcc agg ggg gac cta gag caa ctt act agt     144
Glu Leu Ala Ser Ala Ala Ala Arg Gly Asp Leu Glu Gln Leu Thr Ser
        35                  40                  45 ttg ttg caa aat aat gta aac gtc aat gca caa aat gga ttt gga agg     192
Leu Leu Gln Asn Asn Val Asn Val Asn Ala Gln Asn Gly Phe Gly Arg
50                  55                  60 act gcg ctg cag gtt atg aaa ctt gga aat ccc gag att gcc agg aga     240
Thr Ala Leu Gln Val Met Lys Leu Gly Asn Pro Glu Ile Ala Arg Arg
65                  70                  75                  80 ctg cta ctt aga ggt gca gcc gtt ctt ctc cct gtt ctt ctt gcc gca     288
Leu Leu Leu Arg Gly Ala Ala Val Leu Leu Pro Val Leu Leu Ala Ala
                85                  90                  95 ccc taa                                                              294
Pro

<210> SEQ ID NO 32
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Gly Ser Ser His His His His His His Ser Ser Gly Leu Val Pro
1               5                   10                  15

Arg Gly Ser His Met Lys Lys Lys Arg Lys Ala Glu Pro Trp Gly Asn
            20                  25                  30

Glu Leu Ala Ser Ala Ala Ala Arg Gly Asp Leu Glu Gln Leu Thr Ser
        35                  40                  45

Leu Leu Gln Asn Asn Val Asn Val Asn Ala Gln Asn Gly Phe Gly Arg
50                  55                  60

Thr Ala Leu Gln Val Met Lys Leu Gly Asn Pro Glu Ile Ala Arg Arg
65                  70                  75                  80

Leu Leu Leu Arg Gly Ala Ala Val Leu Leu Pro Val Leu Leu Ala Ala
                85                  90                  95

Pro

<210> SEQ ID NO 33
<211> LENGTH: 297
<212> TYPE: DNA
<213> ORGANISM: Artificial Sequence
<220> FEATURE:
<223> OTHER INFORMATION: His-p18S-MTD1 recombinant protein
<220> FEATURE:
<223> OTHER INFORMATION: Description of Artificial Sequence: Synthetic
```

```
                           polynucleotide
<220> FEATURE:
<221> NAME/KEY: CDS
<222> LOCATION: (1)..(294)

<400> SEQUENCE: 33 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag gct aat ccc gat ttg aaa      96
Arg Gly Ser His Met Lys Lys Lys Arg Lys Ala Asn Pro Asp Leu Lys
            20                  25                  30 gac cga act ggt ttc gct gtc att cat gat gcg gcc aga gca ggt ttc     144
Asp Arg Thr Gly Phe Ala Val Ile His Asp Ala Ala Arg Ala Gly Phe
        35                  40                  45 ctg gac act tta cag act ttg ctg gag ttt caa gct gat gtt aac atc     192
Leu Asp Thr Leu Gln Thr Leu Leu Glu Phe Gln Ala Asp Val Asn Ile
50                  55                  60 gag gat aat gaa ggg aac ctg ccc ttg cac ttg gct gcc aaa gaa ggc     240
Glu Asp Asn Glu Gly Asn Leu Pro Leu His Leu Ala Ala Lys Glu Gly
65                  70                  75                  80 cac ctc cgg gtg gtg gag gca gcc gtt ctt ctc cct gtt ctt ctt gcc     288
His Leu Arg Val Val Glu Ala Ala Val Leu Leu Pro Val Leu Leu Ala
                85                  90                  95 gcc ccc tga                                                         297
Ala Pro

<210> SEQ ID NO 34
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Gly Ser Ser His His His His His His Ser Ser Gly Leu Val Pro
1               5                   10                  15

Arg Gly Ser His Met Lys Lys Lys Arg Lys Ala Asn Pro Asp Leu Lys
            20                  25                  30

Asp Arg Thr Gly Phe Ala Val Ile His Asp Ala Ala Arg Ala Gly Phe
        35                  40                  45

Leu Asp Thr Leu Gln Thr Leu Leu Glu Phe Gln Ala Asp Val Asn Ile
    50                  55                  60

Glu Asp Asn Glu Gly Asn Leu Pro Leu His Leu Ala Ala Lys Glu Gly
65                  70                  75                  80

His Leu Arg Val Val Glu Ala Ala Val Leu Leu Pro Val Leu Leu Ala
                85                  90                  95

Ala Pro

<210> SEQ ID NO 35
<211> LENGTH: 261
<212> TYPE: DNA
<213> ORGANISM: Artificial Sequence
<220> FEATURE:
<223> OTHER INFORMATION: His-p18C-MTD1 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(258)

<400> SEQUENCE: 35
```

```
atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag ttc ctg gtg aag cac acg      96
Arg Gly Ser His Met Lys Lys Lys Arg Lys Phe Leu Val Lys His Thr
                20                  25                  30 gcc agc aat gtg ggg cat cgg aac cat aag ggg gac acc gcc tgt gat     144
Ala Ser Asn Val Gly His Arg Asn His Lys Gly Asp Thr Ala Cys Asp
            35                  40                  45 ttg gcc agg ctc tat ggg agg aat gag gtt gtt agc ctg atg cag gca     192
Leu Ala Arg Leu Tyr Gly Arg Asn Glu Val Val Ser Leu Met Gln Ala
        50                  55                  60 aac ggg gct ggg gga gcc aca aat ctt caa gca gcc gtt ctt ctc cct     240
Asn Gly Ala Gly Gly Ala Thr Asn Leu Gln Ala Ala Val Leu Leu Pro
65                  70                  75                  80 gtt ctt ctt gcc gca ccc tga                                         261
Val Leu Leu Ala Ala Pro
                85
```

<210> SEQ ID NO 36
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Gly Ser Ser His His His His His His Ser Ser Gly Leu Val Pro
1               5                   10                  15

Arg Gly Ser His Met Lys Lys Lys Arg Lys Phe Leu Val Lys His Thr
                20                  25                  30

Ala Ser Asn Val Gly His Arg Asn His Lys Gly Asp Thr Ala Cys Asp
            35                  40                  45

Leu Ala Arg Leu Tyr Gly Arg Asn Glu Val Val Ser Leu Met Gln Ala
        50                  55                  60

Asn Gly Ala Gly Gly Ala Thr Asn Leu Gln Ala Ala Val Leu Leu Pro
65                  70                  75                  80

Val Leu Leu Ala Ala Pro
                85
```

<210> SEQ ID NO 37
<211> LENGTH: 474
<212> TYPE: DNA
<213> ORGANISM: Artificial Sequence
<220> FEATURE:
<223> OTHER INFORMATION: His-p18NS-MTD1 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(471)

<400> SEQUENCE: 37

```
atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag gcc gag cct tgg ggg aac      96
Arg Gly Ser His Met Lys Lys Lys Arg Lys Ala Glu Pro Trp Gly Asn
                20                  25                  30 gag ttg gcg tcc gca gct gcc agg ggg gac cta gag caa ctt act agt     144
Glu Leu Ala Ser Ala Ala Ala Arg Gly Asp Leu Glu Gln Leu Thr Ser
```

```
                35                  40                  45
ttg ttg caa aat aat gta aac gtc aat gca caa aat gga ttt gga agg       192
Leu Leu Gln Asn Asn Val Asn Val Asn Ala Gln Asn Gly Phe Gly Arg
        50                  55                  60 act gcg ctg cag gtt atg aaa ctt gga aat ccc gag att gcc agg aga       240
Thr Ala Leu Gln Val Met Lys Leu Gly Asn Pro Glu Ile Ala Arg Arg
65                  70                  75                  80 ctg cta ctt aga ggt gct aat ccc gat ttg aaa gac cga act ggt ttc       288
Leu Leu Leu Arg Gly Ala Asn Pro Asp Leu Lys Asp Arg Thr Gly Phe
                85                  90                  95 gct gtc att cat gat gcg gcc aga gca ggt ttc ctg gac act tta cag       336
Ala Val Ile His Asp Ala Ala Arg Ala Gly Phe Leu Asp Thr Leu Gln
            100                 105                 110 act ttg ctg gag ttt caa gct gat gtt aac atc gag gat aat gaa ggg       384
Thr Leu Leu Glu Phe Gln Ala Asp Val Asn Ile Glu Asp Asn Glu Gly
        115                 120                 125 aac ctg ccc ttg cac ttg gct gcc aaa gaa ggc cac ctc cgg gtg gtg       432
Asn Leu Pro Leu His Leu Ala Ala Lys Glu Gly His Leu Arg Val Val
130                 135                 140 gag gca gcc gtt ctt ctc cct gtt ctt ctt gcc gca ccc tga               474
Glu Ala Ala Val Leu Leu Pro Val Leu Leu Ala Ala Pro
145                 150                 155
```

<210> SEQ ID NO 38
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Gly Ser Ser His His His His His His Ser Ser Gly Leu Val Pro
1               5                   10                  15

Arg Gly Ser His Met Lys Lys Arg Lys Ala Glu Pro Trp Gly Asn
            20                  25                  30

Glu Leu Ala Ser Ala Ala Arg Gly Asp Leu Glu Gln Leu Thr Ser
        35                  40                  45

Leu Leu Gln Asn Asn Val Asn Val Asn Ala Gln Asn Gly Phe Gly Arg
        50                  55                  60

Thr Ala Leu Gln Val Met Lys Leu Gly Asn Pro Glu Ile Ala Arg Arg
65                  70                  75                  80

Leu Leu Leu Arg Gly Ala Asn Pro Asp Leu Lys Asp Arg Thr Gly Phe
                85                  90                  95

Ala Val Ile His Asp Ala Ala Arg Ala Gly Phe Leu Asp Thr Leu Gln
            100                 105                 110

Thr Leu Leu Glu Phe Gln Ala Asp Val Asn Ile Glu Asp Asn Glu Gly
        115                 120                 125

Asn Leu Pro Leu His Leu Ala Ala Lys Glu Gly His Leu Arg Val Val
    130                 135                 140

Glu Ala Ala Val Leu Leu Pro Val Leu Leu Ala Ala Pro
145                 150                 155
```

<210> SEQ ID NO 39
<211> LENGTH: 441
<212> TYPE: DNA
<213> ORGANISM: Artificial Sequence
<220> FEATURE:
<223> OTHER INFORMATION: His-p18SC-MTD1 recombinant protein
<220> FEATURE:
<223> OTHER INFORMATION: Description of Artificial Sequence: Synthetic

```
                polynucleotide
<220> FEATURE:
<221> NAME/KEY: CDS
<222> LOCATION: (1)..(438)

<400> SEQUENCE: 39 atg ggc agc agc cat cat cat cat cat cac agc agc ggc ctg gtg ccg        48
Met Gly Ser Ser His His His His His His Ser Ser Gly Leu Val Pro
1               5                   10                  15 cgc ggc agc cat atg aag aag aag agg aag gct aat ccc gat ttg aaa        96
Arg Gly Ser His Met Lys Lys Lys Arg Lys Ala Asn Pro Asp Leu Lys
            20                  25                  30 gac cga act ggt ttc gct gtc att cat gat gcg gcc aga gca ggt ttc       144
Asp Arg Thr Gly Phe Ala Val Ile His Asp Ala Ala Arg Ala Gly Phe
        35                  40                  45 ctg gac act tta cag act ttg ctg gag ttt caa gct gat gtt aac atc       192
Leu Asp Thr Leu Gln Thr Leu Leu Glu Phe Gln Ala Asp Val Asn Ile
50                  55                  60 gag gat aat gaa ggg aac ctg ccc ttg cac ttg gct gcc aaa gaa ggc       240
Glu Asp Asn Glu Gly Asn Leu Pro Leu His Leu Ala Ala Lys Glu Gly
65                  70                  75                  80 cac ctc cgg gtg gtg gag ttc ctg gtg aag cac acg gcc agc aat gtg       288
His Leu Arg Val Val Glu Phe Leu Val Lys His Thr Ala Ser Asn Val
                85                  90                  95 ggg cat cgg aac cat aag ggg gac acc gcc tgt gat ttg gcc agg ctc       336
Gly His Arg Asn His Lys Gly Asp Thr Ala Cys Asp Leu Ala Arg Leu
            100                 105                 110 tat ggg agg aat gag gtt gtt agc ctg atg cag gca aac ggg gct ggg       384
Tyr Gly Arg Asn Glu Val Val Ser Leu Met Gln Ala Asn Gly Ala Gly
        115                 120                 125 gga gcc aca aat ctt caa gca gcc gtt ctt ctc cct gtt ctt ctt gcc       432
Gly Ala Thr Asn Leu Gln Ala Ala Val Leu Leu Pro Val Leu Leu Ala
130                 135                 140 gca ccc tga                                                            441
Ala Pro
145

<210> SEQ ID NO 40
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Gly Ser Ser His His His His His His Ser Ser Gly Leu Val Pro
1               5                   10                  15

Arg Gly Ser His Met Lys Lys Lys Arg Lys Ala Asn Pro Asp Leu Lys
            20                  25                  30

Asp Arg Thr Gly Phe Ala Val Ile His Asp Ala Ala Arg Ala Gly Phe
        35                  40                  45

Leu Asp Thr Leu Gln Thr Leu Leu Glu Phe Gln Ala Asp Val Asn Ile
    50                  55                  60

Glu Asp Asn Glu Gly Asn Leu Pro Leu His Leu Ala Ala Lys Glu Gly
65                  70                  75                  80

His Leu Arg Val Val Glu Phe Leu Val Lys His Thr Ala Ser Asn Val
                85                  90                  95

Gly His Arg Asn His Lys Gly Asp Thr Ala Cys Asp Leu Ala Arg Leu
            100                 105                 110

Tyr Gly Arg Asn Glu Val Val Ser Leu Met Gln Ala Asn Gly Ala Gly
```

```
                115                 120                 125
Gly Ala Thr Asn Leu Gln Ala Val Leu Leu Pro Val Leu Leu Ala
            130                 135                 140

Ala Pro
145

<210> SEQ ID NO 41
<211> LENGTH: 609
<212> TYPE: DNA
<213> ORGANISM: Artificial Sequence
<220> FEATURE:
<223> OTHER INFORMATION: His-MTD2-p18 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(606)

<400> SEQUENCE: 41 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag ctg att ctg ctg ctg ctg      96
Arg Gly Ser His Met Lys Lys Lys Arg Lys Leu Ile Leu Leu Leu Leu
            20                  25                  30 ccg att att gcc gag cct tgg ggg aac gag ttg gcg tcc gca gct gcc     144
Pro Ile Ile Ala Glu Pro Trp Gly Asn Glu Leu Ala Ser Ala Ala Ala
        35                  40                  45 agg ggg gac cta gag caa ctt act agt ttg ttg caa aat aat gta aac     192
Arg Gly Asp Leu Glu Gln Leu Thr Ser Leu Leu Gln Asn Asn Val Asn
50                  55                  60 gtc aat gca caa aat gga ttt gga agg act gcg ctg cag gtt atg aaa     240
Val Asn Ala Gln Asn Gly Phe Gly Arg Thr Ala Leu Gln Val Met Lys
65                  70                  75                  80 ctt gga aat ccc gag att gcc agg aga ctg cta ctt aga ggt gct aat     288
Leu Gly Asn Pro Glu Ile Ala Arg Arg Leu Leu Leu Arg Gly Ala Asn
                85                  90                  95 ccc gat ttg aaa gac cga act ggt ttc gct gtc att cat gat gcg gcc     336
Pro Asp Leu Lys Asp Arg Thr Gly Phe Ala Val Ile His Asp Ala Ala
            100                 105                 110 aga gca ggt ttc ctg gac act tta cag act ttg ctg gag ttt caa gct     384
Arg Ala Gly Phe Leu Asp Thr Leu Gln Thr Leu Leu Glu Phe Gln Ala
        115                 120                 125 gat gtt aac atc gag gat aat gaa ggg aac ctg ccc ttg cac ttg gct     432
Asp Val Asn Ile Glu Asp Asn Glu Gly Asn Leu Pro Leu His Leu Ala
    130                 135                 140 gcc aaa gaa ggc cac ctc cgg gtg gtg gag ttc ctg gtg aag cac acg     480
Ala Lys Glu Gly His Leu Arg Val Val Glu Phe Leu Val Lys His Thr
145                 150                 155                 160 gcc agc aat gtg ggg cat cgg aac cat aag ggg gac acc gcc tgt gat     528
Ala Ser Asn Val Gly His Arg Asn His Lys Gly Asp Thr Ala Cys Asp
                165                 170                 175 ttg gcc agg ctc tat ggg agg aat gag gtt gtt agc ctg atg cag gca     576
Leu Ala Arg Leu Tyr Gly Arg Asn Glu Val Val Ser Leu Met Gln Ala
            180                 185                 190 aac ggg gct ggg gga gcc aca aat ctt caa taa                         609
Asn Gly Ala Gly Gly Ala Thr Asn Leu Gln
        195                 200

<210> SEQ ID NO 42
<211> LENGTH: 202
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 42

```
Met Gly Ser Ser His His His His His His Ser Ser Gly Leu Val Pro
1               5                   10                  15

Arg Gly Ser His Met Lys Lys Lys Arg Lys Leu Ile Leu Leu Leu
            20                  25                  30

Pro Ile Ile Ala Glu Pro Trp Gly Asn Glu Leu Ala Ser Ala Ala Ala
        35                  40                  45

Arg Gly Asp Leu Glu Gln Leu Thr Ser Leu Leu Gln Asn Asn Val Asn
    50                  55                  60

Val Asn Ala Gln Asn Gly Phe Gly Arg Thr Ala Leu Gln Val Met Lys
65                  70                  75                  80

Leu Gly Asn Pro Glu Ile Ala Arg Arg Leu Leu Leu Arg Gly Ala Asn
            85                  90                  95

Pro Asp Leu Lys Asp Arg Thr Gly Phe Ala Val Ile His Asp Ala Ala
        100                 105                 110

Arg Ala Gly Phe Leu Asp Thr Leu Gln Thr Leu Leu Glu Phe Gln Ala
    115                 120                 125

Asp Val Asn Ile Glu Asp Asn Glu Gly Asn Leu Pro Leu His Leu Ala
130                 135                 140

Ala Lys Glu Gly His Leu Arg Val Val Glu Phe Leu Val Lys His Thr
145                 150                 155                 160

Ala Ser Asn Val Gly His Arg Asn His Lys Gly Asp Thr Ala Cys Asp
            165                 170                 175

Leu Ala Arg Leu Tyr Gly Arg Asn Glu Val Val Ser Leu Met Gln Ala
        180                 185                 190

Asn Gly Ala Gly Gly Ala Thr Asn Leu Gln
    195                 200
```

<210> SEQ ID NO 43
<211> LENGTH: 609
<212> TYPE: DNA
<213> ORGANISM: Artificial Sequence
<220> FEATURE:
<223> OTHER INFORMATION: His-p18-MTD2 recombinant protein
<220> FEATURE:
<223> OTHER INFORMATION: Description of Artificial Sequence: Synthetic polynucleotide
<220> FEATURE:
<221> NAME/KEY: CDS
<222> LOCATION: (1)..(606)

<400> SEQUENCE: 43

```
atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag gcc gag cct tgg ggg aac      96
Arg Gly Ser His Met Lys Lys Lys Arg Lys Ala Glu Pro Trp Gly Asn
            20                  25                  30 gag ttg gcg tcc gca gct gcc agg ggg gac cta gag caa ctt act agt     144
Glu Leu Ala Ser Ala Ala Ala Arg Gly Asp Leu Glu Gln Leu Thr Ser
        35                  40                  45 ttg ttg caa aat aat gta aac gtc aat gca caa aat gga ttt gga agg     192
Leu Leu Gln Asn Asn Val Asn Val Asn Ala Gln Asn Gly Phe Gly Arg
    50                  55                  60 act gcg ctg cag gtt atg aaa ctt gga aat ccc gag att gcc agg aga     240
Thr Ala Leu Gln Val Met Lys Leu Gly Asn Pro Glu Ile Ala Arg Arg
```

```
                65                  70                  75                  80
ctg cta ctt aga ggt gct aat ccc gat ttg aaa gac cga act ggt ttc     288
Leu Leu Leu Arg Gly Ala Asn Pro Asp Leu Lys Asp Arg Thr Gly Phe
                85                  90                  95 gct gtc att cat gat gcg gcc aga gca ggt ttc ctg gac act tta cag     336
Ala Val Ile His Asp Ala Ala Arg Ala Gly Phe Leu Asp Thr Leu Gln
            100                 105                 110 act ttg ctg gag ttt caa gct gat gtt aac atc gag gat aat gaa ggg     384
Thr Leu Leu Glu Phe Gln Ala Asp Val Asn Ile Glu Asp Asn Glu Gly
        115                 120                 125 aac ctg ccc ttg cac ttg gct gcc aaa gaa ggc cac ctc cgg gtg gtg     432
Asn Leu Pro Leu His Leu Ala Ala Lys Glu Gly His Leu Arg Val Val
    130                 135                 140 gag ttc ctg gtg aag cac acg gcc agc aat gtg ggg cat cgg aac cat     480
Glu Phe Leu Val Lys His Thr Ala Ser Asn Val Gly His Arg Asn His
145                 150                 155                 160 aag ggg gac acc gcc tgt gat ttg gcc agg ctc tat ggg agg aat gag     528
Lys Gly Asp Thr Ala Cys Asp Leu Ala Arg Leu Tyr Gly Arg Asn Glu
                165                 170                 175 gtt gtt agc ctg atg cag gca aac ggg gct ggg gga gcc aca aat ctt     576
Val Val Ser Leu Met Gln Ala Asn Gly Ala Gly Gly Ala Thr Asn Leu
            180                 185                 190 caa ctg att ctg ctg ctg ctg ccg att att taa                         609
Gln Leu Ile Leu Leu Leu Leu Pro Ile Ile
        195                 200

<210> SEQ ID NO 44
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Gly Ser Ser His His His His His Ser Ser Gly Leu Val Pro
1               5                   10                  15

Arg Gly Ser His Met Lys Lys Arg Lys Ala Glu Pro Trp Gly Asn
            20                  25                  30

Glu Leu Ala Ser Ala Ala Arg Gly Asp Leu Glu Gln Leu Thr Ser
        35                  40                  45

Leu Leu Gln Asn Asn Val Asn Val Asn Ala Gln Asn Gly Phe Gly Arg
    50                  55                  60

Thr Ala Leu Gln Val Met Lys Leu Gly Asn Pro Glu Ile Ala Arg Arg
65                  70                  75                  80

Leu Leu Leu Arg Gly Ala Asn Pro Asp Leu Lys Asp Arg Thr Gly Phe
                85                  90                  95

Ala Val Ile His Asp Ala Ala Arg Ala Gly Phe Leu Asp Thr Leu Gln
            100                 105                 110

Thr Leu Leu Glu Phe Gln Ala Asp Val Asn Ile Glu Asp Asn Glu Gly
        115                 120                 125

Asn Leu Pro Leu His Leu Ala Ala Lys Glu Gly His Leu Arg Val Val
    130                 135                 140

Glu Phe Leu Val Lys His Thr Ala Ser Asn Val Gly His Arg Asn His
145                 150                 155                 160

Lys Gly Asp Thr Ala Cys Asp Leu Ala Arg Leu Tyr Gly Arg Asn Glu
                165                 170                 175

Val Val Ser Leu Met Gln Ala Asn Gly Ala Gly Gly Ala Thr Asn Leu
            180                 185                 190
```

-continued

```
Gln Leu Ile Leu Leu Leu Pro Ile Ile
        195                 200

<210> SEQ ID NO 45
<211> LENGTH: 636
<212> TYPE: DNA
<213> ORGANISM: Artificial Sequence
<220> FEATURE:
<223> OTHER INFORMATION: His-MTD2-p18-MTD2 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(633)

<400> SEQUENCE: 45 atg ggc agc agc cat cat cat cat cat cac agc agc ggc ctg gtg ccg       48
Met Gly Ser Ser His His His His His His Ser Ser Gly Leu Val Pro
1               5                   10                  15 cgc ggc agc cat atg aag aag aag agg aag ctg att ctg ctg ctg           96
Arg Gly Ser His Met Lys Lys Lys Arg Lys Leu Ile Leu Leu Leu Leu
            20                  25                  30 ccg att att gcc gag cct tgg ggg aac gag ttg gcg tcc gca gct gcc      144
Pro Ile Ile Ala Glu Pro Trp Gly Asn Glu Leu Ala Ser Ala Ala Ala
        35                  40                  45 agg ggg gac cta gag caa ctt act agt ttg ttg caa aat aat gta aac      192
Arg Gly Asp Leu Glu Gln Leu Thr Ser Leu Leu Gln Asn Asn Val Asn
    50                  55                  60 gtc aat gca caa aat gga ttt gga agg act gcg ctg cag gtt atg aaa      240
Val Asn Ala Gln Asn Gly Phe Gly Arg Thr Ala Leu Gln Val Met Lys
65                  70                  75                  80 ctt gga aat ccc gag att gcc agg aga ctg cta ctt aga ggt gct aat      288
Leu Gly Asn Pro Glu Ile Ala Arg Arg Leu Leu Leu Arg Gly Ala Asn
                85                  90                  95 ccc gat ttg aaa gac cga act ggt ttc gct gtc att cat gat gcg gcc      336
Pro Asp Leu Lys Asp Arg Thr Gly Phe Ala Val Ile His Asp Ala Ala
            100                 105                 110 aga gca ggt ttc ctg gac act tta cag act ttg ctg gag ttt caa gct      384
Arg Ala Gly Phe Leu Asp Thr Leu Gln Thr Leu Leu Glu Phe Gln Ala
        115                 120                 125 gat gtt aac atc gag gat aat gaa ggg aac ctg ccc ttg cac ttg gct      432
Asp Val Asn Ile Glu Asp Asn Glu Gly Asn Leu Pro Leu His Leu Ala
    130                 135                 140 gcc aaa gaa ggc cac ctc cgg gtg gtg gag ttc ctg gtg aag cac acg      480
Ala Lys Glu Gly His Leu Arg Val Val Glu Phe Leu Val Lys His Thr
145                 150                 155                 160 gcc agc aat gtg ggg cat cgg aac cat aag ggg gac acc gcc tgt gat      528
Ala Ser Asn Val Gly His Arg Asn His Lys Gly Asp Thr Ala Cys Asp
                165                 170                 175 ttg gcc agg ctc tat ggg agg aat gag gtt gtt agc ctg atg cag gca      576
Leu Ala Arg Leu Tyr Gly Arg Asn Glu Val Val Ser Leu Met Gln Ala
            180                 185                 190 aac ggg gct ggg gga gcc aca aat ctt caa ctg att ctg ctg ctg          624
Asn Gly Ala Gly Gly Ala Thr Asn Leu Gln Leu Ile Leu Leu Leu
        195                 200                 205 ccg att att taa                                                       636
Pro Ile Ile
    210

<210> SEQ ID NO 46
<211> LENGTH: 211
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 46

Met Gly Ser Ser His His His His His His Ser Ser Gly Leu Val Pro
1               5                   10                  15

Arg Gly Ser His Met Lys Lys Lys Arg Lys Leu Ile Leu Leu Leu Leu
            20                  25                  30

Pro Ile Ile Ala Glu Pro Trp Gly Asn Glu Leu Ala Ser Ala Ala Ala
        35                  40                  45

Arg Gly Asp Leu Glu Gln Leu Thr Ser Leu Leu Gln Asn Asn Val Asn
    50                  55                  60

Val Asn Ala Gln Asn Gly Phe Gly Arg Thr Ala Leu Gln Val Met Lys
65                  70                  75                  80

Leu Gly Asn Pro Glu Ile Ala Arg Arg Leu Leu Leu Arg Gly Ala Asn
                85                  90                  95

Pro Asp Leu Lys Asp Arg Thr Gly Phe Ala Val Ile His Asp Ala Ala
            100                 105                 110

Arg Ala Gly Phe Leu Asp Thr Leu Gln Thr Leu Leu Glu Phe Gln Ala
        115                 120                 125

Asp Val Asn Ile Glu Asp Asn Glu Gly Asn Leu Pro Leu His Leu Ala
    130                 135                 140

Ala Lys Glu Gly His Leu Arg Val Val Glu Phe Leu Val Lys His Thr
145                 150                 155                 160

Ala Ser Asn Val Gly His Arg Asn His Lys Gly Asp Thr Ala Cys Asp
                165                 170                 175

Leu Ala Arg Leu Tyr Gly Arg Asn Glu Val Val Ser Leu Met Gln Ala
            180                 185                 190

Asn Gly Ala Gly Gly Ala Thr Asn Leu Gln Leu Ile Leu Leu Leu Leu
        195                 200                 205

Pro Ile Ile
    210

<210> SEQ ID NO 47
<211> LENGTH: 609
<212> TYPE: DNA
<213> ORGANISM: Artificial Sequence
<220> FEATURE:
<223> OTHER INFORMATION: His-MTD3-p18 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(606)

<400> SEQUENCE: 47 atg ggc agc agc cat cat cat cat cat cac agc agc ggc ctg gtg ccg      48
Met Gly Ser Ser His His His His His His Ser Ser Gly Leu Val Pro
1               5                   10                  15 cgc ggc agc cat atg aag aag aag agg aag ctg gcg ctg ccg gtg ctg      96
Arg Gly Ser His Met Lys Lys Lys Arg Lys Leu Ala Leu Pro Val Leu
            20                  25                  30 ctg ctg gcg gcc gag cct tgg ggg aac gag ttg gcg tcc gca gct gcc     144
Leu Leu Ala Ala Glu Pro Trp Gly Asn Glu Leu Ala Ser Ala Ala Ala
        35                  40                  45 agg ggg gac cta gag caa ctt act agt ttg ttg caa aat aat gta aac     192
Arg Gly Asp Leu Glu Gln Leu Thr Ser Leu Leu Gln Asn Asn Val Asn
    50                  55                  60

```
gtc aat gca caa aat gga ttt gga agg act gcg ctg cag gtt atg aaa     240
Val Asn Ala Gln Asn Gly Phe Gly Arg Thr Ala Leu Gln Val Met Lys
 65                  70                  75                  80 ctt gga aat ccc gag att gcc agg aga ctg cta ctt aga ggt gct aat     288
Leu Gly Asn Pro Glu Ile Ala Arg Arg Leu Leu Leu Arg Gly Ala Asn
                 85                  90                  95 ccc gat ttg aaa gac cga act ggt ttc gct gtc att cat gat gcg gcc     336
Pro Asp Leu Lys Asp Arg Thr Gly Phe Ala Val Ile His Asp Ala Ala
             100                 105                 110 aga gca ggt ttc ctg gac act tta cag act ttg ctg gag ttt caa gct     384
Arg Ala Gly Phe Leu Asp Thr Leu Gln Thr Leu Leu Glu Phe Gln Ala
         115                 120                 125 gat gtt aac atc gag gat aat gaa ggg aac ctg ccc ttg cac ttg gct     432
Asp Val Asn Ile Glu Asp Asn Glu Gly Asn Leu Pro Leu His Leu Ala
130                 135                 140 gcc aaa gaa ggc cac ctc cgg gtg gtg gag ttc ctg gtg aag cac acg     480
Ala Lys Glu Gly His Leu Arg Val Val Glu Phe Leu Val Lys His Thr
145                 150                 155                 160 gcc agc aat gtg ggg cat cgg aac cat aag ggg gac acc gcc tgt gat     528
Ala Ser Asn Val Gly His Arg Asn His Lys Gly Asp Thr Ala Cys Asp
                165                 170                 175 ttg gcc agg ctc tat ggg agg aat gag gtt gtt agc ctg atg cag gca     576
Leu Ala Arg Leu Tyr Gly Arg Asn Glu Val Val Ser Leu Met Gln Ala
            180                 185                 190 aac ggg gct ggg gga gcc aca aat ctt caa taa                         609
Asn Gly Ala Gly Gly Ala Thr Asn Leu Gln
        195                 200

<210> SEQ ID NO 48
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Ser Ser His His His His His His Ser Ser Gly Leu Val Pro
 1               5                  10                  15

Arg Gly Ser His Met Lys Lys Arg Lys Leu Ala Leu Pro Val Leu
             20                  25                  30

Leu Leu Ala Ala Glu Pro Trp Gly Asn Glu Leu Ala Ser Ala Ala Ala
         35                  40                  45

Arg Gly Asp Leu Glu Gln Leu Thr Ser Leu Leu Gln Asn Asn Val Asn
     50                  55                  60

Val Asn Ala Gln Asn Gly Phe Gly Arg Thr Ala Leu Gln Val Met Lys
 65                  70                  75                  80

Leu Gly Asn Pro Glu Ile Ala Arg Arg Leu Leu Leu Arg Gly Ala Asn
                 85                  90                  95

Pro Asp Leu Lys Asp Arg Thr Gly Phe Ala Val Ile His Asp Ala Ala
             100                 105                 110

Arg Ala Gly Phe Leu Asp Thr Leu Gln Thr Leu Leu Glu Phe Gln Ala
         115                 120                 125

Asp Val Asn Ile Glu Asp Asn Glu Gly Asn Leu Pro Leu His Leu Ala
130                 135                 140

Ala Lys Glu Gly His Leu Arg Val Val Glu Phe Leu Val Lys His Thr
145                 150                 155                 160

Ala Ser Asn Val Gly His Arg Asn His Lys Gly Asp Thr Ala Cys Asp
                165                 170                 175
```

```
Leu Ala Arg Leu Tyr Gly Arg Asn Glu Val Val Ser Leu Met Gln Ala
            180                 185                 190

Asn Gly Ala Gly Gly Ala Thr Asn Leu Gln
            195                 200

<210> SEQ ID NO 49
<211> LENGTH: 609
<212> TYPE: DNA
<213> ORGANISM: Artificial Sequence
<220> FEATURE:
<223> OTHER INFORMATION: His-p18-MTD3 recombinant protein
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(606)

<400> SEQUENCE: 49 atg ggc agc agc cat cat cat cat cat cac agc agc ggc ctg gtg ccg       48
Met Gly Ser Ser His His His His His His Ser Ser Gly Leu Val Pro
1               5                   10                  15 cgc ggc agc cat atg aag aag aag agg aag gcc gag cct tgg ggg aac       96
Arg Gly Ser His Met Lys Lys Lys Arg Lys Ala Glu Pro Trp Gly Asn
            20                  25                  30 gag ttg gcg tcc gca gct gcc agg ggg gac cta gag caa ctt act agt      144
Glu Leu Ala Ser Ala Ala Ala Arg Gly Asp Leu Glu Gln Leu Thr Ser
        35                  40                  45 ttg ttg caa aat aat gta aac gtc aat gca caa aat gga ttt gga agg      192
Leu Leu Gln Asn Asn Val Asn Val Asn Ala Gln Asn Gly Phe Gly Arg
    50                  55                  60 act gcg ctg cag gtt atg aaa ctt gga aat ccc gag att gcc agg aga      240
Thr Ala Leu Gln Val Met Lys Leu Gly Asn Pro Glu Ile Ala Arg Arg
65                  70                  75                  80 ctg cta ctt aga ggt gct aat ccc gat ttg aaa gac cga act ggt ttc      288
Leu Leu Leu Arg Gly Ala Asn Pro Asp Leu Lys Asp Arg Thr Gly Phe
                85                  90                  95 gct gtc att cat gat gcg gcc aga gca ggt ttc ctg gac act tta cag      336
Ala Val Ile His Asp Ala Ala Arg Ala Gly Phe Leu Asp Thr Leu Gln
            100                 105                 110 act ttg ctg gag ttt caa gct gat gtt aac atc gag gat aat gaa ggg      384
Thr Leu Leu Glu Phe Gln Ala Asp Val Asn Ile Glu Asp Asn Glu Gly
        115                 120                 125 aac ctg ccc ttg cac ttg gct gcc aaa gaa ggc cac ctc cgg gtg gtg      432
Asn Leu Pro Leu His Leu Ala Ala Lys Glu Gly His Leu Arg Val Val
    130                 135                 140 gag ttc ctg gtg aag cac acg gcc agc aat gtg ggg cat cgg aac cat      480
Glu Phe Leu Val Lys His Thr Ala Ser Asn Val Gly His Arg Asn His
145                 150                 155                 160 aag ggg gac acc gcc tgt gat ttg gcc agg ctc tat ggg agg aat gag      528
Lys Gly Asp Thr Ala Cys Asp Leu Ala Arg Leu Tyr Gly Arg Asn Glu
                165                 170                 175 gtt gtt agc ctg atg cag gca aac ggg gct ggg gga gcc aca aat ctt      576
Val Val Ser Leu Met Gln Ala Asn Gly Ala Gly Gly Ala Thr Asn Leu
            180                 185                 190 caa ctg gcg ctg ccg gtg ctg ctg ctg gcg taa                          609
Gln Leu Ala Leu Pro Val Leu Leu Leu Ala
        195                 200

<210> SEQ ID NO 50
<211> LENGTH: 202
<212> TYPE: PRT
<213> ORGANISM: Artificial Sequence
```

<220> FEATURE:
<223> OTHER INFORMATION: Description of Artificial Sequence: Synthetic
    polypeptide

<400> SEQUENCE: 50

Met Gly Ser Ser His His His His His His Ser Ser Gly Leu Val Pro
1               5                   10                  15

Arg Gly Ser His Met Lys Lys Lys Arg Lys Ala Glu Pro Trp Gly Asn
            20                  25                  30

Glu Leu Ala Ser Ala Ala Ala Arg Gly Asp Leu Glu Gln Leu Thr Ser
        35                  40                  45

Leu Leu Gln Asn Asn Val Asn Val Asn Ala Gln Asn Gly Phe Gly Arg
    50                  55                  60

Thr Ala Leu Gln Val Met Lys Leu Gly Asn Pro Glu Ile Ala Arg Arg
65                  70                  75                  80

Leu Leu Leu Arg Gly Ala Asn Pro Asp Leu Lys Asp Arg Thr Gly Phe
                85                  90                  95

Ala Val Ile His Asp Ala Ala Arg Ala Gly Phe Leu Asp Thr Leu Gln
            100                 105                 110

Thr Leu Leu Glu Phe Gln Ala Asp Val Asn Ile Glu Asp Asn Glu Gly
        115                 120                 125

Asn Leu Pro Leu His Leu Ala Ala Lys Glu Gly His Leu Arg Val Val
    130                 135                 140

Glu Phe Leu Val Lys His Thr Ala Ser Asn Val Gly His Arg Asn His
145                 150                 155                 160

Lys Gly Asp Thr Ala Cys Asp Leu Ala Arg Leu Tyr Gly Arg Asn Glu
                165                 170                 175

Val Val Ser Leu Met Gln Ala Asn Gly Ala Gly Gly Ala Thr Asn Leu
            180                 185                 190

Gln Leu Ala Leu Pro Val Leu Leu Ala
        195                 200

<210> SEQ ID NO 51
<211> LENGTH: 636
<212> TYPE: DNA
<213> ORGANISM: Artificial Sequence
<220> FEATURE:
<223> OTHER INFORMATION: His-MTD3-p18-MTD3 recombinant protein
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(633)

<400> SEQUENCE: 51 atg ggc agc agc cat cat cat cat cac agc agc ggc ctg gtg ccg       48
Met Gly Ser Ser His His His His His His Ser Ser Gly Leu Val Pro
1               5                   10                  15 cgc ggc agc cat atg aag aag aag agg aag ctg gcg ctg ccg gtg ctg   96
Arg Gly Ser His Met Lys Lys Lys Arg Lys Leu Ala Leu Pro Val Leu
            20                  25                  30 ctg ctg gcg gcc gag cct tgg ggg aac gag ttg gcg tcc gca gct gcc   144
Leu Leu Ala Ala Glu Pro Trp Gly Asn Glu Leu Ala Ser Ala Ala Ala
        35                  40                  45 agg ggg gac cta gag caa ctt act agt ttg ttg caa aat aat gta aac   192
Arg Gly Asp Leu Glu Gln Leu Thr Ser Leu Leu Gln Asn Asn Val Asn
    50                  55                  60 gtc aat gca caa aat gga ttt gga agg act gcg ctg cag gtt atg aaa   240
Val Asn Ala Gln Asn Gly Phe Gly Arg Thr Ala Leu Gln Val Met Lys
65                  70                  75                  80

```
ctt gga aat ccc gag att gcc agg aga ctg cta ctt aga ggt gct aat    288
Leu Gly Asn Pro Glu Ile Ala Arg Arg Leu Leu Leu Arg Gly Ala Asn
             85                  90                  95 ccc gat ttg aaa gac cga act ggt ttc gct gtc att cat gat gcg gcc    336
Pro Asp Leu Lys Asp Arg Thr Gly Phe Ala Val Ile His Asp Ala Ala
        100                 105                 110 aga gca ggt ttc ctg gac act tta cag act ttg ctg gag ttt caa gct    384
Arg Ala Gly Phe Leu Asp Thr Leu Gln Thr Leu Leu Glu Phe Gln Ala
    115                 120                 125 gat gtt aac atc gag gat aat gaa ggg aac ctg ccc ttg cac ttg gct    432
Asp Val Asn Ile Glu Asp Asn Glu Gly Asn Leu Pro Leu His Leu Ala
130                 135                 140 gcc aaa gaa ggc cac ctc cgg gtg gtg gag ttc ctg gtg aag cac acg    480
Ala Lys Glu Gly His Leu Arg Val Val Glu Phe Leu Val Lys His Thr
145                 150                 155                 160 gcc agc aat gtg ggg cat cgg aac cat aag ggg gac acc gcc tgt gat    528
Ala Ser Asn Val Gly His Arg Asn His Lys Gly Asp Thr Ala Cys Asp
                165                 170                 175 ttg gcc agg ctc tat ggg agg aat gag gtt gtt agc ctg atg cag gca    576
Leu Ala Arg Leu Tyr Gly Arg Asn Glu Val Val Ser Leu Met Gln Ala
            180                 185                 190 aac ggg gct ggg gga gcc aca aat ctt caa ctg gcg ctg ccg gtg ctg    624
Asn Gly Ala Gly Gly Ala Thr Asn Leu Gln Leu Ala Leu Pro Val Leu
        195                 200                 205 ctg ctg gcg taa                                                    636
Leu Leu Ala
    210
```

<210> SEQ ID NO 52
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Met Gly Ser Ser His His His His His His Ser Ser Gly Leu Val Pro
1               5                   10                  15

Arg Gly Ser His Met Lys Lys Arg Lys Leu Ala Leu Pro Val Leu
            20                  25                  30

Leu Leu Ala Ala Glu Pro Trp Gly Asn Glu Leu Ala Ser Ala Ala Ala
        35                  40                  45

Arg Gly Asp Leu Glu Gln Leu Thr Ser Leu Leu Gln Asn Asn Val Asn
    50                  55                  60

Val Asn Ala Gln Asn Gly Phe Gly Arg Thr Ala Leu Gln Val Met Lys
65                  70                  75                  80

Leu Gly Asn Pro Glu Ile Ala Arg Arg Leu Leu Leu Arg Gly Ala Asn
                85                  90                  95

Pro Asp Leu Lys Asp Arg Thr Gly Phe Ala Val Ile His Asp Ala Ala
            100                 105                 110

Arg Ala Gly Phe Leu Asp Thr Leu Gln Thr Leu Leu Glu Phe Gln Ala
        115                 120                 125

Asp Val Asn Ile Glu Asp Asn Glu Gly Asn Leu Pro Leu His Leu Ala
    130                 135                 140

Ala Lys Glu Gly His Leu Arg Val Val Glu Phe Leu Val Lys His Thr
145                 150                 155                 160

Ala Ser Asn Val Gly His Arg Asn His Lys Gly Asp Thr Ala Cys Asp
                165                 170                 175
```

```
Leu Ala Arg Leu Tyr Gly Arg Asn Glu Val Val Ser Leu Met Gln Ala
            180                 185                 190
Asn Gly Ala Gly Gly Ala Thr Asn Leu Gln Leu Ala Leu Pro Val Leu
            195                 200                 205
Leu Leu Ala
    210

<210> SEQ ID NO 53
<211> LENGTH: 12
<212> TYPE: PRT
<213> ORGANISM: Streptomyces coelicolor
<220> FEATURE:
<223> OTHER INFORMATION: MTD JO-01

<400> SEQUENCE: 53

Ala Val Val Val Cys Ala Ile Val Leu Ala Ala Pro
1               5                   10

<210> SEQ ID NO 54
<211> LENGTH: 12
<212> TYPE: PRT
<213> ORGANISM: Homo sapiens
<220> FEATURE:
<223> OTHER INFORMATION: MTD JO-02

<400> SEQUENCE: 54

Pro Leu Ala Leu Leu Val Leu Leu Leu Leu Gly Pro
1               5                   10

<210> SEQ ID NO 55
<211> LENGTH: 11
<212> TYPE: PRT
<213> ORGANISM: Homo sapiens
<220> FEATURE:
<223> OTHER INFORMATION: MTD JO-03

<400> SEQUENCE: 55

Leu Leu Leu Ala Phe Ala Leu Leu Cys Leu Pro
1               5                   10

<210> SEQ ID NO 56
<211> LENGTH: 13
<212> TYPE: PRT
<213> ORGANISM: Homo sapiens
<220> FEATURE:
<223> OTHER INFORMATION: MTD JO-04

<400> SEQUENCE: 56

Leu Leu Gly Ala Leu Ala Ala Val Leu Leu Ala Leu Ala
1               5                   10

<210> SEQ ID NO 57
<211> LENGTH: 16
<212> TYPE: PRT
<213> ORGANISM: Homo sapiens
<220> FEATURE:
<223> OTHER INFORMATION: MTD JO-05

<400> SEQUENCE: 57

Pro Val Leu Leu Ala Leu Gly Val Gly Leu Val Leu Leu Gly Leu Ala
1               5                   10                  15

<210> SEQ ID NO 58
<211> LENGTH: 9
<212> TYPE: PRT
<213> ORGANISM: Streptomyces coelicolor
```

```
<220> FEATURE:
<223> OTHER INFORMATION: MTD JO-06

<400> SEQUENCE: 58

Ala Ala Ala Ala Val Leu Leu Ala Ala
1               5

<210> SEQ ID NO 59
<211> LENGTH: 8
<212> TYPE: PRT
<213> ORGANISM: Streptomyces coelicolor
<220> FEATURE:
<223> OTHER INFORMATION: MTD JO-07

<400> SEQUENCE: 59

Ile Val Val Ala Val Val Val Ile
1               5

<210> SEQ ID NO 60
<211> LENGTH: 9
<212> TYPE: PRT
<213> ORGANISM: Streptomyces coelicolor
<220> FEATURE:
<223> OTHER INFORMATION: MTD JO-08

<400> SEQUENCE: 60

Ala Val Leu Ala Pro Val Val Ala Val
1               5

<210> SEQ ID NO 61
<211> LENGTH: 13
<212> TYPE: PRT
<213> ORGANISM: Streptomyces coelicolor
<220> FEATURE:
<223> OTHER INFORMATION: MTD JO-09

<400> SEQUENCE: 61

Leu Ala Val Cys Gly Leu Pro Val Val Ala Leu Leu Ala
1               5                   10

<210> SEQ ID NO 62
<211> LENGTH: 16
<212> TYPE: PRT
<213> ORGANISM: Streptomyces coelicolor
<220> FEATURE:
<223> OTHER INFORMATION: MTD JO-10

<400> SEQUENCE: 62

Leu Gly Gly Ala Val Val Ala Ala Pro Val Ala Ala Val Ala Pro
1               5                   10                  15

<210> SEQ ID NO 63
<211> LENGTH: 13
<212> TYPE: PRT
<213> ORGANISM: Streptomyces coelicolor
<220> FEATURE:
<223> OTHER INFORMATION: MTD JO-11

<400> SEQUENCE: 63

Leu Leu Leu Val Leu Ala Val Leu Leu Ala Val Leu Pro
1               5                   10

<210> SEQ ID NO 64
<211> LENGTH: 12
<212> TYPE: PRT
<213> ORGANISM: Homo sapiens
<220> FEATURE:
<223> OTHER INFORMATION: MTD JO-12
```

```
<400> SEQUENCE: 64

Leu Leu Ile Leu Leu Leu Pro Leu Leu Ile Val
1               5                   10

<210> SEQ ID NO 65
<211> LENGTH: 11
<212> TYPE: PRT
<213> ORGANISM: Streptomyces coelicolor
<220> FEATURE:
<223> OTHER INFORMATION: MTD JO-13

<400> SEQUENCE: 65

Leu Ala Ala Ala Ala Leu Ala Val Leu Pro Leu
1               5                   10

<210> SEQ ID NO 66
<211> LENGTH: 14
<212> TYPE: PRT
<213> ORGANISM: Homo sapiens
<220> FEATURE:
<223> OTHER INFORMATION: MTD JO-14

<400> SEQUENCE: 66

Phe Leu Met Leu Leu Leu Pro Leu Leu Leu Leu Val Ala
1               5                   10

<210> SEQ ID NO 67
<211> LENGTH: 15
<212> TYPE: PRT
<213> ORGANISM: Streptomyces coelicolor
<220> FEATURE:
<223> OTHER INFORMATION: MTD JO-15

<400> SEQUENCE: 67

Ala Ala Ala Ala Ala Ala Leu Gly Leu Ala Ala Ala Val Pro Ala
1               5                   10                  15

<210> SEQ ID NO 68
<211> LENGTH: 14
<212> TYPE: PRT
<213> ORGANISM: Neisseria meningitidis
<220> FEATURE:
<223> OTHER INFORMATION: MTD JO-16

<400> SEQUENCE: 68

Leu Leu Leu Ala Ala Leu Leu Leu Ile Ala Phe Ala Ala Val
1               5                   10

<210> SEQ ID NO 69
<211> LENGTH: 14
<212> TYPE: PRT
<213> ORGANISM: Streptomyces coelicolor
<220> FEATURE:
<223> OTHER INFORMATION: MTD JO-17

<400> SEQUENCE: 69

Ala Leu Ala Ala Val Val Leu Ile Pro Leu Gly Ile Ala Ala
1               5                   10

<210> SEQ ID NO 70
<211> LENGTH: 16
<212> TYPE: PRT
<213> ORGANISM: Streptomyces coelicolor
<220> FEATURE:
<223> OTHER INFORMATION: MTD JO-18

<400> SEQUENCE: 70
```

Ala Ala Leu Ala Leu Gly Val Ala Ala Ala Pro Ala Ala Ala Pro Ala
1               5                   10                  15

<210> SEQ ID NO 71
<211> LENGTH: 14
<212> TYPE: PRT
<213> ORGANISM: Streptomyces coelicolor
<220> FEATURE:
<223> OTHER INFORMATION: MTD JO-19

<400> SEQUENCE: 71

Ala Ala Leu Ile Gly Ala Val Leu Ala Pro Val Val Ala Val
1               5                   10

<210> SEQ ID NO 72
<211> LENGTH: 15
<212> TYPE: PRT
<213> ORGANISM: Streptomyces coelicolor
<220> FEATURE:
<223> OTHER INFORMATION: MTD JO-20

<400> SEQUENCE: 72

Ala Ala Gly Ile Ala Val Ala Ile Ala Ala Ile Val Pro Leu Ala
1               5                   10                  15

<210> SEQ ID NO 73
<211> LENGTH: 12
<212> TYPE: PRT
<213> ORGANISM: Streptomyces coelicolor
<220> FEATURE:
<223> OTHER INFORMATION: MTD JO-21

<400> SEQUENCE: 73

Ile Ala Val Ala Ile Ala Ala Ile Val Pro Leu Ala
1               5                   10

<210> SEQ ID NO 74
<211> LENGTH: 15
<212> TYPE: PRT
<213> ORGANISM: Mycobacterium leprae
<220> FEATURE:
<223> OTHER INFORMATION: MTD JO-22

<400> SEQUENCE: 74

Val Ala Met Ala Ala Ala Ala Val Leu Ala Ala Pro Ala Leu Ala
1               5                   10                  15

<210> SEQ ID NO 75
<211> LENGTH: 11
<212> TYPE: PRT
<213> ORGANISM: Streptomyces coelicolor
<220> FEATURE:
<223> OTHER INFORMATION: MTD JO-23

<400> SEQUENCE: 75

Leu Ala Val Leu Val Leu Leu Val Leu Leu Pro
1               5                   10

<210> SEQ ID NO 76
<211> LENGTH: 9
<212> TYPE: PRT
<213> ORGANISM: Streptomyces coelicolor
<220> FEATURE:
<223> OTHER INFORMATION: MTD JO-24

<400> SEQUENCE: 76

Val Val Ala Val Leu Ala Pro Val Leu
1               5

<210> SEQ ID NO 77
<211> LENGTH: 12
<212> TYPE: PRT
<213> ORGANISM: Streptomyces coelicolor
<220> FEATURE:
<223> OTHER INFORMATION: MTD JO-25

<400> SEQUENCE: 77

Ala Ala Leu Leu Leu Pro Leu Leu Leu Leu Leu Pro
1               5                   10

<210> SEQ ID NO 78
<211> LENGTH: 10
<212> TYPE: PRT
<213> ORGANISM: Streptomyces coelicolor
<220> FEATURE:
<223> OTHER INFORMATION: MTD JO-26

<400> SEQUENCE: 78

Pro Ala Ala Val Ala Ala Leu Leu Val Ile
1               5                   10

<210> SEQ ID NO 79
<211> LENGTH: 8
<212> TYPE: PRT
<213> ORGANISM: Streptomyces coelicolor
<220> FEATURE:
<223> OTHER INFORMATION: MTD JO-27

<400> SEQUENCE: 79

Leu Leu Ile Ala Ala Leu Leu Pro
1               5

<210> SEQ ID NO 80
<211> LENGTH: 12
<212> TYPE: PRT
<213> ORGANISM: Streptomyces coelicolor
<220> FEATURE:
<223> OTHER INFORMATION: MTD JO-28

<400> SEQUENCE: 80

Ala Ala Val Val Leu Leu Pro Leu Ala Ala Ala Pro
1               5                   10

<210> SEQ ID NO 81
<211> LENGTH: 10
<212> TYPE: PRT
<213> ORGANISM: Streptomyces coelicolor
<220> FEATURE:
<223> OTHER INFORMATION: MTD JO-29

<400> SEQUENCE: 81

Ala Ala Ala Ala Ala Ala Leu Leu Val Pro
1               5                   10

<210> SEQ ID NO 82
<211> LENGTH: 8
<212> TYPE: PRT
<213> ORGANISM: Streptomyces coelicolor
<220> FEATURE:
<223> OTHER INFORMATION: MTD JO-30

<400> SEQUENCE: 82

Leu Pro Val Val Ala Leu Leu Ala
1               5

```
<210> SEQ ID NO 83
<211> LENGTH: 11
<212> TYPE: PRT
<213> ORGANISM: Streptomyces coelicolor
<220> FEATURE:
<223> OTHER INFORMATION: MTD JO-31

<400> SEQUENCE: 83

Ala Ala Ala Leu Ala Ala Pro Leu Ala Leu Pro
1               5                   10

<210> SEQ ID NO 84
<211> LENGTH: 9
<212> TYPE: PRT
<213> ORGANISM: Homo sapiens
<220> FEATURE:
<223> OTHER INFORMATION: MTD JO-32

<400> SEQUENCE: 84

Leu Leu Leu Ala Leu Leu Leu Ala Ala
1               5

<210> SEQ ID NO 85
<211> LENGTH: 8
<212> TYPE: PRT
<213> ORGANISM: Mycobacterium bovis
<220> FEATURE:
<223> OTHER INFORMATION: MTD JO-33

<400> SEQUENCE: 85

Ala Val Ala Val Val Ala Leu Leu
1               5

<210> SEQ ID NO 86
<211> LENGTH: 11
<212> TYPE: PRT
<213> ORGANISM: Streptomyces coelicolor
<220> FEATURE:
<223> OTHER INFORMATION: MTD JO-34

<400> SEQUENCE: 86

Leu Leu Leu Ile Ile Val Leu Leu Ile Val Pro
1               5                   10

<210> SEQ ID NO 87
<211> LENGTH: 10
<212> TYPE: PRT
<213> ORGANISM: Streptomyces coelicolor
<220> FEATURE:
<223> OTHER INFORMATION: MTD JO-36

<400> SEQUENCE: 87

Pro Ala Ala Leu Ala Leu Leu Leu Val Ala
1               5                   10

<210> SEQ ID NO 88
<211> LENGTH: 17
<212> TYPE: PRT
<213> ORGANISM: Streptomyces coelicolor
<220> FEATURE:
<223> OTHER INFORMATION: MTD JO-37

<400> SEQUENCE: 88

Ile Val Ala Leu Leu Leu Val Pro Leu Val Leu Ala Ile Ala Ala Val
1               5                   10                  15

Leu
```

```
<210> SEQ ID NO 89
<211> LENGTH: 8
<212> TYPE: PRT
<213> ORGANISM: Streptomyces coelicolor
<220> FEATURE:
<223> OTHER INFORMATION: MTD JO-38

<400> SEQUENCE: 89

Ile Val Ala Leu Leu Leu Val Pro
1               5

<210> SEQ ID NO 90
<211> LENGTH: 10
<212> TYPE: PRT
<213> ORGANISM: Streptomyces coelicolor
<220> FEATURE:
<223> OTHER INFORMATION: MTD JO-39

<400> SEQUENCE: 90

Pro Leu Val Leu Ala Ile Ala Ala Val Leu
1               5                   10

<210> SEQ ID NO 91
<211> LENGTH: 9
<212> TYPE: PRT
<213> ORGANISM: Homo sapiens
<220> FEATURE:
<223> OTHER INFORMATION: MTD JO-40

<400> SEQUENCE: 91

Pro Leu Val Leu Ala Ala Leu Val Ala
1               5

<210> SEQ ID NO 92
<211> LENGTH: 8
<212> TYPE: PRT
<213> ORGANISM: Streptomyces coelicolor
<220> FEATURE:
<223> OTHER INFORMATION: MTD JO-41

<400> SEQUENCE: 92

Ala Ala Ala Leu Leu Ala Val Ala
1               5

<210> SEQ ID NO 93
<211> LENGTH: 8
<212> TYPE: PRT
<213> ORGANISM: Homo sapiens
<220> FEATURE:
<223> OTHER INFORMATION: MTD JO-42

<400> SEQUENCE: 93

Pro Leu Leu Leu Leu Ala Leu Ala
1               5

<210> SEQ ID NO 94
<211> LENGTH: 7
<212> TYPE: PRT
<213> ORGANISM: Streptomyces coelicolor
<220> FEATURE:
<223> OTHER INFORMATION: MTD JO-43

<400> SEQUENCE: 94

Ala Leu Ala Leu Val Val Ala
1               5

<210> SEQ ID NO 95
```

```
<211> LENGTH: 8
<212> TYPE: PRT
<213> ORGANISM: Streptomyces coelicolor
<220> FEATURE:
<223> OTHER INFORMATION: MTD JO-44

<400> SEQUENCE: 95

Val Ala Ala Val Val Ala Ala
1               5

<210> SEQ ID NO 96
<211> LENGTH: 9
<212> TYPE: PRT
<213> ORGANISM: Homo sapiens
<220> FEATURE:
<223> OTHER INFORMATION: MTD JO-45

<400> SEQUENCE: 96

Pro Leu Leu Pro Leu Leu Leu Leu Val
1               5

<210> SEQ ID NO 97
<211> LENGTH: 13
<212> TYPE: PRT
<213> ORGANISM: Mycobacterium bovis
<220> FEATURE:
<223> OTHER INFORMATION: MTD JO-46

<400> SEQUENCE: 97

Val Val Leu Val Val Val Leu Pro Leu Ala Val Leu Ala
1               5                   10

<210> SEQ ID NO 98
<211> LENGTH: 10
<212> TYPE: PRT
<213> ORGANISM: Streptomyces coelicolor
<220> FEATURE:
<223> OTHER INFORMATION: MTD JO-47

<400> SEQUENCE: 98

Ala Ala Ala Val Pro Val Leu Val Ala Ala
1               5                   10

<210> SEQ ID NO 99
<211> LENGTH: 12
<212> TYPE: PRT
<213> ORGANISM: Homo sapiens
<220> FEATURE:
<223> OTHER INFORMATION: MTD JO-48

<400> SEQUENCE: 99

Pro Ala Leu Leu Leu Leu Leu Leu Ala Ala Val Val
1               5                   10

<210> SEQ ID NO 100
<211> LENGTH: 12
<212> TYPE: PRT
<213> ORGANISM: Homo sapiens
<220> FEATURE:
<223> OTHER INFORMATION: MTD JO-49

<400> SEQUENCE: 100

Pro Leu Ala Ile Leu Leu Leu Leu Leu Ile Ala Pro
1               5                   10

<210> SEQ ID NO 101
<211> LENGTH: 13
<212> TYPE: PRT
```

<213> ORGANISM: Homo sapiens
<220> FEATURE:
<223> OTHER INFORMATION: MTD JO-50

<400> SEQUENCE: 101

Pro Leu Leu Ala Leu Val Leu Leu Leu Ala Leu Ile Ala
1 5 10

<210> SEQ ID NO 102
<211> LENGTH: 12
<212> TYPE: PRT
<213> ORGANISM: Mus musculus
<220> FEATURE:
<223> OTHER INFORMATION: MTD JO-51

<400> SEQUENCE: 102

Val Val Ala Val Leu Ala Leu Val Leu Ala Ala Leu
1 5 10

<210> SEQ ID NO 103
<211> LENGTH: 9
<212> TYPE: PRT
<213> ORGANISM: Homo sapiens
<220> FEATURE:
<223> OTHER INFORMATION: MTD JO-52

<400> SEQUENCE: 103

Pro Leu Leu Leu Leu Leu Pro Ala Leu
1 5

<210> SEQ ID NO 104
<211> LENGTH: 12
<212> TYPE: PRT
<213> ORGANISM: Streptomyces coelicolor
<220> FEATURE:
<223> OTHER INFORMATION: MTD JO-53

<400> SEQUENCE: 104

Leu Ala Ala Val Ala Ala Leu Ala Val Val Val Pro
1 5 10

<210> SEQ ID NO 105
<211> LENGTH: 12
<212> TYPE: PRT
<213> ORGANISM: Homo sapiens
<220> FEATURE:
<223> OTHER INFORMATION: MTD JO-54

<400> SEQUENCE: 105

Leu Leu Leu Leu Val Leu Ile Leu Pro Leu Ala Ala
1 5 10

<210> SEQ ID NO 106
<211> LENGTH: 9
<212> TYPE: PRT
<213> ORGANISM: Mycobacterium bovis
<220> FEATURE:
<223> OTHER INFORMATION: MTD JO-55

<400> SEQUENCE: 106

Leu Ala Val Val Val Val Ala Ala Val
1 5

<210> SEQ ID NO 107
<211> LENGTH: 9
<212> TYPE: PRT
<213> ORGANISM: Homo sapiens
<220> FEATURE:

```
<223> OTHER INFORMATION: MTD JO-56

<400> SEQUENCE: 107

Val Leu Leu Ala Ala Ala Leu Ile Ala
1               5

<210> SEQ ID NO 108
<211> LENGTH: 10
<212> TYPE: PRT
<213> ORGANISM: Salmonella enterica
<220> FEATURE:
<223> OTHER INFORMATION: MTD JO-57

<400> SEQUENCE: 108

Leu Ile Ala Leu Leu Ala Ala Pro Leu Ala
1               5                   10

<210> SEQ ID NO 109
<211> LENGTH: 8
<212> TYPE: PRT
<213> ORGANISM: Homo sapiens
<220> FEATURE:
<223> OTHER INFORMATION: MTD JO-58

<400> SEQUENCE: 109

Leu Ala Leu Leu Leu Leu Ala Ala
1               5

<210> SEQ ID NO 110
<211> LENGTH: 12
<212> TYPE: PRT
<213> ORGANISM: Homo sapiens
<220> FEATURE:
<223> OTHER INFORMATION: MTD JO-59

<400> SEQUENCE: 110

Leu Leu Ala Ala Ala Leu Leu Leu Leu Leu Leu Ala
1               5                   10

<210> SEQ ID NO 111
<211> LENGTH: 10
<212> TYPE: PRT
<213> ORGANISM: Streptomyces coelicolor
<220> FEATURE:
<223> OTHER INFORMATION: MTD JO-60

<400> SEQUENCE: 111

Val Ile Ile Ala Leu Ile Val Ile Val Ala
1               5                   10

<210> SEQ ID NO 112
<211> LENGTH: 11
<212> TYPE: PRT
<213> ORGANISM: Streptomyces coelicolor
<220> FEATURE:
<223> OTHER INFORMATION: MTD JO-61

<400> SEQUENCE: 112

Val Val Leu Val Val Ala Ala Val Leu Ala Leu
1               5                   10

<210> SEQ ID NO 113
<211> LENGTH: 9
<212> TYPE: PRT
<213> ORGANISM: Mycobacterium bovis
<220> FEATURE:
<223> OTHER INFORMATION: MTD JO-62
```

```
<400> SEQUENCE: 113

Val Ala Val Ala Ile Ala Val Val Leu
1               5

<210> SEQ ID NO 114
<211> LENGTH: 13
<212> TYPE: PRT
<213> ORGANISM: Streptomyces coelicolor
<220> FEATURE:
<223> OTHER INFORMATION: MTD JO-63

<400> SEQUENCE: 114

Pro Leu Ile Val Val Val Ala Ala Ala Val Val Ala Val
1               5                   10

<210> SEQ ID NO 115
<211> LENGTH: 11
<212> TYPE: PRT
<213> ORGANISM: Escherichia coli
<220> FEATURE:
<223> OTHER INFORMATION: MTD JO-64

<400> SEQUENCE: 115

Pro Leu Ala Val Ala Val Ala Ala Val Ala Ala
1               5                   10

<210> SEQ ID NO 116
<211> LENGTH: 10
<212> TYPE: PRT
<213> ORGANISM: Streptomyces avermitilis
<220> FEATURE:
<223> OTHER INFORMATION: MTD JO-65

<400> SEQUENCE: 116

Ala Ala Ile Ala Leu Val Ala Val Val Leu
1               5                   10

<210> SEQ ID NO 117
<211> LENGTH: 10
<212> TYPE: PRT
<213> ORGANISM: Streptomyces coelicolor
<220> FEATURE:
<223> OTHER INFORMATION: MTD JO-66

<400> SEQUENCE: 117

Ala Ala Ala Leu Ala Ala Ile Ala Val Ile
1               5                   10

<210> SEQ ID NO 118
<211> LENGTH: 8
<212> TYPE: PRT
<213> ORGANISM: Streptomyces coelicolor
<220> FEATURE:
<223> OTHER INFORMATION: MTD JO-67

<400> SEQUENCE: 118

Ala Ala Ala Pro Ala Val Ala Ala
1               5

<210> SEQ ID NO 119
<211> LENGTH: 7
<212> TYPE: PRT
<213> ORGANISM: Streptomyces coelicolor
<220> FEATURE:
<223> OTHER INFORMATION: MTD JO-68

<400> SEQUENCE: 119
```

```
Leu Leu Leu Ala Ala Leu Pro
1               5

<210> SEQ ID NO 120
<211> LENGTH: 8
<212> TYPE: PRT
<213> ORGANISM: Mycobacterium leprae
<220> FEATURE:
<223> OTHER INFORMATION: MTD JO-69

<400> SEQUENCE: 120

Ala Leu Leu Ala Val Val Ala Ala
1               5

<210> SEQ ID NO 121
<211> LENGTH: 10
<212> TYPE: PRT
<213> ORGANISM: Streptomyces coelicolor
<220> FEATURE:
<223> OTHER INFORMATION: MTD JO-70

<400> SEQUENCE: 121

Ala Val Val Val Val Leu Pro Ile Leu Leu
1               5                   10

<210> SEQ ID NO 122
<211> LENGTH: 9
<212> TYPE: PRT
<213> ORGANISM: Mus musculus
<220> FEATURE:
<223> OTHER INFORMATION: MTD JO-71

<400> SEQUENCE: 122

Ala Leu Ala Leu Leu Leu Leu Val Pro
1               5

<210> SEQ ID NO 123
<211> LENGTH: 11
<212> TYPE: PRT
<213> ORGANISM: Rattus sp.
<220> FEATURE:
<223> OTHER INFORMATION: MTD JO-72

<400> SEQUENCE: 123

Leu Val Val Leu Leu Ala Ala Leu Leu Val Leu
1               5                   10

<210> SEQ ID NO 124
<211> LENGTH: 8
<212> TYPE: PRT
<213> ORGANISM: Drosophila sp.
<220> FEATURE:
<223> OTHER INFORMATION: MTD JO-73

<400> SEQUENCE: 124

Pro Val Leu Leu Leu Leu Ala Pro
1               5

<210> SEQ ID NO 125
<211> LENGTH: 8
<212> TYPE: PRT
<213> ORGANISM: Streptomyces coelicolor
<220> FEATURE:
<223> OTHER INFORMATION: MTD JO-74

<400> SEQUENCE: 125

Ala Leu Ala Val Val Ala Ala Pro
1               5
```

```
<210> SEQ ID NO 126
<211> LENGTH: 8
<212> TYPE: PRT
<213> ORGANISM: Streptomyces coelicolor
<220> FEATURE:
<223> OTHER INFORMATION: MTD JO-75

<400> SEQUENCE: 126

Val Ile Val Ala Leu Leu Ala Val
1               5

<210> SEQ ID NO 127
<211> LENGTH: 8
<212> TYPE: PRT
<213> ORGANISM: Homo sapiens
<220> FEATURE:
<223> OTHER INFORMATION: MTD JO-76

<400> SEQUENCE: 127

Ala Leu Val Leu Pro Leu Ala Pro
1               5

<210> SEQ ID NO 128
<211> LENGTH: 9
<212> TYPE: PRT
<213> ORGANISM: Streptomyces coelicolor
<220> FEATURE:
<223> OTHER INFORMATION: MTD JO-77

<400> SEQUENCE: 128

Ala Val Ala Leu Leu Ile Leu Ala Val
1               5

<210> SEQ ID NO 129
<211> LENGTH: 7
<212> TYPE: PRT
<213> ORGANISM: Xenopus laevis
<220> FEATURE:
<223> OTHER INFORMATION: MTD JO-78

<400> SEQUENCE: 129

Val Leu Leu Ala Val Ile Pro
1               5

<210> SEQ ID NO 130
<211> LENGTH: 13
<212> TYPE: PRT
<213> ORGANISM: Streptomyces coelicolor
<220> FEATURE:
<223> OTHER INFORMATION: MTD JO-79

<400> SEQUENCE: 130

Leu Ile Val Ala Ala Val Val Val Ala Val Leu Ile
1               5                   10

<210> SEQ ID NO 131
<211> LENGTH: 7
<212> TYPE: PRT
<213> ORGANISM: Streptomyces coelicolor
<220> FEATURE:
<223> OTHER INFORMATION: MTD JO-80

<400> SEQUENCE: 131

Ala Val Val Val Ala Ala Pro
1               5
```

```
<210> SEQ ID NO 132
<211> LENGTH: 9
<212> TYPE: PRT
<213> ORGANISM: Streptomyces coelicolor
<220> FEATURE:
<223> OTHER INFORMATION: MTD JO-81

<400> SEQUENCE: 132

Leu Ala Ala Val Leu Leu Leu Ile Pro
1               5

<210> SEQ ID NO 133
<211> LENGTH: 10
<212> TYPE: PRT
<213> ORGANISM: Homo sapiens
<220> FEATURE:
<223> OTHER INFORMATION: MTD JO-82

<400> SEQUENCE: 133

Leu Leu Leu Leu Leu Leu Ala Val Val Pro
1               5                   10

<210> SEQ ID NO 134
<211> LENGTH: 11
<212> TYPE: PRT
<213> ORGANISM: Phytophthora coelicolor
<220> FEATURE:
<223> OTHER INFORMATION: MTD JO-83

<400> SEQUENCE: 134

Ala Val Ala Leu Val Ala Val Val Ala Val Ala
1               5                   10

<210> SEQ ID NO 135
<211> LENGTH: 9
<212> TYPE: PRT
<213> ORGANISM: Streptomyces coelicolor
<220> FEATURE:
<223> OTHER INFORMATION: MTD JO-84

<400> SEQUENCE: 135

Leu Val Ala Ala Leu Leu Ala Val Leu
1               5

<210> SEQ ID NO 136
<211> LENGTH: 11
<212> TYPE: PRT
<213> ORGANISM: Streptomyces coelicolor
<220> FEATURE:
<223> OTHER INFORMATION: MTD JO-85

<400> SEQUENCE: 136

Leu Leu Ala Ala Ala Ala Ala Leu Leu Leu Ala
1               5                   10

<210> SEQ ID NO 137
<211> LENGTH: 8
<212> TYPE: PRT
<213> ORGANISM: Mycobacterium bovis
<220> FEATURE:
<223> OTHER INFORMATION: MTD JO-86

<400> SEQUENCE: 137

Leu Ala Val Leu Ala Ala Ala Pro
1               5

<210> SEQ ID NO 138
<211> LENGTH: 13
```

```
<212> TYPE: PRT
<213> ORGANISM: Streptomyces coelicolor
<220> FEATURE:
<223> OTHER INFORMATION: MTD JO-87

<400> SEQUENCE: 138

Val Val Val Leu Leu Val Leu Leu Ala Leu Val Val Val
1               5                   10

<210> SEQ ID NO 139
<211> LENGTH: 7
<212> TYPE: PRT
<213> ORGANISM: Streptomyces coelicolor
<220> FEATURE:
<223> OTHER INFORMATION: MTD JO-88

<400> SEQUENCE: 139

Val Val Ile Ala Val Val Pro
1               5

<210> SEQ ID NO 140
<211> LENGTH: 10
<212> TYPE: PRT
<213> ORGANISM: Streptomyces coelicolor
<220> FEATURE:
<223> OTHER INFORMATION: MTD JO-89

<400> SEQUENCE: 140

Leu Ala Ala Val Ala Ala Leu Ala Val Val
1               5                   10

<210> SEQ ID NO 141
<211> LENGTH: 9
<212> TYPE: PRT
<213> ORGANISM: Streptomyces coelicolor
<220> FEATURE:
<223> OTHER INFORMATION: MTD JO-90

<400> SEQUENCE: 141

Val Leu Leu Val Leu Leu Ala Leu Val
1               5

<210> SEQ ID NO 142
<211> LENGTH: 8
<212> TYPE: PRT
<213> ORGANISM: Streptomyces coelicolor
<220> FEATURE:
<223> OTHER INFORMATION: MTD JO-91

<400> SEQUENCE: 142

Pro Val Leu Val Pro Ala Val Pro
1               5

<210> SEQ ID NO 143
<211> LENGTH: 8
<212> TYPE: PRT
<213> ORGANISM: Streptomyces coelicolor
<220> FEATURE:
<223> OTHER INFORMATION: MTD JO-92

<400> SEQUENCE: 143

Pro Ala Leu Ala Leu Ala Leu Ala
1               5

<210> SEQ ID NO 144
<211> LENGTH: 8
<212> TYPE: PRT
<213> ORGANISM: Streptomyces coelicolor
```

```
<220> FEATURE:
<223> OTHER INFORMATION: MTD JO-93

<400> SEQUENCE: 144

Ala Ala Ala Ala Pro Ala Leu Ala
1               5

<210> SEQ ID NO 145
<211> LENGTH: 9
<212> TYPE: PRT
<213> ORGANISM: Streptomyces coelicolor
<220> FEATURE:
<223> OTHER INFORMATION: MTD JO-94

<400> SEQUENCE: 145

Ile Val Leu Pro Val Leu Ala Ala Pro
1               5

<210> SEQ ID NO 146
<211> LENGTH: 10
<212> TYPE: PRT
<213> ORGANISM: Mycobacterium leprae
<220> FEATURE:
<223> OTHER INFORMATION: MTD JO-95

<400> SEQUENCE: 146

Leu Val Leu Leu Leu Leu Pro Leu Leu Ile
1               5                   10

<210> SEQ ID NO 147
<211> LENGTH: 11
<212> TYPE: PRT
<213> ORGANISM: Streptomyces coelicolor
<220> FEATURE:
<223> OTHER INFORMATION: MTD JO-96

<400> SEQUENCE: 147

Leu Ala Ala Val Ala Pro Ala Leu Ala Val Val
1               5                   10

<210> SEQ ID NO 148
<211> LENGTH: 8
<212> TYPE: PRT
<213> ORGANISM: Homo sapiens
<220> FEATURE:
<223> OTHER INFORMATION: MTD JO-97

<400> SEQUENCE: 148

Ile Leu Val Leu Val Leu Pro Ile
1               5

<210> SEQ ID NO 149
<211> LENGTH: 9
<212> TYPE: PRT
<213> ORGANISM: Homo sapiens
<220> FEATURE:
<223> OTHER INFORMATION: MTD JO-98

<400> SEQUENCE: 149

Ile Leu Leu Pro Leu Leu Leu Leu Pro
1               5

<210> SEQ ID NO 150
<211> LENGTH: 10
<212> TYPE: PRT
<213> ORGANISM: Streptomyces coelicolor
<220> FEATURE:
<223> OTHER INFORMATION: MTD JO-99
```

```
<400> SEQUENCE: 150

Ile Ala Pro Ala Val Val Ala Ala Leu Pro
1               5                   10

<210> SEQ ID NO 151
<211> LENGTH: 12
<212> TYPE: PRT
<213> ORGANISM: Homo sapiens
<220> FEATURE:
<223> OTHER INFORMATION: MTD JO-100

<400> SEQUENCE: 151

Leu Leu Leu Val Ala Val Val Pro Leu Leu Val Pro
1               5                   10

<210> SEQ ID NO 152
<211> LENGTH: 10
<212> TYPE: PRT
<213> ORGANISM: Streptomyces coelicolor
<220> FEATURE:
<223> OTHER INFORMATION: MTD JO-102

<400> SEQUENCE: 152

Ala Val Leu Ala Ala Pro Ala Val Leu Val
1               5                   10

<210> SEQ ID NO 153
<211> LENGTH: 7
<212> TYPE: PRT
<213> ORGANISM: Canis familiaris
<220> FEATURE:
<223> OTHER INFORMATION: MTD JO-104

<400> SEQUENCE: 153

Leu Ala Leu Ala Leu Leu Leu
1               5

<210> SEQ ID NO 154
<211> LENGTH: 9
<212> TYPE: PRT
<213> ORGANISM: Streptomyces coelicolor
<220> FEATURE:
<223> OTHER INFORMATION: MTD JO-105

<400> SEQUENCE: 154

Val Ala Val Pro Leu Leu Val Val Ala
1               5

<210> SEQ ID NO 155
<211> LENGTH: 11
<212> TYPE: PRT
<213> ORGANISM: Mycobacterium bovis
<220> FEATURE:
<223> OTHER INFORMATION: MTD JO-106

<400> SEQUENCE: 155

Ala Val Ala Val Ala Pro Val Ala Ala Ala
1               5                   10

<210> SEQ ID NO 156
<211> LENGTH: 11
<212> TYPE: PRT
<213> ORGANISM: Streptomyces coelicolor
<220> FEATURE:
<223> OTHER INFORMATION: MTD JO-107

<400> SEQUENCE: 156
```

Ala Ala Ala Val Val Ala Ala Val Pro Ala Ala
1               5                   10

<210> SEQ ID NO 157
<211> LENGTH: 9
<212> TYPE: PRT
<213> ORGANISM: Homo sapiens
<220> FEATURE:
<223> OTHER INFORMATION: MTD JO-108

<400> SEQUENCE: 157

Ala Leu Leu Ala Ala Leu Leu Ala Pro
1               5

<210> SEQ ID NO 158
<211> LENGTH: 7
<212> TYPE: PRT
<213> ORGANISM: Homo sapiens
<220> FEATURE:
<223> OTHER INFORMATION: MTD JO-109

<400> SEQUENCE: 158

Leu Leu Ala Leu Leu Val Pro
1               5

<210> SEQ ID NO 159
<211> LENGTH: 14
<212> TYPE: PRT
<213> ORGANISM: Homo sapiens
<220> FEATURE:
<223> OTHER INFORMATION: MTD JO-110

<400> SEQUENCE: 159

Ala Leu Leu Ala Ala Leu Leu Ala Leu Leu Ala Leu Leu Val
1               5                   10

<210> SEQ ID NO 160
<211> LENGTH: 11
<212> TYPE: PRT
<213> ORGANISM: Homo sapiens
<220> FEATURE:
<223> OTHER INFORMATION: MTD JO-111

<400> SEQUENCE: 160

Ala Ala Ala Leu Pro Leu Leu Val Leu Leu Pro
1               5                   10

<210> SEQ ID NO 161
<211> LENGTH: 10
<212> TYPE: PRT
<213> ORGANISM: Streptomyces coelicolor
<220> FEATURE:
<223> OTHER INFORMATION: MTD JO-112

<400> SEQUENCE: 161

Ala Ala Ala Val Pro Ala Ala Leu Ala Pro
1               5                   10

<210> SEQ ID NO 162
<211> LENGTH: 10
<212> TYPE: PRT
<213> ORGANISM: Streptomyces coelicolor
<220> FEATURE:
<223> OTHER INFORMATION: MTD JO-113

<400> SEQUENCE: 162

Ala Ala Leu Ala Val Ala Ala Leu Ala Ala

```
                 1               5                  10
```

<210> SEQ ID NO 163
<211> LENGTH: 8
<212> TYPE: PRT
<213> ORGANISM: Streptomyces coelicolor
<220> FEATURE:
<223> OTHER INFORMATION: MTD JO-114

<400> SEQUENCE: 163

Ala Val Leu Ala Ala Ala Val Pro
1               5

<210> SEQ ID NO 164
<211> LENGTH: 8
<212> TYPE: PRT
<213> ORGANISM: Streptomyces coelicolor
<220> FEATURE:
<223> OTHER INFORMATION: MTD JO-115

<400> SEQUENCE: 164

Val Ala Ala Leu Pro Ala Pro Ala
1               5

<210> SEQ ID NO 165
<211> LENGTH: 11
<212> TYPE: PRT
<213> ORGANISM: Streptomyces coelicolor
<220> FEATURE:
<223> OTHER INFORMATION: MTD JO-116

<400> SEQUENCE: 165

Ala Leu Ala Leu Ala Val Pro Ala Val Leu Pro
1               5                   10

<210> SEQ ID NO 166
<211> LENGTH: 11
<212> TYPE: PRT
<213> ORGANISM: Streptomyces coelicolor
<220> FEATURE:
<223> OTHER INFORMATION: MTD JO-117

<400> SEQUENCE: 166

Ala Ala Leu Leu Pro Ala Ala Val Ala Val Pro
1               5                   10

<210> SEQ ID NO 167
<211> LENGTH: 8
<212> TYPE: PRT
<213> ORGANISM: Streptomyces coelicolor
<220> FEATURE:
<223> OTHER INFORMATION: MTD JO-118

<400> SEQUENCE: 167

Ala Val Val Val Ala Leu Ala Pro
1               5

<210> SEQ ID NO 168
<211> LENGTH: 14
<212> TYPE: PRT
<213> ORGANISM: Streptomyces coelicolor
<220> FEATURE:
<223> OTHER INFORMATION: MTD JO-119

<400> SEQUENCE: 168

Ala Ala Ala Val Ala Leu Pro Ala Ala Ala Ala Leu Leu Ala
1               5                   10

```
<210> SEQ ID NO 169
<211> LENGTH: 13
<212> TYPE: PRT
<213> ORGANISM: Homo sapiens
<220> FEATURE:
<223> OTHER INFORMATION: MTD JO-120

<400> SEQUENCE: 169

Ala Val Val Leu Pro Leu Ala Leu Val Ala Val Ala Pro
1               5                   10

<210> SEQ ID NO 170
<211> LENGTH: 8
<212> TYPE: PRT
<213> ORGANISM: Mus musculus
<220> FEATURE:
<223> OTHER INFORMATION: MTD JO-121

<400> SEQUENCE: 170

Leu Val Ala Leu Pro Leu Leu Pro
1               5

<210> SEQ ID NO 171
<211> LENGTH: 10
<212> TYPE: PRT
<213> ORGANISM: Streptomyces coelicolor
<220> FEATURE:
<223> OTHER INFORMATION: MTD JO-122

<400> SEQUENCE: 171

Val Val Val Pro Leu Leu Leu Ile Val Pro
1               5                   10

<210> SEQ ID NO 172
<211> LENGTH: 8
<212> TYPE: PRT
<213> ORGANISM: Mycobacterium leprae
<220> FEATURE:
<223> OTHER INFORMATION: MTD JO-123

<400> SEQUENCE: 172

Leu Ala Val Val Leu Ala Val Pro
1               5

<210> SEQ ID NO 173
<211> LENGTH: 10
<212> TYPE: PRT
<213> ORGANISM: Plasmodium cynomolgi
<220> FEATURE:
<223> OTHER INFORMATION: MTD JO-124

<400> SEQUENCE: 173

Leu Leu Ala Val Pro Ile Leu Leu Val Pro
1               5                   10

<210> SEQ ID NO 174
<211> LENGTH: 8
<212> TYPE: PRT
<213> ORGANISM: Homo sapiens
<220> FEATURE:
<223> OTHER INFORMATION: MTD JO-125

<400> SEQUENCE: 174

Leu Val Ala Leu Val Leu Leu Pro
1               5

<210> SEQ ID NO 175
```

```
<211> LENGTH: 14
<212> TYPE: PRT
<213> ORGANISM: Homo sapiens
<220> FEATURE:
<223> OTHER INFORMATION: MTD JO-126

<400> SEQUENCE: 175

Leu Val Leu Leu Leu Ala Val Leu Leu Leu Ala Val Leu Pro
1               5                   10

<210> SEQ ID NO 176
<211> LENGTH: 12
<212> TYPE: PRT
<213> ORGANISM: Salmonella typhi
<220> FEATURE:
<223> OTHER INFORMATION: MTD JO-127

<400> SEQUENCE: 176

Leu Leu Ala Pro Val Val Ala Leu Val Ile Leu Pro
1               5                   10

<210> SEQ ID NO 177
<211> LENGTH: 13
<212> TYPE: PRT
<213> ORGANISM: Streptomyces coelicolor
<220> FEATURE:
<223> OTHER INFORMATION: MTD JO-128

<400> SEQUENCE: 177

Val Leu Ala Val Leu Ala Val Pro Val Leu Leu Leu Pro
1               5                   10

<210> SEQ ID NO 178
<211> LENGTH: 10
<212> TYPE: PRT
<213> ORGANISM: Streptomyces coelicolor
<220> FEATURE:
<223> OTHER INFORMATION: MTD JO-129

<400> SEQUENCE: 178

Val Val Ile Ala Val Val Pro Val Val Val
1               5                   10

<210> SEQ ID NO 179
<211> LENGTH: 11
<212> TYPE: PRT
<213> ORGANISM: Streptomyces coelicolor
<220> FEATURE:
<223> OTHER INFORMATION: MTD JO-130

<400> SEQUENCE: 179

Leu Leu Val Leu Leu Ala Leu Val Val Val Pro
1               5                   10

<210> SEQ ID NO 180
<211> LENGTH: 11
<212> TYPE: PRT
<213> ORGANISM: Streptomyces coelicolor
<220> FEATURE:
<223> OTHER INFORMATION: MTD JO-131

<400> SEQUENCE: 180

Val Leu Leu Ala Leu Pro Val Val Ala Ala Pro
1               5                   10

<210> SEQ ID NO 181
<211> LENGTH: 12
<212> TYPE: PRT
```

```
<213> ORGANISM: Streptomyces coelicolor
<220> FEATURE:
<223> OTHER INFORMATION: MTD JO-132

<400> SEQUENCE: 181

Ala Val Val Val Pro Ala Ile Val Leu Ala Ala Pro
1               5                   10

<210> SEQ ID NO 182
<211> LENGTH: 11
<212> TYPE: PRT
<213> ORGANISM: Streptomyces coelicolor
<220> FEATURE:
<223> OTHER INFORMATION: MTD JO-133

<400> SEQUENCE: 182

Ala Val Leu Val Pro Ala Ala Ala Leu Val Pro
1               5                   10

<210> SEQ ID NO 183
<211> LENGTH: 10
<212> TYPE: PRT
<213> ORGANISM: Streptomyces coelicolor
<220> FEATURE:
<223> OTHER INFORMATION: MTD JO-134

<400> SEQUENCE: 183

Val Val Ala Ala Leu Pro Leu Val Leu Pro
1               5                   10

<210> SEQ ID NO 184
<211> LENGTH: 10
<212> TYPE: PRT
<213> ORGANISM: Streptomyces coelicolor
<220> FEATURE:
<223> OTHER INFORMATION: MTD JO-135

<400> SEQUENCE: 184

Ala Ala Val Ala Leu Pro Ala Ala Ala Pro
1               5                   10

<210> SEQ ID NO 185
<211> LENGTH: 8
<212> TYPE: PRT
<213> ORGANISM: Homo sapiens
<220> FEATURE:
<223> OTHER INFORMATION: MTD JO-136

<400> SEQUENCE: 185

Leu Ile Ala Leu Pro Leu Leu Pro
1               5

<210> SEQ ID NO 186
<211> LENGTH: 13
<212> TYPE: PRT
<213> ORGANISM: Homo sapiens
<220> FEATURE:
<223> OTHER INFORMATION: MTD JO-137

<400> SEQUENCE: 186

Leu Leu Ala Leu Pro Leu Val Leu Val Leu Ala Leu Pro
1               5                   10

<210> SEQ ID NO 187
<211> LENGTH: 9
<212> TYPE: PRT
<213> ORGANISM: Streptomyces coelicolor
<220> FEATURE:
```

<223> OTHER INFORMATION: MTD JO-138

<400> SEQUENCE: 187

Ile Val Pro Leu Leu Ala Ala Pro
1               5

<210> SEQ ID NO 188
<211> LENGTH: 10
<212> TYPE: PRT
<213> ORGANISM: Homo sapiens
<220> FEATURE:
<223> OTHER INFORMATION: MTD JO-139

<400> SEQUENCE: 188

Leu Leu Leu Ala Pro Leu Leu Leu Ala Pro
1               5                   10

<210> SEQ ID NO 189
<211> LENGTH: 10
<212> TYPE: PRT
<213> ORGANISM: Streptomyces coelicolor
<220> FEATURE:
<223> OTHER INFORMATION: MTD JO-140

<400> SEQUENCE: 189

Leu Ala Ala Leu Pro Val Ala Ala Val Pro
1               5                   10

<210> SEQ ID NO 190
<211> LENGTH: 10
<212> TYPE: PRT
<213> ORGANISM: Neisseria meningitidis
<220> FEATURE:
<223> OTHER INFORMATION: MTD JO-141

<400> SEQUENCE: 190

Ala Leu Ala Val Ile Val Leu Val Leu Leu
1               5                   10

<210> SEQ ID NO 191
<211> LENGTH: 10
<212> TYPE: PRT
<213> ORGANISM: Homo sapiens
<220> FEATURE:
<223> OTHER INFORMATION: MTD JO-142

<400> SEQUENCE: 191

Leu Ala Leu Leu Leu Pro Ala Ala Leu Ile
1               5                   10

<210> SEQ ID NO 192
<211> LENGTH: 11
<212> TYPE: PRT
<213> ORGANISM: Streptomyces coelicolor
<220> FEATURE:
<223> OTHER INFORMATION: MTD JO-143

<400> SEQUENCE: 192

Ala Leu Leu Pro Leu Leu Ala Val Val Leu Pro
1               5                   10

<210> SEQ ID NO 193
<211> LENGTH: 10
<212> TYPE: PRT
<213> ORGANISM: Streptomyces coelicolor
<220> FEATURE:
<223> OTHER INFORMATION: MTD JO-144

```
<400> SEQUENCE: 193

Ala Ile Ala Val Pro Val Leu Ala Ala Pro
1               5                   10

<210> SEQ ID NO 194
<211> LENGTH: 10
<212> TYPE: PRT
<213> ORGANISM: Homo sapiens
<220> FEATURE:
<223> OTHER INFORMATION: MTD JO-145

<400> SEQUENCE: 194

Ala Ala Ala Pro Val Leu Leu Leu Leu Leu
1               5                   10

<210> SEQ ID NO 195
<211> LENGTH: 11
<212> TYPE: PRT
<213> ORGANISM: Streptomyces coelicolor
<220> FEATURE:
<223> OTHER INFORMATION: MTD JO-146

<400> SEQUENCE: 195

Ala Ala Ala Val Ala Val Leu Ala Leu Ala Pro
1               5                   10

<210> SEQ ID NO 196
<211> LENGTH: 11
<212> TYPE: PRT
<213> ORGANISM: Streptomyces coelicolor
<220> FEATURE:
<223> OTHER INFORMATION: MTD JO-147

<400> SEQUENCE: 196

Ala Ala Leu Ala Ala Leu Val Val Ala Ala Pro
1               5                   10

<210> SEQ ID NO 197
<211> LENGTH: 12
<212> TYPE: PRT
<213> ORGANISM: Streptomyces coelicolor
<220> FEATURE:
<223> OTHER INFORMATION: MTD JO-148

<400> SEQUENCE: 197

Ala Ala Leu Ala Ala Val Pro Leu Ala Leu Ala Pro
1               5                   10

<210> SEQ ID NO 198
<211> LENGTH: 13
<212> TYPE: PRT
<213> ORGANISM: Streptomyces coelicolor
<220> FEATURE:
<223> OTHER INFORMATION: MTD JO-149

<400> SEQUENCE: 198

Ala Leu Ala Val Ala Ala Pro Ala Leu Ala Leu Leu Pro
1               5                   10

<210> SEQ ID NO 199
<211> LENGTH: 8
<212> TYPE: PRT
<213> ORGANISM: Streptomyces coelicolor
<220> FEATURE:
<223> OTHER INFORMATION: MTD JO-150

<400> SEQUENCE: 199
```

```
Ala Ala Leu Pro Ala Ala Ala Pro
1               5

<210> SEQ ID NO 200
<211> LENGTH: 9
<212> TYPE: PRT
<213> ORGANISM: Streptomyces coelicolor
<220> FEATURE:
<223> OTHER INFORMATION: MTD JO-151

<400> SEQUENCE: 200

Ala Ala Ala Pro Val Ala Ala Val Pro
1               5

<210> SEQ ID NO 201
<211> LENGTH: 10
<212> TYPE: PRT
<213> ORGANISM: Homo sapiens
<220> FEATURE:
<223> OTHER INFORMATION: MTD JO-152

<400> SEQUENCE: 201

Leu Leu Ala Val Leu Leu Ala Leu Leu Pro
1               5                   10

<210> SEQ ID NO 202
<211> LENGTH: 10
<212> TYPE: PRT
<213> ORGANISM: Streptomyces coelicolor
<220> FEATURE:
<223> OTHER INFORMATION: MTD JO-153

<400> SEQUENCE: 202

Val Leu Ala Leu Leu Val Ala Val Val Pro
1               5                   10

<210> SEQ ID NO 203
<211> LENGTH: 9
<212> TYPE: PRT
<213> ORGANISM: Streptomyces coelicolor
<220> FEATURE:
<223> OTHER INFORMATION: MTD JO-154

<400> SEQUENCE: 203

Ala Leu Val Val Pro Ala Ala Val Pro
1               5

<210> SEQ ID NO 204
<211> LENGTH: 9
<212> TYPE: PRT
<213> ORGANISM: Streptomyces coelicolor
<220> FEATURE:
<223> OTHER INFORMATION: MTD JO-155

<400> SEQUENCE: 204

Ala Val Val Leu Pro Leu Leu Leu Pro
1               5

<210> SEQ ID NO 205
<211> LENGTH: 10
<212> TYPE: PRT
<213> ORGANISM: Mycobacterium tuberculosis
<220> FEATURE:
<223> OTHER INFORMATION: MTD JO-156

<400> SEQUENCE: 205

Ala Val Ile Pro Val Ala Val Leu Val Pro
1               5                   10
```

```
<210> SEQ ID NO 206
<211> LENGTH: 11
<212> TYPE: PRT
<213> ORGANISM: Streptomyces coelicolor
<220> FEATURE:
<223> OTHER INFORMATION: MTD JO-157

<400> SEQUENCE: 206

Ala Ala Ala Val Pro Ala Ala Val Leu Ala Pro
1               5                   10

<210> SEQ ID NO 207
<211> LENGTH: 11
<212> TYPE: PRT
<213> ORGANISM: Streptomyces coelicolor
<220> FEATURE:
<223> OTHER INFORMATION: MTD JO-158

<400> SEQUENCE: 207

Val Ala Val Pro Val Val Leu Ala Ile Leu Pro
1               5                   10

<210> SEQ ID NO 208
<211> LENGTH: 12
<212> TYPE: PRT
<213> ORGANISM: Bacillus subtilis
<220> FEATURE:
<223> OTHER INFORMATION: MTD JO-159

<400> SEQUENCE: 208

Ile Ala Ile Ala Ala Ile Pro Ala Ile Leu Ala Leu
1               5                   10

<210> SEQ ID NO 209
<211> LENGTH: 10
<212> TYPE: PRT
<213> ORGANISM: Neisseria meningitidis
<220> FEATURE:
<223> OTHER INFORMATION: MTD JO-160

<400> SEQUENCE: 209

Ala Leu Ile Ala Pro Ala Leu Ala Ala Pro
1               5                   10

<210> SEQ ID NO 210
<211> LENGTH: 10
<212> TYPE: PRT
<213> ORGANISM: Streptomyces coelicolor
<220> FEATURE:
<223> OTHER INFORMATION: MTD JO-161

<400> SEQUENCE: 210

Ala Ala Ile Ala Leu Val Ala Pro Ala Leu
1               5                   10

<210> SEQ ID NO 211
<211> LENGTH: 9
<212> TYPE: PRT
<213> ORGANISM: Streptomyces coelicolor
<220> FEATURE:
<223> OTHER INFORMATION: MTD JO-162

<400> SEQUENCE: 211

Leu Ala Pro Ala Val Ala Ala Ala Pro
1               5
```

```
<210> SEQ ID NO 212
<211> LENGTH: 15
<212> TYPE: PRT
<213> ORGANISM: Streptomyces coelicolor
<220> FEATURE:
<223> OTHER INFORMATION: MTD JO-163

<400> SEQUENCE: 212

Val Ala Ile Ile Val Pro Ala Val Val Ala Ile Ala Leu Ile Ile
1               5                   10                  15

<210> SEQ ID NO 213
<211> LENGTH: 9
<212> TYPE: PRT
<213> ORGANISM: Streptomyces coelicolor
<220> FEATURE:
<223> OTHER INFORMATION: MTD JO-164

<400> SEQUENCE: 213

Ala Val Val Ala Ile Ala Leu Ile Ile
1               5

<210> SEQ ID NO 214
<211> LENGTH: 9
<212> TYPE: PRT
<213> ORGANISM: Streptomyces coelicolor
<220> FEATURE:
<223> OTHER INFORMATION: MTD JO-165

<400> SEQUENCE: 214

Leu Ala Ala Val Pro Ala Ala Ala Pro
1               5

<210> SEQ ID NO 215
<211> LENGTH: 10
<212> TYPE: PRT
<213> ORGANISM: Streptomyces coelicolor
<220> FEATURE:
<223> OTHER INFORMATION: MTD JO-166

<400> SEQUENCE: 215

Ala Val Ala Ala Leu Pro Leu Ala Ala Pro
1               5                   10

<210> SEQ ID NO 216
<211> LENGTH: 9
<212> TYPE: PRT
<213> ORGANISM: Streptomyces coelicolor
<220> FEATURE:
<223> OTHER INFORMATION: MTD JO-167

<400> SEQUENCE: 216

Leu Ala Ala Pro Ala Ala Ala Ala Pro
1               5

<210> SEQ ID NO 217
<211> LENGTH: 12
<212> TYPE: PRT
<213> ORGANISM: Streptomyces coelicolor
<220> FEATURE:
<223> OTHER INFORMATION: MTD JO-168

<400> SEQUENCE: 217

Leu Ala Ala Val Val Pro Val Ala Ala Ala Val Pro
1               5                   10

<210> SEQ ID NO 218
<211> LENGTH: 9
```

```
<212> TYPE: PRT
<213> ORGANISM: Streptomyces coelicolor
<220> FEATURE:
<223> OTHER INFORMATION: MTD JO-169

<400> SEQUENCE: 218

Val Ala Ala Pro Ala Ala Ala Pro
1               5

<210> SEQ ID NO 219
<211> LENGTH: 8
<212> TYPE: PRT
<213> ORGANISM: Streptomyces coelicolor
<220> FEATURE:
<223> OTHER INFORMATION: MTD JO-170

<400> SEQUENCE: 219

Ala Val Pro Val Pro Val Pro Leu
1               5

<210> SEQ ID NO 220
<211> LENGTH: 10
<212> TYPE: PRT
<213> ORGANISM: Homo sapiens
<220> FEATURE:
<223> OTHER INFORMATION: MTD JO-171

<400> SEQUENCE: 220

Leu Leu Ile Leu Pro Ile Val Leu Leu Pro
1               5                   10

<210> SEQ ID NO 221
<211> LENGTH: 11
<212> TYPE: PRT
<213> ORGANISM: Streptomyces coelicolor
<220> FEATURE:
<223> OTHER INFORMATION: MTD JO-172

<400> SEQUENCE: 221

Ala Leu Ala Leu Pro Ala Leu Ala Ile Ala Pro
1               5                   10

<210> SEQ ID NO 222
<211> LENGTH: 9
<212> TYPE: PRT
<213> ORGANISM: Streptomyces coelicolor
<220> FEATURE:
<223> OTHER INFORMATION: MTD JO-173

<400> SEQUENCE: 222

Ala Val Ile Pro Ile Leu Ala Val Pro
1               5

<210> SEQ ID NO 223
<211> LENGTH: 11
<212> TYPE: PRT
<213> ORGANISM: Streptomyces coelicolor
<220> FEATURE:
<223> OTHER INFORMATION: MTD JO-174

<400> SEQUENCE: 223

Leu Ile Leu Leu Leu Pro Ala Val Ala Leu Pro
1               5                   10

<210> SEQ ID NO 224
<211> LENGTH: 10
<212> TYPE: PRT
<213> ORGANISM: Streptomyces coelicolor
```

```
<220> FEATURE:
<223> OTHER INFORMATION: MTD JO-175

<400> SEQUENCE: 224

Ile Val Leu Ala Pro Val Pro Ala Ala Ala
1               5                   10

<210> SEQ ID NO 225
<211> LENGTH: 11
<212> TYPE: PRT
<213> ORGANISM: Streptomyces coelicolor
<220> FEATURE:
<223> OTHER INFORMATION: MTD JO-176

<400> SEQUENCE: 225

Val Val Val Val Pro Val Leu Ala Ala Ala Ala
1               5                   10

<210> SEQ ID NO 226
<211> LENGTH: 7
<212> TYPE: PRT
<213> ORGANISM: Bacillus amyloliquefaciens
<220> FEATURE:
<223> OTHER INFORMATION: MTD JO-177

<400> SEQUENCE: 226

Leu Val Ala Val Ala Ala Pro
1               5

<210> SEQ ID NO 227
<211> LENGTH: 10
<212> TYPE: PRT
<213> ORGANISM: Streptomyces coelicolor
<220> FEATURE:
<223> OTHER INFORMATION: MTD JO-178

<400> SEQUENCE: 227

Leu Val Leu Ala Ala Pro Ala Ala Leu Pro
1               5                   10

<210> SEQ ID NO 228
<211> LENGTH: 9
<212> TYPE: PRT
<213> ORGANISM: Streptomyces coelicolor
<220> FEATURE:
<223> OTHER INFORMATION: MTD JO-179

<400> SEQUENCE: 228

Leu Ile Ala Pro Ala Ala Ala Val Pro
1               5

<210> SEQ ID NO 229
<211> LENGTH: 10
<212> TYPE: PRT
<213> ORGANISM: Homo sapiens
<220> FEATURE:
<223> OTHER INFORMATION: MTD JO-180

<400> SEQUENCE: 229

Ala Leu Ala Ala Leu Pro Ile Ala Leu Pro
1               5                   10

<210> SEQ ID NO 230
<211> LENGTH: 9
<212> TYPE: PRT
<213> ORGANISM: Neisseria meningitidis
<220> FEATURE:
<223> OTHER INFORMATION: MTD JO-181
```

```
<400> SEQUENCE: 230

Ala Val Leu Leu Leu Pro Ala Ala Ala
1               5

<210> SEQ ID NO 231
<211> LENGTH: 9
<212> TYPE: PRT
<213> ORGANISM: Escherichia coli
<220> FEATURE:
<223> OTHER INFORMATION: MTD JO-182

<400> SEQUENCE: 231

Ile Ala Leu Ala Leu Leu Pro Leu Leu
1               5

<210> SEQ ID NO 232
<211> LENGTH: 10
<212> TYPE: PRT
<213> ORGANISM: Homo sapiens
<220> FEATURE:
<223> OTHER INFORMATION: MTD JO-183

<400> SEQUENCE: 232

Val Leu Leu Ala Ala Ala Leu Ile Ala Pro
1               5                   10

<210> SEQ ID NO 233
<211> LENGTH: 11
<212> TYPE: PRT
<213> ORGANISM: Streptomyces coelicolor
<220> FEATURE:
<223> OTHER INFORMATION: MTD JO-184

<400> SEQUENCE: 233

Ala Pro Ala Val Leu Pro Pro Val Val Val Ile
1               5                   10

<210> SEQ ID NO 234
<211> LENGTH: 9
<212> TYPE: PRT
<213> ORGANISM: Mycobacterium leprae
<220> FEATURE:
<223> OTHER INFORMATION: MTD JO-185

<400> SEQUENCE: 234

Val Val Gly Leu Leu Val Ala Ala Leu
1               5

<210> SEQ ID NO 235
<211> LENGTH: 11
<212> TYPE: PRT
<213> ORGANISM: Streptomyces coelicolor
<220> FEATURE:
<223> OTHER INFORMATION: MTD JO-186

<400> SEQUENCE: 235

Ala Ala Ile Ala Ala Ala Ala Pro Leu Ala Ala
1               5                   10

<210> SEQ ID NO 236
<211> LENGTH: 7
<212> TYPE: PRT
<213> ORGANISM: Homo sapiens
<220> FEATURE:
<223> OTHER INFORMATION: MTD JO-187

<400> SEQUENCE: 236
```

Leu Leu Leu Ala Val Ala Pro
1               5

<210> SEQ ID NO 237
<211> LENGTH: 10
<212> TYPE: PRT
<213> ORGANISM: Homo sapiens
<220> FEATURE:
<223> OTHER INFORMATION: MTD JO-188

<400> SEQUENCE: 237

Leu Ile Leu Leu Leu Pro Leu Ala Ala Leu
1               5                   10

<210> SEQ ID NO 238
<211> LENGTH: 8
<212> TYPE: PRT
<213> ORGANISM: Mus musculus
<220> FEATURE:
<223> OTHER INFORMATION: MTD JO-189

<400> SEQUENCE: 238

Ala Leu Leu Leu Leu Val Leu Ala
1               5

<210> SEQ ID NO 239
<211> LENGTH: 9
<212> TYPE: PRT
<213> ORGANISM: Homo sapiens
<220> FEATURE:
<223> OTHER INFORMATION: MTD JO-190

<400> SEQUENCE: 239

Leu Leu Leu Leu Leu Leu Pro Leu Ala
1               5

<210> SEQ ID NO 240
<211> LENGTH: 8
<212> TYPE: PRT
<213> ORGANISM: Homo sapiens
<220> FEATURE:
<223> OTHER INFORMATION: MTD JO-191

<400> SEQUENCE: 240

Leu Ala Leu Pro Leu Leu Leu Pro
1               5

<210> SEQ ID NO 241
<211> LENGTH: 8
<212> TYPE: PRT
<213> ORGANISM: Streptomyces coelicolor
<220> FEATURE:
<223> OTHER INFORMATION: MTD JO-192

<400> SEQUENCE: 241

Leu Leu Val Leu Pro Leu Leu Ile
1               5

<210> SEQ ID NO 242
<211> LENGTH: 9
<212> TYPE: PRT
<213> ORGANISM: Homo sapiens
<220> FEATURE:
<223> OTHER INFORMATION: MTD JO-193

<400> SEQUENCE: 242

Leu Pro Leu Leu Pro Ala Ala Leu Val

```
<210> SEQ ID NO 243
<211> LENGTH: 9
<212> TYPE: PRT
<213> ORGANISM: Bacillus subtilis
<220> FEATURE:
<223> OTHER INFORMATION: MTD JO-35

<400> SEQUENCE: 243

Leu Ala Leu Ala Ala Ala Val Val Pro
1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 244

His His His His His His
1               5
```

CELL PERMEABLE P18 RECOMBINANT PROTEINS, POLYNUCLEOTIDES ENCODING THE SAME, AND ANTICANCER COMPOSITION COMPRISING THE SAME

CROSS-REFERENCE TO RELATED APPLICATIONS

The present application is a 35 U.S.C. §371 National Stage patent application of International patent application PCT/KR2008/005222, filed on Sep. 4, 2008, which claims priority to Korean patent application KR 10-2008-0059938, filed on Jun. 25, 2008 and U.S. provisional patent application 60/969,762, filed on Sep. 4, 2007.

TECHNICAL FIELD

The present invention relates to cell permeable p18 recombinant proteins in which a tumor suppressor p18 is fused to a macromolecule transduction domain (MTD), polynucleotides encoding the same, expression vectors for producing the same, and anticancer pharmaceutical compositions including the same as effective ingredients for treating p18 deficiency or failure.

BACKGROUND ART

A eukaryotic cell goes through a series of events in the cell cycle resulting in replication and proliferation. The cell cycle consists of four distinct phases: $G_1$ phase which is a quiescent phase from the end of the previous M phase till the beginning of DNA synthesis; S phase when DNA replication occurs; $G_2$ phase when significant protein synthesis occurs in preparation of cell mitosis (the $G_1$, S and $G_2$ phases being collectively known as an interphase); and M phase when nuclear division (i.e., chromosomes separate) and cytoplasmic division (i.e., cytokinesis) occur. As these events are repeated, cell replication and proliferation are accomplished.

Cell cycle check points are control mechanisms that ensure the fidelity of cell division in eukaryotic cells. These check points verify whether the process at each phase of the cell cycle has been properly completed before progression into the next phase. For example, if the cells are damaged or exposed to radiation, the cell cycle may be interrupted at three check points during the oncogenesis: the G1 check point for blocking the progress from the $G_1$ phase to the S phase; the S check point for delaying the progress of the S phase; and the G2 check point for blocking the progress from the $G_2$ phase to the M phase (Kastan, M. B. *Nature* 410: 766-7, 2001).

Such delicate regulation of the cell cycle is controlled by various regulatory molecules, the most important of which is cyclin-dependent kinase (CDK). CDKs couple with regulatory proteins called cyclins that are specifically expressed at each phase of the cell cycle to form functional units, resulting in the generation of various combinations of cyclin-CDK complexes specifically activated at each phase of the cell cycle. Upon receiving a pro-mitotic extracellular signal, the cell proceeds to the S phase. Specifically, the cyclin D-CDK2 or cyclin D-CDK6 complex is activated first, the cyclin E-CDK2 complex is next activated upon entering S phase, and then, cyclin A interacts with CDK2 to carry out the cell cycle progression during late $G_1$ and early S phases.

As indicated above, cell cycle progression is regulated by the various cyclins and kinases interacting therewith, and the coupling with CDK inhibitory factors, such as CDK4 inhibitor (INK4) and CDK interacting protein/kinase inhibitory protein (CIP/KIP) family, plays an important role in cell cycle regulation (Balomenos, D. and Martinez, A. C. *Immunol. Today* 21: 551-5, 2000). Further, ataxia telangiectasia mutated (ATM), which is a serine/threonine protein kinase of the phosphatidylinositol 3-kinase related kinases (PIKK) family, has been found to control cell-cycle check points in response to DNA damage or oncogenic signals, thereby ensuring genomic integrity and stability. ATM is necessary for the phosphorylation and activation of downstream factors, such as p53, murine double minute 2 (MDM2) and BRCA1 (Lu, S. et al., *Carcinogenesis* 27: 848-55, 2006). For instance, if the cells receive an oncogenic signal, such as damage to the double-strand DNA, ATM activates target proteins that induce cell cycle arrest and apoptosis, resulting in the regulation of gene transcription and DNA repair (Abraham, R. T. *Nat. Med.* 11: 257-8, 2005).

It has been found that p18 relating to ATM acts as a tumor suppressor in mice and humans. p18 deficiency or failure increases susceptibility to cancer by suppressing apoptosis of cells with DNA damage or mutations, thereby leading to malignant transformation of cells (Abraham, R. T. *Nat. Med.* 11: 257-8, 2005). In previous studies using p18 knock out mice, p18 homozygous knock out mice caused embryonic lethality, while p18 heterozygous knock out mice showed high susceptibility to various tumors including liver cancer, breast cancer, lung cancer, and the like (Park, B. J. et al., *Cell* 120: 209-21, 2005). p18 is transported into the nucleus and activated in response to DNA damage, where an increase in p18 expression leads to the phosphorylation and activation of p53 (French, J. E. et al., *Carcinogenesis* 22: 99-106, 2001; Ide, F. et al., *Am. J. Pathol.* 163: 1729-33, 2003), which is another tumor suppressor that controls cell proliferation and death. In contrast, p18 depletion inhibits the expression of p53 (Park, B. J. et al., *Cell* 120: 209-21, 2005).

The tumor suppressor gene p18 is located on chromosome region 6p24-25, where a loss-of-heterozygosity (LOH) region was found in lymphoma (Baumgartner, A. K. et al., *Lab. Invest.* 83: 1509-16, 2003). It has been suggested that LOH in this chromosome is responsible for the lower expression of p18. According to recent studies, reduced levels of endogenous p18 have generally and frequently been detected in various human cancer cell lines as well as primary tissues, suggesting that p18 is a rate-limiting factor in the mechanism for ATM-mediated p53 activation, as well as a haploinsufficient tumor suppressor (Park, B. J. et al., *Cell* 120: 209-21, 2005).

Based on the fact that p18 is a potent tumor suppressor which directly interacts with ATM to activate p53 in response to oncogenic signals such as DNA damage (Savitsky, K. et al., *Hum. Mol. Genet.* 4: 2025-32, 1995) and is an attractive target protein as a haploinsufficient tumor suppressor involved in the signaling pathway of cell-cycle checkpoints including ATM and p53 (Kastan, M. B. *Nature* 410: 766-7, 2001; Balomenos, D. and Martinez, A. C. *Immunol. Today* 21: 551-5, 2000; Abraham, R. T. *Nat. Med.* 11: 257-8, 2005; Park, B. J. et al., *Cell* 120: 209-21, 2005), the present inventors have endeavored to develop new anticancer agents.

Meanwhile, small molecules derived from synthetic compounds or natural compounds can be transported into the cells, whereas macromolecules, such as proteins, peptides, and nucleic acids, cannot. It is widely understood that macromolecules larger than 500 kDa are incapable of penetrating the plasma membrane, i.e., the lipid bilayer structure, of live cells. To overcome this problem, a macromolecule intracellular transduction technology (MITT) was developed (Jo et al., *Nat. Biotech.* 19: 929-33, 2001), which allows the delivery of therapeutically effective macromolecules into cells, making the development of new drugs using peptides, proteins and genetic materials possible. According to this method, if a target macromolecule is fused to a hydrophobic macromolecule transduction domain (MTD) and other cellular delivery regulators, synthesized, expressed, and purified in the form of a recombinant protein, it can penetrate the plasma membrane lipid bilayer of the cells, be accurately delivered to a target site, and then, effectively exhibit its therapeutic effect. Such MTDs facilitate the transport of many impermeable materials which are fused to peptides, proteins, DNA, RNA, synthetic compounds, and the like into the cells.

Accordingly, the inventors of the present invention have developed a method of mediating the transport of tumor suppressor p18 into the cells, where cell permeable p18 recombinant proteins are engineered by fusing a MTD to the tumor suppressor p18. Such cell permeable p18 recombinant proteins have been found to efficiently mediate the transport of tumor suppressor p18 into the cells in vivo as well as in vitro and can be used as anticancer agents for treating p18 deficiency or failure occurring in various human cancers.

DISCLOSURE

Technical Problem

Accordingly, the objective of the present invention is to provide cell permeable p18 recombinant proteins effective for the treatment of p18 deficiency or failure occurring in various kinds of human cancers as an anticancer agent.

Technical Solution

One aspect of the present invention relates to cell permeable p18 recombinant proteins capable of mediating the transport of a tumor suppressor p18 into a cell by fusing a macromolecule transduction domain (MTD) having cell permeability to the tumor suppressor protein.

Another aspect of the present invention relates to polynucleotides encoding the above cell permeable p18 recombinant proteins.

The present invention also relates to expression vectors containing the above polynucleotides, and transformants transformed with the above expression vectors.

Another aspect of the present invention relates to a method of producing cell permeable p18 recombinant proteins involving culturing the above transformants.

Another aspect of the present invention relates to a pharmaceutical composition including the above cell permeable p18 recombinant proteins as an effective ingredient for treating p18 deficiency or failure.

BEST MODE FOR CARRYING OUT THE INVENTION

The present invention provides cell permeable p18 recombinant proteins (CP-p18) capable of mediating the transport of a tumor suppressor p18 into a cell in which the tumor suppressor p18 is fused to a macromolecule transduction domain and, thereby, imparted with cell permeability; and polynucleotides encoding each of the cell permeable p18 recombinant proteins.

The present invention is characterized in that a tumor suppressor p18 which is a macromolecule incapable of being introduced into a cell is fused to a specific macromolecule transduction domain (hereinafter, "MTD") peptide so as to provide cell permeability, and thus, can be effectively transported into a cell. The MTD peptide may be fused to the N-terminus, the C-terminus, or both termini of the tumor suppressor p18.

The present invention relates to cell permeable p18 recombinant proteins that are engineered by fusing a tumor suppressor p18 to one of three MTD domains capable of mediating the transport of a macromolecule into a cell.

The term "cell permeable p18 recombinant protein" as used herein refers to a covalent bond complex bearing a MTD and a tumor suppressor protein p18, where they are functionally linked by genetic fusion or chemical coupling. Here, the term "genetic fusion" refers to a co-linear, covalent linkage of two or more proteins or fragments thereof via their individual peptide backbones, through genetic expression of a polynucleotide molecule encoding those proteins.

p18 is a tumor suppressor protein which directly interacts with ATM in response to oncogenic signals, such as DNA damage, for the activation of p53 which induces cell cycle arrest and apoptosis. p18 has an amino acid sequence represented by SEQ ID NO: 2, while a polynucleotide encoding the same has a nucleotide sequence represented by SEQ ID NO: 1. p18 functions as an important target protein in signal transduction pathways including ATM p53.

Figure 1A:
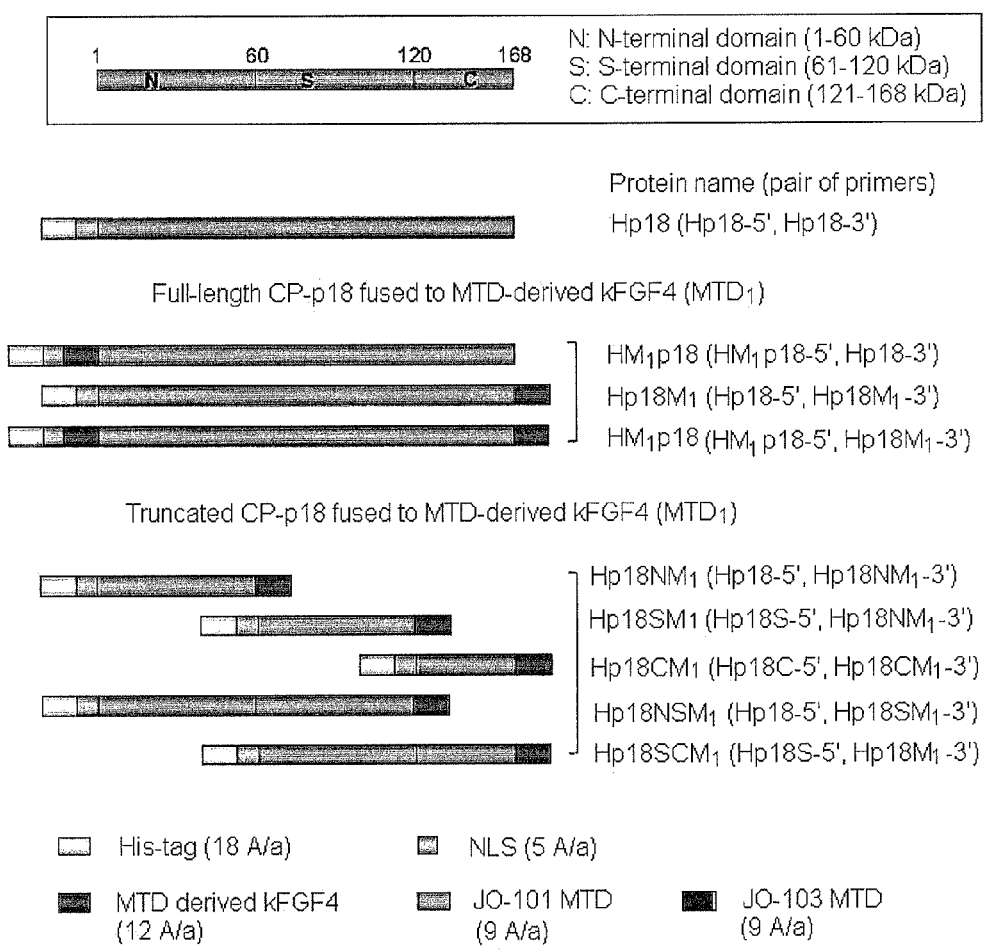
FIG. 1a is a schematic diagram illustrating the structures of cell permeable p18 recombinant proteins being fused to a kFGF4-derived MTD and constructed in the full-length and truncated forms according to the present invention.

The amino acid sequence of the tumor suppressor p18, i.e., SEQ ID NO: 2, is composed of a N-terminal domain corresponding to amino acid residues 1-60, a S-terminal domain corresponding to amino acid residues 61-120, and a C-terminal domain corresponding to amino acid residues 121-168 (see FIG. 1a).

For the MTD capable of being fused to the tumor suppressor p18, cell permeable peptides having an amino acid sequence selected from the group consisting of SEQ ID NOS: 4, 6, 8, and 53 to 243 may be used. The MTD having one of the amino acid sequences represented by SEQ ID NOS: 4, 6, 8 and 53 to 243 is a cell permeable polypeptide which is capable of mediating the transport of a biologically active molecule, such as a polypeptide, a protein domain, or a full-length protein across the cell membrane. Suitable MTDs for the present invention include a hydrophobic region showing cell membrane targeting activity by forming a helix structure at a signal peptide which is composed of an N-terminal domain, a hydrophobic domain and a C-terminal domain containing a secreted protein cleavage site. These MTDs can directly penetrate the cell membrane without causing any cell damage, transport a target protein into a cell, and thus, allow the target protein to exhibit its desired function.

The MTDs having the amino acid sequences represented by SEQ ID NOS: 4, 6, 8, and 53 to 243 and capable of being fused to a tumor suppressor p18 according to the present invention are summarized in the following Tables 1a to 1l.

TABLE 1a

| MTD | Origin | Amino acid sequence | SEQ ID NO |
|---|---|---|---|
| JO-01 | CAC04038 putative NLP/P60-family secreted protein [*Streptomyces coelicolor* A3(2)] | Ala Val Val Val Cys Ala Ile Val Leu Ala Ala Pro | 53 |
| JO-02 | NP_057021 phosphatidylinositol glycan, class T precursor [*Homo sapiens*] | Pro Leu Ala Leu Leu Val Leu Leu Leu Leu Gly Pro | 54 |
| JO-03 | NP_072171 chorionic somatomammotropin hormone 2 isoform 3 [*Homo sapiens*] | Leu Leu Leu Ala Phe Ala Leu Leu Cys Leu Pro | 55 |
| JO-04 | NP_932156 nudix-type motif 9 isoform a [*Homo sapiens*] | Leu Leu Gly Ala Leu Ala Ala Val Leu Leu Ala Leu Ala | 56 |
| JO-05 | NP_057327 NAD(P)H:quinone oxidoreductase type 3, polypeptide A2 [*Homo sapiens*] | Pro Val Leu Leu Ala Leu Gly Val Gly Leu Val Leu Leu Gly Leu Ala | 57 |
| JO-06 | CAD55300 putative secreted protein. [*Streptomyces coelicolor* A3(2)] | Ala Ala Ala Ala Val Leu Leu Ala Ala | 58 |
| JO-07 | NP_629514 secreted protein [*Streptomyces coelicolor* A3(2)] | Ile Val Val Ala Val Val Val Ile | 59 |
| JO-08 | CAB57190 putative secreted chitin binding protein [*Streptomyces coelicolor* A3(2)] | Ala Val Leu Ala Pro ValVal Ala Val | 60 |
| JO-09 | CAB51015 putative secreted protein [*Streptomyces coelicolor* A3(2)] | Leu Ala Val Cys Gly Leu Pro Val Val Ala Leu Leu Ala | 61 |
| JO-10 | NP_625021glycosyl hydrolase (secreted protein) [*Streptomyces coelicolor* A3(2)] | Leu Gly Gly Ala Val Val Ala Ala Pro Val Ala Ala Val Ala Pro | 62 |
| JO-11 | NP_630686 secreted protein [*Streptomyces coelicolor* A3(2)] | Leu Leu Leu Val Leu Ala Val Leu Leu Ala Val Leu Pro | 63 |
| JO-12 | NP_057329 dehydrogenase/reductase (SDR family) member 8 [*Homo sapiens*] | Leu Leu Ile Leu Leu Leu Leu Pro Leu Leu Ile Val | 64 |
| JO-13 | NP_639877putative secreted protein [*Streptomyces coelicolor* A3(2)] | Leu Ala Ala Ala Ala Leu Ala Val Leu Pro Leu | 65 |
| JO-14 | NP_699201 protease inhibitor 16 precursor [*Homo sapiens*] | Phe Leu Met Leu Leu Leu Pro Leu Leu Leu Leu Val Ala | 66 |
| JO-15 | NP_639871putative secreted protein [*Streptomyces coelicolor* A3(2)] | Ala Ala Ala Ala Ala Ala Leu Gly Leu Ala Ala Ala Val Pro Ala | 67 |
| JO-16 | CAB85250 putative secreted protein [*Neisseria meningitidis* Z2491] | Leu Leu Leu Ala Ala Leu Leu Leu Ile Ala Phe Ala Ala Val | 68 |

TABLE 1b

| MTD | Origin | Amino acid sequence | SEQ ID NO |
|---|---|---|---|
| JO-17 | NP_626397small secreted hydrophilic protein [Streptomyces coelicolor A3(2)] | Ala Leu Ala Ala Val Val Leu Ile Pro Leu Gly Ile Ala Ala | 69 |
| JO-18 | CAB38593putative secreted protein [Streptomyces coelicolor A3(2)] | Ala Ala Leu Ala Leu Gly Val Ala Ala Ala Pro Ala Ala Ala Pro Ala | 70 |
| JO-19 | CAB57190 putative secreted chitin binding protein [Streptomyces coelicolor A3(2)] | Ala Ala Leu Ile Gly Ala Val Leu Ala Pro Val Val Ala Val | 71 |
| JO-20 | NP_626007 secreted cellulose-binding protein [Streptomyces coelicolor A3(2)] | Ala Ala Gly Ile Ala Val Ala Ile Ala Ala Ile Val Pro Leu Ala | 72 |
| JO-21 | NP_625632 secreted protein [Streptomyces coelicolor A3(2)] | Ile Ala Val Ala Ile Ala Ala Ile Val Pro Leu Ala | 73 |
| JO-22 | CAC31790 putative secreted protein [Mycobacterium leprae] | Val Ala met Ala Ala Ala Ala Val Leu Ala Ala Pro Ala Leu Ala | 74 |
| JO-23 | NP_630266secreted Protein [StrePtomyces coelicolor A3(2)] | Leu Ala Val Leu Val Leu Leu Val Leu Leu pro | 75 |
| JO-24 | NP_630165secreted Protein [StrePtomyces coelicolor A3(2)] | Val Val Ala Val Leu Ala pro Val Leu | 76 |
| JO-25 | NC_003888secreted Protein [StrePtomyces coelicolor A3(2)] | Ala Ala Leu Leu Leu Pro Leu Leu Leu Leu pro | 77 |
| JO-26 | NP_627363secreted Protein [StrePtomyces coelicolor A3(2)] | Pro Ala Ala Val Ala Ala Leu Leu Val Ile | 78 |
| JO-27 | NP_631288secreted Protein [StrePtomyces coelicolor A3(2)] | Leu Leu Ile Ala Ala Leu Leu Pro | 79 |
| JO-28 | NP_630325secreted Protein [StrePtomyces coelicolor A3(2)] | Ala Ala Val Val Leu Leu Pro Leu Ala Ala Pro | 80 |
| JO-29 | NP_631289secreted Protein [StrePtomyces coelicolor A3(2)] | Ala Ala Ala Ala Ala Ala Leu Leu Val Pro | 81 |
| JO-30 | CAB51015 Putative secreted Protein [StrePtomyces coelicolor A3(2)] | Leu Pro Val Val Ala Leu Leu Ala | 82 |
| JO-31 | NP_629515chitinase C (secreted Protein) [StrePtomyces coelicolor A3(2)] | Ala Ala Ala Leu Ala Ala Pro Leu Ala Leu Pro | 83 |
| JO-32 | NP_940995 C1q and tumor necrosis factor related Protein 1 isoform 1 [Homo saPiens] | Leu Leu Leu Ala Leu Leu Leu Ala Ala | 84 |
| JO-33 | NP_854150POSSIBLE CONSERVED SECRETED PROTEIN [Mycobacterium bovis AF2122/97] | Ala Val Ala Val Val Ala Leu Leu | 85 |

TABLE 1c

| MTD | Origin | Amino acid sequence | SEQ ID NO |
|---|---|---|---|
| JO-34 | NP_630361Probable secreted Protein [StrePtomyces coelicolor A3(2)] | Leu Leu Leu Ile Ile Val Leu Leu Ile Val Pro | 86 |
| JO-35 | P39790 Extracellular metalloProtease Precursor | Leu Ala Leu Ala Ala Ala Val Val Pro | 243 |
| JO-36 | CAA19252 Putative liPoProtein [StrePtomyces coelicolor A3(2)] | Pro Ala Ala Leu Ala Leu Leu Leu Val Ala | 87 |

TABLE 1c-continued

| MTD | Origin | Amino acid sequence | SEQ ID NO |
|---|---|---|---|
| JO-37 | P_625685large secreted Protein [StrePtomyces coelicolor A3(2)] | Ile Val Ala Leu Leu Leu Val Pro Leu Val Leu Ala Ile Ala Ala Val Leu | 88 |
| JO-38 | NP_625685large secreted Protein [StrePtomyces coelicolor A3(2)] | Ile Val Ala Leu Leu Leu Val Pro | 89 |
| JO-39 | NP_625685large secreted Protein [StrePtomyces coelicolor A3(2)] | Pro Leu Val Leu Ala Ile Ala Ala Val Leu | 90 |
| JO-40 | NP_808800 golgi PhosPhoProtein 2 [Homo sapiens] | Pro Leu Val Leu Ala Ala Leu Val Ala | 91 |
| JO-41 | NP_626993secreted Protein [StrePtomyces coelicolor A3(2)] | Ala Ala Ala Leu Leu Ala Val Ala | 92 |
| JO-42 | NP_004863 thymic dendritic cell-derived factor 1 [Homo saPiens] | Pro Leu Leu Leu Leu Ala Leu Ala | 93 |
| JO-43 | NP_631398 secreted Protein [StrePtomyces coelicolor A3(2)] | Ala Leu Ala Leu Val Val Ala | 94 |
| JO-44 | NP_627373Penicillin-binding Protein (secreted Protein) [StrePtomyces coelicolor A3(2)] | Val Ala Ala Val Val Val Ala Ala | 95 |
| JO-45 | NP_056226 sulfatase modifying factor 2 [Homo sapiens] | Pro Leu Leu Pro Leu Leu Leu Leu Val | 96 |
| JO-46 | NP_854998Conserved hypothelial secreted protein [Mycobacterium bovis AF2122/97] | Val Val Leu Val Val Val Leu Pro Leu Ala Val Leu Ala | 97 |
| JO-47 | NP_627512secreted Protein [StrePtomyces coelicolor A3(2)] | Ala Ala Ala Val Pro Val Leu Val Ala Ala | 98 |
| JO-48 | NP_110448 phospholipase A2, group XIIA [Homo sapiens] | Pro Ala Leu Leu Leu Leu Leu Leu Ala Ala Val Val | 99 |
| JO-49 | NP_003245 tissue inhibitor of metalloproteinase 1 precursor [Homo sapiens] | Pro Leu Ala Ile Leu Leu Leu Leu Leu Ile Ala Pro | 100 |
| JO-50 | NP_002978 small inducible cytokine A17 precursor [Homo sapiens] | Pro Leu Leu Ala Leu Val Leu Leu Leu Ala Leu Ile Ala | 101 |
| JO-51 | NP_001012495 stromal cell derived factor 1 isoform gamma precursor [Mus musculus] | Val Val Ala Val Leu Ala Leu Val Leu Ala Ala Leu | 102 |

TABLE 1d

| MTD | Origin | Amino acid sequence | SEQ ID NO |
|---|---|---|---|
| JO-52 | NP_775628 ficolin 3 isoform 2 precursor [Homo sapiens] | Pro Leu Leu Leu LeuLeu Pro Ala Leu | 103 |
| JO-53 | NP_624483secreted Protein [Streptomyces coelicolor A3(2)] | Leu Ala Ala Val Ala Ala Leu Ala Val Val Val Pro | 104 |
| JO-54 | NP_997465 HERV-FRD provirus ancestral Env polyprotein [Homo sapiens] | Leu Leu Leu Leu Val Leu Ile Leu Pro Leu Ala Ala | 105 |
| JO-55 | NP_854234 possible conserved secreted protein [Mycobacterium bovis AF2122/97] | Leu Ala Val Val Val Val Ala Ala Val | 106 |
| JO-56 | P23284 Peptidyl-prolyl cis-trans isomerase B precursor (PPIase) (Rotamase) (Cyclophilin B) | Val Leu Leu Ala Ala Ala Leu Ile Ala | 107 |

TABLE 1d-continued

| MTD | Origin | Amino acid sequence | SEQ ID NO |
|---|---|---|---|
| JO-57 | CAD05047 hypothetical secreted protein [*Salmonella enterica* subsp. *Enterica serovar Typhi*] | Leu Ile Ala Leu Leu Ala Ala Pro Leu Ala | 108 |
| JO-58 | P05067 Amyloid beta A4 protein precursor (APP) (ABPP) (Alzheimer disease amyloid protein) | Leu Ala Leu Leu Leu Leu Ala Ala | 109 |
| JO-59 | NP_004878 small inducible cytokine B14 precursor [*Homo sapiens*] | Leu Leu Ala Ala Ala Leu Leu Leu Leu Leu Leu Ala | 110 |
| JO-60 | NP_626589 secreted protein [*Streptomyces coelicolor* A3(2)] | Val Ile Ile Ala Leu Ile Val Ile Val Ala | 111 |
| JO-61 | NP_626589 secreted protein [*Streptomyces coelicolor* A3(2)] | Val Val Leu Val Val Ala Ala Val Leu Ala Leu | 112 |
| JO-62 | NP_856548 SOLUBLE SECRETED ANTIGEN MPB53 [*Mycobacterium bovis* AF2122/97] | Val Ala Val Ala Ile Ala Val Val Leu | 113 |
| JO-63 | NP_629854 secreted protein [*Streptomyces coelicolor* A3(2)] | Pro Leu Ile Val Val Val Ala Ala Ala Val Val Ala Val | 114 |
| JO-64 | AAB59058 lambda receptor protein [*Escherichia coli*] | Pro Leu Ala Val Ala Val Ala Ala Val Ala Ala | 115 |
| JO-65 | NP_825185 NLP/P60-family secreted protein [*Streptomyces avermitilis* MA-4680] | Ala Ala Ile Ala Leu Val Ala Val Val Leu | 116 |
| JO-66 | NP_626568 secreted protein [*Streptomyces coelicolor* A3(2)] | Ala Ala Ala Leu Ala Ala Ile Ala Val Ile | 117 |
| JO-67 | NP_626568 secreted protein [*Streptomyces coelicolor* A3(2)] | Ala Ala Ala Pro Ala Val Ala Ala | 118 |

[TABLE 1e]

| MTD | Origin | Amino acid sequenc | SEQ ID NO |
|---|---|---|---|
| JO-68 | NP_625639 secreted protein [*Streptomyces coelicolor* A3(2)] | Leu Leu Leu Ala Ala Leu Pro | 119 |
| JO-69 | CAC32053 putative secreted protein [*Mycobacterium leprae*] | Ala Leu Leu Ala Val Val Ala Ala | 120 |
| JO-70 | NP_630954 secreted protein [*Streptomyces coelicolor* A3(2)] | Ala Val Val Val Val Leu Pro Ile Leu Leu | 121 |
| JO-71 | P97300 Neuroplastin precursor (Stromal cell-derived receptor 1) (SDR-1) | Ala Leu Ala Leu Leu Leu Leu Val Pro | 122 |
| JO-72 | AAA41949 Rat parotid gland acidic proline-rich protein mRNA, complete CDS | Leu Val Val Leu Leu Ala Ala Leu Leu Val Leu | 123 |
| JO-73 | AAA17887 *Drosophila melanogaster* spatzle (spz) gene | Pro Val Leu Leu Leu Leu Ala Pro | 124 |
| JO-74 | NP_627867 conserved secreted protein [*Streptomyces coelicolor* A3(2)] | Ala Leu Ala Val Val Ala Ala Pro | 125 |
| JO-75 | NP_631283 secreted protein [*Streptomyces coelicolor* A3(2)] | Val Ile Val Ala Leu Leu Ala Val | 126 |
| JO-76 | NP_003231 endometrial bleeding associated factor preproprotein [*Homo sapiens*] | Ala Leu Val Leu Pro Leu Ala Pro | 127 |
| JO-77 | CAB76313 putative secreted protein [*Streptomyces coelicolor* A3(2)] | Ala Val Ala Leu Leu Ile Leu Ala Val | 128 |

[TABLE 1e]-continued

| MTD | Origin | Amino acid sequenc | SEQ ID NO |
|---|---|---|---|
| JO-78 | P07198 Xenopsin precursor [Contains: Xenopsin precursor fragment (XPF); Xenopsin] | Val Leu Leu Ala Val Ile Pro | 129 |
| JO-79 | NP_631293secreted protein [*Streptomyces coelicolor* A3(2)] | Leu Ile Val Ala Ala Val Val Val Val Ala Val Leu Ile | 130 |
| JO-80 | NP_626373secreted protein [*Streptomyces coelicolor* A3(2)] | Ala Val Val Val Ala Ala Pro | 131 |
| JO-81 | NP_624952secreted cellulose-binding protein [*Streptomyces coelicolor* A3(2)] | Leu Ala Ala Val Leu Leu Leu Ile Pro | 132 |
| JO-82 | NP_009104 protease, serine, 23 precursor [*Homo sapiens*] | Leu Leu Leu Leu Leu Leu Ala Val Val Pro | 133 |
| JO-83 | AAK63068 phytotoxic protein PcF precursor [*Phytophthora cactorum*] | Ala Val Ala Leu Val Ala Val Val Ala Val Ala | 134 |
| JO-84 | NC_003903Streptomyces coelicolor A3(2) plasmid SCP1, complete sequence | Leu Val Ala Ala Leu Leu Ala Val Leu | 135 |

TABLE 1f

| MTD | Origin | Amino acid sequence | SEQ ID NO |
|---|---|---|---|
| JO-85 | NP_629842peptide transport system secreted peptide binding protein [*Streptomyces coelicolor* A3(2)] | Leu Leu Ala Ala Ala Ala Ala Leu Leu Leu Ala | 136 |
| JO-86 | NP_854067Posible secreted protein [*Mycobacterium bovis* AF2122/97] | Leu Ala Val Leu Ala Ala Ala Pro | 137 |
| JO-87 | NP_627802secreted protein [*Streptomyces coelicolor* A3(2)] | Val Val Val Leu Leu Val Leu Leu Ala Leu Val Val Val | 138 |
| JO-88 | NP_627802secreted protein [*Streptomyces coelicolor* A3(2)] | Val Val Ile Ala Val Val Pro | 139 |
| JO-89 | NP_624483secreted protein [*Streptomyces coelicolor* A3(2)] | Leu Ala Ala Val Ala Ala Leu Ala Val Val | 140 |
| JO-90 | NP_627802secreted protein [*Streptomyces coelicolor* A3(2)] | Val Leu Leu Val Leu Leu Ala Leu Val | 141 |
| JO-91 | NP_625203secreted protein [*Streptomyces coelicolor* A3(2)] | Pro Val Leu Val Pro Ala Val Pro | 142 |
| JO-92 | NP_630960secreted protein [*Streptomyces coelicolor* A3(2)] | Pro Ala Leu Ala Leu Ala Leu Ala | 143 |
| JO-93 | NP_630670secreted protein [*Streptomyces coelicolor* A3(2)] | Ala Ala Ala Ala Pro Ala Leu Ala | 144 |
| JO-94 | NP_630493secreted protein [*Streptomyces coelicolor* A3(2)] | Ile Val Leu Pro Val Leu Ala Ala Pro | 145 |
| JO-95 | CAC29994putative secreted protein [*Mycobacterium leprae*] | Leu Val Leu Leu Leu Leu Pro Leu Leu Ile | 146 |
| JO-96 | NP_624483secreted protein [*Streptomyces coelicolor* A3(2)] | Leu Ala Ala Val Ala Pro Ala Leu Ala Val Val | 147 |
| JO-97 | NP_037375 secretogranin III [*Homo sapiens*] | Ile Leu Val Leu Val Leu Pro Ile | 148 |
| JO-98 | NP_009199 V-set and immunoglobulin domain containing 4 [*Homo sapiens*] | Ile Leu Leu Pro Leu Leu Leu Leu Pro | 149 |

TABLE 1f-continued

| MTD | Origin | Amino acid sequence | SEQ ID NO |
|---|---|---|---|
| JO-99 | NP_733650 secreted hydrolase [Streptomyces coelicolor A3(2)] | Ile Ala Pro Ala Val Val Ala Ala Leu Pro | 150 |
| JO-100 | NP_057540 transmembrane protein 9 [Homo sapiens] | Leu Leu Leu Val Ala Val Val Pro Leu Val Pro | 151 |
| JO-101 | CAI74362 hypothetical protein [Theileria annulata] | Leu Ile Leu Leu Leu Leu Pro Ile Ile | 6 |
| JO-102 | NP_630671 secreted protein [Streptomyces coelicolor A3(2)] | Ala Val Leu Ala Ala Pro Ala Val Leu Val | 152 |
| JO-103 | NP_065695 TMEM9 domain family, member B [Homo sapiens] | Leu Ala Leu Pro Val Leu Leu Leu Ala | 8 |
| JO-104 | P06908 Pulmonary surfactant-associated protein A precursor (SP-A) (PSP-A) (PSAP) | Leu Ala Leu Ala Leu Leu Leu | 153 |

TABLE 1g

| MTD | Origin | Amino acid sequence | SEQ ID NO |
|---|---|---|---|
| JO-105 | NP_639721 putative secreted protein [Streptomyces coelicolor A3(2)] | Val Ala Val Pro Leu Leu Val Val Ala | 154 |
| JO-106 | NP_854954 CONSERVED PROBABLE SECRETED PROTEIN [Mycobacterium bovis AF2122/97] | Ala Val Ala Val Ala Pro Val Ala Ala Ala Ala | 155 |
| JO-107 | NP_627759 secreted protein [Streptomyces coelicolor A3(2)] | Ala Ala Ala Val Val Ala Ala Val Pro Ala Ala | 156 |
| JO-108 | NP_003842 cellular repressor of E1A-stimulated genes [Homo sapiens] | Ala Leu Leu Ala Ala Leu Leu Ala Pro | 157 |
| JO-109 | NP_003842 cellular repressor of E1A-stimulated genes [Homo sapiens] | Leu Leu Ala Leu Leu Val Pro | 158 |
| JO-110 | NP_003842 cellular repressor of E1A-stimulated genes [Homo sapiens] | Ala Leu Leu Ala Ala Leu Leu Ala Leu Leu Ala Leu Leu Val | 159 |
| JO-111 | NP_000589 Homo sapiens insulin-like growth factor binding protein 3 (IGFBP3) | Ala Ala Ala Leu Pro Leu Leu Val Leu Leu Pro | 160 |
| JO-112 | CAB59459 putative secreted protein [Streptomyces coelicolor A3(2)] | Ala Ala Ala Val Pro Ala Ala Leu Ala Pro | 161 |
| JO-113 | NP_628917 secreted protein [Streptomyces coelicolor A3(2)] | Ala Ala Leu Ala Val Ala Ala Leu Ala Ala | 162 |
| JO-114 | NP_624695 secreted protein [Streptomyces coelicolor A3(2)] | Ala Val Leu Ala Ala Ala Val Pro | 163 |
| JO-115 | NP_624695 secreted protein [Streptomyces coelicolor A3(2)] | Val Ala Ala Leu Pro Ala Pro Ala | 164 |
| JO-116 | NP_624791 secreted protein [Streptomyces coelicolor A3(2)] | AlaLeu Ala Leu Ala Val Pro Ala Val Leu Pro | 165 |
| JO-117 | CAB45579 putative secreted protein [Streptomyces coelicolor A3(2)] | Ala Ala Leu Leu Pro Ala Ala Val Ala Val Pro | 166 |
| JO-118 | NP_627066 secreted protein [Streptomyces coelicolor A3(2)] | Ala Val Val Val Ala Leu Ala Pro | 167 |
| JO-119 | NP_630174 secreted substrate-binding protein [Streptomyces coelicolor A3(2)] | Ala Ala Ala Val Ala Leu Pro Ala Ala Ala Ala Leu Leu Ala | 168 |
| JO-120 | P06727 Apolipoprotein A-IV precursor (Apo-AIV) (ApoA-IV) Homo sapiens | Ala Val Val Leu Pro Leu Ala Leu Val Ala Val Ala Pro | 169 |

TABLE 1g-continued

| MTD Origin | Amino acid sequence | SEQ ID NO |
|---|---|---|
| JO-121 Q62087 Serum paraoxonase/lactonase 3. *Mus musculus* | Leu Val Ala Leu Pro Leu Leu Pro | 170 |
| JO-122 NP_627123 probable secreted penicillin-binding protein[*Streptomyces coelicolor* A3(2)] | Val Val Val Pro Leu Leu Leu Ile Val Pro | 171 |

TABLE 1h

| MTD Origin | Amino acid sequence | SEQ ID NO |
|---|---|---|
| JO-123 CAC30224 putative secreted hydrolase [*Mycobacterium leprae*] | Leu Ala Val Val Leu Ala Val Pro | 172 |
| JO-124 OZZQAM circumsporozoite protein precursor - *Plasmodium cynomolgi* | Leu Leu Ala Val Pro Ile Leu Leu Val Pro | 173 |
| JO-125 Q15166 Serum paraoxonase/lactonase 3 [*Homo sapiens*] | Leu Val Ala Leu Val Leu Leu Pro | 174 |
| JO-126 NP_060220 all-trans-13,14-dihydroretinol saturase [*Homo sapiens*] | Leu Val Leu Leu Leu Ala Val Leu Leu Ala Val Leu Pro | 175 |
| JO-127 AL627273 *Salmonella enterica serovar Typhi (Salmonella typhi)* strain CT18 | Leu Leu Ala Pro Val Val Ala Leu Val Ile Leu Pro | 176 |
| JO-128 NP_625987 secreted protein [*Streptomyces coelicolor* A3(2)] | Val Leu Ala Val Leu Ala Val Pro Val Leu Leu Leu Pro | 177 |
| JO-129 CAB45474 putative secreted protein [*Streptomyces coelicolor* A3(2)] | Val Val Ile Ala Val Val Pro Val Val Val | 178 |
| JO-130 CAB45474 putative secreted protein [*Streptomyces coelicolor* A3(2)] | Leu Leu Val Leu Leu Ala Leu Val Val Val Pro | 179 |
| JO-131 CAB36605 putative secreted protein [*Streptomyces coelicolor* A3(2)] | Val Leu Leu Ala Leu Pro Val Val Ala Ala Pro | 180 |
| JO-132 NP_628377 NLP/P60-family secreted protein [*Streptomyces coelicolor* A3(2)] | Ala Val Val Val Pro Ala Ile Val Leu Ala Ala Pro | 181 |
| JO-133 CAB59594 putative secreted protein [*Streptomyces coelicolor* A3(2)] | Ala Val Leu Val Pro Ala Ala Ala Leu Val Pro | 182 |
| JO-134 NP_624974 secreted protein [*Streptomyces coelicolor* A3(2)] | Val Val Ala Ala Leu Pro Leu Val Leu Pro | 183 |
| JO-135 NP_733682 secreted ATP/GTP binding protein [*Streptomyces coelicolor* A3(2)] | Ala Ala Val Ala Leu Pro Ala Ala Ala Pro | 184 |
| JO-136 P27169 Serum paraoxonase/arylesterase 1 (PON 1) (Serum aryldialkylphosphatase 1) (A-esterase 1) *Homo sapiens* | Leu Ile Ala Leu Pro Leu Leu Pro | 185 |
| JO-137 P52430 Serum paraoxonase/arylesterase 1 (PON 1) (Serum aryldialkylphosphatase 1) (A-esterase 1) *Homo sapiens* | Leu Leu Ala Leu Pro Leu Val Leu Val Leu Ala Leu Pro | 186 |

TABLE 1i

| MTD Origin | Amino acid sequence | SEQ ID NO |
|---|---|---|
| JO-NP_626569 secreted protein 138 [*Streptomyces coelicolor* A3(2)] | Ile Val Pro Leu Leu Leu Ala Ala Pro | 187 |
| JO-NP_940995 C1q and tumor necrosis 139 factor related protein 1 isoform 1 [*Homo sapiens*] | Leu Leu Leu Ala Pro Leu Leu Leu Ala Pro | 188 |
| JO-NP_626174 large secreted protein1 140 [*Streptomyces coelicolor* A3(2)] | Leu Ala Ala Leu Pro Val Ala Ala Val Pro | 189 |
| JO-CAB83860 putative protein-export 141 integral membrane protein [*Neisseria meningitidis* Z2491] | Ala Leu Ala Val Ile Val Leu Val Leu Leu | 190 |
| JO-NP_001009551 cornichon-like 142 isoform 2 [*Homo sapiens*] | Leu Ala Leu Leu Leu Pro Ala Ala Leu Ile | 191 |
| JO-NP_626808 secreted protein 143 [*Streptomyces coelicolor* A3(2)] | Ala Leu Leu Pro Leu Leu Ala Val Val Leu Pro | 192 |
| JO-NP_639798 putative secreted protein 144 [*Streptomyces coelicolor* A3(2)] | Ala Ile Ala Val Pro Val Leu Ala Ala Pro | 193 |
| JO-NP_000492 *Homo sapiens* elastin 145 (supravalvular aortic stenosis) | Ala Ala Ala Pro Val Leu Leu Leu Leu Leu | 194 |
| JO-NP_630680 secreted sugar binding 146 protein [*Streptomyces coelicolor* A3(2)] | Ala Ala Ala Val Ala Val Leu Ala Leu Ala Pro | 195 |
| JO-CAB56129 putative secreted protein 147 [*Streptomyces coelicolor* A3(2)] | Ala Ala Leu Ala Ala Leu Val Val Ala Ala Pro | 196 |
| JO-NP_625109 secreted solute-binding 148 lipoprotein [*Streptomyces coelicolor* A3(2)] | Ala Ala Leu Ala Ala Val Pro Leu Ala Leu Ala Pro | 197 |
| JO-NP_733579 secreted sugar-binding 149 protein [*Streptomyces coelicolor* A3(2)] | Ala Leu Ala Val Ala Ala Pro Ala Leu Ala Leu Leu Pro | 198 |
| JO-NP_630126 secreted chitinase 150 (secreted protein) [*Streptomyces coelicolor* A3(2)] | Ala Ala Leu Pro Ala Ala Ala Pro | 199 |
| JO-NP_630126 secreted chitinase 151 (secreted protein) [*Streptomyces coelicolor* A3(2)] | Ala Ala Ala Pro Val Ala Ala Val Pro | 200 |
| JO-NP_872425 secretory protein 152 LOC348174 [*Homo sapiens*] | Leu Leu Ala Val Leu Leu Ala Leu Leu Pro | 201 |
| JO-NP_630107 secreted protein 153 [*Streptomyces coelicolor* A3(2)] | Val Leu Ala Leu Leu Val Ala Val Val Pro | 202 |

TABLE 1j

| MTD Origin | Amino acid sequence | SEQ ID NO |
|---|---|---|
| JO-NP_733688 peptide-binding 154 transport protein [*Streptomyces coelicolor* A3(2)] | Ala Leu Val Val Pro Ala Ala Val Pro | 203 |
| JO-NP_629904 secreted protein 155 [*Streptomyces coelicolor* A3(2)] | Ala Val Val Leu Pro Leu Leu Leu Pro | 204 |
| JO-YP_177852 MCE-FAMILY 156 PROTEIN MCE3A [*Mycobacterium tuberculosis* H37Rv] | Ala Val Ile Pro Val Ala Val Leu Val Pro | 205 |
| JO-CAA19627 putative secreted solute 157 binding protein [*Streptomyces coelicolor* A3(2)] | Ala Ala Ala Val Pro Ala Ala Val Leu Ala Pro | 206 |

TABLE 1j-continued

| MTD Origin | Amino acid sequence | SEQ ID NO |
|---|---|---|
| JO-158 NP_639884 putative large secreted protein [Streptomyces coelicolor A3(2)] | Val Ala Val Pro Val Val Leu Ala Ile Leu Pro | 207 |
| JO-159 P24327 Foldase protein prsA precursor | Ile Ala Ile Ala Ala Ile Pro Ala Ile Leu Ala Leu | 208 |
| JO-160 CAB84808 putative membrane lipoprotein [Neisseria meningitidis Z2491] | Ala Leu Ile Ala Pro Ala Leu Ala Ala Pro | 209 |
| JO-161 NP_639883 putative large secreted protein [Streptomyces coelicolor A3(2)] | Ala Ala Ile Ala Leu Val Ala Pro Ala Leu | 210 |
| JO-162 NP_639883 putative large secreted protein [Streptomyces coelicolor A3(2)] | Leu Ala Pro Ala Val Ala Ala Ala Pro | 211 |
| JO-163 NP_627362 secreted protein [Streptomyces coelicolor A3(2)] | Val Ala Ile Ile Val Pro Ala Val Val Ala Ile Ala Leu Ile Ile | 212 |
| JO-164 NP_627362 secreted protein [Streptomyces coelicolor A3(2)] | Ala Val Val Ala Ile Ala Leu Ile Ile | 213 |
| JO-165 NP_624625 secreted protein [Streptomyces coelicolor A3(2)] | Leu Ala Ala Val Pro Ala Ala Ala Pro | 214 |
| JO-166 NP_624625 secreted protein [Streptomyces coelicolor A3(2)] | Ala Val Ala Ala Leu Pro Leu Ala Ala Pro | 215 |
| JO-167 NP_624625 secreted protein [Streptomyces coelicolor A3(2)] | Leu Ala Ala Pro Ala Ala Ala Ala Pro | 216 |
| JO-168 NP_626936 secreted protein [Streptomyces coelicolor A3(2)] | Leu Ala Ala Val Val Pro Val Ala Ala Ala Val Pro | 217 |
| JO-169 NP_626936 secreted protein [Streptomyces coelicolor A3(2)] | Val Ala Ala Pro Ala Ala Ala Ala Pro | 218 |
| JO-170 NP_626936 secreted protein [Streptomyces coelicolor A3(2)] | Ala Val Pro Val Pro Val Pro Leu | 219 |

TABLE 1k

| MTD Origin | Amino acid sequence | SEQ ID NO |
|---|---|---|
| JO-171 NP_085072 matrilin 2 isoform b precursor [Homo sapiens] | Leu Leu Ile Leu Pro Ile Val Leu Leu Pro | 220 |
| JO-172 CAB94057 putative secreted protein [Streptomyces coelicolor A3(2)] | Ala Leu Ala Leu Pro Ala Leu Ala Ile Ala Pro | 221 |
| JO-173 NP_624384 secreted protein [Streptomyces coelicolor A3(2)] | Ala Val Ile Pro Ile Leu Ala Val Pro | 222 |
| JO-174 NP_733505 large, multifunctional secreted protein [Streptomyces coelicolor A3(2)] | Leu Ile Leu Leu Leu Pro Ala Val Ala Leu Pro | 223 |
| JO-175 CAB45630 putative secreted protein [Streptomyces coelicolor A3(2)] | Ile Val Leu Ala Pro Val Pro Ala Ala Ala | 224 |
| JO-176 NP_627887 secreted protein [Streptomyces coelicolor A3(2)] | Val Val Val Val Pro Val Leu Ala Ala Ala Ala | 225 |
| JO-177 P06832 Bacillolysin precursor | Leu Val Ala Val Ala Ala Pro | 226 |
| JO-178 NP_625998 secreted hydrolase [Streptomyces coelicolor A3(2)] | Leu Val Leu Ala Ala Pro Ala Ala Leu Pro | 227 |

TABLE 1k-continued

| MTD Origin | Amino acid sequence | SEQ ID NO |
|---|---|---|
| JO-179 | NP_625057 secreted protein [Streptomyces coelicolor A3(2)] | Leu Ile Ala Pro Ala Ala Ala Val Pro | 228 |
| JO-180 | NP_443750 ADP-ribosyltransferase 5 precursor [Homo sapiens] | Ala Leu Ala Ala Leu Pro Ile Ala Leu Pro | 229 |
| JO-181 | CAB84257 putative secreted protein [Neisseria meningitidis Z2491] | Ala Val Leu Leu Leu Pro Ala Ala Ala | 230 |
| JO-182 | P00634 Alkaline phosphatase precursor (APase) | Ile Ala Leu Ala Leu Leu Pro Leu Leu | 231 |
| JO-183 | NP_000933 peptidylprolyl isomerase B precursor [Homo sapiens] | Val Leu Leu Ala Ala Ala Leu Ile Ala Pro | 232 |
| JO-184 | CAB71258 putative secreted protein. [Streptomyces coelicolor A3(2)] | Ala Pro Ala Val Leu Pro Pro Val Val Val Ile | 233 |
| JO-185 | CAC31847 possible secreted protein [Mycobacterium leprae] | Val Val Gly Leu Leu Val Ala Ala Leu | 234 |
| JO-186 | NP_626948 secreted protein [Streptomyces coelicolor A3(2)] | Ala Ala Ile Ala Ala Ala Ala Pro Leu Ala Ala | 235 |
| JO-187 | NP_059120 cat eye syndrome critical region protein 1 isoform a precursor [Homo sapiens] | Leu Leu Leu Ala Val Ala Pro | 236 |
| JO-188 | NP_006519 tissue factor pathway inhibitor 2 [Homo sapiens] | Leu Ile Leu Leu Leu Pro Leu Ala Ala Leu | 237 |

In some embodiments, the present invention may employ a kaposi fibroblast growth factor 4 (kFGF4)-derived MTD having the nucleotide sequence of SEQ ID NO: 3 and the amino acid sequence of SEQ ID NO: 4 (hereinafter, "MTD$_1$"), a JO-101 MTD having the nucleotide sequence of SEQ ID NO: 5 and the amino acid sequence of SEQ ID NO: 6 which is a hypothetical protein derived from *Theileria annulata* (hereinafter, "MTD$_2$"), and a JO-103 MTD having the nucleotide sequence of SEQ ID NO: 7 and the amino acid sequence of SEQ ID NO: 8 which belongs to member B of a human TMEM9 domain family (hereinafter, "MTD$_3$"), as the MTD capable of mediating the transport of the tumor suppressor p18 into a cell.

The cell permeable p18 recombinant proteins according to the present invention have a structure where one of the three MTDs (kFGF4-derived MTD: MTD$_1$, JO-101: MTD$_2$, JO-103: MTD$_3$) is fused to one terminus or both termini of a tumor suppressor protein p18, and a SV40 large T antigen-derived nuclear localization sequence (NLS) (nucleotide sequence of SEQ ID NO: 9, amino acid sequence of SEQ ID NO:10) and a histidine-tag (His-Tag) affinity domain for easy purification are fused to one terminus of the resulting construct.

In another embodiment, the present invention relates to the construction of three full-length forms and five truncated forms of a cell permeable p18 recombinant protein by using a kFGF4-derived MTD.

As used herein, the term "full-length form" refers to a construct including the entire N-, S-, and C-terminal domains of the tumor suppressor protein p18, while the term "truncated form" refers to a construct lacking any one or more of the N-, S-, and C-terminal domains thereof.

Referring to FIG. 1a, the full-length forms of the cell permeable p18 recombinant protein are as follows:

1) HM$_1$p18, where a kFGF4-derived MTD is fused to the N-terminus of a full-length p18, 2) Hp18M$_1$, where a kFGF4-derived MTD is fused to the C-terminus of a full-length p18, and 3) HM$_1$p18M$_1$, where a kFGF4-derived MTD is fused to both termini of a full-length p18, where a His-tag and a NLS derived from SV40 large T antigen are covalently coupled to the N-terminus of the above constructs.

As for the full-length forms of the cell permeable p18 recombinant protein as described above, HM$_1$p18 has an amino acid sequence represented by SEQ ID NO: 26, while a polynucleotide encoding the same has a nucleotide sequence represented by SEQ ID NO: 25; Hp18M$_1$ has an amino acid sequence represented by SEQ ID NO: 28, while a polynucleotide encoding the same has a nucleotide sequence represented by SEQ ID NO: 27; HM$_1$p18M$_1$ has an amino acid sequence represented by SEQ ID NO: 30, while a polynucleotide encoding the same has a nucleotide sequence represented by SEQ ID NO: 29.

Further, the truncated forms of the cell permeable p18 recombinant protein are as follows:

1) Hp18NM$_1$, where a kFGF4-derived MTD is fused to the C-terminus of a p18 N-terminal domain fragment lacking S- and C-terminal domains, 2) Hp18SM$_1$, where a kFGF4-derived MTD is fused to the C-terminus of a p18 S-terminal domain fragment lacking N- and C-terminal domains, 3) Hp18CM$_1$, where a kFGF4-derived MTD is fused to C-terminus of a p18 C-terminal domain fragment lacking N- and S-terminal domains, 4) Hp18NSM$_1$, where a kFGF4-derived MTD is fused to the C-terminus of a p18 N- and S-terminal domain fragment lacking a C-terminal domain, and 5) Hp18SCM$_1$, where a kFGF4-derived MTD is fused to the C-terminus of a p18 S- and C-terminal domain fragment lacking an N-terminal domain, where a His-tag and a NLS derived from SV40 large T antigen are covalently coupled to the N-terminus of the above constructs.

As for the truncated forms of the cell permeable p18 recombinant protein as described above, Hp18NM$_1$ has an amino acid sequence represented by SEQ ID NO: 32, while a polynucleotide encoding the same has a nucleotide sequence represented by SEQ ID NO: 31; Hp18SM$_1$ has an amino acid sequence represented by SEQ ID NO: 34, while a polynucleotide encoding the same has a nucleotide sequence represented by SEQ ID NO: 33; Hp18CM$_1$ has an amino acid sequence represented by SEQ ID NO: 36, while a polynucleotide encoding the same has a nucleotide sequence represented by SEQ ID NO: 35; Hp18NSM$_1$ has an amino acid sequence represented by SEQ ID NO: 38, while a polynucleotide encoding the same has a nucleotide sequence represented by SEQ ID NO: 37; Hp18SCM$_1$ has an amino acid sequence represented by SEQ ID NO: 40, while a polynucleotide encoding the same has a nucleotide sequence represented by SEQ ID NO: 39.

In another embodiment, the present invention relates to the construction of three full-length forms of a cell permeable p18 recombinant protein by using a JO-101 MTD and a JO-103 MTD, respectively.

Figure 1B:
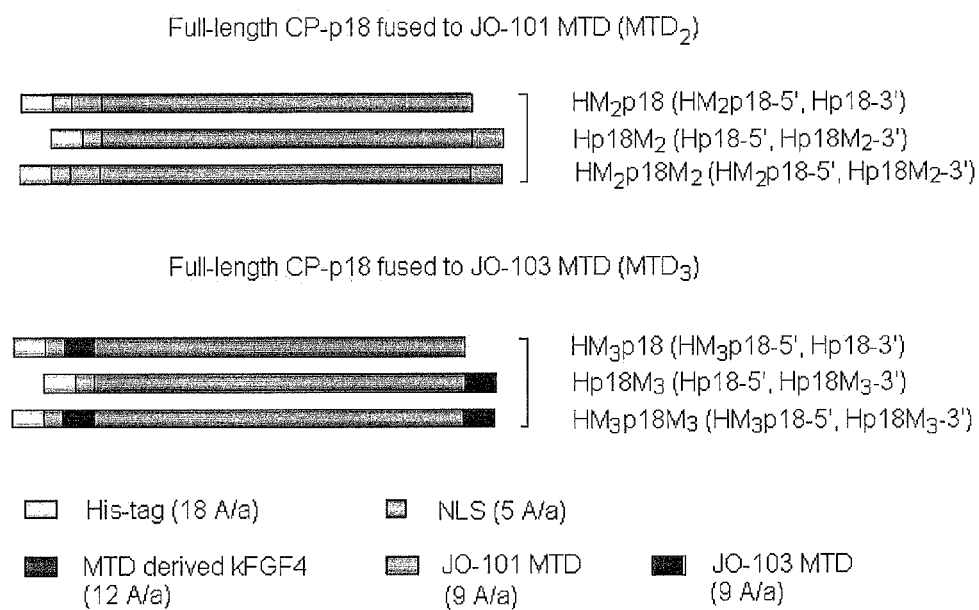
FIG. 1b is a schematic diagram illustrating the structures of cell permeable p18 recombinant proteins being fused to JO-101 and JO-103 MTDs, respectively, and constructed in the full-length form according to the present invention.

Referring to FIG. 1b, the full-length forms of the cell permeable p18 recombinant protein are as follows:

1) HM$_2$p18, where a JO-101 MTD is fused to the N-terminus of a full-length p18,
2) Hp18M$_2$, where a JO-101 MTD is fused to the C-terminus of a full-length p18,
3) HM$_2$p18M$_2$, where a JO-101 MTD is fused to both termini of a full-length p18,
4) HM$_3$p18, where a JO-103 MTD is fused to the N-terminus of a full-length p18,
5) Hp18M$_3$, where a JO-103 MTD is fused to the C-terminus of a full-length p18, and
6) HM$_3$p18M$_3$, where a JO-103 MTD is fused to both termini of a full-length p18, where a His-tag and a NLS derived from SV40 large T antigen are covalently coupled to the N-terminus of the above constructs.

As for the full-length forms of a cell permeable p18 recombinant protein as described above, HM$_2$p18 has an amino acid sequence represented by SEQ ID NO: 42, while a polynucleotide encoding the same has a nucleotide sequence represented by SEQ ID NO: 41; Hp18M$_2$ has an amino acid sequence represented by SEQ ID NO: 44, while a polynucleotide encoding the same has a nucleotide sequence represented by SEQ ID NO: 43; HM$_2$p18M$_2$ has an amino acid sequence represented by SEQ ID NO: 46, while a polynucleotide encoding the same has a nucleotide sequence represented by SEQ ID NO: 45; HM$_3$p18 has an amino acid sequence represented by SEQ ID NO: 48, while a polynucleotide encoding the same has a nucleotide sequence represented by SEQ ID NO: 47; Hp18M$_3$ has an amino acid sequence represented by SEQ ID NO: 50, while a polynucleotide encoding the same has a nucleotide sequence represented by SEQ ID NO: 49; and HM$_3$p18M$_3$ has an amino acid sequence represented by SEQ ID NO: 52, while a polynucleotide encoding the same has a nucleotide sequence represented by SEQ ID NO: 51.

As a control for the cell permeable p18 recombinant proteins, Hp18, where a full-length p18 is fused only to a nuclear localization sequence (NLS) derived from SV40 large T antigen and a histidine-tag (His-Tag) without any MTD, is constructed. The control protein has an amino acid sequence represented by SEQ ID NO: 24, while a polynucleotide encoding the same has a nucleotide sequence represented by SEQ ID NO: 23.

Further, the present invention provides an expression vector containing the polynucleotide encoding each of the cell permeable p18 recombinant proteins described above, and a transformant capable of producing each of the cell permeable p18 recombinant proteins at high levels, which is obtainable by transforming a host cell using the expression vector.

As used herein, the term "expression vector" is a vector capable of expressing a target protein or a target RNA in a suitable host cell. The nucleotide sequence of the present invention may be present in a vector in which the nucleotide sequence is operably linked to regulatory sequences capable of providing for the expression of the nucleotide sequence by a suitable host cell.

Within an expression vector, the term "operably linked" is intended to mean that the nucleotide sequence of interest is linked to the regulatory sequence(s) in a manner which allows for expression of the nucleotide sequence. The term "regulatory sequence" is intended to include promoters, enhancers, and other expression control elements. Such operable linkage with the expression vector can be achieved by conventional gene recombination techniques known in the art, while site-directed DNA cleavage and linkage are carried out by using conventional enzymes known in the art.

The expression vectors suitable for the present invention may include plasmid vectors, cosmid vectors, bacteriophage vectors, viral vectors and the like, but are not limited thereto. The expression vectors for use in the present invention may contain a signal sequence or a leader sequence for membrane targeting or secretion, as well as regulatory sequences such as a promoter, an operator, an initiation codon, a termination codon, a polyadenylation signal, an enhancer and the like. The promoter may be a constitutive or an inducible promoter. Further, the expression vector may include one or more selectable marker genes for selecting the host cell containing the expression vector, and may further include a nucleotide sequence that enables the vector to replicate in the host cell in question.

The expression vector constructed according to the present invention may be exemplified by pHp18M$_1$ where the polynucleotide encoding the recombinant protein Hp18M$_1$ where a kFGF4-derived MTD is fused to the N-terminus of a full-length p18 is inserted into a cleavage site of NdeI restriction enzyme within the multiple cloning sites (MCS) of a pET-28a (+) vector.

In another embodiment, the polynucleotide of the present invention is cloned into a pET-28a(+) vector (NOVAGEN, USA) bearing a His-tag sequence so as to fuse six histidine residues to the N-terminus of the cell permeable p18 recombinant protein to allow easy purification.

Accordingly, the cell permeable p18 recombinant protein expressed in the above expression vector has a structure where one of a kFGF4-derived MTD, a JO-101 MTD and a JO-103 MTD is fused to the full-length or truncated p18, and a His-tag and NLS are linked to the N-terminus thereof.

The present invention further provides a transformant capable of producing each of the cell permeable p18 recombinant proteins at high levels which is obtainable by transforming a host cell using the expression vector. The host cell suitable for the present invention may be eukaryotic cells, such as E. coli. In one embodiment of the present invention, E. coli used as a host cell is transformed with the expression vector, for example, pHp18M$_1$ containing the polynucleotide encoding the cell permeable recombinant protein Hp18M$_1$ where a kFGF4-derived MTD is fused to the C-terminus of a full-length p18 according to the present invention so as to produce the cell permeable p18 recombinant protein at high levels. Methods for transforming bacterial cells are well known in the art, and include, but are not limited to, biochemical means such as transformation, transfection, conjugation, protoplast fusion, calcium phosphate-precipitation, and application of polycations such as diethylaminoethyl (DEAE) dextran, and mechanical means such as electroporation, direct microinjection, microprojectile bombardment, calcium phosphate ($CaPO_4$) precipitation, calcium chloride ($CaCl_2$) precipitation, PEG-mediated fusion and liposome-mediated method.

In some embodiments, the transformants obtained by transforming E. coli DH5α with the expression vector containing the cell permeable p18 recombinant protein $Hp18M_1$ where a kFGF4-derived MTD is fused to the C-terminus of a full-length p18, the expression vector containing the cell permeable p18 recombinant protein $HM_2p18M_2$ where a JO-101 MTD is fused to the both termini thereof, and the expression vector containing the cell permeable p18 recombinant protein $HM_3p18$ where a JO-103 MTD is fused to the N-terminus thereof, respectively, were deposited under accession numbers KCTC-110310BP, KCTC-110311BP and KCTC-11312BP, respectively, with the Korean Collection for Type Cultures (KCTC), Korea Research Institute of Bioscience and Biotechnology (KRIBB), 52, Oun-Dong, Yusong-Ku, Taejon 305-333, Republic of Korea. All deposits referred to herein were made on Apr. 12, 2008 in accordance with the Budapest Treaty, and all restrictions imposed by the depositor on the availability to the public of the deposited biological material will be irrevocably removed upon the granting of the patent.

The present invention provides a method of producing the cell permeable p18 recombinant proteins at high levels, which includes the step of culturing the above transformant.

The method of the present invention may be carried out by culturing the transformant in a suitable medium under suitable conditions for expressing a cell permeable p18 recombinant protein of the present invention in the expression vector introduced into the transformant. Methods for expressing a recombinant protein by culturing a transformant are well known in the art, and for example, may be carried out by inoculating a transformant in a suitable medium for growing the transformant, performing a subculture, transferring the same to a main culture medium, culturing under suitable conditions, for example, supplemented with a gene expression inducer, isopropyl-β-D-thiogalactoside (IPTG) and, thereby, inducing the expression of a recombinant protein. After the culture is completed, it is possible to recover a "substantially pure" recombinant protein from the culture solution. The term "substantially pure" means that the recombinant protein and polynucleotide encoding the same of the present invention are essentially free of other substances with which they may be found in nature or in vivo systems to the extent practical and appropriate for their intended use.

A recombinant protein of the present invention obtained as above may be isolated from the inside or outside (e.g., medium) of host cells, and purified as a substantially pure homogeneous polypeptide. The method for polypeptide isolation and purification is not limited to any specific method. In fact, any standard method may be used. For instance, chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the polypeptide. As for chromatography, affinity chromatography, ion-exchange chromatography, hydrophobic chromatography, gel filtration chromatography, reverse phase chromatography, adsorption chromatography, etc., for example, may be used (Maniatis et al., Molecular Cloning: A Laboratory Manual, Cold Spring Harbor Laboratory, Cold Spring Harbor, N.Y., 1982; Sambrook et al., Molecular Cloning: A Laboratory Manual, 2d Ed., Cold Spring Harbor Laboratory Press, 1989; Deutscher, M., Guide to Protein Purification Methods Enzymology vol. 182. Academic Press. Inc., San Diego, Calif., 1990).

Meanwhile, the recombinant protein expressed in the transformants according to the present invention can be classified into a soluble fraction and an insoluble fraction according to protein characteristics during the protein purification process. If the majority of the expressed recombinant proteins are present in the soluble fraction, the recombinant protein can be isolated and purified according to the method as described above. However, when the majority of the expressed recombinant proteins are present in the insoluble fraction, i.e., as inclusion bodies, the recombinant proteins are first solubilized by using polypeptide denaturing agents, e.g., urea, guanidine HCl, or detergents, and then, purified by performing a series of centrifugation, dialysis, electrophoresis and column chromatography. Since there is the risk of losing the recombinant protein's activity due to a structural modification caused by the polypeptide denaturing agent, the process of purifying the recombinant protein from the insoluble fraction requires desalting and refolding steps. That is, the desalting and refolding steps can be performed by dialysis and dilution with a solution that does not include a polypeptide denaturing agent or by centrifugation with a filter. Further, if a salt concentration of the solution used for the purification of a recombinant protein from a soluble fraction is relatively high, such desalting and refolding steps may be performed.

In some embodiments, it has been found that the cell permeable p18 recombinant protein of the present invention mostly exists in the insoluble fraction as an inclusion body. In order to purify the recombinant protein from the insoluble fraction, the insoluble fraction may be dissolved in a lysis buffer containing a non-ionic surfactant such as Triton X-100, subjected to ultrasonification, and then centrifuged to separate a precipitate. The separated precipitate may be dissolved in a buffer supplemented with a strong denaturing agent, such as urea, and centrifuged to separate the supernatant. The above separated supernatant is purified by means of a histidin-tagged protein purification kit and subjected to ultrafiltration, for example, by using an amicon filter for salt removal and protein refolding, thereby obtaining a purified recombinant protein of the present invention.

Further, the present invention provides an anticancer pharmaceutical composition comprising the cell permeable p18 recombinant protein as an effective ingredient for treating p18 deficiency or failure.

The cell permeable p18 recombinant proteins of the present invention can activate cell signaling mechanisms involved in the activation of ATM and p53 that induce cell cycle arrest and apoptosis in response to DNA damage or oncogenic signals by efficiently introducing a tumor suppressor protein p18 into a cell. Therefore, the cell permeable p18 recombinant proteins of the present invention can be effectively used as an anticancer agent for treating various kinds of human cancers.

The pharmaceutical composition comprising the recombinant protein of the present invention as an effective ingredient may further include pharmaceutically acceptable carriers suitable for oral administration or parenteral administration.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (*Remington's Pharmaceutical Sciences*, 19th ed., Mack Publishing Company, Easton, Pa., 1995). The carriers for oral administration may include lactose, starch, cellulose derivatives, magnesium stearate, stearic acid and the like. In case of oral administration, the recombinant protein of the present invention can be formulated in the form of chewable tablets, buccal tablets, troches, capsules, elixir, suspensions, syrup, wafers or combination thereof by mixing with the carriers. Further, the carriers for parenteral administration may include water, suitable oil, saline, aqueous glucose, glycol and the like, and may further include stabilizers and preservatives. The stabilizers suitable for the present invention may include antioxidants such as sodium bisulfite, sodium sulfite and ascorbic acid. Suitable preservatives may include benzalconium chloride, methyl-paraben, propyl-paraben and chlorobutanol.

The pharmaceutical composition of the present invention may be formulated into various parenteral or oral administration forms. Representative examples of the parenteral formulation include those designed for administration by injection. For injection, the recombinant proteins of the present invention may be formulated in aqueous solutions, specifically in physiologically compatible buffers or physiological saline buffer. These injection formulations may be formulated by conventional methods using one or more dispersing agents, wetting agents and suspending agents. For oral administration, the proteins can be readily formulated by combining the proteins with pharmaceutically acceptable carriers well known in the art. Such carriers enable the proteins of the invention to be formulated as tablets, pills, capsules, liquids, gels, syrups, slurries, suspensions and the like, for oral ingestion by a patient to be treated. Such oral solid formulations may include suitable excipients such as diluents (e.g., lactose, dextrose, sucrose, mannitol, sorbitol cellulose and/or glycin) and lubricants (e.g., colloidal silica, talc, stearic acid, magnesium stearate, calcium stearate, and/or polyethylene glycol). The tablets may include binders, such as aluminum silicate, starch, gelatin, gum tragacanth, methyl cellulose, hydroxypropylmethyl-cellulose, sodium carboxymethylcellulose, and/or polyvinylpyrrolidone (PVP), and disintegrating agents, such as cross-linked polyvinylpyrrolidone, agar, or alginic acid or a salt thereof such as sodium alginate. If desired, absorbents, coloring agents, flavoring agents and/or sweeteners may be added. The formulations can be prepared by mixing, granulating or coating according to conventional methods well-known in the art.

If necessary, the pharmaceutical compositions of the present invention may further include pharmaceutical additives, such as preservatives, antioxidants, emulsifiers, buffering agents and/or salts for regulating osmosis and other therapeutically effective materials, and can be formulated according to conventional methods known in the art.

In addition, the pharmaceutical composition of the present invention can be administered via oral routes or parenteral routes such as intravenously, subcutaneously, intranasally or intraperitoneally. The oral administration may include sublingual application. The parenteral administration may include drip infusion and injection such as subcutaneous injection, intramuscular injection, intravenous injection and introtumoral injection.

The total effective amount of the recombinant protein of the present invention can be administered to patients in a single dose or can be administered by a fractionated treatment protocol, in which multiple doses are administered over a more prolonged period of time. Although the amount of the recombinant protein or nucleic acid encoding the same in the pharmaceutical composition of the present invention may vary depending on the severity of diseases, the protein or the nucleic acid may be generally administered several times a day at an effective dose of 5 to 20 mg. However, a suitable dose of the recombinant protein in the pharmaceutical composition of the present invention may depend on many factors, such as age, body weight, health condition, sex, disease severity, diet and excretion of patients, as well as the route of administration and the number of treatments to be administered. In view of the above factors, any person skilled in the art may determine the effective dose of the recombinant protein as an anticancer agent for treating or preventing p18 deficiency or failure. The pharmaceutical composition of the present invention containing the recombinant protein has no special limitations on its formulation, administration route and/or administration mode insofar as it exhibits the effects of the present invention.

EXAMPLES

The following examples are provided to illustrate the embodiments of the present invention in more detail, but are by no means intended to limit its scope.

Example 1

Construction of Cell Permeable p18 Recombinant Proteins (CP-p18)

<1-1> Construction of p18 Recombinant Proteins by Using kFGF4-Derived MTD

Three full-length forms and five truncated forms of a cell permeable p18 (CP-p18) recombinant protein were constructed by using a kFGF4-derived MTD ($MTD_1$).

Figure 2A:
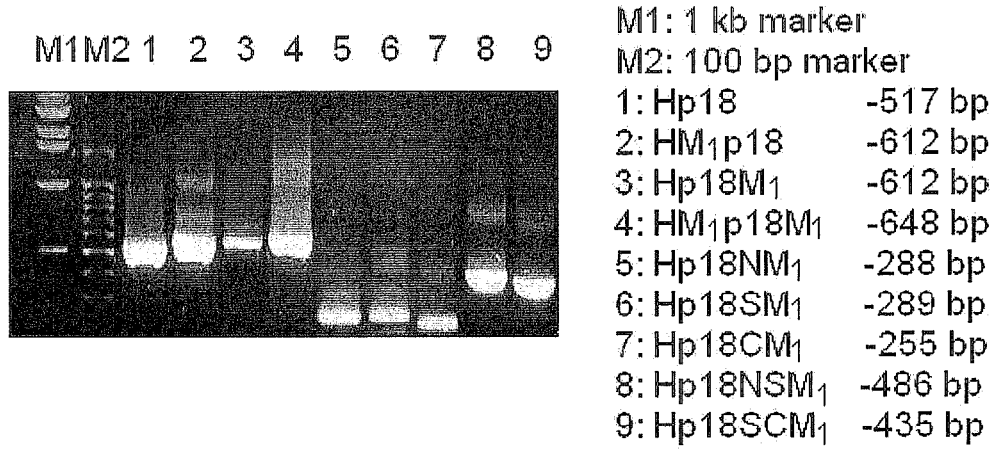
FIG. 2a is a photograph of an agarose gel electrophoresis analysis showing PCR-amplified DNA fragments encoding cell permeable p18 recombinant proteins being fused to a kFGF4-derived MTD and constructed in the full-length and truncated forms according to the present invention.

Referring to FIG. 1a, the full-length forms of CP-p18 recombinant constructs were as follows: 1) $HM_1p18$, where a kFGF4-derived MTD is fused to the N-terminus of a full-length p18; 2) $Hp18M_1$, where a kFGF4-derived MTD is fused to the C-terminus of a full-length p18; and 3) $HM_1p18M_1$, where a kFGF4-derived MTD is fused to both termini of a full-length p18, where a His-tag and a NLS derived from SV40 large T antigen are covalently coupled to the N-terminus of the above constructs. In order to prepare the full-length CP-p18 recombinant constructs, polymerase chain reactions (PCRs) were carried out by using the oligonucleotides described in Table 1 below as a primer pair specific for each recombinant construct and a human p18 cDNA (SEQ ID NO: 1) as a template (FIG. 2a). The forward and reverse primers for amplifying $HM_1p18$ have nucleotide sequences represented by SEQ ID NOS: 13 and 12, respectively; those for amplifying $Hp18M_1$ have nucleotide sequences represented by SEQ ID NOS: 11 and 14, respectively; those for amplifying $HM_1p18M_1$ have nucleotide sequences represented by SEQ ID NOS: 13 and 14, respectively.

Further, the truncated forms of a CP-p18 recombinant protein were as follows: 1) $Hp18NM_1$, wherein a kFGF4-derived MTD is fused to the C-terminus of a p18 N-terminal domain fragment lacking S- and C-terminal domains; 2) Hp18SM₁, wherein a kFGF4-derived MTD is fused to the C-terminus of a p18 S-terminal domain fragment lacking N- and C-terminal domains; 3) Hp18CM₁, wherein a kFGF4-derived MTD is fused to C-terminus of a p18 C-terminal domain fragment lacking N- and S-terminal domains; 4) Hp18NSM₁, wherein a kFGF4-derived MTD is fused to the C-terminus of a p18 N- and S-terminal domain fragment lacking a C-terminal domain; and 5) Hp18SCM₁, wherein a kFGF4-derived MTD is fused to the C-terminus of a p18 S- and C-terminal domain fragment lacking an N-terminal domain, wherein a His-tag and a NLS derived from SV40 large T antigen are covalently coupled to the N-terminus of all constructs. In order to prepare the truncated CP-p18 recombinant proteins, PCR was carried out by using the oligonucleotides described in Table 1 as a primer set specific for each recombinant protein and a human p18 cDNA (SEQ ID NO: 1) as a template (FIG. 2a). The forward and reverse primers for amplifying Hp18NM₁ have nucleotide sequences represented by SEQ ID NOS: 11 and 15, respectively, while those for amplifying Hp18SM₁ have nucleotide sequences represented by SEQ ID NOS: 16 and 17, respectively, those for amplifying Hp18CM₁ have nucleotide sequences represented by SEQ ID NOS: 14 and 18, respectively, those for amplifying Hp18NSM₁ have nucleotide sequences represented by SEQ ID NOS: 11 and 17, respectively, and those for amplifying Hp18SCM₁ have nucleotide sequences represented by SEQ ID NOS: 14 and 16, respectively.

The PCR was performed in a 50 µl reaction mixture containing 100 ng of human p18 cDNA as a template, 0.2 mM dNTP mixture (dGTP, dATP, dTTP, and dCTP, each at 2 mM), 0.6 µM of each primer, 5 µl of 10×Taq buffer, 1 µl of Taq polymerase (TAKARA, Japan). The PCR was performed for 30 cycles at 94° C. for 45 seconds, at 57° C. for 45 seconds and at 72° C. for 45 seconds after the initial denaturation of 94° C. for 3 minutes, followed by the final extension at 72° C. for 4 minutes. After the PCR was completed, the amplified PCR product was digested with restriction enzyme NdeI and loaded onto a 1.0% agarose gel and fractionated. As shown in FIG. 2a, it was confirmed that the expected fragment for each recombinant construct fused to a kFGF4-derived MTD was successfully amplified.

Figure 3A:
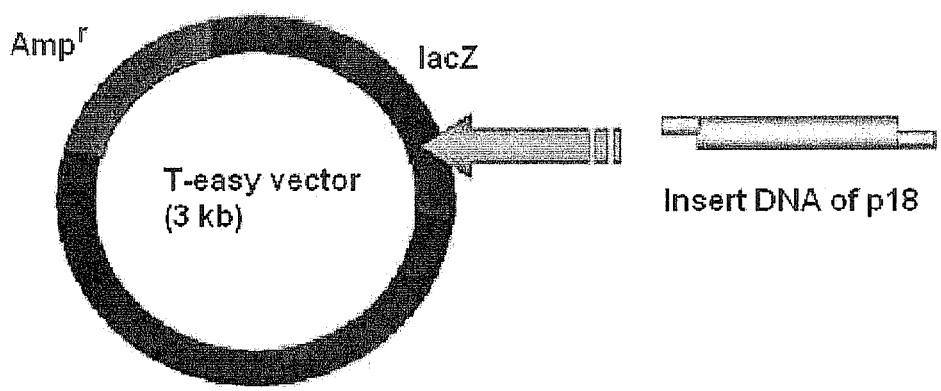
FIG. 3a is a schematic diagram illustrating the subcloning of a PCR product encoding a cell permeable p18 recombinant protein into the pGEM-T Easy vector according to the present invention.

The DNA band of expected size was excised from the gel, eluted, and purified by using a QIAquick™ Gel extraction kit (QIAGEN, USA). The eluted DNA was precipitated with ethanol and resuspended in 6 µl of distilled water for ligation. As shown in FIG. 3a, the PCR amplified DNA fragment containing the coding region was subcloned into a pGEM-T Easy vector (PROMEGA, Madison WI, USA) with a T4 ligase according to the TA cloning method, and then, followed by transformation of E. coli JM109 competent cells with the pGEM-T Easy vector. The cells were plated onto LB plate media supplemented with 100 µg/ml of ampicillin and cultured at 37° C. for overnight. After the recombinant fragment-inserted pGEM-T Easy vector was isolated by treating with restriction enzyme NdeI 37° C. for 1 hour, it was subjected to a 0.8% agarose gel electrophoresis.

Figure 3B:
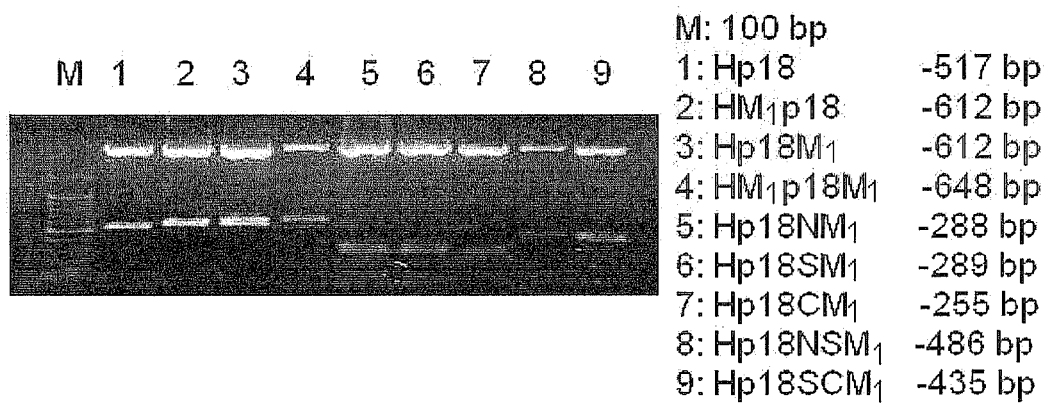
FIGS. 3b and 3c are photographs of an agarose gel electrophoresis analysis showing the PCR products encoding the cell permeable p18 recombinant proteins from FIGS. 2a and 2b subcloned in the pGEM-T Easy vector according to the present invention, respectively.

As shown in FIG. 3b, the DNA fragments of about 0.6 kb for the full-length form and about 0.2-0.4 kb for the truncated forms and vector fragments of about 3 kb were detected, confirming that the insert DNA of the CP-p18 recombinant construct was appropriately subcloned into the pGEM-T Easy vector.

Figure 4A:
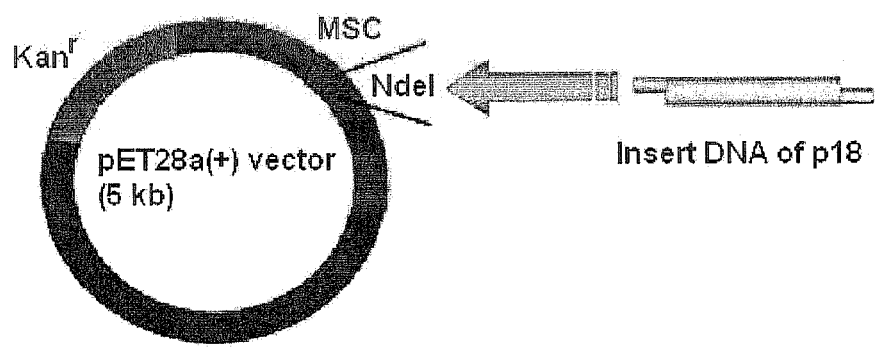
FIG. 4a is a schematic diagram illustrating the cloning of a recombinant DNA fragment encoding a cell permeable p18 recombinant protein into the pET 28(+) vector according to the present invention.

A pET-28(+)a vector (NOVAGEN, Madison, WI) bearing a histidine-tag and a T7 promoter was digested with a restriction enzyme NdeI (Enzynomics, Korea). The pGEM-T Easy vector fragments containing the CP-p18 recombinant fragment and pET-28(+)a vector fragment were purified by using a QIAquick™ Gel extraction kit. Each of the pGEM-T Easy vector fragments was cloned into the pre-treated pET-28a(+) with a T4 ligase at 16° C. for 12 hours, followed by transformation of E. coli DH5α competent cells with the resulting pET-28a(+) vector (FIG. 4a).

Figure 4B:
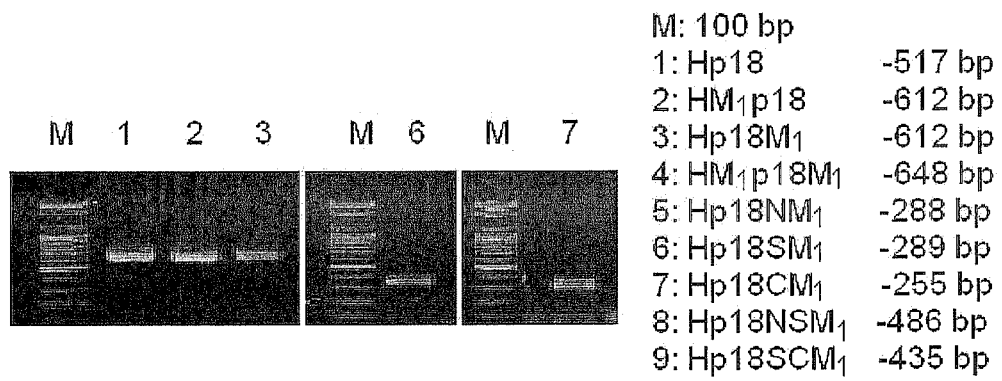
FIGS. 4b and 4c are photographs of an agarose gel electrophoresis analysis showing the recombinant DNA fragments encoding cell permeable p18 recombinant proteins subcloned in the pET 28(+) vector according to the present invention.

After the clones were treated with the restriction enzyme NdeI (Enzynomics, Korea) and subjected to 0.8% agarose gel electrophoresis, it was verified that DNA fragments of about 0.6 kb for the full-length form and about 0.2-0.4 kb for the truncated forms and vector fragments of about 5 kb were detected, confirming the cloning of the insert DNA of CP-p18 recombinant construct into pET-28a(+) vector, as shown in FIG. 4b.

The successfully cloned expression vectors for expressing cell permeable p18 recombinant proteins were designated pHp18, pHM₁p18, pHp18M₁, pHM₁p18M₁, pHp18NM₁, pHp18SM₁, pHp18CM₁, pHp18NSM₁, and pHp18SCM₁, respectively. Among them, the E. coli transformant DH5α/ Hp18M₁ obtained by transforming E. coli DH5α with the expression vector pHp18M₁ was deposited on Apr. 12, 2008 in accordance with the Budapest Treaty under accession number KCTC-110310BP with the Korean Collection for Type Cultures (KCTC), Korea Research Institute of Bioscience and Biotechnology (KRIBB), 52, Oun-Dong, Yusong-Ku, Taejon 305-333, Republic of Korea.

<1-2> Construction of p18 Recombinant Proteins by Using JO-101 MTD and JO-103 MTD In order to construct a cell permeable p18 recombinant protein by using a JO-101 MTD (MTD₂) and a JO-103 MTD (MTD₃), three full-length forms of a CP-p18 recombinant construct for each MTD were constructed.

Figure 2B:
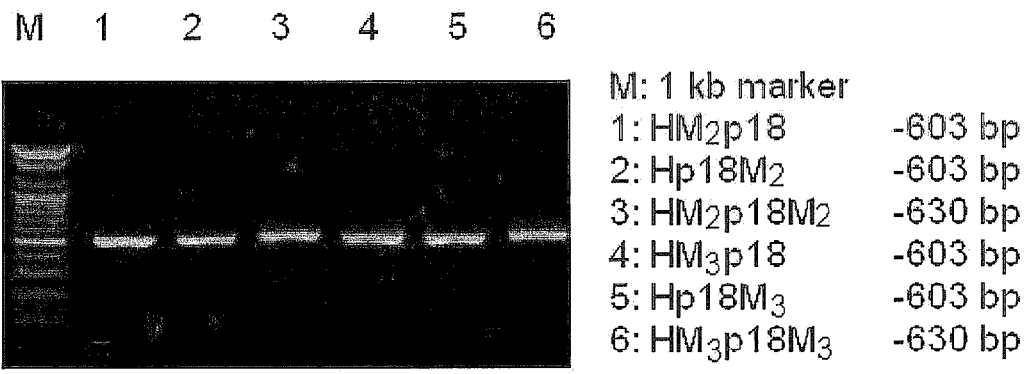
FIG. 2b is a photograph of an agarose gel electrophoresis analysis showing PCR-amplified DNA fragments encoding cell permeable p18 recombinant proteins being fused to JO-101 and JO-103 MTDs, respectively, and constructed in the full-length and truncated forms according to the present invention.

Referring to FIG. 2b, the full-length forms of the CP-p18 recombinant constructs fused to a JO-101 MTD were as follows: 1) HM₂p18, where a JO-101 MTD is fused to the N-terminus of a full-length p18; 2) Hp18M₂, where a JO-101 MTD is fused to the C-terminus of a full-length p18; and 3) HM₂p18M₂, where a JO-101 MTD is fused to both termini of a full-length p18, where a His-tag and a NLS derived from SV40 large T antigen are covalently coupled to the N-terminus of the above constructs. In order to prepare the full-length CP-p18 recombinant proteins, PCR was carried out according to the same method as described in section <1-1> of Example 1 above. The forward and reverse primers for amplifying HM₂p18 have nucleotide sequences represented by SEQ ID NOS: 19 and 12, respectively, while those for amplifying Hp18M₂ have nucleotide sequences represented by SEQ ID NOS: 11 and 20, respectively and those for amplifying HM₂p18M₂ have nucleotide sequences represented by SEQ ID NOS: 19 and 20, respectively.

Further, the full-length forms of a CP-p18 recombinant construct fused to a JO-103 MTD were as follows: 1) HM₃p18, where a JO-103 MTD is fused to the N-terminus of a full-length p18; 2) Hp18M₃, where a JO-103 MTD is fused to the C-terminus of a full-length p18; and 3) HM₃p18M₃, where a JO-103 MTD is fused to both termini of a full-length p18, where a His-tag and a NLS derived from SV40 large T antigen are covalently coupled to the N-terminus of the above constructs. In order to prepare the full-length CP-p18 recombinant proteins, PCR was carried out according to the same method as described in section <1-1> of Example 1 above. The forward and reverse primers for amplifying HM₃p18 have nucleotide sequences represented by SEQ ID NOS: 21 and 12, respectively, while those for amplifying Hp18M₃ have nucleotide sequences represented by SEQ ID NOS: 11 and 22, respectively and those for amplifying HM₃p18M₃ have nucleotide sequences represented by SEQ ID NOS: 21 and 22, respectively.

Figure 3C:
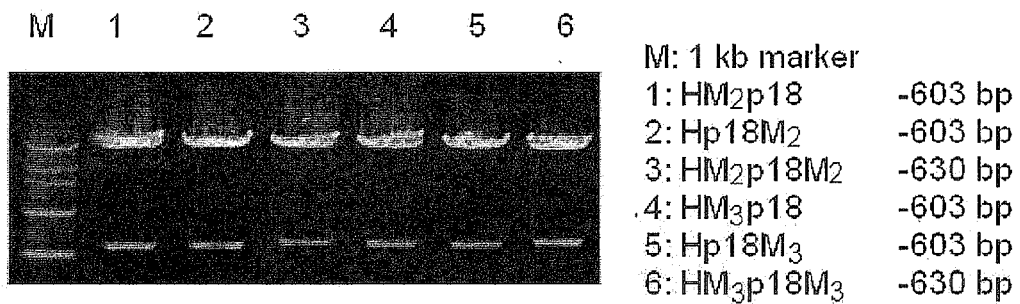
Figure 4C:
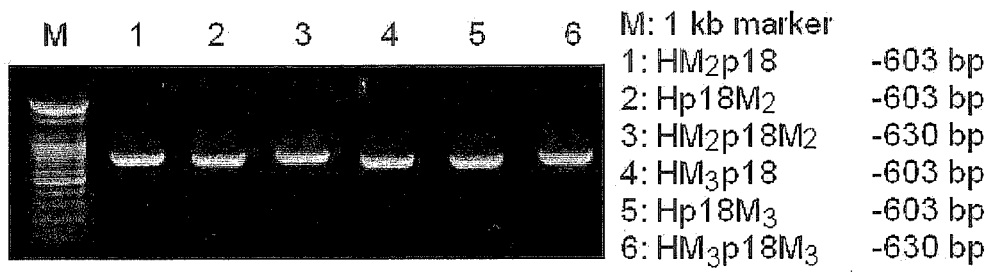

Each of the PCR amplified DNA fragments was subcloned into a pGEM-T Easy vector, followed by cloning into a pET-28(+)a vector according to the same method as described in section <1-1> of Example 1 above, to thereby obtain expression vectors for expressing cell permeable p18 recombinant proteins. The successful insertion of the recombinant fragment into the pGEM-T Easy and pET-28(+)a vectors is confirmed in FIGS. 3c and 4c.

The thus obtained expression vectors for expressing cell permeable p18 recombinant proteins were designated pHM₂p18, pHp18M₂, pHM₂p18M₂, pHM₃p18, pHp18M₃, and pHM₃p18M₃, respectively. Among them, the *E. coli* transformants DH5α/HM₂p18M₂ and DH5α/HM₃p18 obtained by transforming *E. coli* DH5α with each of the expression vectors pHM₂p18M₂ and pHM₃p18 were deposited on Apr. 12, 2008 in accordance with the Budapest Treaty under accession numbers KCTC-110311BP and KCTC-11312BP, respectively, with the Korean Collection for Type Cultures (KCTC), Korea Research Institute of Bioscience and Biotechnology (KRIBB), 52, Oun-Dong, Yusong-Ku, Taej on 305-333, Republic of Korea.

The oligonucleotides as a forward and reverse primer set specific for each recombinant protein are summarized in Table 2 below.

Example 2

Expression of Recombinant Proteins

<2-1> Selection of Optimal Bacterial Strains

To select the optimal bacterial strain for the expression of cell permeable p18 recombinant proteins prepared in Example 1 above, the following experiments were carried out in *E. coli* BL21(DE3), BL21-Gold(DE3), BL21-CodonPlus (DE3) and BL21-Gold(DE3) pLysS strains (STRATAGENE, USA), all of which contain the LacI promoter.

First, each of the expression vectors pHM₁p18, pHp18M₁, and pHp18 (control) was transformed into *E. coli* BL21 (DE3), BL21-Gold(DE3), BL21-CodonPlus(DE3) and BL21-Gold(DE3) pLysS strains, respectively, according to the heat shock method, followed by culturing in an LB medium containing 50 μg/ml of kanamycin. After that, the cells transformed with the recombinant protein encoding gene were grown in 1 ml of LB medium at 37° C. overnight, followed by culturing at 37° C. in 100 ml of LB medium with vigorous shaking until the optical density 600 ($OD_{600}$) reached 0.5. IPTG (isopropyl-β-D-thiogalactoside) was then added thereto at a final concentration of 0.65 mM to induce the expression of the CP-p18 recombinant proteins. Protein induction was prolonged for 3 hours at 37° C. The *E. coli* culture solutions were harvested by centrifugation at 4° C., 7,000×g for 20 minutes, resuspended in a lysis buffer (100

TABLE 2

| Primer | SEQ ID NO | Sequence |
|---|---|---|
| Hp18-5' (45nts) | 11 | CCG CAT ATG AAG AAG AAG AGG AAG GCC GAG CCT TGG GGG AAC GAG |
| Hp18-3' (30nts) | 12 | CCG CAT ATG TCA TTG AAG ATT TGT GGC TCC |
| HM₁p18-5' (84nts) | 13 | CCG CAT ATG AAG AAG AAG AGG AAG GCA GCC GTT CTT CTC CCT GTT CTT CTT GCC GCA CCC GCC GAG CCT TGG GGG AAC GAG TTG |
| Hp18M₁-3' (72nts) | 14 | CCG CAT ATG TCA GGG TGC GGC AAG AAG AAC AGG GAG AAG AAC GGC TGC TTG AAG ATT TGT GGC TCC CCC AGC |
| Hp18NM₁-3' (72nts) | 15 | CCG CAT ATG TCA AAT AAT CGG CAG CAG CAG CAG AAT CAG TTG AAG ATT TGT GGC TCC CCC AGC |
| Hp18S-5' (45nts) | 16 | CCG CAT ATG AAG AAG AAG AGG AAG GCT AAT CCC GAT TTG AAA GAC |
| Hp18SM₁-3' (72nts) | 17 | CCG CAT ATG TCA GGG TGC GGC AAG AAG AAC AGG GAG AAG AAC GGV TGC CTC CAC CAC CCG GAG GTG GCC TTC |
| Hp18C-5' (45nts) | 18 | CCG CAT ATG AAG AAG AAG AGG AAG TTC CTG GTG AAG CAC ACG GCC |
| HM₂p18-5' (75nts) | 19 | CCG CAT ATG AAG AAG AAG AGG AAG CTG ATT CTG CTG CTG CTG CCG ATT ATT GCC GAG CCT TGG GGG AAC GAG TTG |
| Hp18M₂-3' (63nts) | 20 | CCG CAT ATG TCA AAT AAT CGG CAG CAG CAG CAG AAT CAG TTG AAG ATT TGT GGC TCC CCC AGC |
| HM₃p18-5' (75nts) | 21 | CCG CAT ATG AAG AAG AAG AGG AAG CTG GCG CTG CCG GTG CTG CTG CTG GCG GCC GAG CCT TGG GGG AAC GAG TTG |
| Hp18M₃-3' (63nts) | 22 | CCG CAT ATG TCA CGC CAG CAG CAG CAC CGG CAG CGC CAG TTG AAG ATT TGT GGC TCC CCC AGC | mM NaH$_2$PO$_4$, 10 mM Tris-HCl, 8 M urea, pH 8.0), and subjected to ultrasonication on ice using a sonicator equipped with a probe. The cell lysates were centrifuged at 14,000×g for 15 minutes, so as to separate the insoluble fraction from the soluble fraction. The thus obtained soluble and insoluble fractions of CP-p18 recombinant proteins expressed in the *E. coli* strain with IPTG were loaded on a SDS-PAGE gel.

Figure 5A:
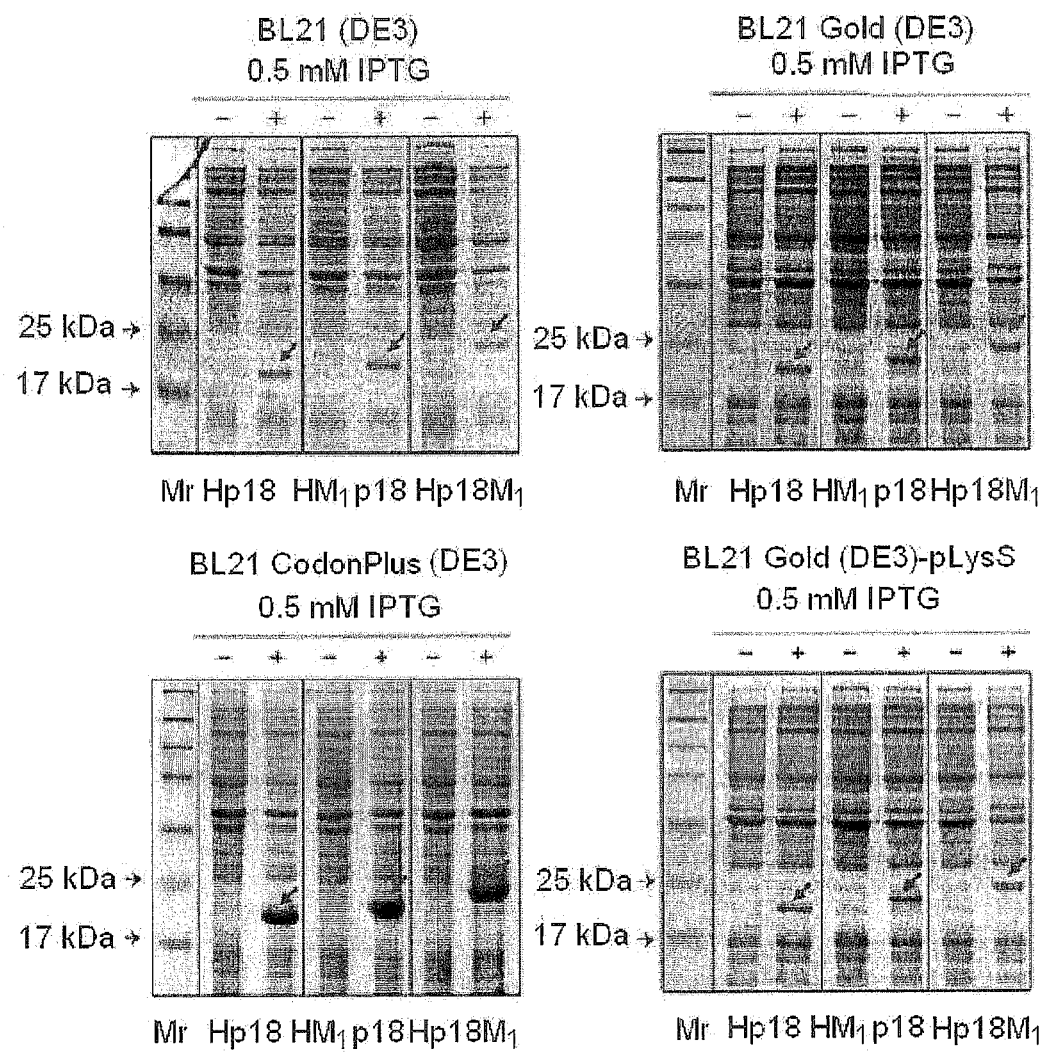
FIG. 5a is a photograph of a SDS-PAGE analysis showing the inducible expression of cell permeable p18 recombinant proteins according to the present invention in various kinds of host cells.

As shown in FIG. 5a, the highest expression level of the CP-p18 recombinant proteins were observed in BL21-Gold-Plus(DE3). From these results, BL21-GoldPlus(DE3) was selected as the optimal strain for the expression of cell permeable p18 recombinant proteins according to the present invention.

<2-2> Expression of Recombinant Proteins

Each of the expression vectors pHM$_1$p18, pHp18M$_1$, and pHp18 (control) was transformed into *E. coli* BL21-Codon-Plus(DE3), selected as the optimal strain in section <2-1> of Example 2 above, according to the heat shock method, followed by culturing in an LB medium containing 50 µg/ml of kanamycin. After that, the cells transformed with the recombinant protein encoding gene were grown in 25 ml of LB medium at 37° C. overnight, followed by culturing at 37° C. in 1 l of LB medium with vigorous shaking until the optical density 600 (OD$_{600}$) reached 0.5. IPTG was then added thereto at a final concentration of 0.65 mM to induce the expression of the CP-p18 recombinant proteins. Protein induction was prolonged for 3 hours at 37° C. The *E. coli* culture solutions were harvested by centrifugation at 4° C., 7,000×g for 20 minutes, resuspended in a lysis buffer (100 mM NaH$_2$PO$_4$, 10 mM Tris-HCl, 8 M urea, pH 8.0), and subjected to ultrasonication on ice using a sonicator equipped with a probe. The cell lysates were centrifuged at 14,000×g for 15 minutes, so as to separate the insoluble fraction from the soluble fraction. The thus obtained soluble and insoluble fractions of CP-p18 recombinant proteins expressed in the *E. coli* strain with IPTG were loaded on a SDS-PAGE gel.

Figure 5B:
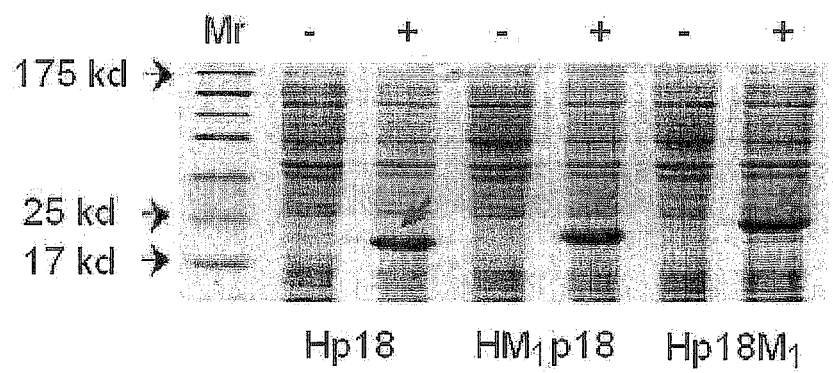
FIG. 5b is a photograph of a SDS-PAGE analysis showing the inducible expression of cell permeable p18 recombinant proteins according to the present invention in the presence or the absence of IPTG as an inducer.

As shown in FIG. 5b, it was confirmed that the cell permeable p18 recombinant proteins (~21 kDa) expressed in the host cell were mostly included in the insoluble fraction as an inclusion body, and their expression was significantly increased in the presence of IPTG.

Example 3

Purification of Recombinant Proteins

The inducible expression of cell permeable p18 recombinant proteins in an *E. coli* system leads to the formation of insoluble aggregates, which are known as inclusion bodies. To completely solubilize these inclusion bodies, all of the above expressed proteins were denatured by dissolving them in 8 M urea used as a strong denaturing agent.

First, the BL21 CodonPlus(DE3) strains transformed with each of the expression vectors pHp18, pHM$_1$p18, pHp18M$_1$, pHM$_2$p18, pHp18M$_2$, pHM$_2$p18M$_2$, pHM$_3$p18, pHp18M$_3$, and pHM$_3$p18M$_3$ were cultured in 1 l of an LB medium as described in Example 2. Each culture solution was harvested by centrifugation, gently resuspended in 20 ml of a lysis buffer (100 mM NaH$_2$PO$_4$, 10 mM Tris-HCl, 8 M urea, pH 8.0) without forming bubbles, and subjected to ultrasonication on ice using a sonicator equipped with a microtip. The cells were intermittently sonicated for 30 seconds, followed by cooling for 10 seconds, while setting the power to 25% of the maximum power. The total sonication time was 5 minutes. The cell lysates were centrifuged at 3,000×g for 25 minutes, so as to separate the supernatant and the cellular debris pellet. The supernatant was loaded onto a Ni-NTA agarose resin where nitrilotriacetic acid agarose was charged with nickel (Ni). The Ni-NTA agarose resin was equilibrated with the lysis buffer. The supernatant was allowed to absorb onto the resin by gently shaking (using a rotary shaker) at 4° C. for 8 hours or more. The resin absorbed with the inclusion bodies containing the recombinant protein was centrifuged at 4° C., 1,000×g for 5 minutes, to remove the reaction solution and washed with a washing buffer (100 mM NaH$_2$PO$_4$, 10 mM Tris-HCl, 8 M urea, pH 6.3) five times to remove nonspecific absorbed materials. After washing, the proteins absorbed to the resin were eluted with an elution buffer (100 mM NaH$_2$PO$_4$, Tris-HCl, 8 M urea, pH 4.0) for 2 hours or 8 hours. The eluted proteins were analyzed with 12% SDS-PAGE gel electrophoresis, stained with Coomassie Brilliant Blue R by gently shaking, and destained with a destaining solution.

Figure 6A:
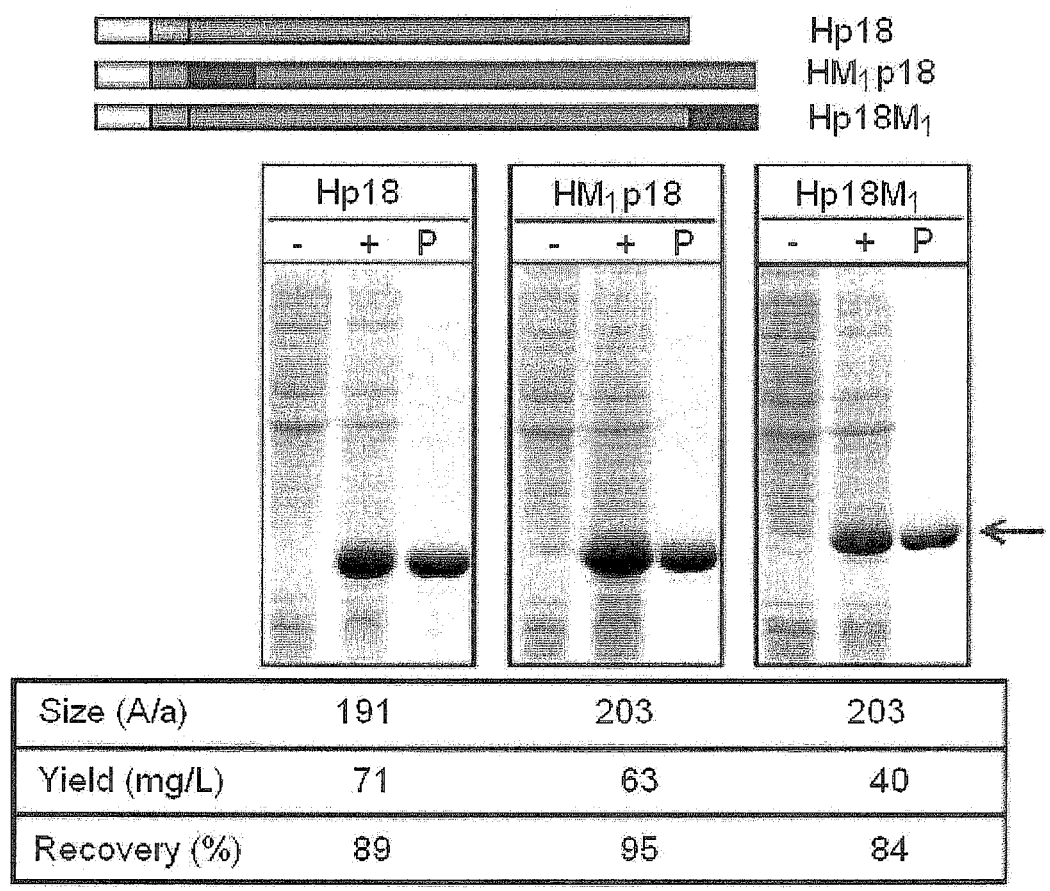
FIGS. 6a to 6c are photographs of a SDS-PAGE analysis showing the results of purification of cell permeable p18 recombinant proteins in full-length forms fused to a kFGF4-derived MTD, a JO-101 MTD, and a JO-103 MTD, respectively, according to the present invention.
Figure 6B:
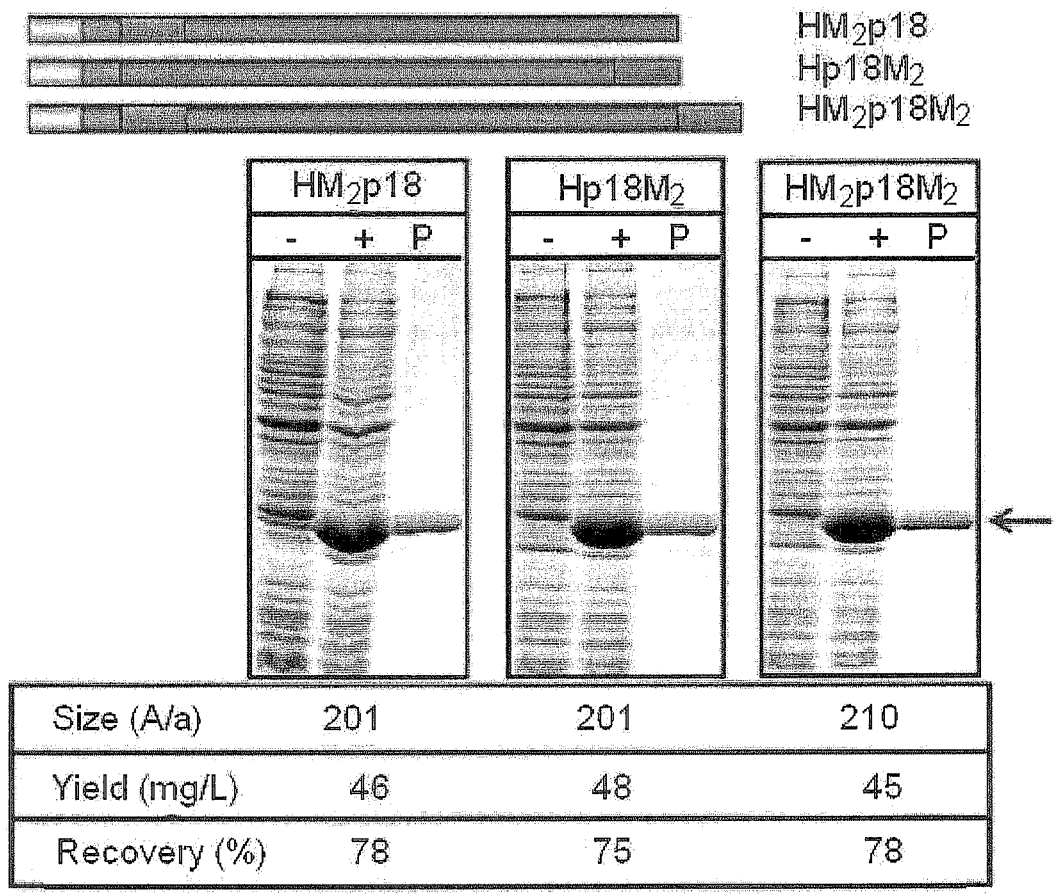
Figure 6C:
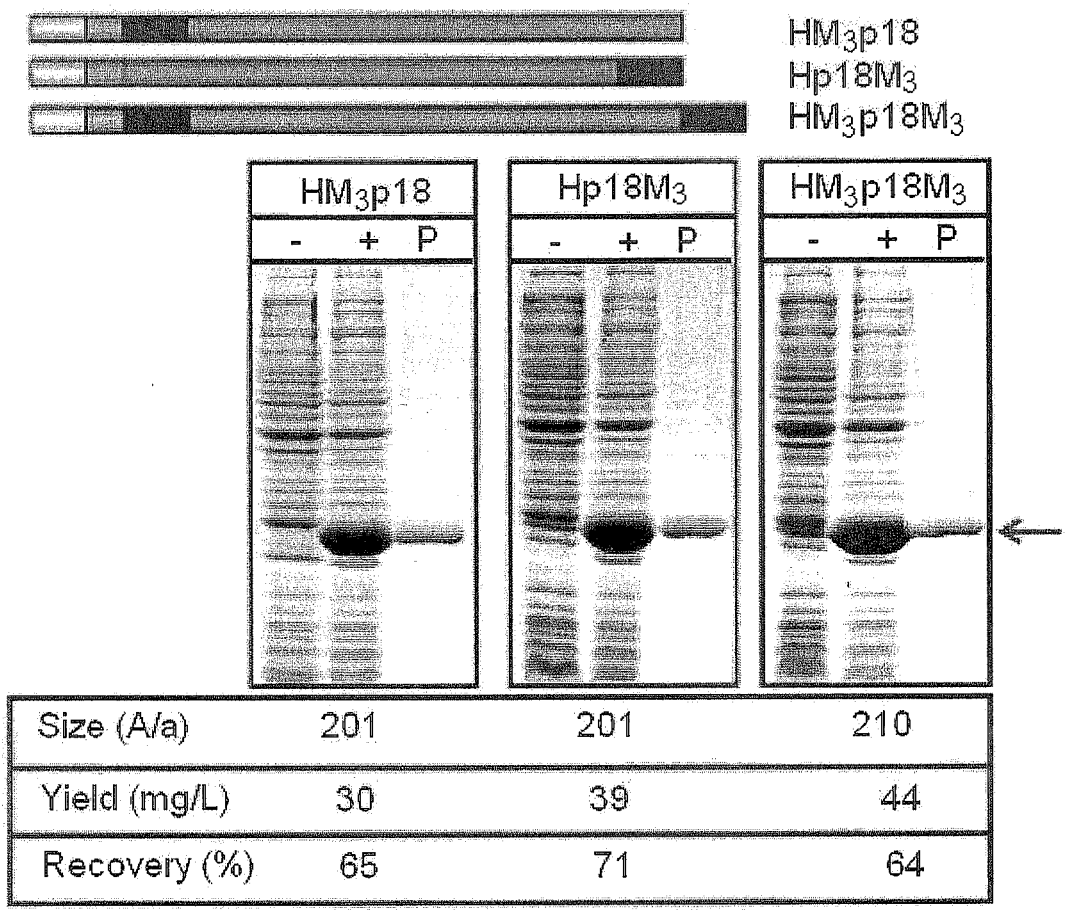

According to the results shown in FIGS. 6a to 6c, all of the cell permeable p18 recombinant proteins fused to kFGF4-derived MTD, a JO-101 MTD and a JO-103 MTD, respectively, were detected as a single band corresponding to about 21 kDa, which confirms that the cell permeable p18 recombinant proteins of the present invention have been purified from the insoluble fraction.

Example 4

Refolding of Recombinant Proteins

Since the cell permeable p18 recombinant proteins of the present invention purified from the insoluble fraction as described in Example 3 above were denatured by a strong denaturing agent, such as 8 M urea, the denatured proteins must be converted into an active form by a refolding process, as follows.

First, the purified recombinant proteins were subjected to a refolding process by dialyzing them against a refolding buffer (0.55 M guanidine HCl, 0.44 M L-arginine, 50 mM Tris-HCl, 150 mM NaCl, 1 mM EDTA, 100 mM NDSB, 2 mM glutathione oxidized, and 0.2 mM glutathione reduced) at 4° C. for 24 hours, thereby removing the denaturing agent. All of the refolded recombinant proteins were dialyzed against a cell culture medium DMEM (Dulbecco's Modified Eagle Medium) by using a dialysis bag (Snakeskin pleated, PIERCE) at 4° C. for 8 hours. The medium was replaced with fresh DMEM every 3 hours.

In order to quantitatively determine the cell permeability of the CP-p18 recombinant proteins refolded into their active form above, they were labeled with FITC (fluorescein-5-isothiocyanate, MOLECULAR PROBE). The recombinant protein (2 to 20 mg) was mixed with 1 µl of FITC at a concentration of 333 mg/ml and reacted in a dark room at room temperature for 1 hour by gentle stirring. The reaction solution was subjected to a dialysis against DMEM at 4□ for 1 day until the unreacted FITC was completely removed, thereby obtaining FITC-conjugated recombinant proteins. The thus obtained FITC-conjugated recombinant proteins were subjected to a Bradford protein assay to measure the protein concentration. As a result, each of the FITC-conjugated recombinant proteins was measured to have a concentration of about 1 µg/µl.

Example 5

Determination of Cell Permeability

<5-1> Flow Cytometry

In order to quantitatively determine the cell permeability of the CP-p18 recombinant proteins according to the present invention, RAW 264.7 cells derived from mouse macrophage were incubated with 10 μM of each of the FITC-conjugated recombinant proteins prepared above for 1 hour at 37°. The RAW 264.7 cells were maintained in DMEM supplemented with 10% fetal bovine serum and 5% penicillin/streptomycin (500 mg/ml) and incubated at 37° in a humidified atmosphere of 5% $CO_2$ in air. After the incubation, the cells were treated with trypsin/EDTA (T/E, INVITROGEN, Carlsbad, CA) to remove cell surface bound proteins, washed with cold PBS three times, and then, subjected to flow cytometry analysis by using a CellQuest™ Pro software program of the FACS (fluorescence-activated cell sorting) Calibur system (Beckton-Dickinson).

Figure 7A:
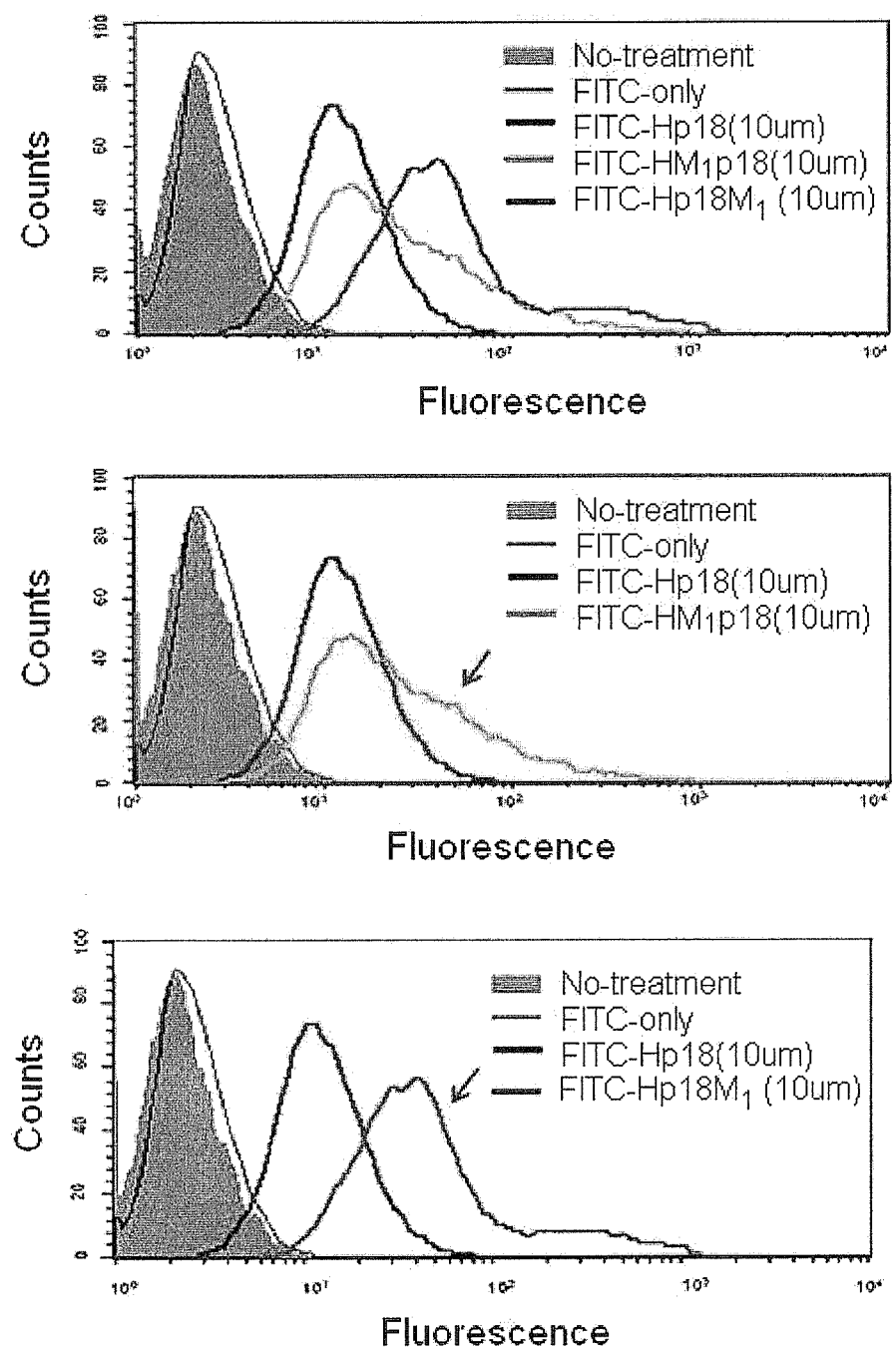
FIGS. 7a to 7c are graphs illustrating the results of flow cytometry analysis of cell permeabilities of cell permeable p18 recombinant proteins in full-length forms fused to a kFGF4-derived MTD, a JO-101 MTD, and a JO-103 MTD, respectively, according to the present invention.
Figure 7B:
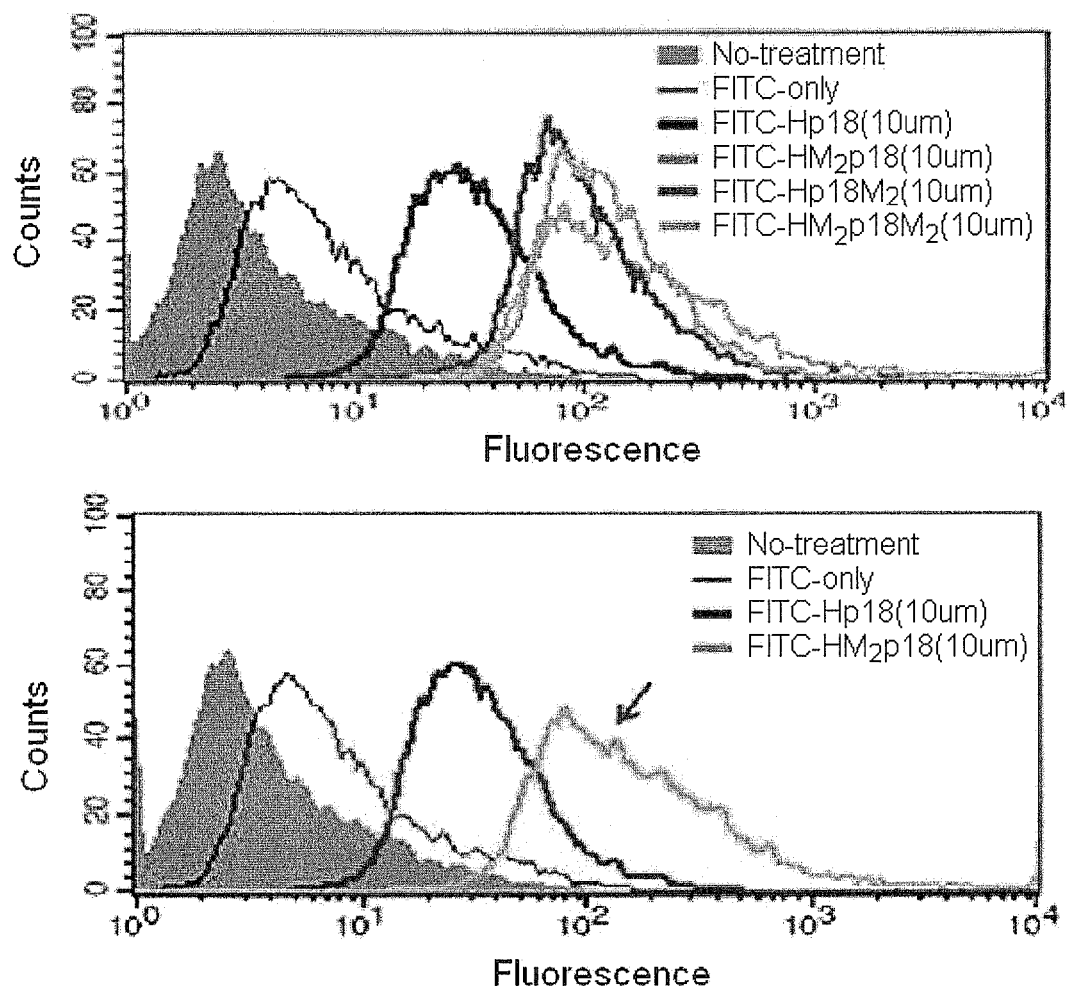
Figure 7B:
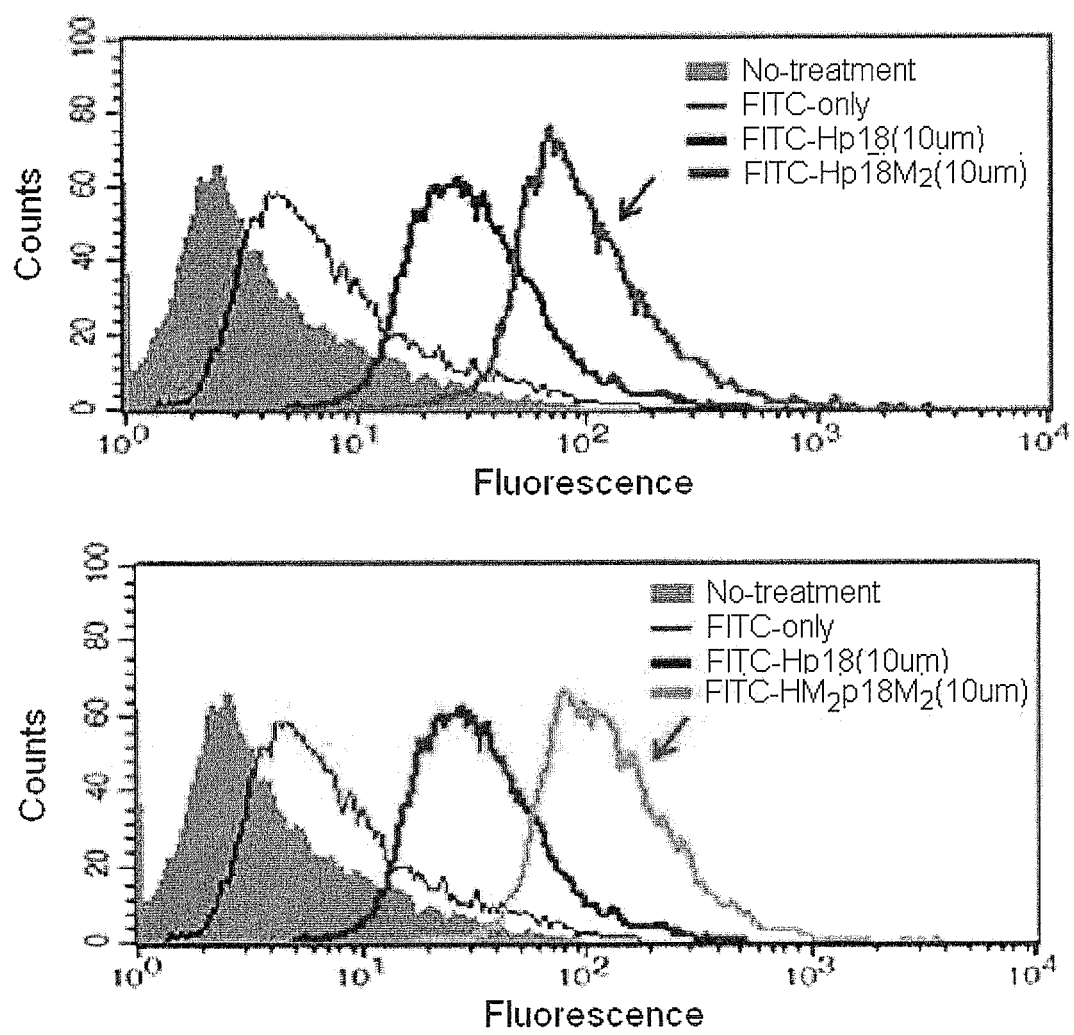
Figure 7C:
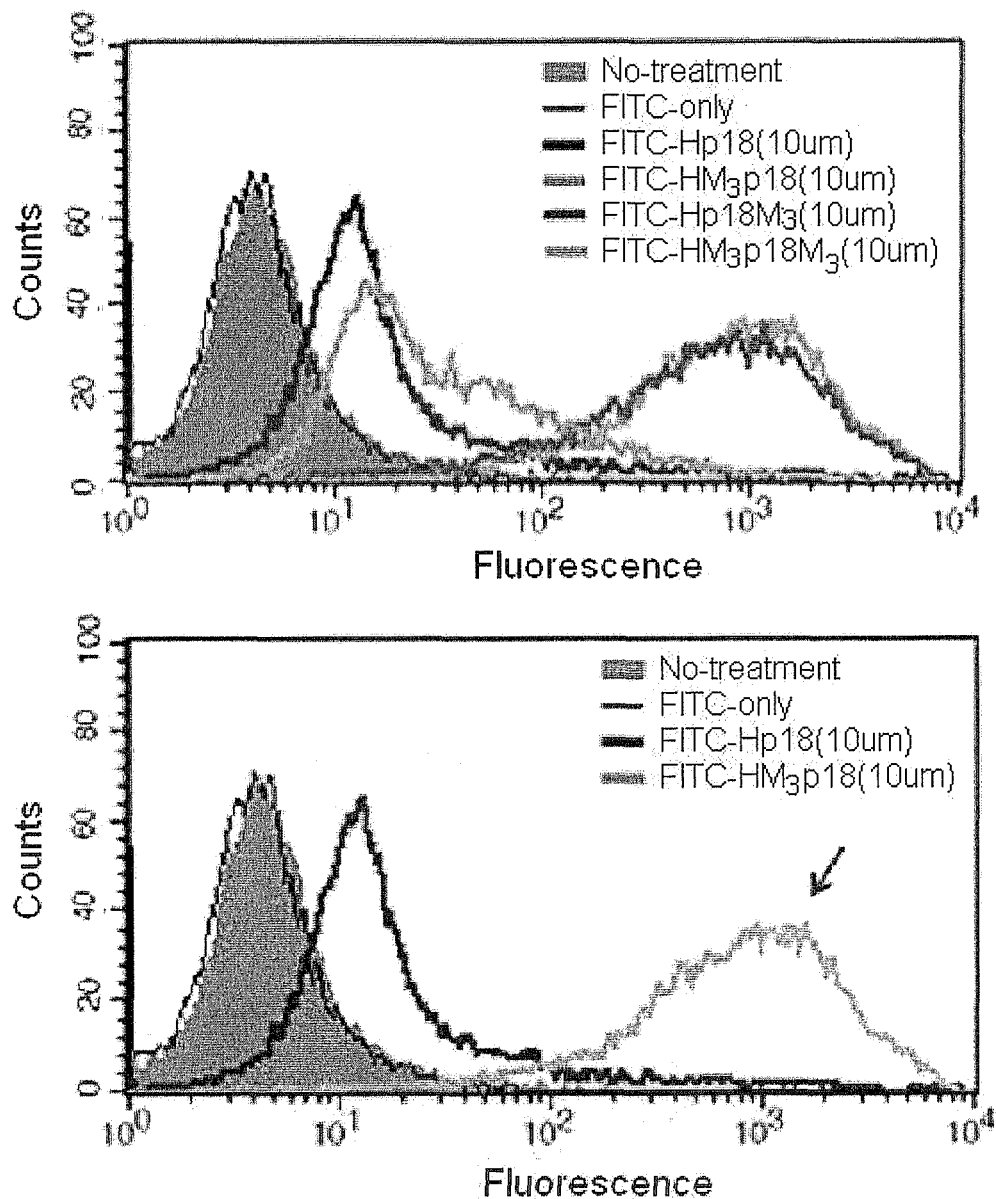
Figure 7C:
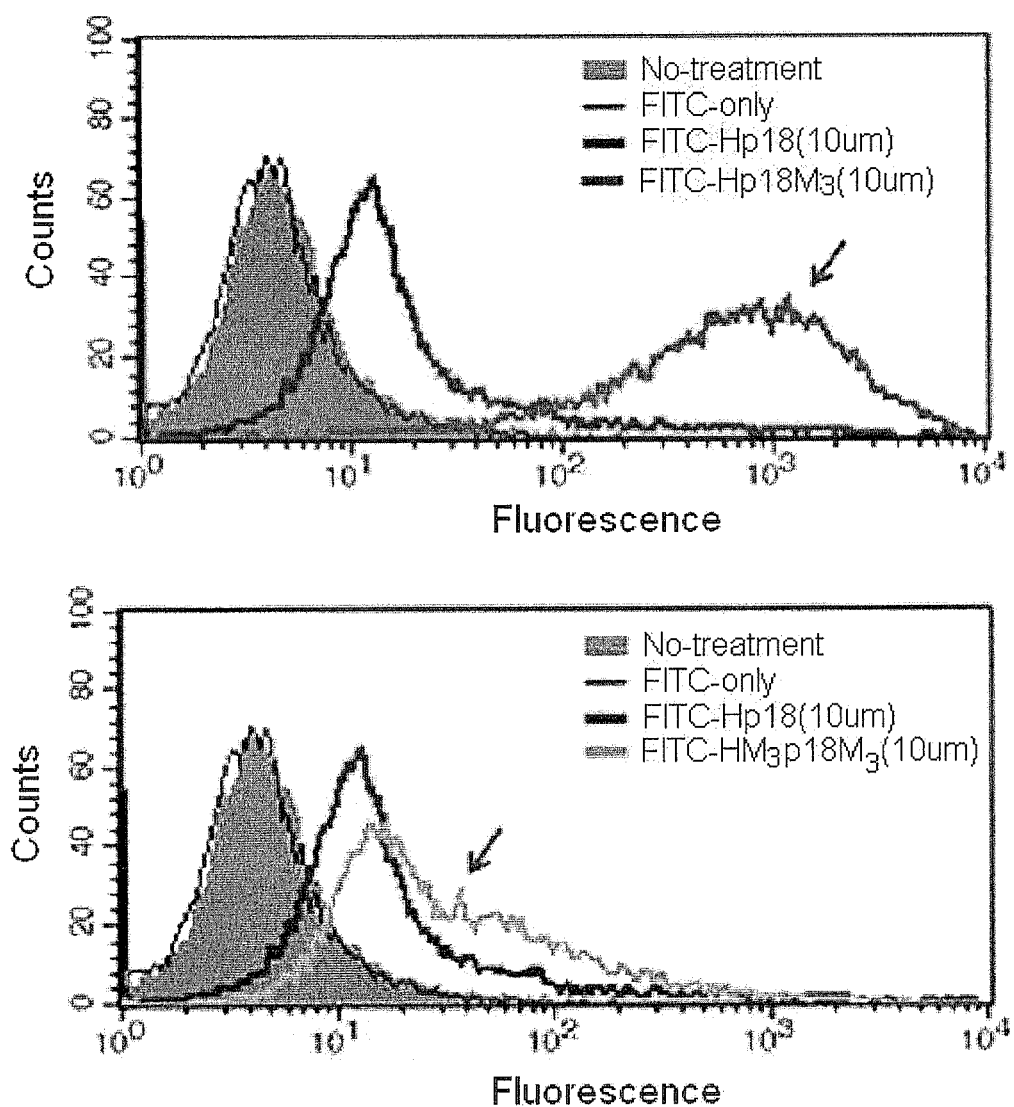

FIGS. 7a to 7c show the results of the flow cytometry analysis where the gray filled curve represents cell only, the black curve represents FITC only, the blue curve represents the cell permeability of Hp18 not fused to a MTD (control), the green curve represents the cell permeability of HMp18 where a MTD ($MTD_1$, $MTD_2$ or $MTD_3$) was fused to its N-terminus, the red curve represents the cell permeability of HMp18 where a MTD ($MTD_1$, $MTD_2$ or $MTD_3$) was fused to its C-terminus, and the orange curve represents the cell permeability of HMp18 where a MTD ($MTD_1$, $MTD_2$ or $MTD_3$) was fused to both termini thereof. Referring to the results shown in FIGS. 7a to 7c, it was found that in case of the cell permeable p18 recombinant protein (CP-p18) to which kFGF4-derived MTD ($MTD_1$) was fused, $Hp18M_1$ containing the MTD fused to its C-terminus showed higher cell permeability than $HM_1p18$ containing the MTD fused to its N-terminus. In case of CP-p18 to which JO-101 MTD ($MTD_2$) was fused, $HM_2p18$ containing the MTD fused to its N-terminus, $Hp18M_2$ containing the MTD fused to its C-terminus, and $HM_2p18M_2$ containing the MTD fused to both termini thereof showed similar levels of cell permeability, which were higher than a control not being fused to a MTD. Further, in case of CP-p18 to which JO-103 MTD ($MTD_3$) was fused, $HM_3p18$ containing the MTD fused to its N-terminus and $Hp18M_3$ containing the MTD fused to its C-terminus showed higher cell permeability than $HM_3p18M_3$ containing the MTD fused to both termini thereof.

<5-2> Confocal Laser Scanning Microscope Analysis I

To visualize the intracellular localization of human p18 proteins delivered into a cell, NIH 3T3 cells were treated for 1 hour without (cell only) or with FITC (FITC only), or 10 μM FITC-conjugated recombinant proteins lacking kFGF4-derived MTD (Hp18) or 10 μM FITC-conjugated recombinant proteins fused to a kFGF4-derived MTD ($HM_1p18$, $Hp18M_1$), and visualized by confocal laser scanning microscopy. The NIH3T3 cells were maintained in DMEM supplemented with 10% fetal bovine serum, 5% penicillin/streptomycin (500 mg/ml) in 5% $CO_2$ at 37°. In order to preserve the FITC fluorescence of the recombinant protein, the glass slide was fixed in 10 μl of a mounting medium for 15 minutes before the observation. For a direct detection of FITC-conjugated recombinant proteins that were internalized, the cells were washed with PBS three times and counterstained with a nuclear fluorescent stain solution, propidium iodide (PI, SIGMA ALDRICH, St. Louis, MO). The intracellular distribution of the fluorescence was determined at the middle of a single cell analyzed by a confocal laser scanning microscope using a normaski filter.

Figure 8A:
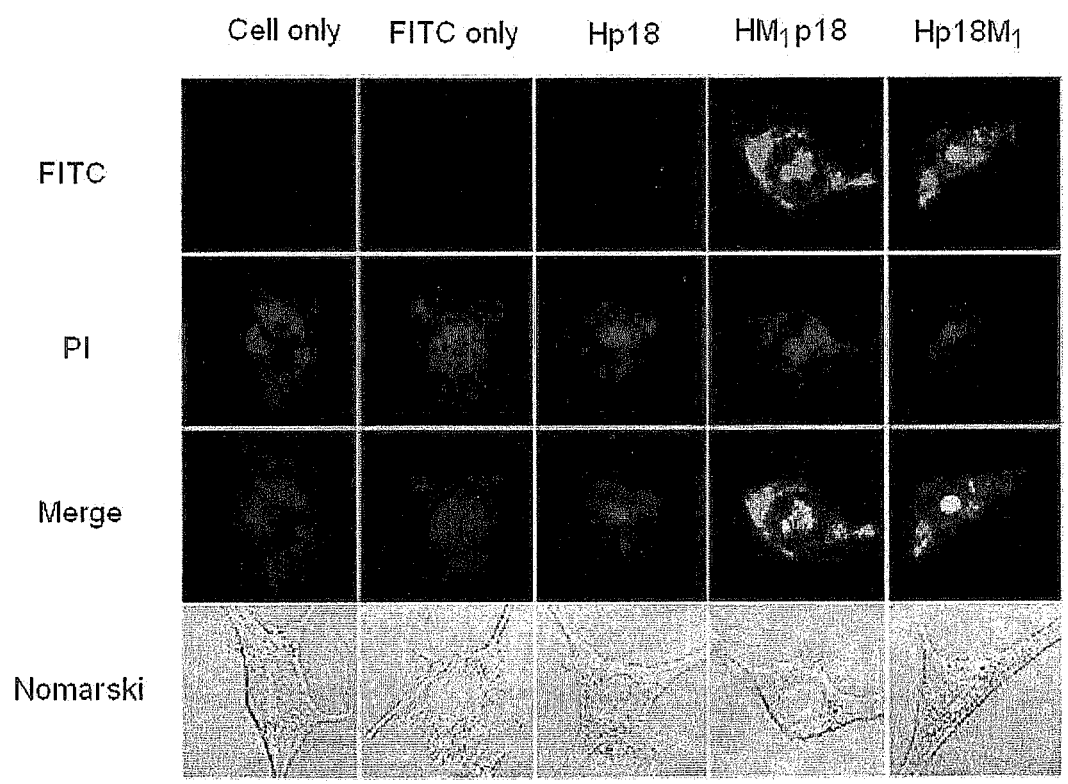
FIGS. 8a to 8c are confocal laser scanning microscopy photographs visualizing the cell permeabilities of cell permeable p18 recombinant proteins in full-length forms fused to a kFGF4-derived MTD, a JO-101 MTD, and a JO-103 MTD, respectively, according to the present invention in mouse fibroblasts.
Figure 8B:
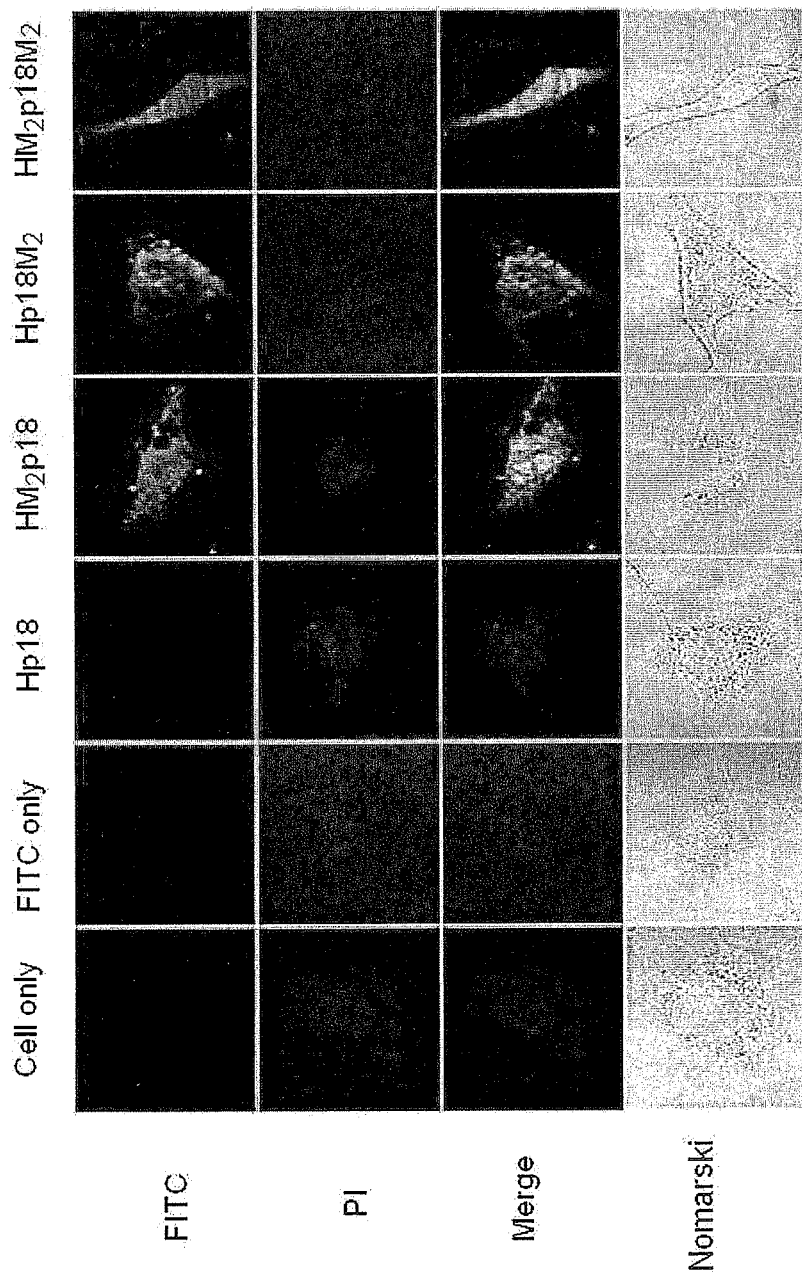
Figure 8C:
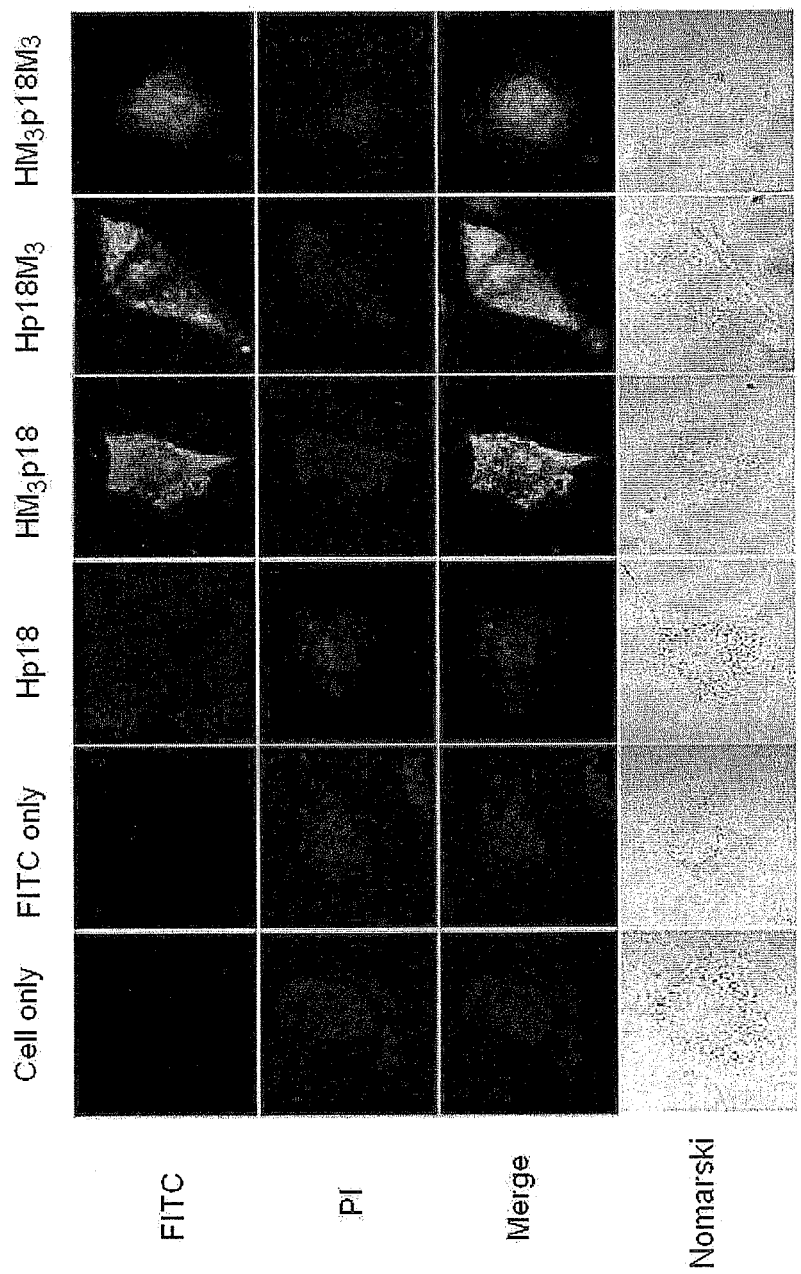

As shown in FIGS. 8a to 8c, it was observed that the cell permeable p18 recombinant proteins stained with FITC (green) and PI (red) were well distributed largely in the nucleus, which is consistent with the cell permeability of the CP-p18 recombinant proteins determined by flow cytometry.

From these results, it was confirmed that the cell permeable p18 recombinant proteins of the present invention exhibited high cell permeability.

<5-3> Confocal Laser Scanning Microscope Analysis II

In order to examine whether the cell permeable p18 recombinant proteins according to the present invention exhibit cell permeability with respect to a tissue, the following experiment was performed.

In this experiment, 7-week old MHC (major histocompatibility complex)-deficient Balb/c nu/nu mice (Central Lab. Animal Inc., Seoul) were used. The mice were subcutaneously injected with a human colon cancer cell line, HCT-116 cells ($1 \times 10^7$) (Korean Cell Line Bank) on their right leg by using a syringe (omnican, Germany, B. BRAUN), so as to induce tumor formation. Meanwhile, $Hp18M_1$ where a kFGF4-derived MTD ($MTD_1$) was fused to its C-terminus, $HM_2p18M_2$ where a JO-101 MTD ($MTD_2$) was fused to both termini thereof, $HM_3p18$ where a JO-103 MTD ($MTD_3$) was fused to its N-terminus, and Hp18 not being fused to a MTD were labeled with FITC. The tumor-bearing mice were administered with 300 μg of each of the FITC-conjugated recombinant proteins via intraperitoneal injection. Two hours later, the mice were sacrificed, and various tissue samples were extracted from the liver, kidney, spleen, lung, heart, brain, and tumor. The extracted tissues were embedded in an OCT compound, freezed, and then sectioned with a microtome to have a thickness of 14 ţµm. The tissue specimens were mounted on a glass slide and observed with a confocal laser scanning microscope. In order to preserve the FITC fluorescence of the recombinant protein, the glass slide was fixed in 10 μl of a mounting medium for 15 minutes before the observation.

Figure 9:
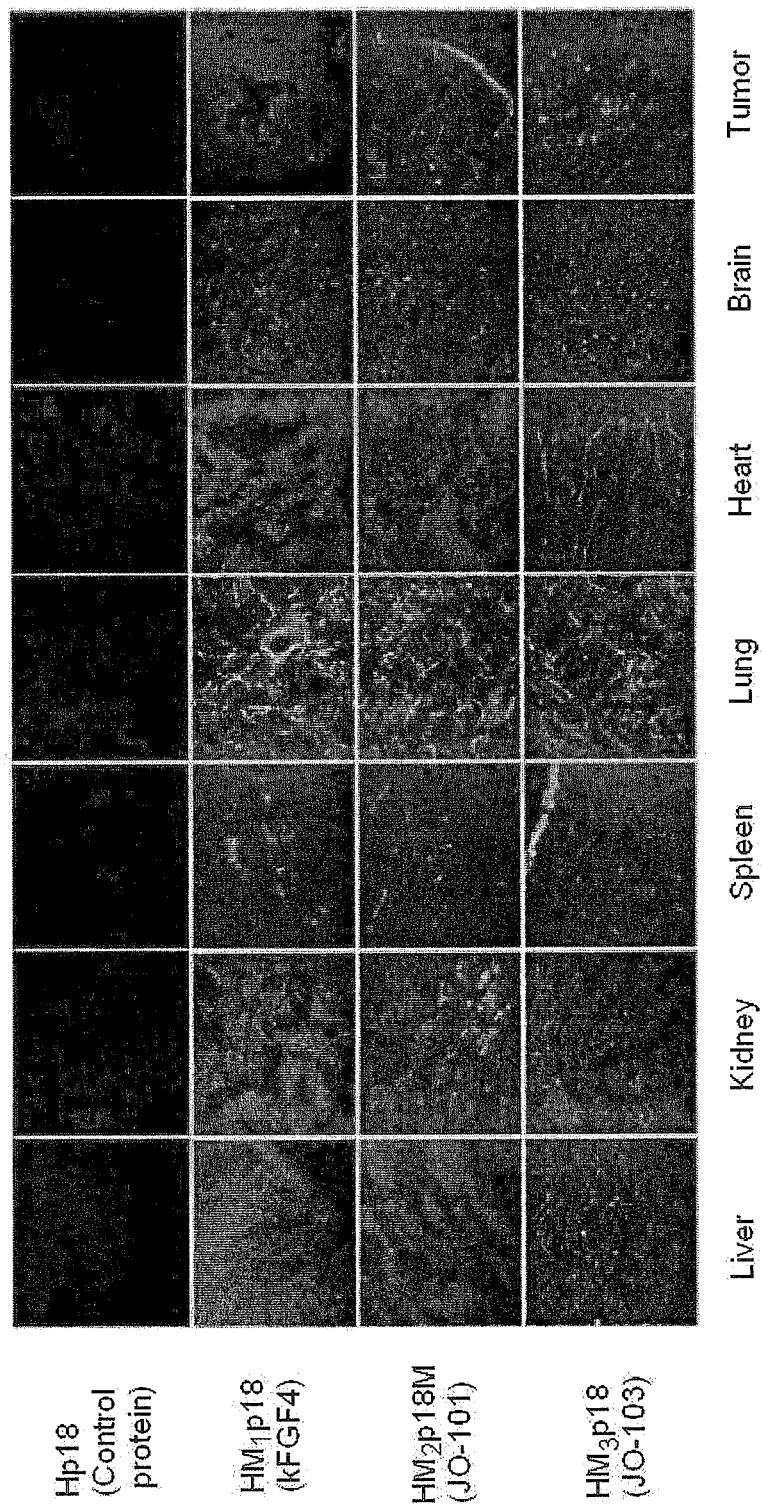
FIG. 9 is a confocal laser scanning microscopy photograph visualizing the cell permeabilities of cell permeable p18 recombinant proteins in full-length forms fused to a kFGF4-derived MTD, a JO-101 MTD, and a JO-103 MTD according to the present invention in various kinds of mouse tissues.

As illustrated in FIG. 9, it was found that protein transport into the nucleus clearly stained with FITC (green) and PI (red) was observed in all of the tissue specimens, which is consistent with the cell permeability of the CP-p18 recombinant proteins determined by flow cytometry. These results demonstrate that the cell permeable p18 recombinant proteins according to the present invention can be effectively used for transporting a tumor suppressor p18 into a target tissue.

Example 6

In Vivo Function of Cell Permeable p18 Recombinant Proteins

<6-1> Western Blot Analysis

To evaluate the in vivo function of the cell permeable p18 recombinant proteins according to the present invention, a Western blot analysis was performed as follows. HCT-116 cells, a human colon cancer cell line used in this experiment, were purchased from Korean Cell Line Bank (Seoul, Republic of Korea). HCT-116 cells were maintained in a RPMI 1640 medium (L-glutamine 300 mg/f, 25 mM HEPES, 25 mM $NaHCO_3$ 89.3%, heat-inactivated fetal bovine serum 9.8%, streptomycin/penicillin 0.9%) in a 5% $CO_2$ incubator at 37° C. After 2 ml of the RPMI 1640 medium was added to each well of a 6-well plate, HCT-116 cells were inoculated thereto, grown at 37° C. for 1 day, and then, further cultured for another day in the absence of serum. After removing the medium, the HCT-116 cells were washed with cold PBS (phosphate-buffered saline) and treated with each of $HM_1p18$ where kFGF4-derived MTD was fused to its N-terminus, $Hp18M_1$ where kFGF4-derived MTD was fused to its C-terminus, and Hp18 not being fused to a MTD at a concentration of 10 μM, 10 μM, and 20 μM, respectively. The cells treated with the recombinant proteins were reacted in a 5% $CO_2$ incubator at 37° C. for 4 hours so as to induce the expression of p21, or for 1 hour so as to induce the phosphorylation of p53, ATM, MEK, ERK and Rb. After the reaction was completed, the cells were resuspended in 200 μl of a lysis buffer (20 mM HEPES, pH 7.2, 1% Triton-X, 10% glycerol) and subjected to ultrasonication on ice for 30 minutes, to thereby obtain a cell lysate. The cell lysate was centrifuged at 12,000 rpm for 20 minutes at 4° C. to separate the supernatant. The thus obtained supernatant was subjected to a Bradford protein assay to quantitatively measure the protein concentration, and stored at −80° C. until use.

For Western blot analysis, p21Waf1/Cip1 (21 kDa, CELL SIGNALING TECHNOLOGY), phospho-p53 (Ser15, 53 kDa, CELL SIGNALING TECHNOLOGY), phospho-ATM (Ser1981, 350 kDa, SANTA CRUZ BIOTECHNOLOGY), phospho-MEK1/2 (Ser217/221, 45 kDa, CELL SIGNALING TECHNOLOGY), phospho-Erk (Thr202/Tyr204, 42/44 kDa, CELL SIGNALING TECHNOLOGY), and phospho-Rb (Ser No.807/811, 110 kDa, Santa Cruz Biotechnology) were used as primary antibodies, and goat anti-mouse IgG-HRP (Santa Cruz Biotechnology) and goat anti-rabbit IgG-HRP (SANTA CRUZ BIOTECHNOLOGY) were used as secondary antibodies. The supernatant was applied to a 12% sodium dodecyl sulfate-polyacrylamide gel (SDS-PAGE) at 100 V and transferred onto a PDVF membrane at 70 V for 2 hours. In order to prevent the nonspecific interaction between blotted proteins and unrelated antibodies, the PVDF membrane was blocked with 5% non-fat dry milk in TBS/T (10 mM Tris-C1, 150 mM NaCl, 0.05% Tween 20, pH 8.0) for 1 hour, followed by incubating with each of the primary antibodies for 1 hour at 4°. The membrane was washed with TBS/T five times and incubated with the secondary antibody for 1 hour at room temperature. After washing with TBS/T five times, the membrane was stained using an ECL (enhanced chemiluminescence) detection system (GE Healthcare Amersham UK) to visualize the antigen/antibody interaction.

Figure 10:
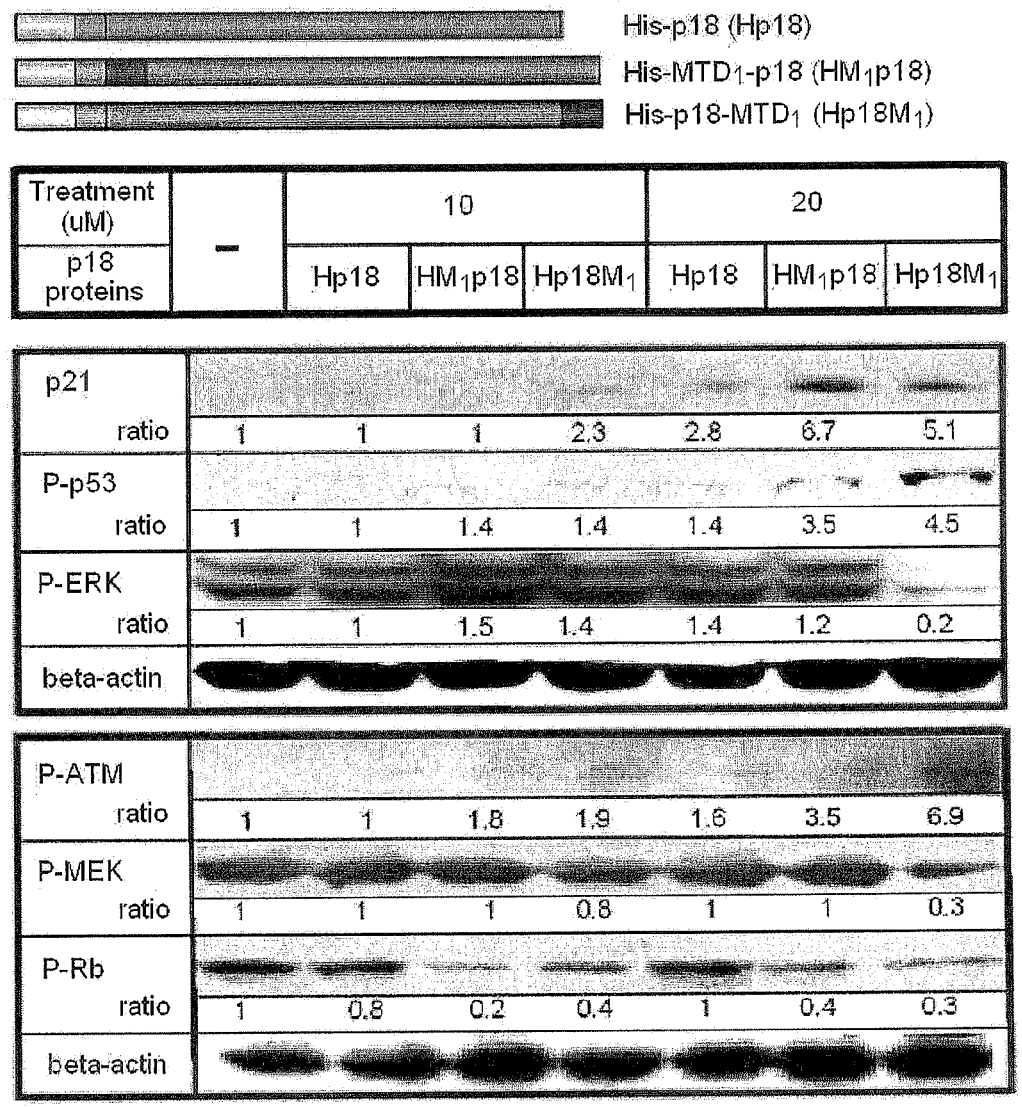
FIG. 10 is a photograph of a Western blot analysis showing the in vivo function of cell permeable p18 recombinant proteins, $HM_1p18$ and $Hp18M_1$, according to the present invention.

As shown in FIG. 10, in the cells treated with the cell permeable p18 recombinant protein to which kFGF4-derived MTD was fused, the expression of p21 and phosphorylation of ATM (P-ATM) and p53 (P-p53) that induce cell cycle arrest were increased, while the phosphorylation of MEK (P-MEK), ERK (P-ERK) and Rb (P-Rb) that induces the activation of tumor cell cycle was decreased. In particular, the Hp18M$_1$ recombinant protein where a kFGF4-derived MTD was fused to its C-terminus strongly inhibited the cell cycle of the cultured cancer cells, suggesting that it can be effectively used as a cell cycle inhibitor capable of preventing tumor formation.

Meanwhile, the Western blot analysis was conducted for the JO-101 MTD (MTD$_2$) fused recombinant proteins (HM$_2$p18, Hp18M$_2$ and HM$_2$p18M$_2$), JO-103 MTD (MTD$_3$) fused recombinant proteins (HM$_3$p18, Hp18M$_3$ and HM$_3$p18M$_3$), and the control recombinant protein not being fused to a MTD (Hp18) according to the same method as described above.

Figure 11:
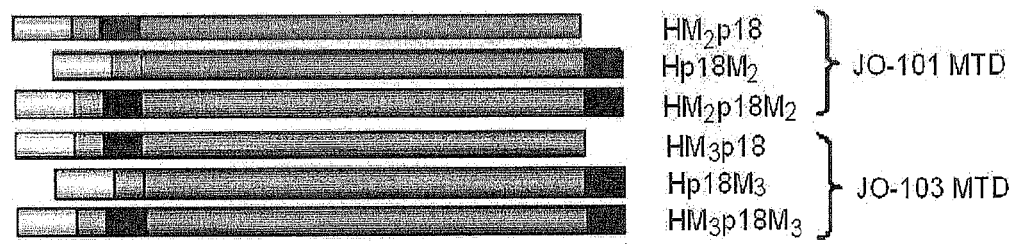
FIG. 11 is a photograph of a Western blot analysis showing the in vivo function of cell permeable p18 recombinant proteins, $HM_2p18$, $Hp18M_2$, $HM_2p18M_2$, $HM_3p18$, $Hp18M_3$ and $HM_3p18M_3$, according to the present invention.
Figure 11:
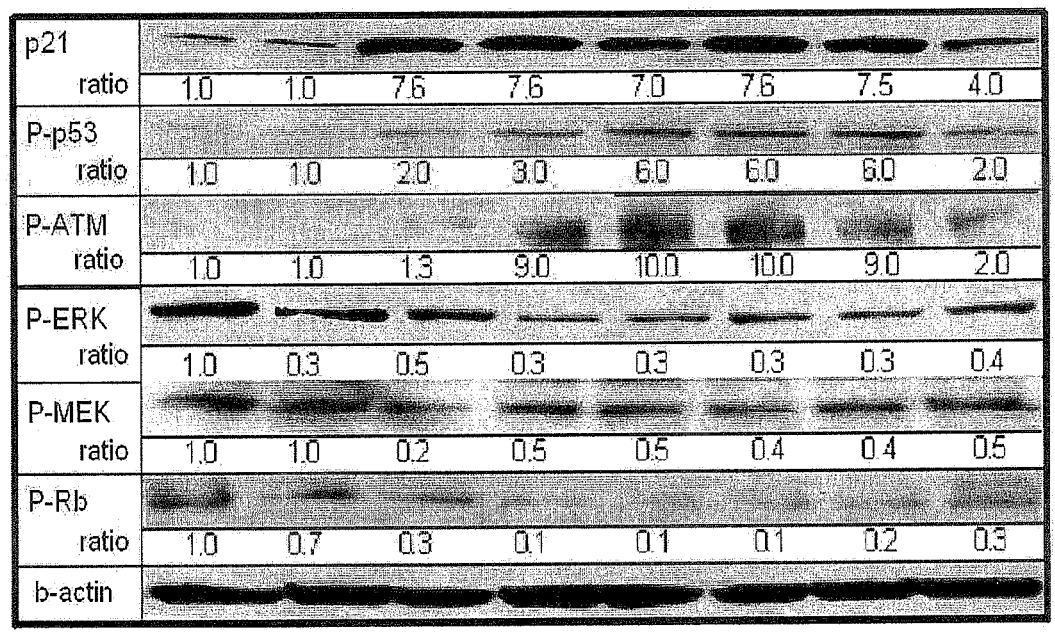

Referring to the results shown in FIG. 11, in the cells treated with the cell permeable p18 recombinant protein, the expression of p21 and phosphorylation of ATM (P-ATM) and p53 (P-p53) that induces cell cycle arrest were increased, while the phosphorylation of MEK (P-MEK), ERK (P-ERK) and Rb (P-Rb) that induces the activation of tumor cell cycle was decreased. In particular, the HM$_2$p18M$_2$ recombinant protein where kFGF4-derived MTD was fused to both termini thereof and HM$_3$p18 recombinant protein where kFGF4-derived MTD was fused to its C-terminus strongly inhibited the cell cycle of the cultured cancer cells, suggesting that they can be effectively used as a cell cycle inhibitor capable of preventing tumor formation.

<6-2> Cellular DNA Content Analysis

In order to examine the in vivo function of the cell permeable p18 recombinant proteins according to the present invention, the apoptosis-inducing effect of the recombinant protein was examined by cellular DNA content analysis as follows.

HCT-116 cells (Korean Cell Line Bank), a human colon cancer cell line, were cultured in a RPMI 1640 medium (L-glutamine 300 mg/l, 25 mM HEPES, 25 mM NaHCO$_3$ 89.3%, heat-inactivated fetal bovine serum 9.8%, streptomycin/penicillin 0.9%) in a 5% CO$_2$ incubator at 37° C. After 2 ml of the RPMI 1640 medium was added to each well of a 6-well plate, the HCT-116 cells cultured above were inoculated thereto, and grown at 37° C. for 1 day. Each of the HM$_1$p18 and Hp18M$_1$, all of which contain a kFGF4-derived MTD (MTD$_1$) fused thereto, HM$_2$p18M$_2$ to which JO-101 MTD (MTD$_2$) was fused, HM$_3$p18 to which JO-103 MTD (MTD$_3$) was fused, and Hp18 not being fused to a MTD was added to each well at a concentration of 20 μM, followed by culturing them in a serum-free medium for 1 hour. After washing the well plate with cold PBS twice, 2 ml of the RPMI 1640 medium was added to each well, and the well plate was further incubated for 0, 2, 4, and 8 hours, respectively. After that, the cells were washed with cold PBS twice, suspended in 200 of PBS, and gently soaked in 4 ml of 70% ethanol. The thus obtained cell suspension was kept on ice for 45 minutes and stored at −20° C. for 1 day. The cell suspension was treated with PI (40 μg/ml) and RNase A (100 μg/ml) and subjected to flow cytometry analysis to quantify the degree of apoptosis induced.

Figure 12:
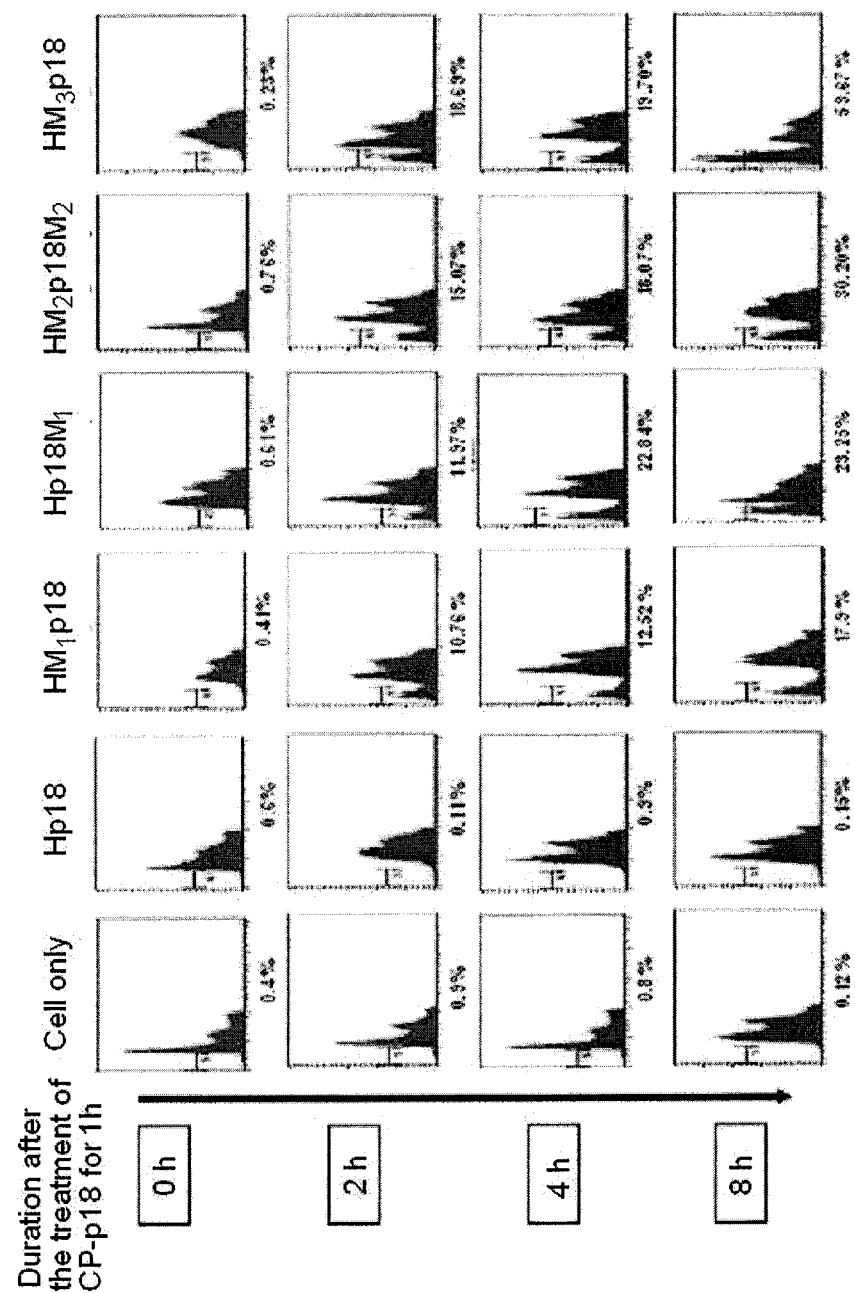
FIG. 12 is a photograph of a cellular DNA content analysis showing the apoptosis-inducing effect of cell permeable p18 recombinant proteins, $HM_1p18$, $Hp18M_1$, $HM_2p18M_2$ and $HM_3p18$, according to the present invention.

According to the results shown in FIG. 12, it has been found that the cell cycle progression in the cancer cell line was significantly suppressed at a higher rate, and thereby apoptosis was strongly induced in the cells treated with the cell permeable p18 recombinant proteins (HM$_1$p18, Hp18M$_1$, HM$_2$p18M$_2$, HM$_3$p18) rather than the untreated and control protein (Hp18) treated cells. In particular, when the cells were treated with the cell permeable p18 recombinant protein for 8 hours, the highest level of apoptosis was observed, and HM$_3$p18 to which JO-103 MTD was fused showed the highest apoptosis-inducing effect.

<6-3> Analysis of the Apoptosis-Inducing Effect Using Annexin-V

In order to examine the in vivo function of the cell permeable p18 recombinant proteins according to the present invention, the apoptosis-inducing effect of the recombinant protein was examined by an Annexin-V assay as follows.

HCT-116 cells (Korean Cell Line Bank), a human colon cancer cell line, were cultured in a RPMI 1640 medium (L-glutamine 300 mg/l, 25 mM HEPES, 25 mM NaHCO$_3$ 89.3%, heat-inactivated fetal bovine serum 9.8%, streptomycin/penicillin 0.9%) in a 5% CO$_2$ incubator at 37° C. After 2 ml of the RPMI 1640 medium was added to each well of a 6-well plate, the HCT-116 cells cultured above were inoculated thereto, and grown at 37° C. for 1 day. Each of HM$_3$p18 to which JO-103 MTD (MTD$_3$) was fused and Hp18 not being fused to a MTD was added to each well at a concentration of 20 μM, followed by culturing them in a serum-free medium for 1 hour. After that, the cells were washed with cold PBS twice, and suspended in 1 ml of a binding buffer (1×) at a concentration of 1×10$^6$ cells/ml. Subsequently, 100 ml of the cell suspension was transferred to an EP-tube, 5 ml of Annexin-V and 5 ml of PI were added thereto, and then, the EP-tube was reacted at room temperature for 15 minutes. After the reaction was completed, 400 ml of the binding buffer (1×) was added to the EP-tube, and the cells were subjected to a flow cytometry analysis to quantify the degree of apoptosis induced.

Figure 13:
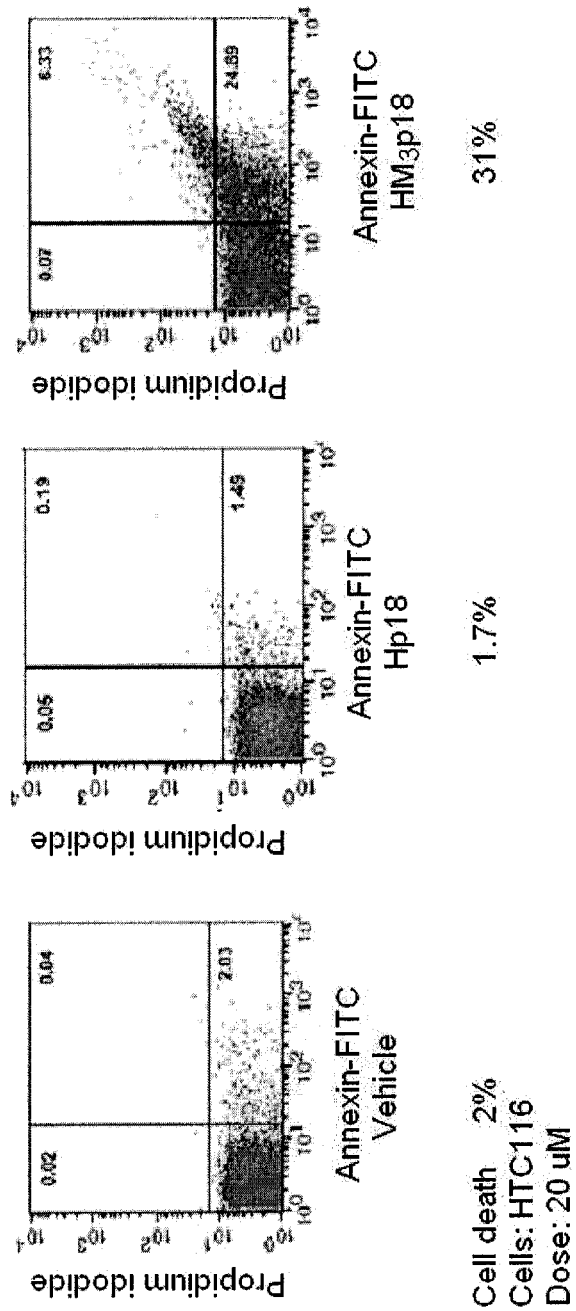
FIG. 13 is a photograph of in vivo annexin-V staining showing the apoptosis-inducing effect of cell permeable p18 recombinant protein $HM_3p18$ according to the present invention.

Referring to the results shown in FIG. 13, it was found that apoptosis was induced to a significantly higher extent in the cells treated with the cell permeable p18 recombinant protein ($HM_3p18$) than the untreated and control protein (Hp18) treated cells.

Example 7

In Vivo Function of Cell Permeable p18 Recombinant Proteins—Peritoneal Injection <7-1> Anticancer Effect During Administration In order to examine the in vivo function of the cell permeable p18 recombinant proteins according to the present invention, the anticancer effect of the recombinant protein was investigated by using an animal model as follows.

In this experiment, 7-week old MHC-deficient Balb/c nu/nu mice (Central Lab. Animal Inc., Seoul) were employed. The mice were subcutaneously injected with a human colon cancer cell line, HCT-116 cells ($1 \times 10^7$) (Korean Cell Line Bank) on their right leg by using a syringe (omnican, Germany, B. BRAUN), so as to induce tumor formation. Twenty four mice were subdivided into 4 groups of 6 mice each. From the day when the tumor size (width$^2$×length/2) measured by using a vernier caliper reached 100 mm$^3$, 300 µg of each of the cell permeable p18 recombinant proteins $HM_1p18$ (Group 3, 1 µg/µl) and $Hp18M_1$ (Group 4, 1 µl/µg), all of which contain a kFGF4-derived MTD fused thereto, was administered daily to the mice for 21 days via intraperitoneal injection. As a control, 300 µl of each of the vehicle (RPMI 1640 medium, Group 1) and Hp18 not being fused to a MTD (Group 2) was administered to the mice via intraperitoneal injection for 21 days. After the injection was completed, the tumor size and body weight of the mouse in each group were measured, where the results are shown in FIGS. 14a and 14b.

Figure 14A:
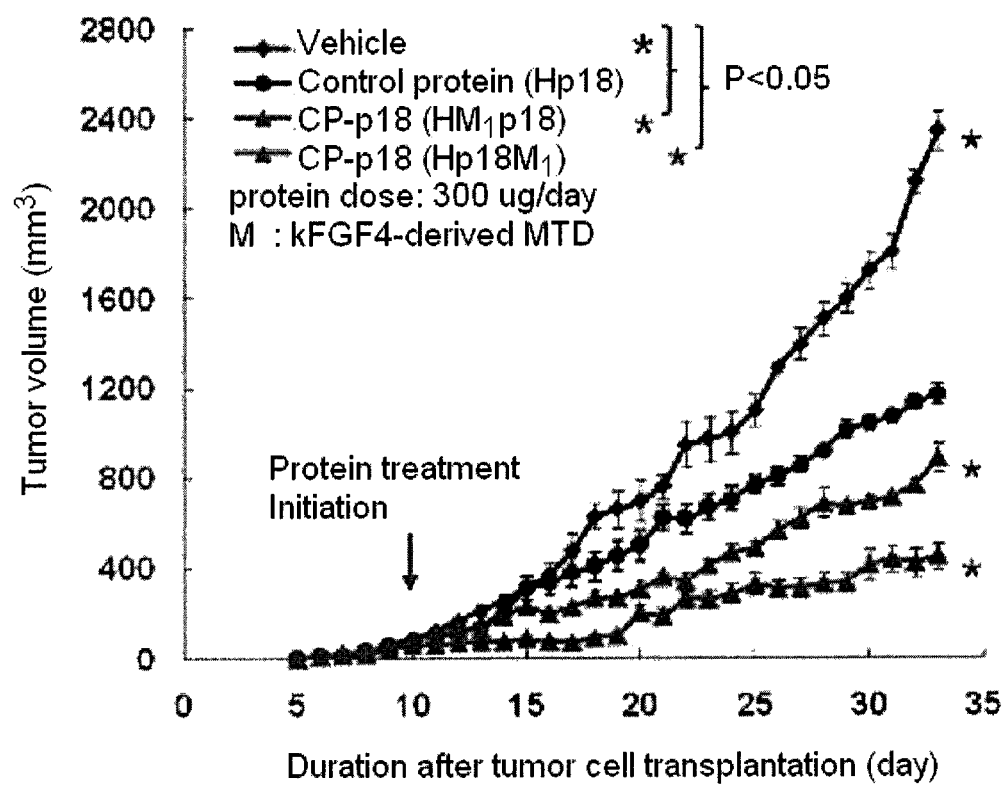
FIGS. 14a and 14b are graphs illustrating the change in tumor size and body weight, respectively, in a tumor-bearing mouse where each of the cell permeable p18 recombinant proteins, $HM_1p18$ and $Hp18M_1$, according to the present invention was administered via intraperitoneal injection for 21 days.
Figure 14B:
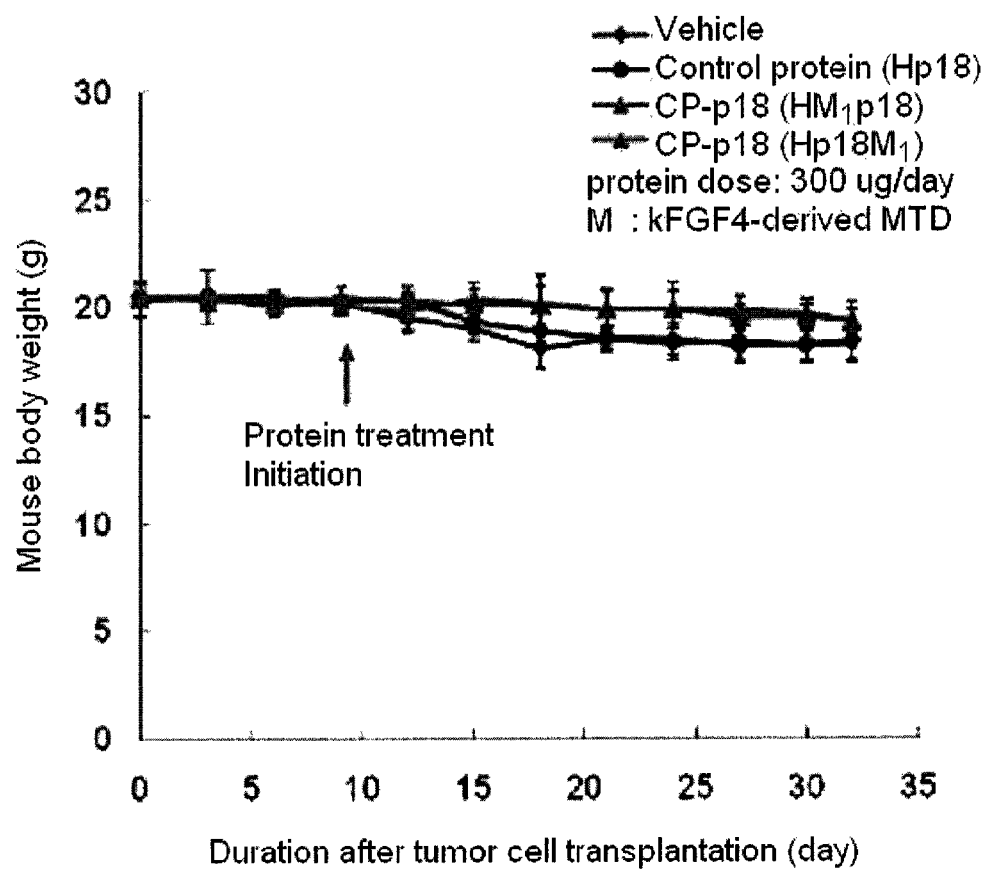
Figure 15:
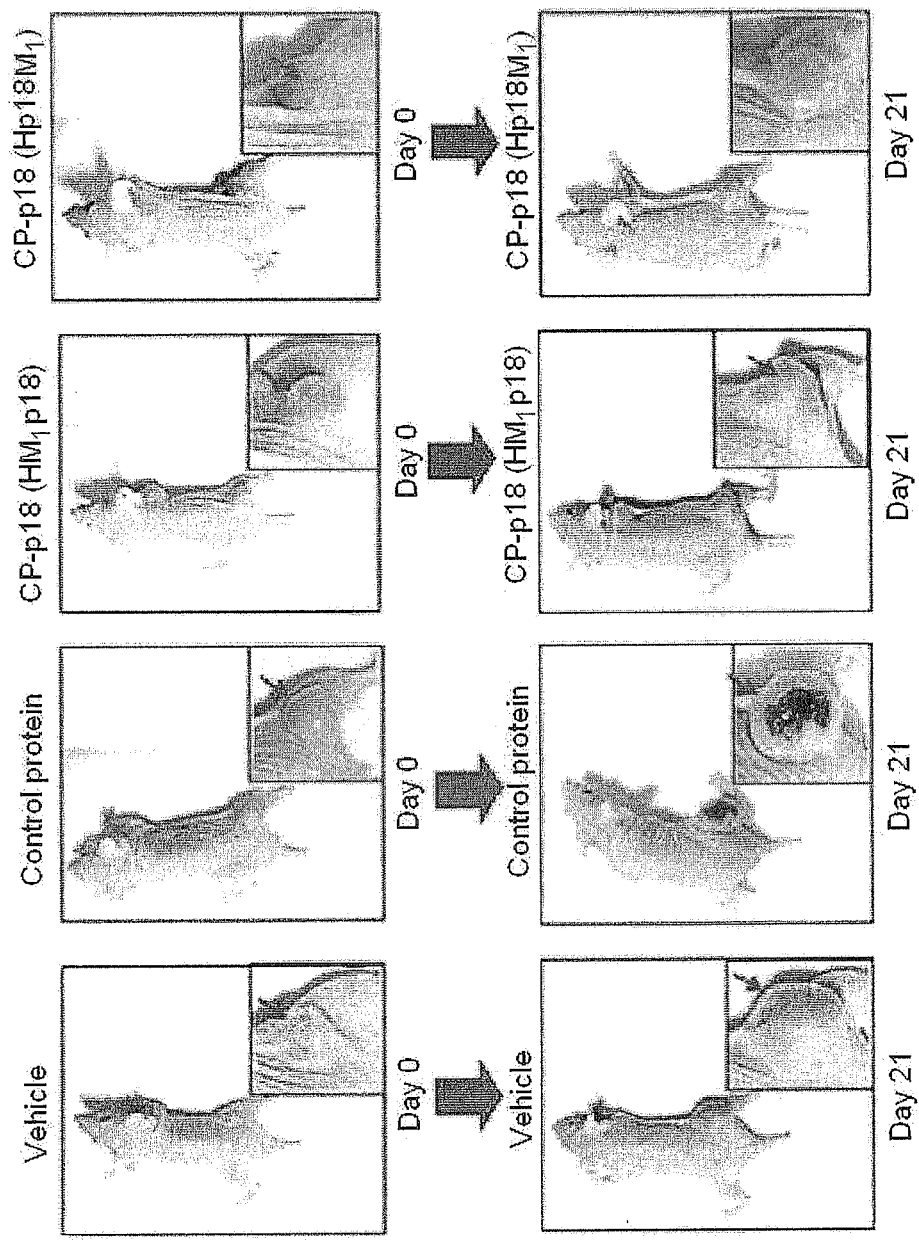
FIG. 15 is a photograph illustrating the change in tumor size in a tumor-bearing mouse, where each of the cell permeable p18 recombinant proteins $HM_1p18$ and $Hp18M_1$ according to the present invention was administered via intraperitoneal injection for 21 days, as compared with a control mouse.

Referring to the results shown in FIGS. 14a and 14b, while the tumor size of the mice treated with the cell permeable p18 recombinant proteins $HM_1p18$ and $Hp18M_1$ (Groups 3 and 4) was significantly reduced compared to that of the control (Groups 1 and 2), there was no meaningful difference in body weight between the control mice and cell permeable p18 recombinant protein treated mice. The mean value P for the tumor size and body weight in the mice treated with the cell permeable p18 recombinant proteins was less than 0.05, indicating that the results are meaningful. FIG. 15 shows photographs visualizing the change in tumor size and body weight in mice administered with the cell permeable p18 recombinant proteins according to the present invention for 21 days. It was visually observed that the mice treated with the cell permeable p18 recombinant protein showed significantly reduced tumor size than the control mice.

<7-2> Anticancer Effect after Administration

In order to examine the durability of the in vivo anticancer effect of the cell permeable p18 recombinant proteins ($HM_1p18$, $Hp18M_1$) after administration, each of the recombinant proteins was administered to the mice for 21 days according to the same method as described in section <7-1> of Example 7 above. After the administration was terminated, 2 mice were selected from each group, and their tumor size was observed for 7 days.

Figure 16A:
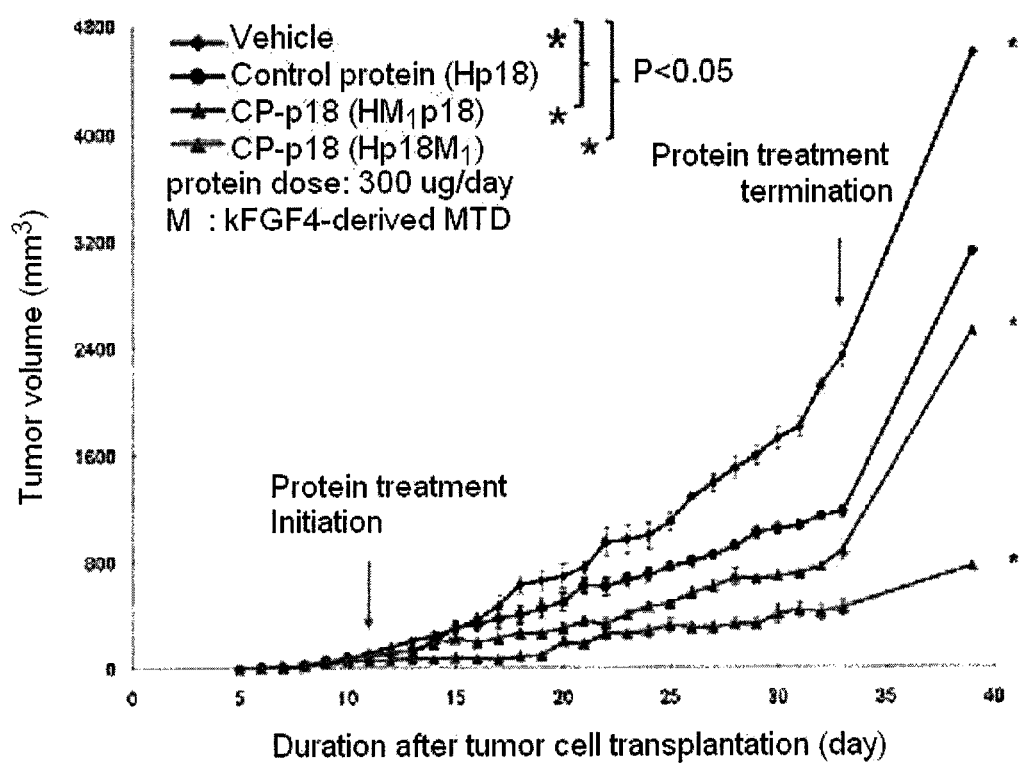
FIGS. 16a and 16b are graphs illustrating the change in tumor size and body weight, respectively, in a tumor-bearing mouse where each of the cell permeable p18 recombinant proteins, $HM_1p18$ and $Hp18M_1$, according to the present invention was administered via intraperitoneal injection for 21 days, after which the administration was terminated for 7 days.
Figure 16B:
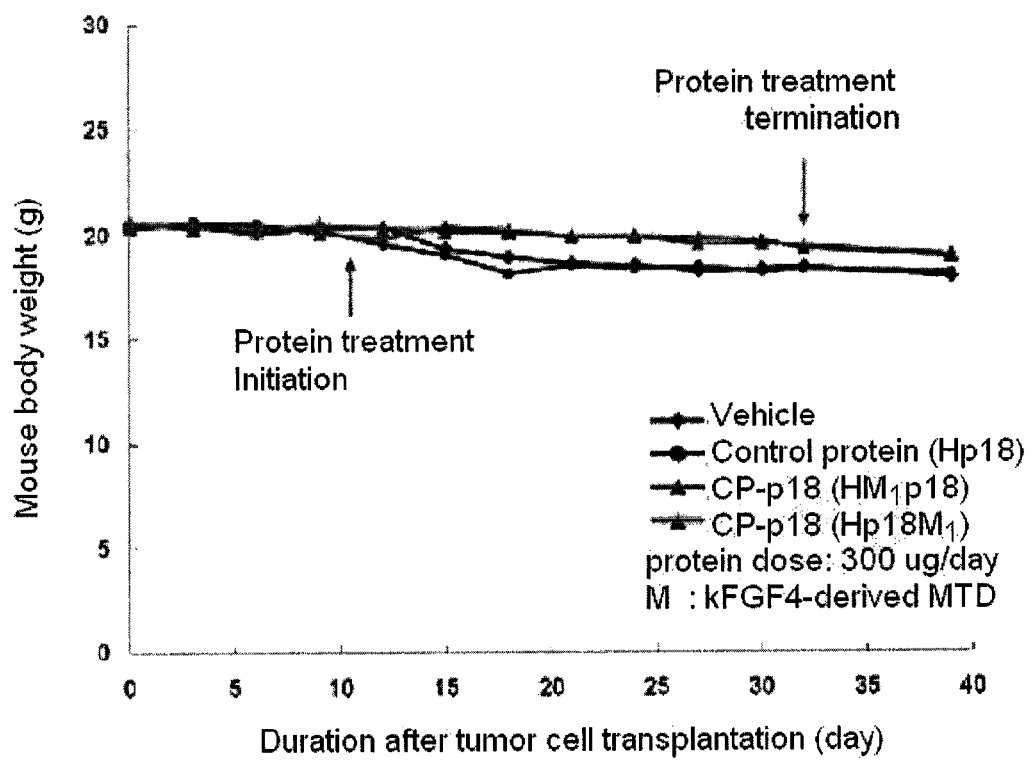

According to the results shown in FIGS. 16a and 16b, the tumor size was increased in all of the experimental groups. In particular, while the tumor size was remarkably increased in the $HM_1p18$ treated mice (Group 3) that showed significantly reduced tumor size during the administration, as similar to the control, the $Hp18M_1$ treated mice (Group 4) showed a significantly smaller increase in tumor size. Further, while the control and vehicle treated mice exhibited gradually decreased body weight, the mice treated with the cell permeable p18 recombinant protein ($Hp18M_1$) did not show a decrease in body weight compared to the control mice. These results suggest that the cell permeable p18 recombinant protein $Hp18M_1$ can stably maintain its anticancer effect for a prolonged period, and thus can be effectively used as a cell cycle inhibitor in cancer cells.

Example 8

In Vivo Function of Cell Permeable p18 Recombinant Proteins—Intravenous Injection <8-1> Anticancer Effect During Administration In order to examine the in vivo function of the cell permeable p18 recombinant proteins according to the present invention, HCT-116 cells ($1 \times 10^7$) were subcutaneously injected to the right leg of a 5-week old MHC-deficient Balb/c nu/nu mice by using a syringe according to the same method as described in Example 7 above. Fifteen mice were subdivided into 3 groups of 5 mice. The mice bearing a tumor of 70 to 80 mm$^3$ in size (width$^2$×length/2) were selected by using a vernier caliper. Each of the cell permeable p18 recombinant protein ($HM_3p18$, 300 µg) to which JO-103 MTD was fused, a vehicle (RPMI 1640 medium, 300 µl) and the recombinant protein Hp18 not being fused to a MTD (300 µg) as a control was daily administered to the tumor-bearing mice via intravenous injection for 14 days.

Figure 17A:
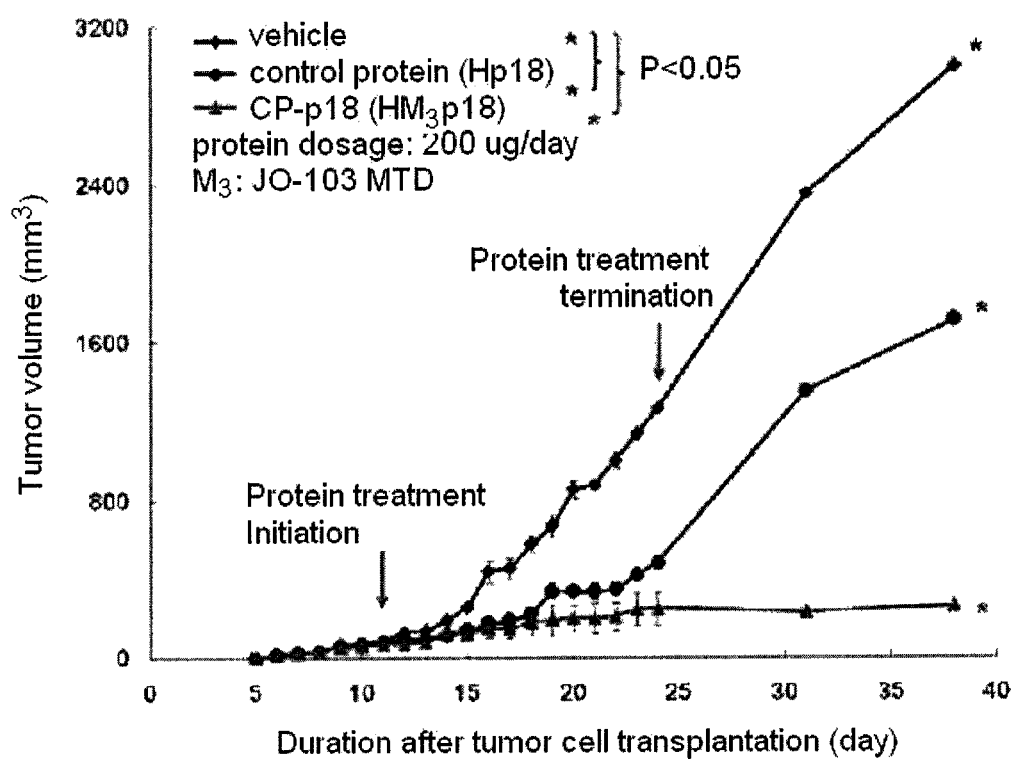
FIGS. 17a and 17b are graphs illustrating the change in tumor size and body weight, respectively, in a tumor-bearing mouse where the cell permeable p18 recombinant protein $HM_3p18$ according to the present invention was administered via intravenous injection for 14 days, after which the administration was terminated for 14 days.
Figure 17B:
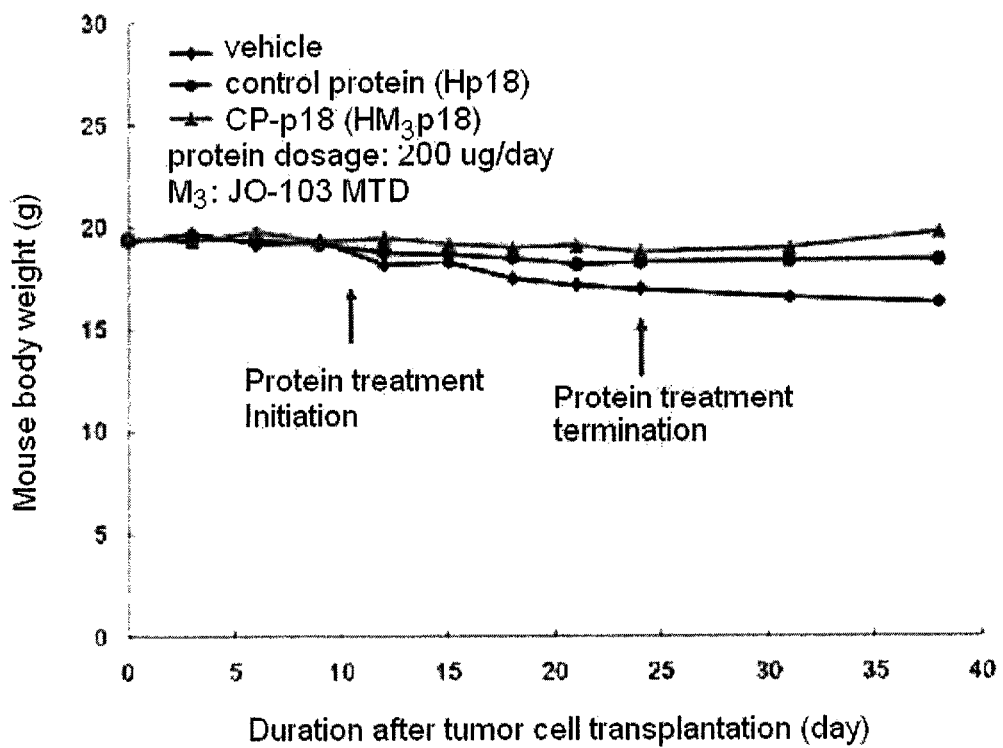
Figure 18:
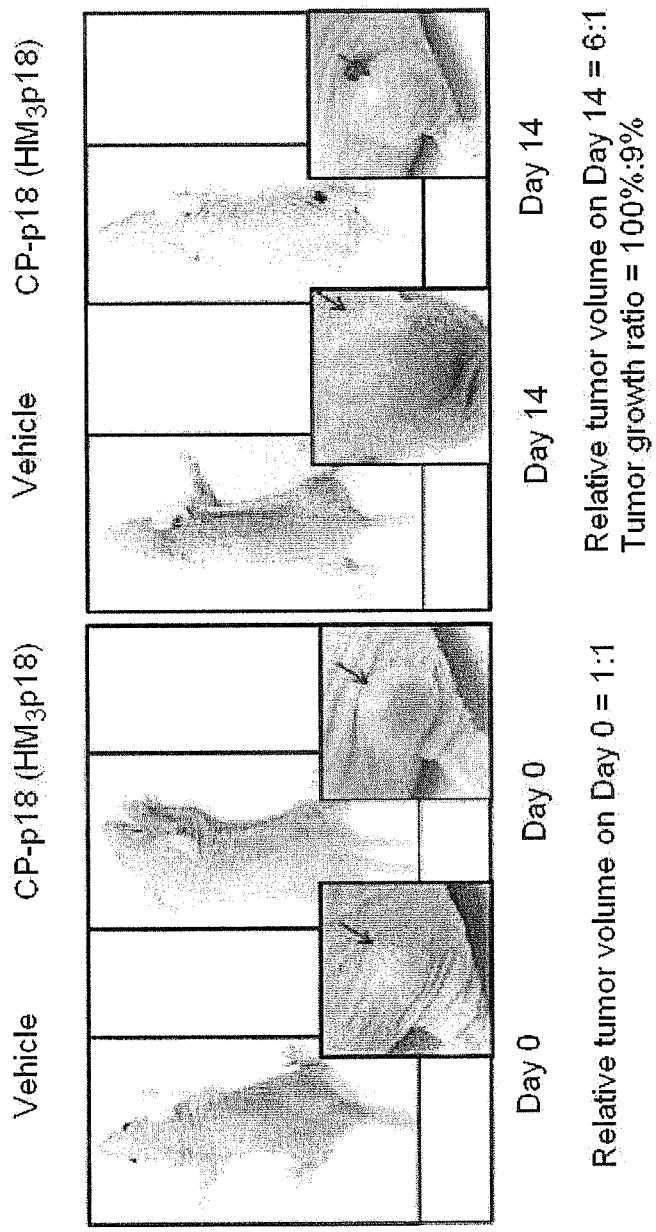
FIG. 18 is a photograph illustrating the change in tumor size and body weight in a tumor-bearing mouse where the cell permeable p18 recombinant protein $HM_3p18$ according to the present invention was administered via intravenous injection for 14 days, as compared with a control mouse.

According to the results shown in FIGS. 17a and 17b, tumor growth was significantly suppressed in the mice treated with the cell permeable p18 recombinant protein ($HM_3p18$) compared to the control mice. Further, while the control mice exhibited gradually decreased body weight, the mice treated with the cell permeable p18 recombinant protein ($HM_3p18$) did not show a decrease in body weight compared to the control mice and gained body weight as tumor growth was suppressed. FIG. 18 shows photographs visualizing the change in tumor size in mice administered with the cell permeable p18 recombinant protein according to the present invention via intravenous injection for 14 days, as compared with a control mouse.

<8-2> Anticancer Effect after Administration

In order to examine the durability of the in vivo anticancer effect of the cell permeable p18 recombinant proteins ($HM_3p18$) after administration, each of the recombinant proteins was administered to the mice for 14 days according to the same method as described in section <8-1> of Example 8. After the administration was terminated, 2 mice were selected from each group and their tumor size was observed for 14 days.

Figure 19:
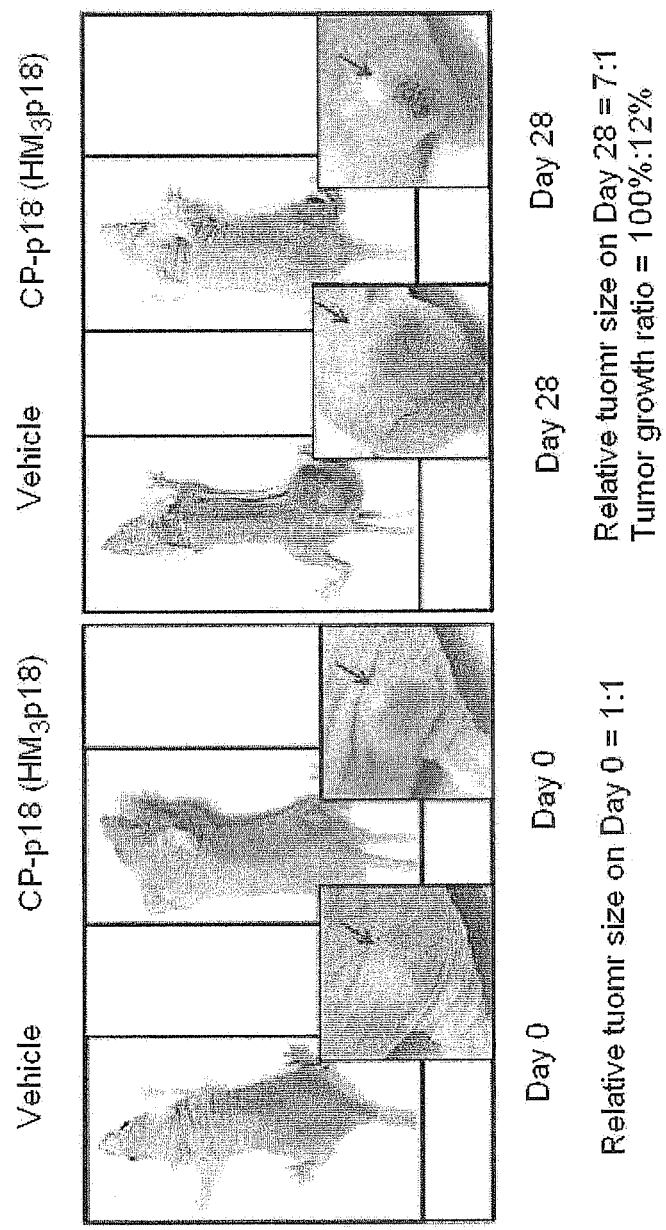
FIG. 19 is a photograph illustrating the change in tumor size and body weight in a tumor-bearing mouse where the cell permeable p18 recombinant protein $HM_3p18$ according to the present invention was administered via intravenous injection for 14 days, after which the administration was terminated for 14 days, as compared with a control mouse.

Referring to the results shown in FIG. 19, while the tumor size was remarkably increased in the control mice (vehicle), the mice where administration of the cell permeable p18 recombinant protein ($HM_3p18$) was terminated maintained similar tumor size to the tumor during administration without causing any sudden change in tumor size. These results suggest that the cell permeable p18 recombinant protein can completely reprogram cancer cells into normal cells by suppressing cell cycle progression and cell division, and thus, can be effectively used as a cell cycle inhibitor in cancer cells.

Example 9

In Vivo Function of Cell Permeable p18 Recombinant Proteins—Intratumoral Injection <9-1> Anticancer Effect During Administration In order to examine the in vivo function of the cell permeable p18 recombinant proteins according to the present invention, HCT-116 cells ($1\times10^7$) were subcutaneously injected to the right leg of a 5-week old MHC-deficient Balb/c nu/nu mice by using a syringe according to the same method as described in Example 7 above. Twenty five mice were subdivided into 5 groups of 5 mice. The mice bearing a tumor of 90 to 100 mm$^3$ in size (width$^2$×length/2) were selected by using a vernier caliper. Each of the cell permeable p18 recombinant proteins Hp18M$_1$ (300 µg) to which kFGF-derived MTD was fused, HM$_2$p18M$_2$ (300 µg) to which JO-101 MTD was fused, HM$_3$p18 (300 µg) to which JO-103 MTD was fused, Hp18 not being fused to a MTD (300 µg), and a vehicle (RPMI 1640 medium, 300 µl) as a control was administered to the tumor-bearing mice via intratumoral injection.

Figure 20A:
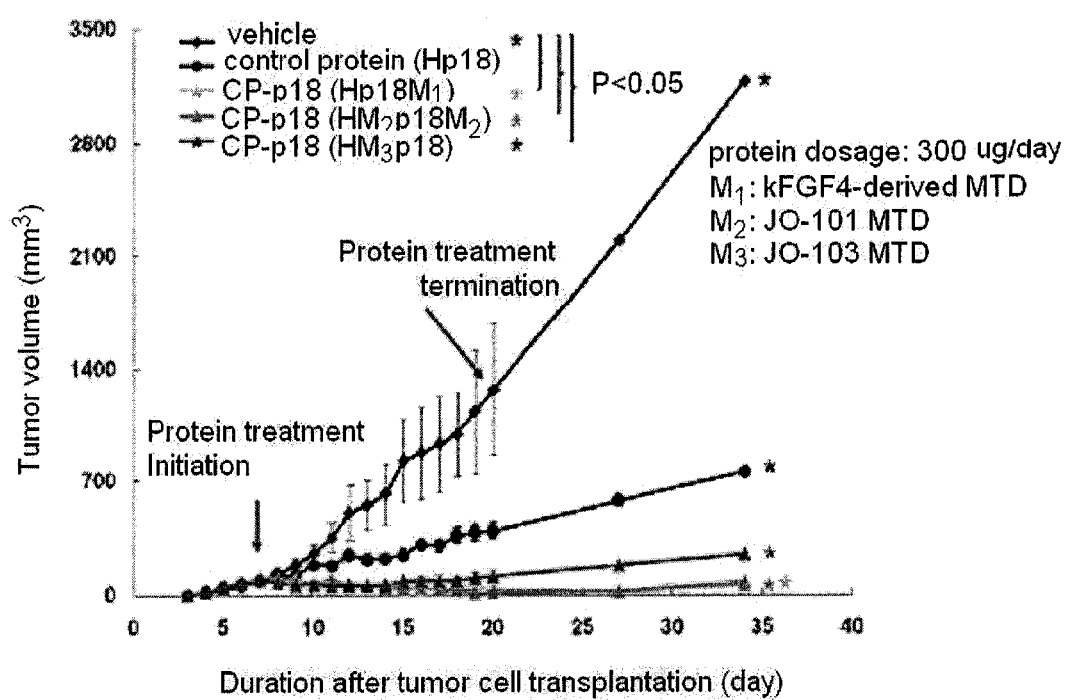
FIGS. 20a and 20b are graphs illustrating the change in tumor size and body weight, respectively, in a tumor-bearing mouse where each of the cell permeable p18 recombinant proteins, $Hp18M_1$, $HM_2p18M_2$ and $HM_3p18$, according to the present invention was administered via intratumoral injection, after which the administration was terminated for 14 days.
Figure 20B:
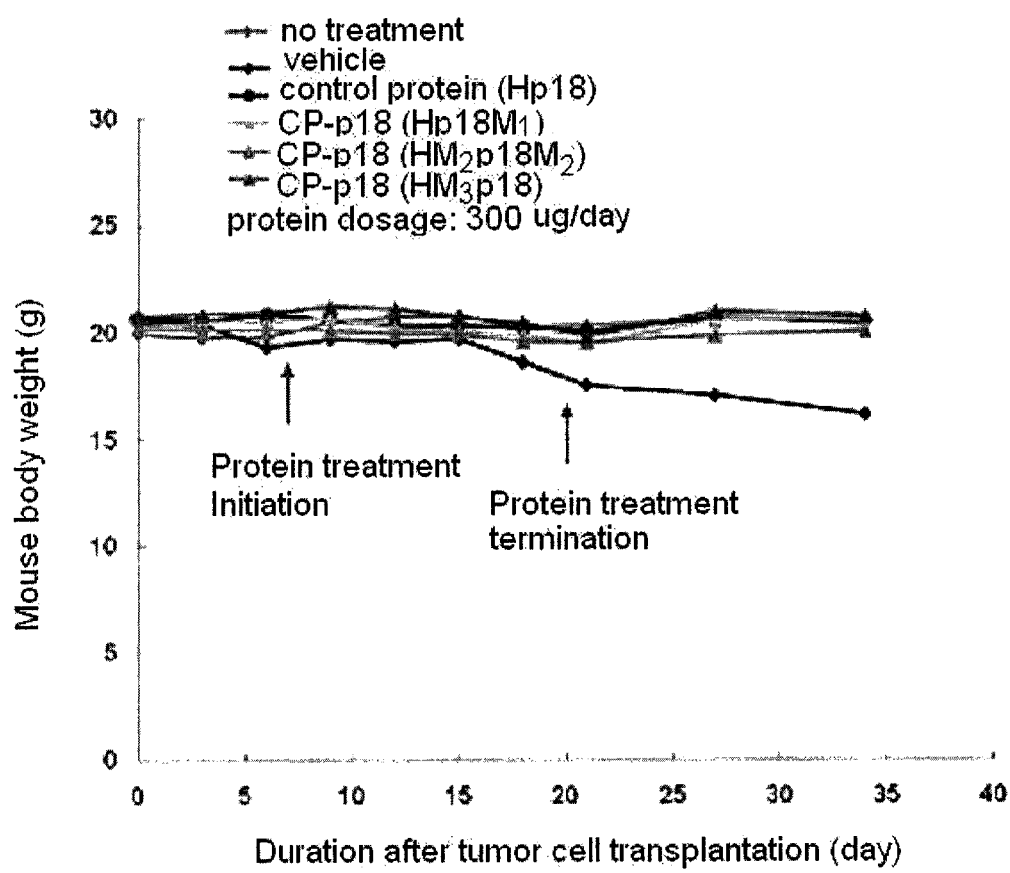
Figure 21:
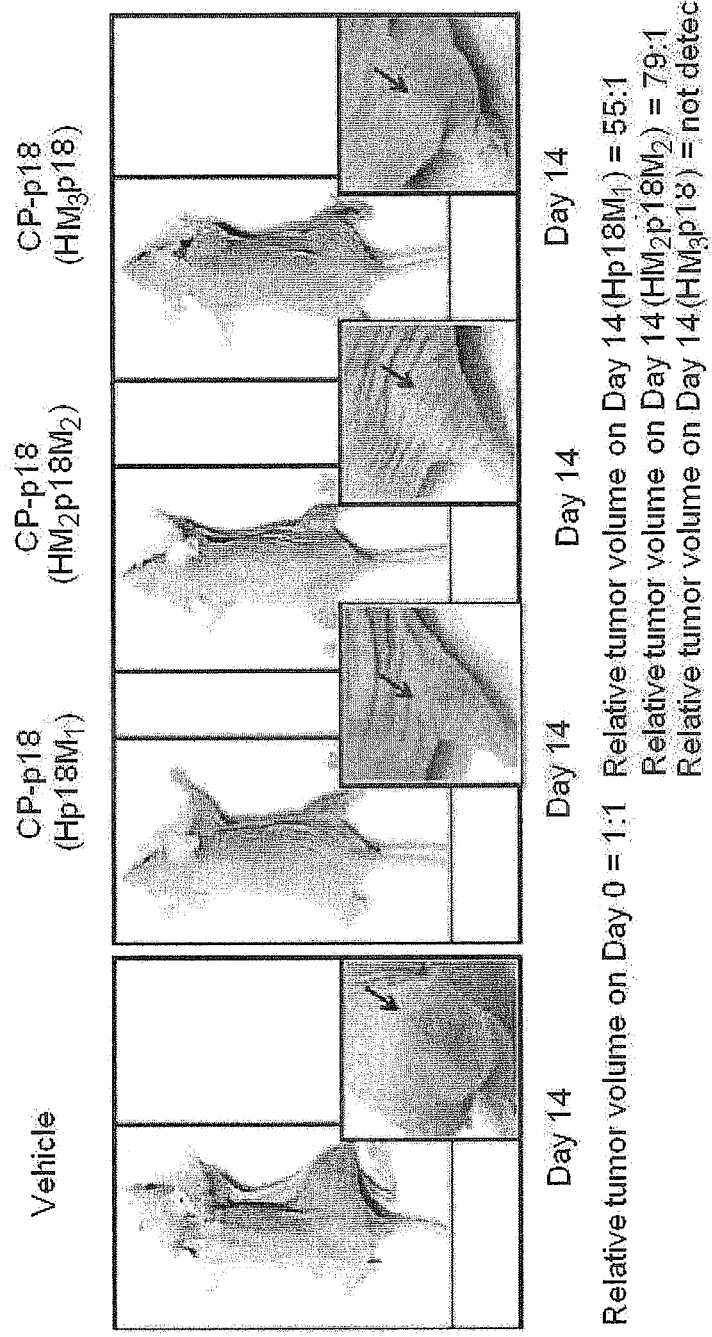
FIG. 21 is a photograph illustrating the change in tumor size and body weight in a tumor-bearing mouse where each of the cell permeable p18 recombinant proteins, $Hp18M_1$, $HM_2p18M_2$ and $HM_3p18$, according to the present invention was administered via intratumoral injection for 14 days, as compared with a control mouse.

According to the results shown in FIGS. 20a and 20b, tumor growth was significantly reduced in the mice treated with the cell permeable p18 recombinant protein (Hp18M$_1$, HM$_2$p18M$_2$, HM$_3$p18) compared to the control mice. Further, while the control mice showed gradually decreased body weight, the mice treated with the cell permeable p18 recombinant proteins (Hp18M$_1$, HM$_2$p18M$_2$, HM$_3$p18) did not show a decrease in body weight compared to the control mice and gained body weight as tumor growth was suppressed. FIG. 21 shows photographs visualizing the change in tumor size in the mice administered with the cell permeable p18 recombinant protein according to the present invention via intratumoral injection for 14 days, as compared with a control mouse.

<9-2> Anticancer Effect after Administration

In order to examine the durability of in vivo anticancer effect of the cell permeable p18 recombinant proteins (Hp18M$_1$, HM$_2$p18M$_2$, HM$_3$p18) after administration, each of the recombinant proteins was administered to the mice for 14 days according to the same method as described in section <9-1> of Example 9. After the administration was terminated, two mice were selected from each group, and their tumor size was observed for 14 days.

Figure 22:
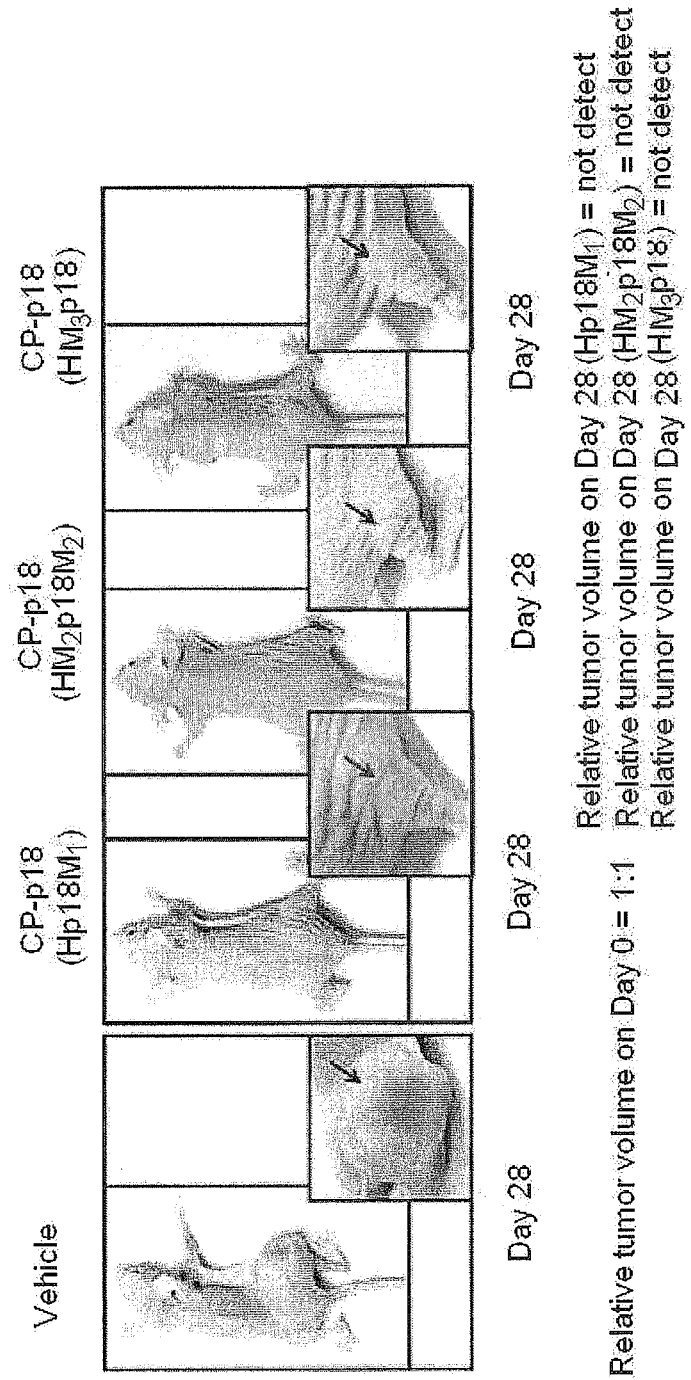
FIG. 22 is a photograph illustrating the change in tumor size and body weight in a tumor-bearing mouse where each of the cell permeable p18 recombinant proteins, $Hp18M_1$, $HM_2p18M_2$ and $HM_3p18$, according to the present invention was administered via intratumoral injection for 14 days, after which the administration was terminated for 14 days, as compared with a control mouse.

According to the results shown in FIG. 22, while the tumor size was remarkably increased in the control mice (vehicle), tumor growth was clearly suppressed in the mice administered with the cell permeable p18 recombinant proteins according to the present invention.

Example 10

Histological Analysis after the Administration of Cell Permeable p18 Recombinant Protein I In order to examine the effect of inducing apoptosis in tumor tissues after the administration of the cell permeable p18 recombinant proteins, a histological analysis using hematoxylin & eosin staining was performed on the same mouse model as used in Example 8.

In particular, the cell permeable p18 recombinant protein (HM$_3$p18), vehicle, and Hp18 (control) were administered to the mice subdivided into three groups (5 mice per group) via intravenous injection for 14 days, respectively, according to the same method as described in Example 8. After three mice were selected from each group and sacrificed, tumor tissue samples were extracted therefrom. The other two mice remaining in each group had undergone further observation for 14 days after the administration was terminated, and then, tumor tissue samples were extracted therefrom. Each tumor tissue extracted above was fixed in formalin and embedded in paraffin melted at 62° C. in an embedding center, to thereby prepare a paraffin block. The paraffin block was sliced with a microtome to have a thickness of 4 µm, where the slices were mounted on a slide glass and treated with xylene for 5 minutes three times to remove paraffin. Next, the glass slide was hydrated by successively treating with 100%, 95%, 90%, 80% and 70% ethanol each for 2 minutes, washed with water for 5 minutes, and then, stained with hematoxylin & eosin. Finally, the glass slide was dehydrated by successively treating with 70%, 80%, 90%, 95%, and 100% ethanol each for 10 seconds and dewaxed by treating with xylene twice each for 3 minutes. And then, the glass slide was sealed with Canada balsam as a mounting medium and observed with an optical microscope.

Figure 23:
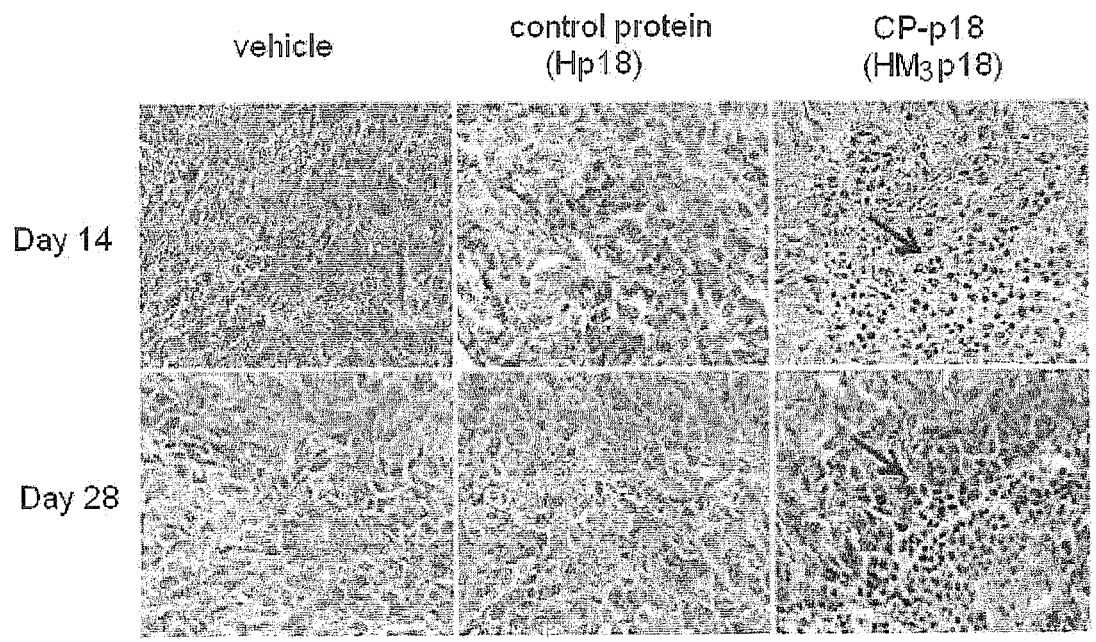
FIG. 23 is a photograph of haematoxylin & eosin staining showing the histological change in a mouse tumor tissue extracted from a mouse administered with the cell permeable p18 recombinant protein $HM_3p18$ via intravenous injection.

Referring to the results shown in FIG. 23, there was no significant histological change in tumor tissue extracted from the mice treated with the vehicle and control protein (Hp18), while the morphological changes characteristic of apoptotic cell death including nuclear condensation or fragmentation and DNA fragmentation were observed in the tumor tissue extracted from the mice treated with the cell permeable p18 recombinant protein (HM$_3$p18) according to the present invention. Further, it was also observed that in the mice treated with the cell permeable p18 recombinant protein according to the present invention, apoptosis is still induced in cancer cells after the administration was terminated.

Example 11

Histological Analysis after the Administration of Cell Permeable p18 Recombinant Protein II In order to examine the effect of inducing apoptosis in tumor tissues after the administration of the cell permeable p18 recombinant proteins, a histological analysis using hematoxylin & eosin staining was performed on the same mouse model as used in Example 9.

The hematoxylin & eosin staining was performed according to the same method as described in Example 10, except that each of the cell permeable p18 recombinant proteins (Hp18M$_1$, HM$_2$p18M$_2$, HM$_3$p18), vehicle, and Hp18 (control) was administered to the mice subdivided into five groups (5 mice per group) via intratumoral injection for 14 days according to the same method as described in Example 9, and tumor tissue samples were extracted from a mouse in each group.

Figure 24:
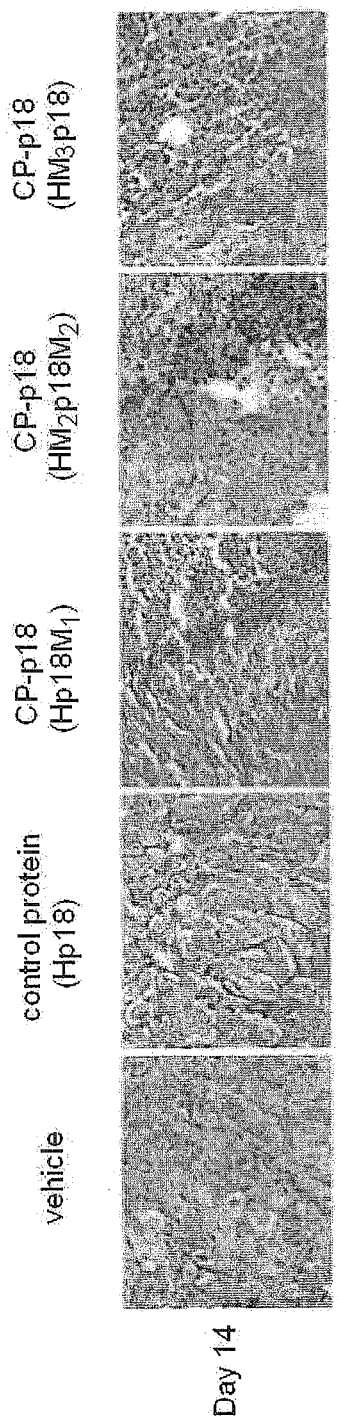
FIG. 24 is a photograph of haematoxylin & eosin staining showing the histological change in a mouse tumor tissue extracted from a mouse administered with each of the cell permeable p18 recombinant proteins, $Hp18M_1$, $HM_2p18M_2$ and $HM_3p18$, via intratumoral injection.

According to the results shown in FIG. 24, there was no significant histological change in tumor tissue extracted from the mice treated with the vehicle and control protein (Hp18), while the morphological changes characteristic of apoptotic cell death including nuclear condensation or fragmentation and DNA fragmentation were observed in the tumor tissue extracted from the mice treated with the cell permeable p18 recombinant protein (Hp18M$_1$, HM$_2$p18M$_2$, HM$_3$p18) according to the present invention.

Example 12

Analysis of Apoptosis-Inducing Effect after the Administration of Cell Permeable p18 Recombinant Protein I In order to examine the effect of inducing apoptosis in tumor tissues after the administration of the cell permeable p18 recombinant proteins, a TUNEL assay was performed by using the same mouse model as described in Example 8.

In particular, each of the cell permeable p18 recombinant protein (HM$_3$p18), vehicle, and Hp18 (control) was administered to the mice subdivided into three groups (5 mice per group) via intravenous injection for 14 days according to the same method as described in Example 8. After three mice were selected from each group and sacrificed, tumor tissue samples were extracted therefrom. The other two mice remaining in each group had undergone further observation for 14 days after the administration was terminated, and then, tumor tissue samples were extracted therefrom. The tissue specimen was prepared by using the extracted tumor tissue according to the same method as described in Example 10 and mounted on a glass slide. The glass slide was treated with xylene for 5 minutes three times, to thereby remove paraffin. It was then successively treated with 100%, 95%, 90%, 80%, and 70% ethanol each for 2 minutes so as to dehydrate the tumor tissue, followed by incubation in PBS for 5 minutes. The glass slide was treated with 0.1% Trition® X-100 dissolved in a 0.1% sodium citrate solution for 8 minutes, and washed with PBS twice for 2 minutes. After a drop of TUNEL reaction buffer (50 µl, ROCHE, USA) was added to the glass slide, the glass slide was incubated in a humidified incubator at 37□ for 1 hour, washed with PBS three times, and then, observed with a fluorescence microscope.

Figure 25:
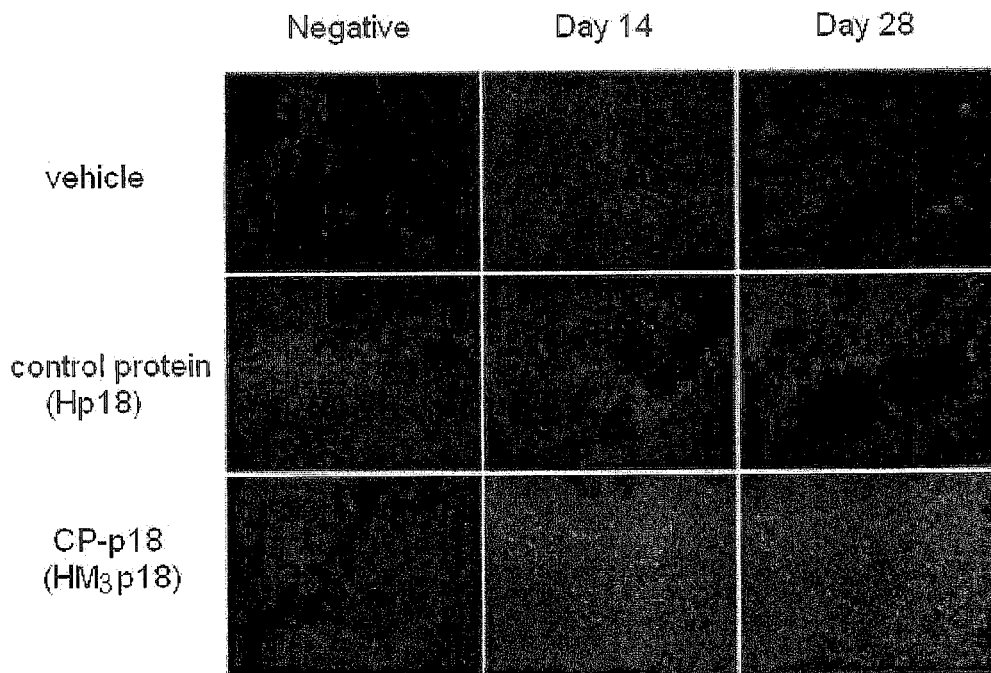
FIG. 25 is a photograph of a terminus deoxynucleotidyl transferase-mediated dUTP nick-end labeling (TUNEL) analysis showing the apoptosis-inducing effect in a mouse tumor tissue extracted from a mouse administered with the cell permeable p18 recombinant protein $HM_3p18$ via an intravenous injection.

Referring to the results shown in FIG. 25, there was no significant histological change in tumor tissue extracted from the mice treated with the vehicle and control protein (Hp18), while in the mouse tumor tissues treated with the cell permeable p18 recombinant protein (HM$_3$p18), a region stained in red representing the characteristic of apoptosis was observed, confirming the effect of inducing apoptosis of the cell permeable p18 recombinant protein according to the present invention. Further, it was also observed that in the mouse group treated with the cell permeable p18 recombinant protein according to the present invention, apoptosis was still induced in cancer cells 14 days after the administration was terminated.

Example 13

Analysis of Apoptosis-Inducing Effect after the Administration of Cell Permeable p18 Recombinant Proteins II In order to examine the effect of inducing apoptosis in tumor tissues after the administration of the cell permeable p18 recombinant proteins, the following histochemical assay was performed by using an ApopTag Peroxidase in situ Apoptosis Detection Kit (CHEMICON, S7100).

In particular, each of the cell permeable p18 recombinant protein (HM$_3$p18), vehicle, and Hp18 (control) was administered to the mice subdivided into three groups (5 mice per group) via intravenous injection for 14 days according to the same method as described in Example 8. After three mice were selected from each group and sacrificed, tumor tissue was extracted therefrom. The other two mice remaining in each group had undergone further observation for 14 days after the administration was terminated, and then, tumor tissue samples were extracted therefrom. The tissue specimen was prepared by using the extracted tumor tissue according to the same method as described in Example 10 and mounted on a glass slide. The glass slide was treated with xylene for 5 minutes three times, to thereby remove paraffin. It was then successively treated with 100%, 90%, and 70% ethanol each for 3 minutes so as to dehydrate the tumor tissue, followed by incubation in PBS for 5 minutes. The glass slide was treated with 20 µg/ml of proteinase K (SIGMA) for 15 minutes, washed with distilled water, and then, treated with 3% H$_2$O$_2$ (vol/vol, in PBS) for 5 minutes, to thereby inhibit the activity of endogenous peroxidase. The glass slide was treated with an equilibration buffer for 10 seconds, followed by treating with a terminus dexoynucleotidyl transferase (TdT) at 37° for 1 hour. After the reaction was completed, the glass slide was treated with a stop buffer and washed. Next, the glass slide was treated with a DAB coloring agent for 5 minutes, and counterstained with methyl green. After the staining, the glass slide was dehydrated, sealed with a cover slip, and observed with an optical microscope.

Figure 26:
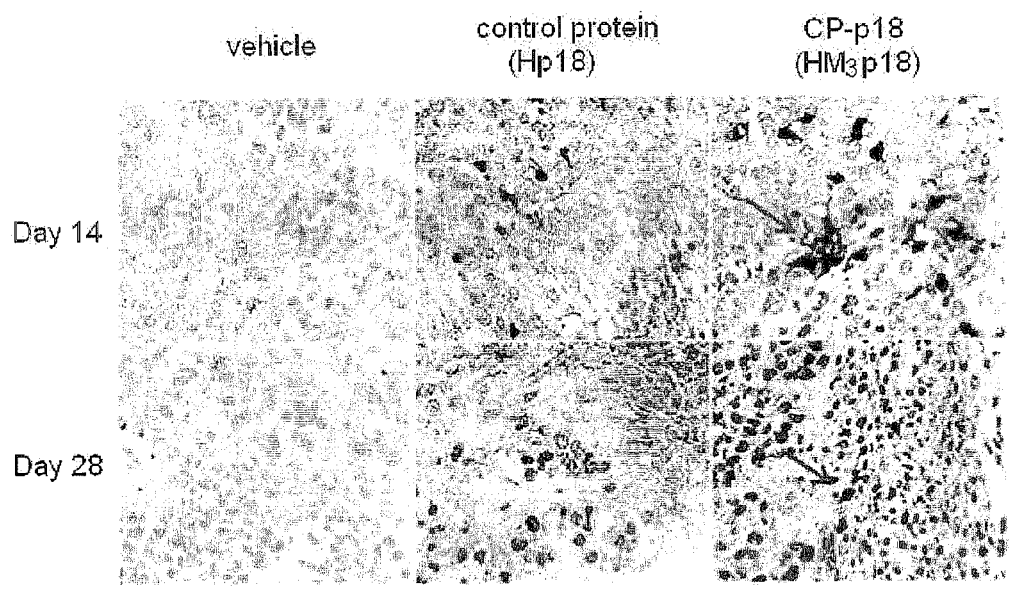
FIG. 26 is a photograph of an ApopTag analysis showing the apoptosis-inducing effect in a mouse tumor tissue extracted from a mouse administered with the cell permeable p18 recombinant protein $HM_3p18$ via intravenous injection.

According to the results shown in FIG. 26, there was no significant histological change in tumor tissue extracted from the mice treated with the vehicle and control protein (Hp18), while in the mouse tumor tissues treated with the cell permeable p18 recombinant protein (HM$_3$p18), a region stained in brown representing the characteristic of apoptosis was observed, confirming the effect of inducing apoptosis of the cell permeable p18 recombinant protein according to the present invention. Further, it was also observed that in the mice treated with the cell permeable p18 recombinant protein according to the present invention, apoptosis is still induced in cancer cells 14 days after the administration was terminated.

Example 14

Analysis of Apoptosis-Inducing Effect after the Administration of Cell Permeable p18 Recombinant Proteins III The TUNEL assay was performed according to the same method as described in Example 12 except that each of the cell permeable p18 recombinant protein (Hp18M$_1$, HM$_2$p18M$_2$, HM$_3$p18), vehicle and Hp18 (control) was administered to the mice subdivided into five groups (5 mice per group) via intratumoral injection for 14 days according to the same method as described in Example 9, and tumor tissue samples were extracted from a mouse in each group.

Figure 27:
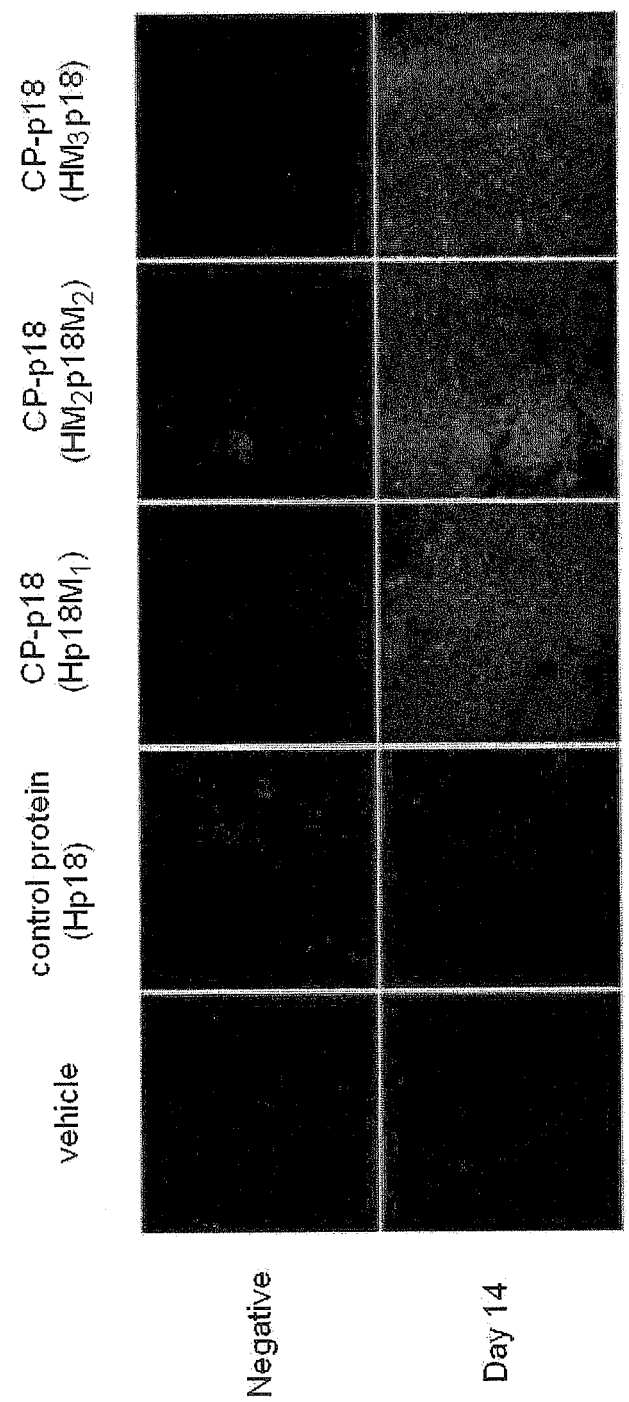
FIG. 27 is a photograph of a TUNEL analysis showing the apoptosis-inducing effect in a mouse tumor tissue extracted from a mouse administered with the cell permeable p18 recombinant proteins $Hp18M_1$, $HM_2p18M_2$ and $HM_3p18$ via intratumoral injection.

Referring to the results shown in FIG. 27, there was no significant histological change in tumor tissue extracted from the mice treated with the vehicle and control protein (Hp18), while in the mouse tumor tissues treated with the cell permeable p18 recombinant protein (Hp18M$_1$, HM$_2$p18M$_2$, HM$_3$p18), a region stained in red representing the characteristic of apoptosis was observed, confirming the effect of inducing apoptosis of the cell permeable p18 recombinant protein according to the present invention.

Example 15

Analysis of Apoptosis-Inducing Effect after the Administration of Cell Permeable p18 Recombinant Proteins IV The ApopTag assay was performed according to the same method as described in Example 13 except that each of the cell permeable p18 recombinant proteins (Hp18M$_1$, HM$_2$p18M$_2$, HM$_3$p18), vehicle, and Hp18 (control) was administered to the mice subdivided into five groups (5 mice per group) via intratumoral injection for 14 days according to the same method as described in Example 9, and tumor tissue samples were extracted from a mouse in each group.

Figure 28:
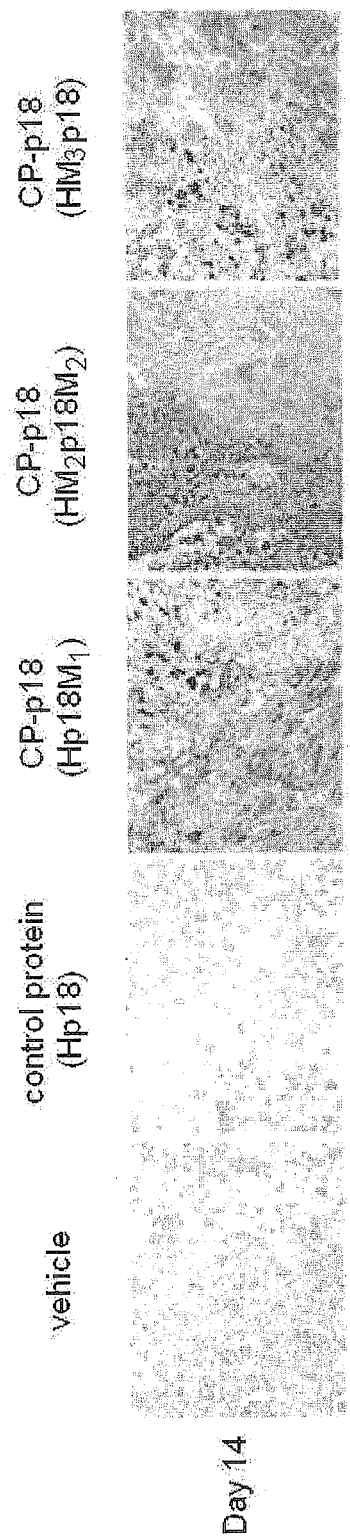
FIG. 28 is a photograph of an ApopTag analysis showing the apoptosis-inducing effect in a mouse tumor tissue extracted from a mouse administered with each of the cell permeable p18 recombinant proteins $Hp18M_1$, $HM_2p18M_2$ and $HM_3p18$ via intratumoral injection.

According to the results shown in FIG. 28, there was no significant histological change in tumor tissue extracted from the mice treated with the vehicle and control protein (Hp18), while in the mouse tumor tissues treated with the cell permeable p18 recombinant protein (Hp18M$_1$, HM$_2$p18M$_2$, HM$_3$p18), a region stained in brown representing the characteristics of apoptosis was observed, confirming the effect of inducing apoptosis of the cell permeable p18 recombinant protein according to the present invention.

Example 16

Comparison of Protein Expression Pattern after the Administration of Cell Permeable p18 Recombinant Proteins In order to examine the change in protein expression pattern in the tumor tissue treated with the cell permeable p18 recombinant protein according to the present invention, a microarray assay was performed as follows.

In particular, each of the cell permeable p18 recombinant protein (HM$_2$p18M$_2$), vehicle and Hp18 (control) was administered to the mice subdivided into three groups via intratumoral injection for 14 days, and then left alone for 14 days after the administration was terminated, according to the same method as described in Example 8 above. Fourteen days after the administration was terminated, tumor tissue samples were extracted from the mouse of each group and freezed with liquid nitrogen. Total RNA was isolated from the tumor tissue by using a TRIZOL reagent (INVITROGEN) according to the manufacturer's instruction, and treated with an RNase-free DNase (LIFE TECHNOLOGIES, Inc.), to thereby completely remove the remaining genomic DNA.

The thus isolated RNA was subjected to synthesis and hybridization of a target cRNA probe by using a Low RNA Input Linear Amplification kit (AGILENT TECHNOLOGY) according to the manufacturer's instruction. In brief, 1 μg of total RNA was mixed with a T7 promoter specific primer and reacted at 65° for 10 minutes. A cDNA master mix was prepared by mixing a first strand buffer (5×), 0.1 M DTT, 10 mM dNTP mix, RNase-Out and MMLV-RT (reverse transcriptase), and added to the reaction mixture. The resulting mixture was reacted at 40° C. for 2 hours, followed by reacting at 65° for 15 minutes, to thereby terminate the reverse transcription and dsDNA synthesis. A transcription master mix was prepared by mixing a transcription buffer (4×), 0.1 M DTT, NTP mix, 50% PEG, RNase-Out, inorganic pyrophosphatase, T7-RNA polymerase and cyanine (3/5-CTP) according to the manufacturer's instruction. The thus prepared transcription master mix was added to the dsDNA reaction mixture and reacted at 40° for 2 hours so as to perform dsDNA transcription. The thus amplified and labeled cRNA was purified with a cRNA Cleanup Module (AGILENT TECHNOLOGY) according to the manufacturer's instruction. The labeled target cRNA was quantified by using a ND-1000 spectrophotometer (NANODROP TECHNOLOGIES, Inc.). After the labeling efficiency was examined, cRNA was mixed with a blocking agent (10×) and a fragmentation buffer (25×), and reacted at 60° for 30 minutes so as to carry out the fragmentation of cRNA. The fragmented cRNA was resuspended in a hybridization buffer (2×) and directly dropped on a Whole Human Genome Oligo Microarray (44K). The microarray was subjected to hybridization in a hybridization oven (AGILENT TECHNOLOGY) at 65° for 17 hours, followed by washing according to the manufacturer's instruction (AGILENT TECHNOLOGY).

The hybridization pattern was read by using a DNA microarray scanner (AGILENT TECHNOLOGY) and quantified by using a Feature Extraction Software (AGILENT TECHNOLOGY). Data normalization and selection of fold-changed genes were carried out by using a Gene Spring GX 7.3 soft wear (AGILENT TECHNOLOGY). The average of the normalized ratio was calculated by dividing a normalized signal channel strength by a normalized control channel strength. Functional annotation for a gene was conducted by using a Gene Spring GX 7.3 software (AGILENT TECHNOLOGY) according to the Gene Ontology™ Consortium.

Figure 29:
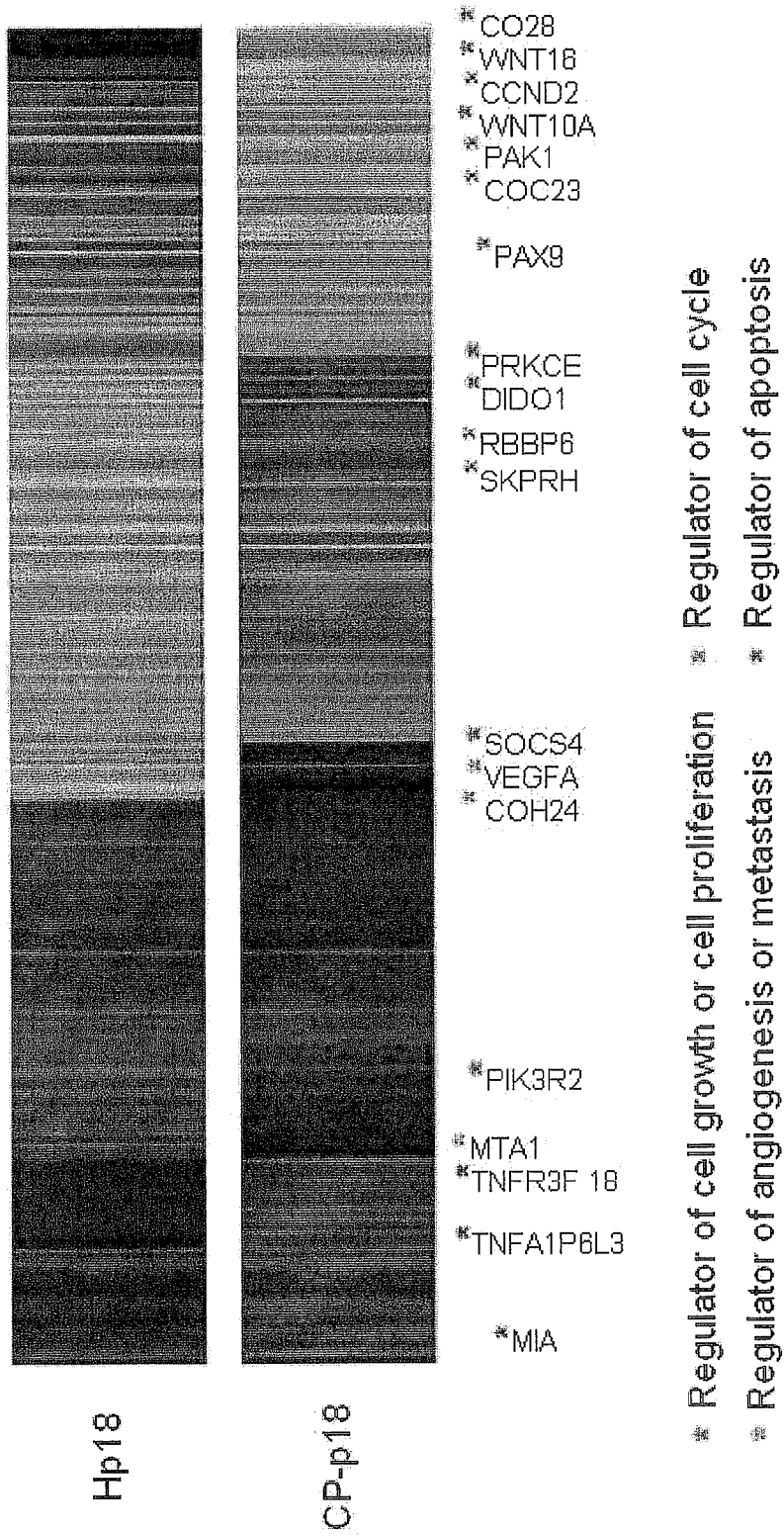
FIG. 29 is a photograph of a microarray analysis showing differential gene expression in a mouse tumor extracted from a mouse administered with the cell permeable p18 recombinant protein $HM_2p18M_2$ via intravenous injection.

The results of the microarray analysis are summarized in FIG. 29 and Tables 3 to 7, where Table 3 shows the expression pattern of apoptosis-relating genes, Tables 4a and 4b show that of cell cycle regulation-relating genes, Tables 5a to 5c show that of cell growth-relating genes, Table 6 shows that of cell proliferation-relating genes, and Table 7 shows that of metastasis and angiogenesis-relating genes.

TABLE 3

| Gene | Genbank ID | Exp. pattern Veh. vs Hp18 | Exp. pattern Veh. vs Cp-p18 | Total relative ratio | t-test/ p-값 |
|---|---|---|---|---|---|
| CD28 molecule | NM_006139 | 0.93 | 0.19 | 0.20 | 0.77/0.05 |
| Arachidonate 12-lipoxygenase | NM_000697 | 0.90 | 0.42 | 0.46 | 0.53/0.04 |
| Protein kinase C, epsilon | NM_005400 | 0.47 | 0.77 | 1.63 | 0.04/0.22 |
| Fem-1 homolog b (C. elegans) | NM_015322 | 0.43 | 0.77 | 1.76 | 0.02/0.13 |
| Death inducer-obliterator 1 | NM_080797 | 0.48 | 0.76 | 1.58 | 0.02/0.11 |
| Serum/glucocorticoid regulated kinase | NM_005627 | 0.48 | 0.73 | 1.51 | 0.02/0.09 |
| Serine/threonine kinase 17b | NM_04226 | 0.48 | 0.64 | 1.33 | 0.03/0.05 |
| v-abl Abelson murine leukemia viral oncogene homolog 1 | NM_007313 | 0.35 | 0.57 | 1.61 | 0.01/0.03 |
| Tumor necrosis factor (ligand) superfamily, member 18 | NM_005092 | 0.58 | 0.31 | 0.53 | 0.05/0.02 |
| p21/Cdc42/Rac1-activated kinase 1 (STE20 homolog, yeast) | NM_002576 | 0.63 | 0.31 | 0.50 | 0.05/0.01 |
| TAO kinase 2 | NM_004783 | 0.58 | 0.42 | 0.72 | 0.18/0.02 |
| Q9Y5L6 Apoptosis related protein APR-5 (Fragment) | | 0.54 | 0.36 | 0.67 | 0.03/0.01 |
| Tumor necrosis factor, alpha-induced protein 3 | NM_006290 | 0.53 | 0.42 | 0.80 | 0.03/0.02 |
| Forkhead box 01 | NM_002015 | 0.39 | 0.26 | 0.67 | 0.02/0.01 |
| BCL2-associated athanogene 4 | NM_004874 | 0.40 | 0.51 | 1.28 | 0.01/0.03 |
| SON DNA binding protein | NM_032195 | 0.44 | 0.55 | 1.23 | 0.02/0.03 |

TABLE 3-continued

| Gene | Genbank ID | Exp. pattern Veh. vs Hp18 | Exp. pattern Veh. vs Cp-p18 | Total relative ratio | t-test/ p- |
|---|---|---|---|---|---|
| FAST kinase domains 2 | NM_014929 | 0.48 | 0.58 | 1.20 | 0.02/0.03 |
| GULP, engulfment adaptor PTB domain containing 1 | NM_016315 | 0.44 | 0.52 | 1.19 | 0.02/0.03 |
| Vascular endothelial growth factor A | NM_001025366 | 2.07 | 1.42 | 0.69 | 0.00/0.00 |
| Coagulation factor II (thrombin) | NM_000506 | 2.14 | 1.18 | 0.55 | 0.02/0.02 |
| Phosphoinositide-3-kinase, regulatory subunit 2 (p85 beta) | NM_005027 | 4.96 | 1.56 | 0.32 | 0.01/0.05 |
| Tumor necrosis factor receptor superfamily, member 18 | NM_148901 | 1.54 | 3.66 | 2.38 | 0.08/0.01 |
| NADPH oxidase, EF-hand calcium binding domain 5 | NM_024505 | 1.14 | 2.15 | 1.88 | 0.38/0.02 |

TABLE 4a

| Gene | Genbank ID | Exp. pattern Veh. vs Hp18 | Exp. pattern Veh. vs Cp-p18 | Total relative ratio | t-test/ p- |
|---|---|---|---|---|---|
| Patched homolog 1 (*Drosophila*) | NM_000264 | 2.49 | 1.37 | 0.55 | 0.03/0.21 |
| Coagulation factor II (thrombin) | NM_000506 | 2.14 | 1.18 | 0.55 | 0.02/0.24 |
| Sjogren's syndrome/scleroderma autoantigen 1 | NM_006396 | 2.12 | 1.21 | 0.57 | 0.02/0.20 |
| Metastasis associated 1 | BC006177 | 2.42 | 0.97 | 0.40 | 0.02/0.79 |
| Cell division cycle 34 homolog (*S. cerevisiae*) | NM_004359 | 2.07 | 1.58 | 0.76 | 0.02/0.05 |
| B-cell CLL/lymphoma 2 | NM_000657 | 2.27 | 1.66 | 0.73 | 0.02/0.04 |
| v-mos Moloney murine sarcoma viral oncogene homolog | NM_005372 | 4.62 | 2.79 | 0.60 | 0.01/0.01 |
| centrin, EF-hand protein, 1 | NM_004066 | 2.10 | 1.63 | 0.78 | 0.02/0.03 |
| Vascular endothelial growth factor A | NM_001025366 | 2.07 | 1.42 | 0.69 | 0.00/0.00 |
| Rho guanine nucleotide exchange factor (GEF) 11 | NM_198236 | 1.16 | 2.21 | 1.91 | 0.61/0.04 |
| NADPH oxidase, EF-hand calcium binding domain 5 | NM_024505 | 1.14 | 2.15 | 1.88 | 0.38/0.02 |
| Cell division cycle 25 homolog A (*S. pombe*) | NM_001789 | 1.44 | 2.03 | 1.41 | 0.08/0.02 |
| SH3-domain binding protein 4 | NM_014521 | 2.08 | 3.99 | 1.92 | 0.02/0.01 |
| Transcription factor 7-like 2 (T-cell specific, HMG-box) | NM_030756 | 1.53 | 2.10 | 1.37 | 0.05/0.02 |
| Structural maintenance of chromosomes 1A | NM_006306 | 1.67 | 2.05 | 1.23 | 0.04/0.02 |
| Cyclin D2 | NM_001759 | 1.26 | 0.41 | 0.33 | 0.26/0.05 |
| Neurofibromin 1 | NM_000267 | 0.62 | 0.46 | 0.74 | 0.10/0.04 |
| Cyclin K | NM_003858 | 0.63 | 0.43 | 0.68 | 0.06/0.02 |
| Dystonin | NM_015548 | 0.55 | 0.44 | 0.79 | 0.04/0.02 |
| Cell division cycle 23 homolog (*S. cerevisiae*) | BC010944 | 0.68 | 0.39 | 0.57 | 0.07/0.02 |
| Centrosomal protein 250 kDa | NM_007186 | 0.71 | 0.44 | 0.63 | 0.08/0.02 |
| Myosin, heavy chain 10, non-muscle | NM_005964 | 0.17 | 0.56 | 3.31 | 0.02/0.07 |
| Cyclin N-terminal domain containing 1 | NM_173478 | 0.27 | 0.62 | 2.28 | 0.01/0.07 |
| Retinoblastoma binding protein 6 | BC051317 | 0.36 | 0.66 | 1.83 | 0.01/0.06 |

TABLE 4b

| | | | | | |
|---|---|---|---|---|---|
| Tuberous sclerosis 1 | NM_000368 | 0.45 | 0.69 | 1.54 | 0.02/0.07 |
| Retinoblastoma binding protein 6 | NM_032626 | 0.49 | 0.62 | 1.27 | 0.03/0.05 |
| Structural maintenance of chromosomes 1B | NM_148674 | 0.39 | 0.54 | 1.38 | 0.02/0.03 |
| v-abl Abelson murine leukemia viral oncogene homolog 1 | NM_007313 | 0.35 | 0.57 | 1.61 | 0.01/0.03 |

TABLE 5a

| | | Exp. pattern | | Total | |
|---|---|---|---|---|---|
| Gene | Genbank ID | Veh. vs Hp18 | Veh. vs Cp-p18 | relative ratio | t-test/ p-at |
| ADAM metallopeptidase with thrombospondin type 1 motif, 4 | NM_005099 | 2.15 | 1.62 | 0.76 | 0.04/0.16 |
| Nuclear receptor subfamily 5, group A, member 1 | NM_004959 | 2.18 | 1.64 | 0.75 | 0.02/0.05 |
| Adrenergic, alpha-1D-, receptor | NM_000678 | 2.22 | 1.66 | 0.75 | 0.02/0.04 |
| MT1L_HUMAN (P80297) (MT1X), complete | | 2.33 | 1.70 | 0.73 | 0.02/0.04 |
| v-mos Moloney murine sarcoma viral oncogene homolog | NM_005372 | 4.62 | 2.79 | 0.60 | 0.01/0.01 |
| Keratin 5 | NM_000424 | 1.79 | 2.83 | 1.58 | 0.03/0.01 |
| Insulin-like growth factor binding protein 3 isoform a precursor | NM_001013398 | 1.68 | 2.52 | 1.50 | 0.00/0.00 |
| Melanoma inhibitory activity | NM_006533 | 1.86 | 3.52 | 1.90 | 0.03/0.01 |
| Keratin 9 | NM_000226 | 1.43 | 2.32 | 1.62 | 0.08/0.02 |
| Tumor necrosis factor receptor superfamily, member 18 isoform 2 precursor | NM_148901 | 1.54 | 3.66 | 2.38 | 0.08/0.01 |
| Catenin, delta 2 | NM_001332 | 3.33 | 1.58 | 0.47 | 0.03/0.10 |
| Cleft lip and palate associated transmembrane protein 1 | NM_001294 | 2.98 | 1.48 | 0.50 | 0.01/0.06 |
| Secreted and transmembrane 1 precursor | NM_003004 | 2.89 | 1.42 | 0.49 | 0.01/0.08 |
| Phosphorylase kinase gamma subunit 1 | NM_006213 | 2.01 | 1.25 | 0.62 | 0.02/0.16 |
| Myelin oligodendrocyte glycoprotein isoform Alpha4 precursor | NM_206814 | 2.85 | 1.58 | 0.55 | 0.02/0.12 |
| Calsequestrin 1 | NM_001231 | 2.61 | 1.52 | 0.58 | 0.02/0.07 |
| Mesenchyme homeobox 1 isoform 1 | NM_004527 | 2.18 | 1.42 | 0.65 | 0.04/0.15 |
| Lung cancer-related protein 8 | NM_017941 | 2.51 | 1.47 | 0.58 | 0.02/0.08 |
| ADAM metallopeptidase with thrombospondin type 1 motif, 9 preproprotein | NM_182920 | 2.36 | 1.57 | 0.67 | 0.02/0.07 |
| Frizzled 1 | NM_003505 | 2.19 | 1.52 | 0.69 | 0.04/0.08 |
| Myeloid/lymphoid or mixed-lineage leukemia 2 | NM_003482 | 2.94 | 1.18 | 0.40 | 0.02/0.42 |

TABLE 5b

| | | | | | |
|---|---|---|---|---|---|
| Misshapen/NIK-related kinase isoform 3 | NM_153827 | 2.15 | 1.13 | 0.53 | 0.02/0.35 |
| Coagulation factor II precursor | NM_000506 | 2.14 | 1.18 | 0.55 | 0.02/0.24 |
| Rho guanine nucleotide exchange factor (GEF) 11 isoform 2 | NM_198236 | 1.16 | 2.21 | 1.91 | 0.61/0.04 |
| Tumor necrosis factor, alpha-induced protein 8-like 3 | NM_207381 | 1.22 | 2.39 | 1.95 | 0.38/0.03 |
| Keratin 6B | NM_005555 | 1.27 | 3.11 | 2.44 | 0.14/0.01 |
| T-box 1 isoform C | NM_080647 | 2.49 | 0.64 | 0.26 | 0.02/0.05 |
| Transcription factor 21 | NM_003206 | 0.28 | 1.02 | 3.62 | 0.05/0.91 |
| Laminin alpha 3 subunit isoform 1 | NM_198129 | 0.38 | 0.91 | 2.39 | 0.03/0.48 |
| Sprouty-related protein 1 with EVH-1 domain | NM_152594 | 0.45 | 0.89 | 1.96 | 0.03/0.41 |

TABLE 5b-continued

| | | | | | |
|---|---|---|---|---|---|
| Suppressor of cytokine signaling 4 | NM_199421 | 0.43 | 0.85 | 2.00 | 0.02/0.26 |
| Arachidonate 12-lipoxygenase | NM_000697 | 0.90 | 0.42 | 0.46 | 0.53/0.04 |
| 3'-phosphoadenosine 5'-phosphosulfate synthase 2 isoform b | NM_001015880 | 0.46 | 0.72 | 1.57 | 0.02/0.09 |
| casein kinase 2, alpha prime polypeptide | NM_001896 | 0.39 | 0.64 | 1.67 | 0.01/0.05 |
| ADAM metallopeptidase domain 22 isoform 5 preproprotein | NM_021721 | 0.36 | 0.70 | 1.93 | 0.04/0.12 |
| solute carrier family 25, member 25 isoform b | NM_001006641 | 0.38 | 0.59 | 1.55 | 0.03/0.07 |
| v-abl Abelson murine leukemia viral oncogene homolog 1 isoform b | NM_007313 | 0.35 | 0.57 | 1.61 | 0.01/0.03 |
| fibroblast growth factor receptor 1 | NM_023111 | 0.30 | 0.48 | 1.57 | 0.01/0.02 |
| suppressor of cytokine signaling 5 | NM_144949 | 0.42 | 0.50 | 1.20 | 0.02/0.02 |
| C1q and tumor necrosis factor related protein 1 | NM_198594 | 0.55 | 0.42 | 0.76 | 0.06/0.03 |
| flotillin 2 | NM_004475 | 0.52 | 0.38 | 0.74 | 0.09/0.02 |
| myeloid/lymphoid or mixed-lineage leukemia (trithorax homolog, *Drosophila*); translocated to, 4 | NM_005936 | 0.27 | 0.15 | 0.57 | 0.01/0.01 |
| HUMBCGF B-cell growth factor | | 0.54 | 0.45 | 0.83 | 0.03/0.01 |

TABLE 5c

| | | | | | |
|---|---|---|---|---|---|
| tumor necrosis factor receptor superfamily, member 13C | NM_052945 | 0.36 | 0.26 | 0.72 | 0.01/0.01 |
| sema domain, immunoglobulin domain (Ig) | NM_020163 | 0.35 | 0.23 | 0.67 | 0.01/0.01 |
| syntaxin 2 | NM_001980 | 0.52 | 0.36 | 0.70 | 0.03/0.01 |
| TAO kinase 2 | NM_004783 | 0.58 | 0.42 | 0.72 | 0.18/0.02 |
| chemokine (C-X-C motif) ligand 1 (melanoma growth stimulating activity, alpha) | NM_001511 | 0.45 | 0.28 | 0.63 | 0.02/0.01 |
| transcription factor 12 (HTF4) | NM_207038 | 0.61 | 0.44 | 0.72 | 0.04/0.02 |
| tumor necrosis factor (ligand) superfamily, member 18 | NM_005092 | 0.58 | 0.31 | 0.53 | 0.05/0.02 |
| wingless-type MMTV integration site family, member 10A | NM_025216 | 0.59 | 0.35 | 0.59 | 0.05/0.02 |
| *Homo sapiens* fibroblast growth factor receptor 2 | NM_022976 | 0.66 | 0.42 | 0.64 | 0.06/0.02 |
| myeloid/lymphoid or mixed-lineage leukemia 3 | NM_170606 | 0.67 | 0.44 | 0.66 | 0.06/0.02 |
| dickkopf homolog 2 (*Xenopus laevis*) | NM_014421 | 0.52 | 0.28 | 0.53 | 0.03/0.01 |
| doublecortin-like kinase 1 | NM_004734 | 0.55 | 0.20 | 0.37 | 0.10/0.01 |
| RAB11B, member RAS oncogene family | NM_004218 | 0.74 | 0.40 | 0.54 | 0.10/0.02 |
| wingless-type MMTV integration site family, member 16 | NM_057168 | 0.74 | 0.28 | 0.37 | 0.09/0.01 |

TABLE 6

| | | Exp. pattern | | Total | |
|---|---|---|---|---|---|
| Gene | Genbank ID | Veh. vs Hp18 | Veh. vs Cp-p18 | relative ratio | t-test/ p-al |
| Regenerating islet-derived 1 beta | NM_006507 | 2.93 | 1.32 | 0.45 | 0.04/0.33 |
| Patched homolog 1 (*Drosophila*) | NM_000264 | 2.49 | 1.37 | 0.55 | 0.03/0.21 |
| Vascular endothelial growth factor A | NM_001025366 | 2.07 | 1.42 | 0.69 | 0.00/0.00 |
| Oncostatin M | NM_020530 | 2.22 | 1.92 | 0.86 | 0.01/0.03 |

TABLE 6-continued

| Gene | Genbank ID | Exp. pattern Veh. vs Hp18 | Exp. pattern Veh. vs Cp-p18 | Total relative ratio | t-test/ p-값 |
|---|---|---|---|---|---|
| GRB2-associated binding protein 1 | AK074381 | 2.74 | 1.87 | 0.68 | 0.02/0.06 |
| Somatostatin receptor 3 | NM_001051 | 2.06 | 1.57 | 0.76 | 0.02/0.06 |
| B-cell CLL/lymphoma 2 | NM_000657 | 2.27 | 1.66 | 0.73 | 0.02/0.04 |
| MT1L_HUMAN (P80297) (MT1X) | | 2.33 | 1.70 | 0.73 | 0.02/0.04 |
| Adrenergic, alpha-1D-, receptor | NM_000678 | 2.22 | 1.66 | 0.75 | 0.02/0.04 |
| Cell division cycle 25 homo log A (*S. pombe*) | NM_001789 | 1.44 | 2.03 | 1.41 | 0.08/0.02 |
| Melanoma inhibitory activity | NM_006533 | 1.86 | 3.52 | 1.90 | 0.03/0.01 |
| Fms-related tyrosine kinase 3 ligand | NM_001459 | 2.01 | 3.41 | 1.70 | 0.02/0.01 |
| NADPH oxidase, EF-hand calcium binding domain 5 | NM_024505 | 1.14 | 2.15 | 1.88 | 0.38/0.02 |
| CD28 molecule | NM_006139 | 0.93 | 0.19 | 0.20 | 0.77/0.05 |
| Arachidonate 12-lipoxygenase | NM_000697 | 0.90 | 0.42 | 0.46 | 0.53/0.04 |
| ATPase, aminophospholipid transporter-like, Class I, type 8A, member 2 | AL390129 | 1.04 | 0.44 | 0.42 | 0.77/0.05 |
| Cholecystokinin B receptor | NM_176875 | 0.44 | 0.56 | 0.42 | 0.03/0.04 |
| Platelet-derived growth factor receptor, alpha polypeptide | NM_006206 | 0.40 | 0.55 | 1.37 | 0.02/0.03 |
| Aldo-keto reductase family 1, member C3 | NM_003739 | 0.65 | 0.34 | 0.52 | 0.05/0.01 |
| SH2 domain protein 1A, Duncan's disease | NM_002351 | 0.32 | 0.99 | 3.11 | 0.04/0.97 |
| Fms-related tyrosine kinase 1 (vascular endothelial growth factor receptor) | NM_002019 | 0.38 | 1.12 | 2.95 | 0.04/0.65 |

TABLE 7

| Gene | Genbank ID | Exp. pattern Veh. vs Hp18 | Exp. pattern Veh. vs Cp-p18 | Total relative ratio | t-test/ p-값 |
|---|---|---|---|---|---|
| Vascular endothelial growth factor A | NM_001025366 | 2.07 | 1.42 | 0.69 | 0.00/0.00 |
| Metastasis associated protein 1 | BC006177 | 2.42 | 0.97 | 0.40 | 0.02/0.79 |
| Cadherin-like 24 | AK057922 | 2.06 | 1.35 | 0.66 | 0.02/0.11 |
| Fms-related tyrosine kinase 1 (vascular endothelial growth factor receptor) | NM_002019 | 0.38 | 1.12 | 2.95 | 0.04/0.65 |

As described in Table 3 above, in case of the apoptosis-relating genes, while the expressions of protein kinase C (PRKCE), death inducer-obliteratio 1 (DIDO1), and member 8 of a tumor necrosis factor receptor superfamily (TNFRSF18) were up-regulated by 1.5- to 2.0-fold, the expression of phosphoinositide-3-kinase (PIK3R2) was down-regulated by 3-fold in the mouse group treated with the cell permeable p18 recombinant protein compared to that treated with the control protein.

As described in Tables 4a and 4b above, in case of the cell cycle regulation-relating genes, the expression of retinoblastoma binding protein 6 (RBBP6) was up-regulated by 1.8-fold in the mouse group treated with the cell permeable p18 recombinant protein compared to that treated with the control protein.

As described in Tables 5a to 5c above, in case of the cell growth-relating genes, the expressions of a member 10A (WNT10A) and a member 16A (WNT16A) of a wingless-type MMTV integration site family were down-regulated by 2- to 2.5-fold in the mouse group treated with the cell permeable p18 recombinant protein compared to that treated with the control protein.

As described in Table 6 above, in case of the cell proliferation-relating genes, the expression of CD28 was down-regulated by 4-fold in the mouse group treated with the cell permeable p18 recombinant protein compared to that treated with the control protein.

As described in Table 7 above, in case of metastasis and angiogenesis-relating genes, the expression of metastasis associated protein 1 (MTA1) was up-regulated by 2-fold in the mouse group treated with the cell permeable p18 recombinant protein compared to that treated with the control protein.

Although the invention has been described in detail for the purpose of illustration, it is understood that such detail is solely for that purpose, and variations can be made therein by those skilled in the art without departing from the spirit and scope of the invention which is defined by the following claims.

INDUSTRIAL APPLICABILITY

The cell permeable p18 recombinant proteins of the present invention can activate cell signaling mechanisms involved in the activation of ATM and p53 that induce cell cycle arrest and apoptosis in response to DNA damage or oncogenic signals by efficiently introducing a tumor suppressor p18 into a cell. Therefore, the cell permeable p18 recombinant proteins of the present invention can be effectively used as an anticancer agent for various kinds of human cancers.

The invention claimed is:

1. A cell permeable p18 recombinant protein comprising: a macromolecule transduction domain (MTD) fused to the N-terminus or C-terminus of a tumor suppressor p18, wherein the MTD comprises SEQ ID NO: 6 or 8, and the p18 comprises SEQ ID NO: 2 or a truncation of SEQ ID NO: 2 lacking one or more of the N-, S- and C- terminal domains, wherein the N-terminal domain corresponds to amino acid residues 1-60 of SEQ ID NO:2, the S-terminal domain corresponds to amino acid residues 61-120 of SEQ ID NO:2, and the C-terminal domain corresponds to amino acid residues 121-168 of SEQ ID NO:2.

2. The cell permeable p18 recombinant protein according to claim 1, further comprising: a nuclear localization sequence (NLS) and a histidine-tag affinity domain, said nuclear localization sequence and histidine-tag affinity domain being covalently coupled to one end of the recombinant protein.

3. The cell permeable p18 recombinant protein according to claim 1, wherein the recombinant protein is selected from the group consisting of:
a recombinant protein wherein the MTD comprises SEQ ID NO: 6 and is fused to the N-terminus of the; p18;
a recombinant protein wherein the MTD comprises SEQ ID NO: 6 and is fused to the C-terminus of the p18;
a recombinant protein wherein the MTD comprises SEQ ID NO: 8 and is fused to the N-terminus of the p18; and
a recombinant protein wherein the MTD comprises SEQ ID NO: 8 and is fused to the C-terminus of the p18.

4. The cell permeable p18 recombinant protein according to claim 1, wherein the recombinant protein has an amino acid sequence selected from the group consisting of SEQ ID NOS: 42, 44, 48, and 50.

5. A polynucleotide encoding the cell permeable p18 recombinant protein according to claim 1.

6. The polynucleotide according to claim 5, wherein the polynucleotide has a nucleotide sequence selected from the group consisting of SEQ ID NOS: 41, 43, 47, and 49.

7. An expression vector comprising the polynucleotide according to claim 5.

8. The expression vector according to claim 7, wherein the expression vector is selected from the group consisting pHM$_2$p18, pHp18M$_2$, pHM$_3$p18, and pHp18M$_3$.

9. A transformant comprising the expression vector according to claim 7.

10. The transformant according to claim 9, wherein the transformant is *E. coil* DH5α/HM$_3$p18 (Accession No. KCTC-11312BP).

11. A method of producing a cell permeable p18 recombinant protein comprising culturing the transformant according to claim 9.

12. A pharmaceutical composition for treating p18 deficiency or failure comprising the cell permeable p18 recombinant protein according to claim 1 as an effective ingredient and a pharmaceutically acceptable carrier.

13. A cell permeable p18 recombinant protein comprising a first MTD fused to the N-terminus of a human tumor suppressor p18 and a second MTD fused to the C-terminus of said human tumor p18 suppressor, wherein the first and second MTDs independently comprise SEQ ID NO: 6 or 8 and the p18 comprises SEQ ID NO: 2.

14. The cell permeable p18 recombinant protein of claim 13 wherein the first and second MTDs comprises SEQ ID NO 6 or SEQ ID NO:8.

15. The cell permeable p18 recombinant protein according to claim 13, wherein the recombinant protein has an amino acid sequence of SEQ ID NO: 46 or SEQ ID NO: 52.

16. A polynucleotide encoding the cell permeable p18 recombinant protein according to claim 13.

17. The polynucleotide according to claim 16, wherein the polynucleotide has a nucleotide sequence of SEQ ID NO: 45 or SEQ ID NO:51.

18. An expression vector comprising the polynucleotide according to claim 16.

19. The expression vector according to claim 18, wherein the expression vector is pHM$_2$p18M$_2$ or pHM$_3$p18M$_3$.

20. A transformant comprising the expression vector according to claim 18.

21. The transformant according to claim 19, wherein the transformant is *E. coli* DH5α/HM$_2$p18M$_2$ (Accession No. KCTC- 11311BP).

22. The cell permeable p18 recombinant protein according to claim 13, further comprising: a nuclear localization sequence (NLS) and a histidine-tag affinity domain, said nuclear localization sequence and histidine-tag affinity domain being covalently coupled to one end of the recombinant protein.

23. A method of producing a cell permeable p18 recombinant protein comprising culturing the transformant according to claims 20.

24. A pharmaceutical composition for treating p18 deficiency or failure comprising the cell permeable p18 recombinant protein according to claim 13 as an effective ingredient and a pharmaceutically acceptable carrier.

* * * * *